(12) United States Patent
Baker et al.

(10) Patent No.: US 8,153,626 B2
(45) Date of Patent: Apr. 10, 2012

(54) SUBSTITUTED DIAZEPINE SULFONAMIDES AS BOMBESIN RECEPTOR SUBTYPE-3 MODULATORS

(75) Inventors: Robert K. Baker, Cranford, NJ (US); Linda L. Chang, Wayne, NJ (US); Marc Chioda, Metuchen, NJ (US); Harry R. Chobanian, Aberdeen, NJ (US); Ying-Duo Gao, Edison, NJ (US); Yan Guo, Westfield, NJ (US); Linus S. Lin, Westfield, NJ (US); Ping Liu, Westfield, NJ (US); Ravi P. Nargund, East Brunswick, NJ (US); Kathleen M. Rupprecht, Cranford, NJ (US); Shouwu Miao, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 361 days.

(21) Appl. No.: 12/517,836

(22) PCT Filed: Dec. 7, 2007

(86) PCT No.: PCT/US2007/025104
§ 371 (c)(1),
(2), (4) Date: Jun. 5, 2009

(87) PCT Pub. No.: WO2008/073311
PCT Pub. Date: Jun. 19, 2008

(65) Prior Publication Data
US 2010/0317645 A1 Dec. 16, 2010

Related U.S. Application Data

(60) Provisional application No. 60/874,376, filed on Dec. 11, 2006.

(51) Int. Cl.
*A01N 43/62* (2006.01)
*A61K 31/55* (2006.01)
*C07D 491/00* (2006.01)
*C07D 513/00* (2006.01)
*C07D 515/00* (2006.01)
*C07D 243/10* (2006.01)
*C07D 487/12* (2006.01)

(52) U.S. Cl. ..................................... 514/220; 540/557

(58) Field of Classification Search .................. 514/220; 540/557
See application file for complete search history.

(56) References Cited

U.S. PATENT DOCUMENTS
2005/0187277 A1  8/2005  Mjalli et al.
2005/0272778 A1  12/2005  Combs et al.

FOREIGN PATENT DOCUMENTS

| JP | 07-243068 | 9/1995 |
| WO | 93/17681 | 9/1993 |
| WO | 98/28269 | 7/1998 |
| WO | 99/32454 | 7/1999 |
| WO | 03/104196 | 12/2003 |
| WO | 2004/007464 | 1/2004 |
| WO | 2004/046091 | 6/2004 |
| WO | 2004/048351 | 6/2004 |
| WO | 2004/058176 | 7/2004 |
| WO | 2004/071447 | 8/2004 |
| WO | 2005/035551 | 4/2005 |
| WO | 2005/056532 | 6/2005 |
| WO | 2005/080390 | 9/2005 |

OTHER PUBLICATIONS

Tisdale, J. Supportive Oncol., 2003, BioLink Communications, vol. 1, No. 3, pp. 159-168.*
Anker et. al., The Lancet, 2003, The Lancet Publishing Group, vol. 361, pp. 1077-1083.*
Gillette-Guyonnette et. al., American Journal of Clinical Nutrition, 2000, American Society for Clinical Nutrition, vol. 71 (supplemental), pp. 637S-642S.*
Ohki-Hamazaki, "Mice lacking bomesin receptor subtype-3 . . . ", Nature (1997), 165-169, vol. 390.
Liu, "Molecular basis of the pharmacological difference between rat and human . . . ", Biochemistry (2002), 8954-8960, vol. 41.
Tan, "Wound repair and proliferation of bronchial epithelial cells . . . ", Peptides (2006), 1852-1858, vol. 27.
Lebacq-Verheyden, "Bombesin and gastrin-releasing peptide: . . . ", Handbook of Exper. Pharmacol. (1990), 71-124, vol. 95.
Porcher, "Bombesin receptor subtype-3 is expressed by the enteric nervous . . . ", Cell Tissue Res. (2005), 21-31 vol. 320.
Akai, "Efficient lipase-catalyzed enantioselective desymmetrization . . . ", J. Org. Chem. (2002), 411-419, vol. 67.
Lohse, "New synthesis of oxcarbazepine via remote metalation . . . ", Tetra. Letters (2001), 385-389, vol. 42.

* cited by examiner

*Primary Examiner* — Sreeni Padmanabhan
*Assistant Examiner* — Sarah Pihonak
(74) *Attorney, Agent, or Firm* — Baerbel R. Brown; John C. Todaro

(57) ABSTRACT

Certain novel substituted diazepine sulfonamides are ligands of the human bombesin receptor and, in particular, are selective ligands of the human bombesin receptor subtype-3 (BRS-3). They are therefore useful for the treatment, control, or prevention of diseases and disorders responsive to the modulation of BRS-3, such as obesity, and diabetes.

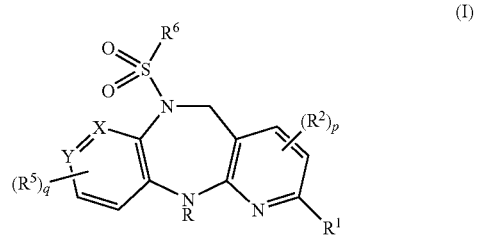

20 Claims, No Drawings

SUBSTITUTED DIAZEPINE SULFONAMIDES AS BOMBESIN RECEPTOR SUBTYPE-3 MODULATORS

CROSS-REFERENCE TO RELATED APPLICATIONS

This application is a U.S. National Phase application under 35 U.S.C. §371 of PCT Application No. PCT/US2007/025104, filed 7 Dec. 2007, which claims priority from and the benefit of U.S. Provisional Application No. 60/874,376, filed Dec. 11, 2006.

BACKGROUND OF THE INVENTION

Obesity is a major health concern in Western societies. It is estimated that about 97 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; hyperinsulinemia; glucose intolerance; dyslipidemias; hyperlipidemia; endometrial, breast, prostate and colon cancer; osteoarthritis; respiratory complications, such as obstructive sleep apnea; cholescystitis; cholelithiasis; gout; gallstones; gall bladder disease; respiratory problems; psychological disorders (such as depression, eating disorders, distorted body image and low self esteem); arteriosclerosis; heart disease; abnormal heart rhythms; angina pectoris; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death. Recent studies have found that obesity and its associated health risks also affect children and adolescents.

Obesity is now recognized as a chronic disease that requires treatment to reduce its associated health risks. Important outcomes for the treatment of obesity include weight loss, and weight management to improve cardiovascular and metabolic health and to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Rodent genetics and pharmacology have implicated BRS-3 in the development of obesity and diabetes (Ohki et al. Nature 390: 165-69 (1997)). Bombesin receptor subtype 3 is a G protein coupled receptor expressed primarily in the central nervous system, particularly the hypothalamus, a major region in the central nervous system for the regulation of food intake, metabolic rate, and body weight (Liu et al. Biochem 41: 8154-8160 (2002)). Bombesin, bombesin-like peptides, and related receptors participate in a diverse array of physiological processes. Although the natural ligand for the BRS-3 receptor has not yet been identified, bombesin-like peptides are widely distributed in the central nervous system and the gastrointestinal tract, where they bind to bombesin receptor subtype 3 (BRS-3), neuromedin B, and gastrin-releasing peptide (GRP-R) receptors, and modulate smooth muscle contraction, exocrine and endocrine processes, metabolism and behavior. BRS-3 has been implicated in the regulation of neuroendocrine function and energy metabolism (Ohki et al. Nature 390: 165-69 (1997)). One study showed that mice lacking the bombesin subtype-3 (BRS-3) receptor develop metabolic defects and obesity (Ohki et al. Nature 390: 165-69 (1997)). Specifically, mice lacking functional BRS-3 are hyperphagic and have a reduced metabolic rate, reduced core temperature which leads to the development of obesity, insulin resistance, diabetes and hypertension as they age. Additionally, bombesin-like peptides may contribute to the pathogenesis of some human carcinomas (For review' see Lebacq-Verheyden et ale in Handbook of Experime'tal Pharmacology, Sporn, M. N. and Roberts, A. B., eds., Vol. 95, pp. 71-124, Springer-Nierlag, Berlin). There is also evidence of a role for BRS-3 in cell growth and wound repair (Tan et al. Peptides 27:1852-58 (2006)) and its distribution in the rat gastrointestinal tract suggests a role in regulation of gut motility (Porcher et al., Cell Tissue Res 320:21-31 (2005).

BRS-3 agonists to treat obesity/diabetes are disclosed in WO 2005/080390, WO 2005/056532, and WO 2003/104196. Imidazole compounds useful for the treatment of obesity and/or diabetes have been disclosed in WO 04/058176, WO 04/071447, WO 04/048351, WO 04/046091, WO 05/035551, US 2005/0187277 and US 2005/0272778. Other imidazoles are disclosed in WO 93/17681, WO 98/28269, WO 99/32454, WO 04/007464, and JP 7-243068.

Weight loss drugs that are currently used in for the treatment of obesity have limited efficacy and significant side effects. Because of the unresolved deficiencies of the various pharmacological agents used in the treatment of obesity and diabetes, there is a continuing need for a weight loss treatment with enhanced efficacy and fewer undesirable side effects. The instant invention addresses this problem by providing bombesin receptor agonists, and in particular selective agonists of the bombesin receptor subtype-3 (BRS-3), useful in the treatment and prevention of obesity, diabetes, obesity-related disorders, and diabetes related disorders.

SUMMARY OF THE INVENTION

The present invention relates to novel substituted diazepines of formula I:

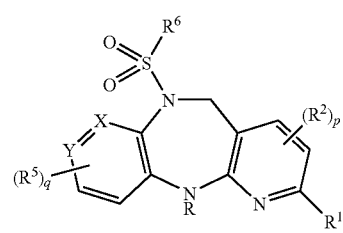

The compounds of formula I are effective as bombesin receptor ligands and are particularly effective as selective ligands of the bombesin receptor subtype-3. They are therefore useful for the treatment and/or prevention of disorders responsive to the modulation of the bombesin receptor subtype-3, such as obesity, diabetes, obesity-related disorders and diabetes-related disorders.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the bombesin receptor subtype-3 in a mammal in need thereof by administering the compounds and pharmaceutical compositions of the present invention.

The present invention further relates to the use of the compounds of the present invention in the preparation of a medicament useful for the treatment or prevention of disorders, diseases, or conditions responsive to the modulation of the bombesin receptor subtype-3 in a mammal in need thereof by administering the compounds and pharmaceutical compositions of the present invention.

DETAILED DESCRIPTION OF THE INVENTION

The present invention relates to substituted diazepines useful as bombesin receptor modulators, in particular, as selective bombesin receptor subtype-3 agonists. Compounds of the present invention are described by formula I:

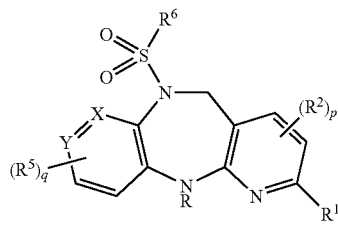

or a pharmaceutically acceptable salt thereof; wherein
X is selected from the group consisting of:
  (1) $CR^3$, and
  (2) N;
Y is selected from the group consisting of:
  (1) $CR^4$, and
  (2) N;
R is selected from the group consisting of:
  (1) hydrogen,
  (2) $-(CH_2)_nC_{2-6}$alkenyl, and
  (3) $-COC_{1-6}$alkyl;
$R^1$, $R^2$, $R^3$, $R^4$ and $R^5$ are each independently selected from the group consisting of:
  (1) hydrogen,
  (2) $-(CH_2)_n$halogen,
  (3) $-C_{1-8}$alkyl,
  (4) $-(CH_2)_nC_{2-8}$alkenyl,
  (5) $-(CH_2)_nC_{2-8}$alkynyl,
  (6) $-(CH_2)_nCN$,
  (7) $-(CH_2)_nCF_3$,
  (8) $-(CH_2)_nCHF_2$,
  (9) $-(CH_2)_nCH_2F$,
  (10) $-(CH_2)_nOCF_3$,
  (11) $-(CH_2)_nOR^b$,
  (12) $-(CH_2)_nCOR^c$,
  (13) $-(CH_2)_nCO_2R^d$,
  (14) $-(CH_2)_nOC(O)R^c$,
  (15) $-(CH_2)_nN(R^c)_2$,
  (16) $-(CH_2)_nNO_2$,
  (17) $-(CH_2)_nCH=NR^a$,
  (18) $-(CH_2)_nCH=N-OR^a$,
  (19) $-(CH_2)_nC(O)N(R^c)_2$,
  (20) $-(CH_2)_nC(O)NR^aN(R^c)_2$,
  (21) $-(CH_2)_nC(O)_{1-2}(CH_2)_nCO_2R^a$,
  (22) $-(CH_2)_nC(O)NR^a(CH_2)_nCO_2R^a$,
  (23) $-(CH_2)_nNR^cC(O)R^c$,
  (24) $-(CH_2)_nNR^aSO_{0-2}C_{1-6}$alkyl,
  (25) $-(CH_2)_nSO_{0-2}N(R^c)_2$,
  (26) $-(CH_2)_nSO_{0-2}C_{1-8}$alkyl,
  (27) $-(CH_2)_nSO_{0-2}C_{3-8}$cycloalkyl,
  (28) $-(CH_2)_nSO_{0-2}$aryl,
  (29) $-(CH_2)_nSO_{0-2}$heteroaryl,
  (30) $-(CH_2)_nC_{3-10}$cycloalkyl,
  (31) $-(CH_2)_nC_{3-10}$cycloalkenyl,
  (32) $-(CH_2)_nC_{2-12}$heterocycloalkyl,
  (33) $-(CH_2)_nC_{2-12}$heterocycloalkenyl,
  (34) $-(CH_2)_n$aryl,
  (35) $-(CH_2)_n$heteroaryl,
  (36) $-(CH_2)_nO(CH_2)_n$heteroaryl,
  (37) $-C(O)C_{3-10}$cycloalkyl,
  (38) $-C(O)C_{3-10}$cycloalkenyl,
  (39) $-C(O)C_{2-12}$heterocycloalkyl,
  (40) $-C(O)C_{2-12}$heterocycloalkenyl,
  (41) $-C(O)$aryl,
  (42) $-C(O)$heteroaryl,
  (43) $-C(O)NR^cC_{3-10}$cycloalkyl,
  (44) $-C(O)NR^cC_{3-10}$cycloalkenyl,
  (45) $-C(O)NR^cC_{2-12}$heterocycloalkyl,
  (46) $-C(O)NR^c$aryl, and
  (47) $-C(O)NR^c$heteroaryl,
wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$;
$R^6$ is independently selected from the group consisting of:
  (1) $C_{1-8}$alkyl,
  (2) $-(CH_2)_nC_{3-10}$cycloalkyl,
  (3) $-(CH_2)_nC_{3-10}$cycloalkenyl,
  (4) $-(CH_2)_nC_{2-12}$heterocycloalkyl,
  (5) $-(CH_2)_nC_{2-12}$heterocycloalkenyl,
  (6) $-(CH_2)_n$aryl, and
  (7) $-(CH_2)_n$heteroaryl,
wherein alkyl, cycloalkyl, cycloalkenyl, heterocycloalkyl, heterocycloalkenyl, aryl, heteroaryl, and $(CH_2)_n$ are unsubstituted or substituted with 1 to 5 substituents selected from $R^f$;
each $R^a$ is independently selected from the group consisting of:
  (1) hydrogen, and
  (2) $-C_{1-6}$alkyl,
wherein alkyl is unsubstituted or substituted with 1 to 3 substituents selected from $-(CH_2)_nOH$;
each $R^b$ is independently selected from the group consisting of:
  (1) hydrogen,
  (2) $-C_{1-6}$alkyl,
  (3) $-(CH_2)_nCF_3$,
  (4) $-(CH_2)_nOC_{1-6}$alkyl,
  (5) $-(CH_2)_nSO_2CF_3$,
  (6) $-(CH_2)_nC_{2-6}$alkenyl,
  (7) $-(CH_2)_nC_{3-8}$cycloalkyl,
  (8) $-(CH_2)_nC_{2-8}$heterocycloalkyl,
  (9) $-(CH_2)_n$aryl, and
  (10) $-(CH_2)_n$heteroaryl,
wherein alkyl, alkenyl, cycloalkyl, heterocycloalkyl, aryl, heteroaryl, and $-(CH_2)_n$ are unsubstituted or substituted with 1-4 substituents selected from $-OH$, halogen, $-CN$, $-CF_3$, $-C_{1-6}$alkyl, and $-CO_2H$;

each $R^c$ is independently selected from the group consisting of:
(1) hydrogen,
(2) —$C_{1-6}$alkyl,
(3) —$(CH_2)_nCF_3$,
(4) —$(CH_2)_nCO_2R^a$,
(5) —$(CH_2)_nSO_2CF_3$,
(6) —$(CH_2)_nC_{3-8}$cycloalkyl,
(7) —$(CH_2)_nC_{2-8}$heterocycloalkyl,
(8) —$(CH_2)_n$aryl, and
(9) —$(CH_2)_n$heteroaryl,
wherein alkyl, cycloalkyl, heterocycloalkyl, aryl, heteroaryl, and —$(CH_2)_n$ are unsubstituted or substituted with 1-4 substituents selected from —OH, halogen, —CN, and $C_{1-6}$alkyl;
each $R^d$ is independently selected from the group consisting of:
(1) hydrogen,
(2) —$C_{1-6}$alkyl, and
(3) —$C_{3-8}$cycloalkyl,
wherein alkyl and cycloalkyl are unsubstituted or substituted with 1-3 substituents selected from halogen, —CN, —OH, —$N(R^2)_2$, and aryl;
each $R^e$ is independently selected from the group consisting of:
(1) —$(CH_2)_n$halogen,
(2) —$C_{1-6}$alkyl,
(3) —$(CH_2)_nCF_3$,
(4) —$(CH_2)_nCN$,
(5) —$(CH_2)_nC_{2-8}$alkenyl,
(6) oxo,
(7) thio,
(8) —$(CH_2)_nOR^a$,
(9) —$(CH_2)_nN(R^a)_2$,
(10) —$(CH_2)_nN(R^a)COR^a$,
(11) —$(CH_2)CON(R^a)_2$,
(12) —$(CH_2)_nCOR^a$,
(13) —$(CH_2)_nN(R^a)CO_2R^a$,
(14) —$(CH_2)_nCO_2R^a$,
(15) —$(CH_2)_nOC(O)R^a$,
(16) —$(CH_2)_nC_{3-8}$cycloalkyl,
(17) —$(CH_2)_nC_{2-8}$heterocycloalkyl,
(18) —$(CH_2)_n$aryl,
(19) —$(CH_2)_n$heteroaryl,
(20) —$(CH_2)_n$—O—$(CH_2)_n$aryl,
(21) —$(CH_2)_nO(CH_2)_n$heteroaryl, and
(22) —$(CH_2)_nOP(O)(OH)_2$,
wherein alkyl, alkenyl, cycloalkyl, heterocycloalkyl, aryl, heteroaryl, and $(CH_2)_n$ are unsubstituted or substituted with 1 to 5 substituents selected from —$(CH_2)_{0-2}$OH, —F, —$CF_3$, —$CO_2C_{1-6}$alkyl, oxo, and —$C_{1-6}$allyl unsubstituted or substituted with —OH;
each $R^f$ is independently selected from the group consisting of:
(1) —$(CH_2)_n$halogen,
(2) —$(CH_2)_nO_mC_{1-8}$alkyl,
(3) —$(CH_2)_nO_mC_{2-8}$alkenyl,
(4) —$(CH_2)_nCN$,
(5) —$(CH_2)_nCCl_3$,
(6) —$(CH_2)_nOH$,
(7) —$(CH_2)_nC(O)H$,
(8) —$(CH_2)_nC(O)C_{1-8}$alkyl,
(9) —$(CH_2)_nCO_2H$,
(10) —$(CH_2)_nCO_2C_{1-8}$alkyl,
(11) —$(CH_2)_nO_mCF_3$,
(12) —$(CH_2)_nO_mCHF_2$,
(13) —$(CH_2)_nO_mCH_2F$,
(14) —$(CH_2)_nO_mC_{3-10}$cycloalkyl,
(15) —$(CH_2)_nO_mC_{3-10}$cycloalkenyl,
(16) —$(CH_2)_nO_mC_{2-12}$heterocycloalkyl,
(17) —$(CH_2)_nO_mC_{2-12}$heterocycloalkenyl,
(18) —$(CH_2)_nO_m$aryl,
(19) —$(CH_2)_nO_m$heteroaryl,
(20) —$SO_{0-2}C_{1-8}$alkyl,
(21) —$SO_{0-2}C_{3-8}$cycloalkyl,
(22) —$(CH_2)_nN(R^c)_2$,
(23) —$(CH_2)_nC(O)N(R^c)_2$, and
(24) —$(CH_2)_nNR^cC(O)R^c$,
wherein alkyl, alkenyl, cycloalkyl, cycloalkenyl, heterocloalkyl, heterocycloalkenyl, aryl, heteroaryl, and —$(CH_2)_n$, are unsubstituted or substituted with 1 to 3 substituents selected from —OH, —$CF_3$, halogen, —$C_{1-6}$alkyl and —CN;
each n is independently 0, 1, 2, 3, 4, or 5;
each m is independently 0 or 1;
each p is independently 0, 1 or 2; and
each q is independently 0, 1 or 2.

In a further embodiment of the compounds of the present invention, there are provided compounds of formula II:

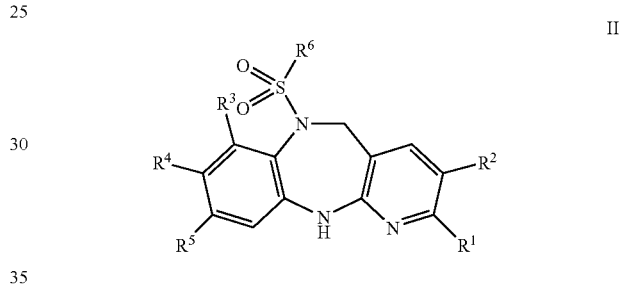

or a pharmaceutically acceptable salt thereof.

In a further embodiment of the compounds of the present invention, there are provided compounds of formula III:

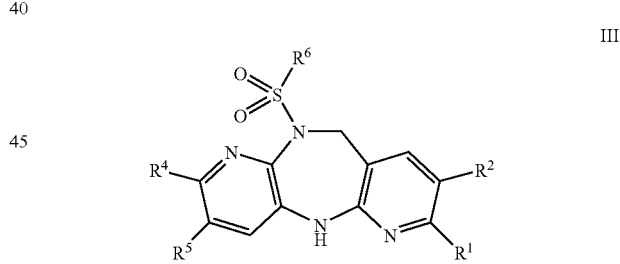

or a pharmaceutically acceptable salt thereof.

In a further embodiment of the compounds of the present invention, there are provided compounds of formula IV:

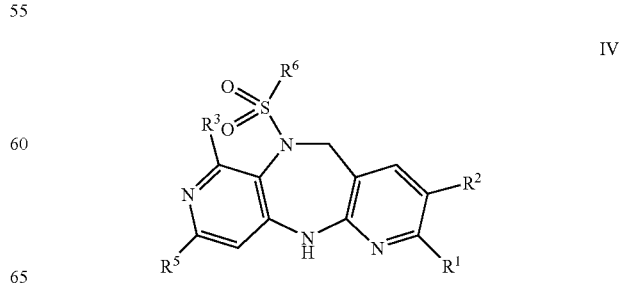

or a pharmaceutically acceptable salt thereof.

In one embodiment of the present invention, X is selected from the group consisting of $CR^3$, and N. In a class of this embodiment, X is $CR^3$. In another class of this embodiment, X is N.

In one embodiment of the present invention, Y is selected from the group consisting of: $CR^4$, and N. In a class of this embodiment, Y is $CR^4$. In another class of this embodiment, Y is N.

In another embodiment of the present invention, R is selected from the group consisting of: hydrogen, $-(CH_2)_n$ $C_{2-6}$alkenyl, and $-COC_{1-6}$alkyl. In another embodiment of the present invention, R is selected from the group consisting of: hydrogen, and $-(CH_2)_nC_{2-6}$alkenyl. In another embodiment of the present invention, R is selected from the group consisting of: hydrogen, and $-CH_2CH=CH_2$. In another embodiment of the present invention, R is $-CH_2CH=CH_2$. In another embodiment of the present invention, R is hydrogen.

In another embodiment of the present invention, $R^1$, $R^2$, $R^3$, $R^4$ and $R^5$ are each independently selected from the group consisting of: hydrogen, $-(CH_2)_n$halogen, $-C_{1-8}$alkyl, $-(CH_2)_nC_{2-8}$alkenyl, $-(CH_2)_nC_{2-8}$alkynyl, $-(CH_2)_nCN$, $-(CH_2)_nCF_3$, $-(CH_2)_nCHF_2$, $-(CH_2)_nCH_2F$, $-(CH_2)_n$ $OCF_3$, $-(CH_2)_nOR^b$, $-(CH_2)_nCOR^c$, $-(CH_2)_nCO_2R^d$, $-(CH_2)_nOC(O)R^c$, $-(CH_2)_nN(R^c)_2$, $-(CH_2)_nNO_2$, $-(CH_2)_nCH=NR^a$, $-(CH_2)_nCH=N-OR^a$, $-(CH_2)_nC$ $(O)N(R^c)_2$, $-(CH_2)_nC(O)NR^aN(R^c)_2$, $-(CH_2)_nC(O)_{1-2}$ $(CH_2)_nCO_2R^a$, $-(CH_2)_nC(O)NR^a(CH_2)_nCO_2R^a$, $-(CH_2)_n$ $NR^cC(O)R^c$, $-(CH_2)_nNR^aSO_{0-2}C_{1-6}$alkyl, $-(CH_2)_nSO_{0-2}$ $N(R^c)_2$, $-(CH_2)_nSO_{0-2}C_{1-8}$alkyl, $-(CH_2)_nSO_{0-2}C_{3-8}$ cycloalkyl, $-(CH_2)_nSO_{0-2}$aryl, $-(CH_2)_nSO_{0-2}$heteroaryl, $-(CH_2)_nC_{3-10}$cycloalkyl, $-(CH_2)_nC_{3-10}$cycloalkenyl, $-(CH_2)_nC_{2-12}$heterocycloalkyl, $-(CH_2)_nC_{2-12}$heterocycloalkenyl, $-(CH_2)_n$aryl, $-(CH_2)_n$heteroaryl, $-(CH_2)_n-$ $O-(CH_2)_n$heteroaryl, $-C(O)C_{3-10}$cycloalkyl, $-C(O)$ $C_{3-10}$cycloalkenyl, $-C(O)C_{2-12}$heterocycloalkyl, $-C(O)$ $C_{2-12}$heterocycloalkenyl, $-C(O)$aryl, $-C(O)$hetero aryl, $-C(O)NR^cC_{3-10}$cycloalkyl, $-C(O)NR^cC_{3-10}$cycloalkenyl, $-C(O)NR^cC_{2-12}$heterocycloalkyl, $-C(O)NR^c$aryl, and $-C(O)NR^c$heteroaryl, wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^1$, $R^2$, $R^3$, $R^4$ and $R^5$ are each independently selected from the group consisting of: hydrogen, $-(CH_2)_n$halogen, $-C_{1-8}$alkyl, $-(CH_2)_nC_{2-8}$alkenyl, $-(CH_2)_nCN$, $-(CH_2)_nCF_3$, $-(CH_2)_nCHF_2$, $-(CH_2)_nCH_2F$, $-(CH_2)_nOCF_3$, $-(CH_2)_n$ $OR^b$, $-(CH_2)_nCOR^c$, $-(CH_2)_nCO_2R^d$, $-(CH_2)_nN(R^c)_2$, $-(CH_2)_nCH=NR^a$, $-(CH_2)_nCH=N-OR^a$, $-(CH_2)_nC$ $(O)N(R^c)_2$, $-(CH_2)_nC(O)NR^aN(R^c)_2$, $-(CH_2)_nC(O)_{1-2}$ $(CH_2)_nCO_2R^a$, $-(CH_2)_nC(O)NR^a(CH_2)_nCO_2R^a$, $-(CH_2)_n$ $NR^cC(O)R^c$, $-(CH_2)_nSO_{0-2}C_{1-8}$alkyl, $-(CH_2)_nC_{3-10}$cycloalkyl, $-(CH_2)_nC_{2-12}$heterocycloalkyl, $-(CH_2)_n$ $C_{2-12}$heterocycloalkenyl, $-(CH_2)_n$aryl, $-(CH_2)_n$heteroaryl, $-C(O)C_{2-12}$heterocycloalkyl, $-C(O)$heteroaryl, $-C(O)$ $NR^cC_{2-12}$heterocycloalkyl, and $-C(O)NR^c$heteroaryl, wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^1$, $R^2$, $R^3$, $R^4$ and $R^5$ are each independently selected from the group consisting of: hydrogen, F, Cl, Br, I, $-(CH_2)_{0-4}CH_3$, $-CF_3$, $-CHF_2$, $-OCF_3$, $-C(OH)(CH_3)CH_2CH_3$, $-C(OH)(CH_3)$ $CF_3$, $-CH(OH)CH(OH)CH_3$, $-CH_2CH(OH)C(OH)$ $(CH_3)_2$, $-(CH_2)_{0-1}C(OH)(CH_3)_2$, $-CH(OH)CF_3$, $-CH$ $(NH_2)CH_3$, $-CH=CH_2$, $-C(CH_3)=CH_2$, $-CH=CH$ $(CH_3)$, $-C=CH$, $-(CH_2)_{0-4}C=C(CH_3)$, $-C=CCH_2OH$, $-CH(OH)-C=C(CH_3)$, $-(CH_2)_{0-1}CN$, $-C(CH_3)_2CN$, $-(CH_2)_{0-4}OH$, $-(CH_2)_{0-2}OCH_3$, $-(CH_2)_{0-2}OCF_3$, $-CH$ $(CH_3)OH$, $-C(CH_3)_2OH$, $-C(CF_3)_2OH$, $-C(CH_3)(CF_3)$ $OH$, $-(CH_2)_{0-1}CH(OH)CH_2OH$, $-C(CH_3)_2CH(OH)$ $CH_2OH$, $-C(CH_3)_2CH_2OH$, $-(CH_2)_{0-1}-C(OH)(CF_3)$ $CH_2OH$, $-(CH_2)_{0-1}C(OH)(CH_3)CH_2OH$, $-CF_2CH_2OH$, $-OCH_2CH=CH_2$, $-(CH_2)_{0-1}NH_2$, $-CH(CH_3)NH_2$, $-C(CH_3)_2CH_2NH_2$, $-NO_2$, $-C(NH_2)=NH$, $-C(CH_3)$ $=N-OH$, $-C(CH_3)=N-OCH_3$, $-(CH_2)_{0-1}C(NH_2)$ $=N-OH$, $-(CH_2)_{0-1}C(O)NH_2$, $-(CH_2)_{0-1}C(O)N(CH_3)_2$, $-C(CH_3)_2C(O)NH_2$, $-C(O)NHCH_2CO_2CH_3$, $-C(O)$ $NHC(CH_3)_2OH$, $-C(O)NH(CH_2)_2OH$, $-C(O)NHNH_2$, $-C(O)NHN(CH_3)_2$, $-CH_2NHC(O)CH_3$, $-(CH_2)_{0-1}C(O)$ $H$, $-(CH_2)_{0-1}C(O)CH_3$, $-C(O)CF_3$, $-C(O)CH_2CH_3$, $-(CH_2)_{0-1}CO_2H$, $-CO_2CH_3$, $-CH(CH_3)CO_2H$, $-C(CH_3)_2CO_2H$, $-C(CH_3)_2CO_2CH_3$, $-CH_2OC(O)CH_3$, $-CH_2NHSOC(CH_3)_3$, $-SO_2CH_3$, $-SO_2CF_3$, cyclopropyl, cyclobutyl, cyclopentyl, cyclohexyl, cyclobutene, -piperidine, morpholine, $-CH_2$-morpholine, tetrahydropyran, $-CH_2$-aziridine, tetrahydropyran, tetrahydroisoxazole, dihydrooxadiazole, dihydrotriazole, dihydropyran, tetrahydropyridine, dihydropyrazole, dihydroisoxazole, dihydrotriazole, phenyl, oxazole, -oxadiazole, triazole, thiadiazole, tetrazole, pyridine, $-(CH_2)_2$pyridine, pyrimidine, pyrazole, thiazole, isoxazole, imidazole, $-CH_2CH(OH)$ $CH_2OCH_2$phenyl, $-C(O)$-aziridine, $-C(O)$-morpholine, $-C(O)$-piperazine, $-C(O)$-piperadine, $-C(O)$-pyrrolidine, $-C(O)$-azepane, $-C(O)$-isoxazolidine, $-C(O)$-thiamorpholine, $-C(O)NH$-piperazine, $-C(O)NH$-piperadine, $-C(O)NH$-morpholine, $-C(O)NH$-azepane, $-C(O)NH$-pyrrolidine, $-C(O)NH$-imidazolidine, $-C(O)NH$-thiazole, $-C(O)NH$-triazole, $-C(O)NH$-pyridine, $-C(O)NH$-pyrrole, $-C(O)NH$-tetrazole, and $-C(O)$-pyrazole, wherein $R^1$, $R^2$, $R^3$, $R^4$ and $R^5$ are each independently unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^1$ and $R^2$ are each independently selected from the group consisting of: hydrogen, $-(CH_2)_n$halogen, $-C_{1-8}$alkyl, $-(CH_2)_nC_{2-8}$alkenyl, $-(CH_2)_nC_{2-8}$alkynyl, $-(CH_2)_nCN$, $-(CH_2)_nCF_3$, $-(CH_2)_nCHF_2$, $-(CH_2)_nCH_2F$, $-(CH_2)_nOCF_3$, $-(CH_2)_n$ $OR^b$, $-(CH_2)_nCOR^c$, $-(CH_2)_nCO_2R^d$, $-(CH_2)_nOC(O)R^c$, $-(CH_2)_nN(R^c)_2$, $-(CH_2)_nNO_2$, $-(CH_2)_nCH=NR^a$, $-(CH_2)_nCH=N-OR^a$, $-(CH_2)_nC(O)N(R^c)_2$, $-(CH_2)_nC$ $(O)NR^aN(R^c)_2$, $-(CH_2)_nC(O)_{1-2}(CH_2)_nCO_2R^a$, $-(CH_2)_nC$ $(O)NR^a(CH_2)_nCO_2R^a$, $-(CH_2)_nNR^cC(O)R^c$, $-(CH_2)_n$ $NR^aSO_{0-2}C_{1-6}$alkyl, $-(CH_2)_nSO_{0-2}N(R^c)_2$, $-(CH_2)_nSO_{0-2}C_{1-8}$alkyl, $-(CH_2)_nSO_{0-2}C_{3-8}$cycloalkyl, $-(CH_2)_nSO_{0-2}$aryl, $-(CH_2)_nSO_{0-2}$heteroaryl, $-(CH_2)_nC_{3-10}$cycloalkyl, $-(CH_2)_nC_{3-10}$cycloalkenyl, $-(CH_2)_nC_{2-12}$heterocycloalkyl, $-(CH_2)_nC_{2-12}$heterocycloalkenyl, $-(CH_2)_n$aryl, $-(CH_2)_n$heteroaryl, $-(CH_2)_n-O-(CH_2)_n$heteroaryl, $-C(O)C_{3-10}$cycloalkyl, $-C(O)C_{3-10}$cycloalkenyl, $-C(O)C_{2-12}$heterocycloalkyl, $-C(O)C_{2-12}$heterocycloalkenyl, $-C(O)$aryl, $-C(O)$heteroaryl, $-C(O)NR^cC_{3-10}$cycloalkyl, $-C(O)NR^cC_{3-10}$cycloalkenyl, $-C(O)NR^cC_{2-12}$heterocycloalkyl, $-C(O)NR^c$aryl, and $-C(O)NR^c$heteroaryl, wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^1$ and $R^2$ are each independently selected from the group consisting of: hydrogen, $-(CH_2)_n$halogen, $-C_{1-8}$alkyl, $-(CH_2)_nC_{2-8}$alkenyl, $-(CH_2)_nCN$, $-(CH_2)_nCF_3$, $-(CH_2)_nCHF_2$, $-(CH_2)_nCH_2F$, $-(CH_2)_nOCF_3$, $-(CH_2)_nOR^b$, $-(CH_2)_nCOR^c$, $-(CH_2)_nCO_2R^d$, $-(CH_2)_nN(R^c)_2$, $-(CH_2)_nCH=NR^a$, $-(CH_2)_nCH=N-OR^a$, $-(CH_2)_nC(O)N(R^c)_2$, $-(CH_2)_nC(O)NR^aN(R^c)_2$, $-(CH_2)_nC(O)_{1-2}(CH_2)_nCO_2R^a$, $-(CH_2)_nC(O)NR^a(CH_2)_nCO_2R^a$, $-(CH_2)_nNR^cC(O)R^c$, $-(CH_2)_nSO_{0-2}C_{1-8}$alkyl, $-(CH_2)_nC_{3-10}$cycloalkyl, $-(CH_2)_nC_{2-12}$heterocycloalkyl, $-(CH_2)_nC_{2-12}$heterocycloalkenyl, $-(CH_2)_n$aryl, $-(CH_2)_n$heteroaryl, $-C(O)C_{2-12}$heterocycloalkyl, $-C(O)$heteroaryl, $-C(O)NR^cC_{2-12}$heterocycloalkyl, and $-C(O)NR^c$heteroaryl, wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^1$ and $R^2$ are each independently selected from the group consisting of: hydrogen, F, Cl, Br, $-(CH_2)_{0-4}CH_3$, $-C(OH)(CH_3)CH_2CH_3$, $-C(OH)(CH_3)CF_3$, $-CH(OH)CH(OH)CH_3$, $-CH_2CH(OH)C(OH)(CH_3)_2$, $-(CH_2)_{0-1}C(OH)(CH_3)_2$, $-CH(OH)CF_3$, $-CH(NH_2)CH_3$, $-CH=CH_2$, $-C(CH_3)=CH_2$, $-CH=CH(CH_3)$, $-C\equiv CH$, $-(CH_2)_{0-1}C\equiv C(CH_3)$, $-C\equiv CCH_2OH$, $-CH(OH)-C\equiv C(CH_3)$, $-(CH_2)_{0-1}CN$, $-C(CH_3)_2CN$, $-(CH_2)_{0-4}OH$, $-(CH_2)_{0-2}OCH_3$, $-(CH_2)_{0-2}OCF_3$, $-CH(CH_3)OH$, $-C(CH_3)_2OH$, $-C(CF_3)_2OH$, $-C(CH_3)(CF_3)OH$, $-(CH_2)_{0-1}CH(OH)CH_2OH$, $-C(CH_3)_2CH(OH)CH_2OH$, $-C(CH_3)_2CH_2OH$, $-(CH_2)_{0-1}C(OH)(CF_3)CH_2OH$, $-(CH_2)_{0-1}C(OH)(CH_3)CH_2OH$, $-CF_2CH_2OH$, $-OCH_2CH=CH_2$, $-(CH_2)_{0-1}NH_2$, $-CH(CH_3)NH_2$, $-C(CH_3)_2CH_2NH_2$, $-NO_2$, $-C(NH_2)=NH$, $-C(CH_3)=N-OH$, $-C(CH_3)=N-OCH_3$, $-(CH_2)_{0-1}C(NH_2)=N-OH$, $-(CH_2)_{0-1}C(O)NH_2$, $-(CH_2)_{0-1}C(O)N(CH_3)_2$, $-C(CH_3)_2C(O)NH_2$, $-C(O)NHCH_2CO_2CH_2CH_3$, $-C(O)NHC(CH_3)_2OH$, $-C(O)NH(CH_2)_2OH$, $-C(O)NHNH_2$, $-C(O)NHN(CH_3)_2$, $-CH_2NHC(O)CH_3$, $-(CH_2)_{0-1}C(O)H$, $-(CH_2)_{0-1}C(O)CH_3$, $-C(O)CF_3$, $-C(O)CH_2CH_3$, $-(CH_2)_{0-1}CO_2H$, $-CO_2CH_3$, $-CH(CH_3)CO_2H$, $-C(CH_3)_2CO_2H$, $-C(CH_3)_2CO_2CH_3$, $-CH_2OC(O)CH_3$, $-CH_2NHSOC(CH_3)_3$, $-SO_2CH_3$, $-SO_2CF_3$, cyclopropyl, cyclobutyl, cyclopentyl, cyclohexyl, cyclobutene, -piperidine, morpholine, $-CH_2$-morpholine, tetrahydropyran, $-CH_2$-aziridine, tetrahydropyran, tetrahydroisoxazole, dihydrooxadiazole, dihydrotriazole, dihydropyran, tetrahydropyridine, dihydropyrazole, dihydroisoxazole, dihydrotriazole, phenyl, oxazole, -oxadiazole, triazole, thiadiazole, tetrazole, pyridine, $-(CH_2)_2$pyridine, pyrimidine, pyrazole, thiazole, isoxazole, imidazole, $-CH_2CH(OH)CH_2OCH_2$phenyl, $-C(O)$-aziridine, $-C(O)$-morpholine, $-C(O)$-piperazine, $-C(O)$-piperadine, $-C(O)$-pyrrolidine, $-C(O)$-azepane, $-C(O)$-isoxazolidine, $-C(O)$-thiamorpholine, $-C(O)NH$-piperazine, $-C(O)NH$-piperadine, $-C(O)NH$-morpholine, $-C(O)NH$-azepane, $-C(O)NH$-pyrrolidine, $-C(O)NH$-imidazolidine, $-C(O)NH$-thiazole, $-C(O)NH$-triazole, $-C(O)NH$-pyridine, $-C(O)NH$-pyrrole, $-C(O)NH$-tetrazole, and $-C(O)$-pyrazole, wherein $R^1$, and $R^2$ are each independently unsubstituted or substituted with 1-5 substituents selected from $R^e$.

In another embodiment of the present invention, $R^1$ and $R^2$ are each independently selected from the group consisting of: hydrogen, $-(CH_2)_n$halogen, $-(CH_2)_nOR^c$, $-(CH_2)_nCN$, $-(CH_2)_nCF_3$, $-(CH_2)_nCHF_2$, $-(CH_2)_nCH_2F$, $-C_{1-8}$alkyl, $-SC_{1-8}$alkyl, and $-SC_{3-8}$cycloalkyl, wherein alkyl, cycloalkyl, and $(CH_2)_n$ are unsubstituted or substituted with 1 to 5 substituents selected from $-C_{1-6}$alkyl, halogen, and $-OH$. In another embodiment of the present invention, $R^1$ and $R^2$ are each independently selected from the group consisting of: hydrogen, $-(CH_2)_n$halogen, $-(CH_2)_nOR^c$, $-(CH_2)_nCN$, $-(CH_2)_nCF_3$, $-(CH_2)_nCHF_2$, $-(CH_2)_nCH_2F$, and $-C_{1-8}$alkyl, wherein alkyl and $(CH_2)_n$ are unsubstituted or substituted with 1 to 5 substituents selected from $-C_{1-6}$alkyl, halogen, and $-OH$. In another embodiment of the present invention, $R^1$ and $R^2$ are each independently selected from the group consisting of: hydrogen, F, Cl, $-OCHF_2$, $-CN$, $-CF_3$, $-CH_2F$, $-CH_3$, wherein $R^1$ and $R^2$ are unsubstituted or substituted with 1 to 5 substituents selected from $-C_{1-6}$alkyl, halogen, and $-OH$.

In another embodiment of the present invention, $R^1$ is selected from the group consisting of: Cl, $-CH_3$, $-CN$, $-CF_3$, $-CHF_2$, and $-CH_2F$, wherein $R^1$ is unsubstituted or substituted with 1 to 5 substituents selected from $-C_{1-6}$alkyl, halogen, and $-OH$. In another embodiment of the present invention, $R^1$ is selected from the group consisting of: Cl, $-CH_3$, $-CN$, and $-CF_3$, wherein $R^1$ is unsubstituted or substituted with 1 to 5 substituents selected from $-C_{1-6}$alkyl, halogen, and $-OH$. In another embodiment of the present invention, $R^1$ is $-CF_3$. In another embodiment of the present invention, $R^1$ is $-CH_3$. In another embodiment of the present invention, $R^1$ is $-Cl$. In another embodiment of the present invention, $R^1$ is $-CN$. In another embodiment of the present invention, $R^1$ is hydrogen.

In another embodiment of the present invention, $R^2$ is independently selected from the group consisting of: hydrogen, and $-(CH_2)_n$halogen, wherein $(CH_2)_n$ is unsubstituted or substituted with 1 to 5 substituents selected from $-C_{1-6}$alkyl, halogen, and $-OH$. In another embodiment of the present invention, $R^2$ is independently selected from the group consisting of: hydrogen, and F. In a class of this embodiment, $R^2$ is hydrogen. In another class of this embodiment, $R^2$ is F.

In another embodiment of the present invention, $R^3$ and $R^4$ are each independently selected from the group consisting of: hydrogen, $-(CH_2)_n$halogen, $-C_{1-8}$alkyl, $-(CH_2)_nC_{2-8}$alkenyl, $-(CH_2)_nC_{2-8}$alkynyl, $-(CH_2)_nCN$, $-(CH_2)_nCF_3$, $-(CH_2)_nCHF_2$, $-(CH_2)_nCH_2F$, $-(CH_2)_nOCF_3$, $-(CH_2)_n$ $OR^b$, —$(CH_2)_nCOR^c$, —$(CH_2)_nCO_2R^d$, —$(CH_2)_nOC(O)R^c$, —$(CH_2)_nN(R^c)_2$, —$(CH_2)_nNO_2$, —$(CH_2)_nCH=NR^a$, —$(CH_2)_nCH=N-OR^a$, —$(CH_2)_nC(O)N(R^c)_2$, —$(CH_2)_nC(O)NR^aN(R^c)_2$, —$(CH_2)_nC(O)_{1-2}(CH_2)_nCO_2R^a$, —$(CH_2)_nC(O)NR^a(CH_2)_nCO_2R^a$, —$(CH_2)_nNR^cC(O)R^c$, —$(CH_2)_nNR^aSO_{0-2}C_{1-6}$alkyl, —$(CH_2)_nSO_{0-2}N(R^c)_2$, —$(CH_2)_nSO_{0-2}C_{1-8}$alkyl, —$(CH_2)_nSO_{0-2}C_{3-8}$cycloalkyl, —$(CH_2)_nSO_{0-2}$aryl, —$(CH_2)_nSO_{0-2}$heteroaryl, —$(CH_2)_nC_{3-10}$cycloalkyl, —$(CH_2)_nC_{3-10}$cycloalkenyl, —$(CH_2)_nC_{2-12}$heterocycloalkyl, —$(CH_2)_nC_{2-12}$heterocycloalkenyl, —$(CH_2)_n$aryl, —$(CH_2)_n$heteroaryl, —$(CH_2)_n$—O—$(CH_2)_n$heteroaryl, —$C(O)C_{3-10}$cycloalkyl, —$C(O)C_{3-10}$cycloalkenyl, —$C(O)C_{2-12}$heterocycloalkyl, —$C(O)C_{2-12}$heterocycloalkenyl, —$C(O)$aryl, —$C(O)$heteroaryl, —$C(O)NR^cC_{3-10}$cycloalkyl, —$C(O)NR^cC_{3-10}$cycloalkenyl, —$C(O)NR^cC_{2-12}$heterocycloalkyl, —$C(O)NR^c$aryl, and —$C(O)NR^c$heteroaryl, wherein alkyl, alkenyl, alkynyl, cycloalkyl, cycloalkenyl, heterocycloalkyl, heterocycloalkenyl, aryl, heteroaryl, —CH, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^3$ and $R^4$ are each independently selected from the group consisting of: hydrogen, —$(CH_2)_n$halogen, —$C_{1-8}$alkyl, —$(CH_2)_nC_{2-8}$alkenyl, —$(CH_2)_nCN$, —$(CH_2)_nCF_3$, —$(CH_2)_nCHF_2$, —$(CH_2)_nCH_2F$, —$(CH_2)_nOCF_3$, —$(CH_2)_nOR^b$, —$(CH_2)_nCOR^c$, —$(CH_2)_nCO_2R^d$, —$(CH_2)_nN(R^c)_2$, —$(CH_2)_nCH=NR^a$, —$(CH_2)_nCH=N-OR^a$, —$(CH_2)_nC(O)N(R^c)_2$, —$(CH_2)_nC(O)NR^aN(R^c)_2$, —$(CH_2)_nC(O)_{1-2}(CH_2)_nCO_2R^a$, —$(CH_2)_nC(O)NR^a(CH_2)_nCO_2R^a$, —$(CH_2)_nNR^cC(O)R^c$, —$(CH_2)_nSO_{0-2}C_{1-8}$alkyl, —$(CH_2)_nC_{3-10}$cycloalkyl, —$(CH_2)_nC_{2-12}$heterocycloalkyl, —$(CH_2)_nC_{2-12}$heterocycloalkenyl, —$(CH_2)_n$aryl, —$(CH_2)_n$heteroaryl, —$C(O)C_{2-12}$heterocycloalkyl, —$C(O)$heteroaryl, —$C(O)NR^cC_{2-12}$heterocycloalkyl, and —$C(O)NR^c$heteroaryl, wherein alkyl, alkenyl, alkynyl, cycloalkyl, cycloalkenyl, heterocycloalkyl, heterocycloalkenyl, aryl, heteroaryl, —CH, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$.

In another embodiment of the present invention, $R^3$ and $R^4$ are each independently selected from the group consisting of: hydrogen, F, Cl, Br, —$(CH_2)_{0-4}CH_3$, —$C(OH)(CH_3)CH_2CH_3$, —$C(OH)(CH_3)CF_3$, —$CH(OH)CH(OH)CH_3$, —$CH_2CH(OH)C(OH)(CH_3)_2$, —$(CH_2)_{0-1}C(OH)(CH_3)_2$, —$CH(OH)CF_3$, —$CH(NH_2)CH_3$, —CH=$CH_2$, —$C(CH_3)$=$CH_2$, —CH=$CH(CH_3)$, —C≡CH, —$(CH_2)_{0-1}$C≡C$(CH_3)$, —C≡$CCH_2OH$, —CH(OH)—C≡$C(CH_3)$, —$(CH_2)_{0-1}CN$, —$C(CH_3)_2CN$, —$(CH_2)_{0-4}OH$, —$(CH_2)_{0-2}OCH_3$, —$(CH_2)_{0-2}OCF_3$, —$CH(CH_3)OH$, —$C(CH_3)_2OH$, —$C(CF_3)_2OH$, —$C(CH_3)(CF_3)OH$, —$(CH_2)_{0-1}CH(OH)CH_2OH$, —$C(CH_3)_2CH(OH)CH_2OH$, —$C(CH_3)_2CH_2OH$, —$(CH_2)_{0-1}C(OH)(CF_3)CH_2OH$, —$(CH_2)_{0-1}C(OH)(CH_3)CH_2OH$, —$CF_2CH_2OH$, —$OCH_2CH$=$CH_2$, —$(CH_2)_{0-1}NH_2$, —$CH(CH_3)NH_2$, —$C(CH_3)_2CH_2NH_2$, —$NO_2$, —$C(NH_2)$=NH, —$C(CH_3)$=N—OH, —$C(CH_3)$=N—$OCH_3$, —$(CH_2)_{0-1}C(NH_2)$=N—OH, —$(CH_2)_{0-1}C(O)NH_2$, —$(CH_2)_{0-1}C(O)N(CH_3)_2$, —$C(CH_3)_2C(O)NH_2$, —$C(O)NHCH_2CO_2CH_2CH_3$, —$C(O)NHC(CH_3)_2OH$, —$C(O)NH(CH_2)_2OH$, —$C(O)NHNH_2$, —$C(O)NHN(CH_3)_2$, —$CH_2NHC(O)CH_3$, —$(CH_2)_{0-1}C(O)H$, —$(CH_2)_{0-1}C(O)CH_3$, —$C(O)CF_3$, —$C(O)CH_2CH_3$, —$(CH_2)_{0-1}CO_2H$, —$CO_2CH_3$, —$CH(CH_3)CO_2H$, —$C(CH_3)_2CO_2H$, —$C(CH_3)_2CO_2CH_3$, —$CH_2OC(O)CH_3$, —$CH_2NHSOC(CH_3)_3$, —$SO_2CH_3$, —$SO_2CF_3$, cyclopropyl, cyclobutyl, cyclopentyl, cyclohexyl, cyclobutene, -piperidine, morpholine, —$CH_2$-morpholine, tetrahydropyran, —$CH_2$-aziridine, tetrahydropyran, tetrahydroisoxazole, dihydrooxadiazole, dihydrotriazole, dihydropyran, tetrahydropyridine, dihydropyrazole, dihydroisoxazole, dihydrotriazole, phenyl, oxazole, -oxadiazole, triazole, thiadiazole, tetrazole, pyridine, —$(CH_2)_2$pyridine, pyrimidine, pyrazole, thiazole, isoxazole, imidazole, —$CH_2CH(OH)CH_2OCH_2$phenyl, —C(O)-aziridine, —C(O)-morpholine, —C(O)-piperazine, —C(O)-piperadine, —C(O)-pyrrolidine, —C(O)-azepane, —C(O)-isoxazolidine, —C(O)-thiamorpholine, —C(O)NH-piperazine, —C(O)NH-piperadine, —C(O)NH-morpholine, —C(O)NH-azepane, —C(O)NH-pyrrolidine, —C(O)NH-imidazolidine, —C(O)NH-thiazole, —C(O)NH-triazole, —C(O)NH-pyridine, —C(O)NH-pyrrole, —C(O)NH-tetrazole, and —C(O)-pyrazole, wherein $R^3$ and $R^4$ are each independently unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$. In another embodiment of the present invention, $R^3$ and $R^4$ are each independently selected from the group consisting of: hydrogen, —$C_{1-8}$alkyl, and —$(CH_2)_n$heteroaryl, wherein alkyl, heteroaryl, and $(CH_2)_n$ are unsubstituted or substituted with 1-5 substituents selected from $R^e$, and wherein $R^3$ and $R^4$ together with the atoms to which they are attached may form a 3-6 membered aromatic or non-aromatic ring containing 0 to 3 heteroatoms independently selected from oxygen, and nitrogen, wherein the 3-6 membered aromatic or non-aromatic ring is unsubstituted or substituted with 1 to 5 substituents selected from $R^e$.

In another embodiment of the present invention, each $R^5$ is independently selected from the group consisting of: hydrogen, —$(CH_2)_n$halogen, —$C_{1-8}$alkyl, —$(CH_2)_nC_{2-8}$alkenyl, —$(CH_2)_nC_{2-8}$alkynyl, —$(CH_2)_nCN$, —$(CH_2)_nOR^b$, —$(CH_2)_nN(R^c)_2$, —$(CH_2)_nNO_2$, —$(CH_2)_nCH=NR^a$, —$(CH_2)_nCH=N-OR^a$, —$(CH_2)_nC(O)N(R^c)_2$, —$(CH_2)_nC(O)NR^aN(R^c)_2$, —$(CH_2)_nNR^cC(O)R^c$, —$(CH_2)_nCOR^c$, —$(CH_2)_nCO_2R^d$, —$(CH_2)_nOC(O)R^c$, —$(CH_2)_nNR^aSO_{0-2}C_{1-6}$alkyl, —$(CH_2)_nSO_{0-2}N(R^c)_2$, —$(CH_2)_nSO_{0-2}C_{1-8}$alkyl, —$(CH_2)_nSO_{0-2}C_{3-8}$cycloalkyl, —$(CH_2)_nSO_{0-2}$aryl, —$(CH_2)_nSO_{0-2}$heteroaryl, —$(CH_2)_nC_{3-10}$cycloalkyl, —$(CH_2)_nC_{3-10}$cycloalkenyl, —$(CH_2)_nC_{2-12}$heterocycloalkyl, —$(CH_2)_nC_{2-12}$heterocycloalkenyl, —$(CH_2)_n$aryl, —$(CH_2)_n$heteroaryl, —$(CH_2)_n$—O—$(CH_2)_n$heteroaryl, —$C(O)C_{3-10}$cycloalkyl, —$C(O)C_{3-10}$cycloalkenyl, —$C(O)C_{2-12}$heterocycloalkyl, —$C(O)C_{2-12}$heterocycloalkenyl, —$C(O)$aryl, —$C(O)$heteroaryl, —$C(O)NR^cC_{3-10}$cycloalkyl, —$C(O)NR^cC_{3-10}$cycloalkenyl, —$C(O)NR^cC_{2-12}$heterocycloalkyl, —$C(O)NR^cC_{2-12}$heterocycloalkenyl, —$C(O)NR^c$aryl, and —$C(O)NR^c$heteroaryl, wherein alkyl, alkenyl, alkynyl, cycloalkyl, cycloalkenyl, heterocycloalkyl, heterocycloalkenyl, aryl, heteroaryl, —CH—, and $(CH_2)_n$ are unsubstituted or substituted with 1-5 substituents selected from $R^e$. In another embodiment of the present invention, each $R^5$ is each independently selected from the group consisting of:

hydrogen, —$(CH_2)_n$halogen, —$C_{1-8}$alkyl, —$(CH_2)_nC_{2-8}$alkenyl, —$(CH_2)_nC_{2-8}$alkynyl, —$(CH_2)_n$CN, —$(CH_2)_nOR^b$, —$(CH_2)_n$ $N(R^c)_2$, —$(CH_2)_n$NO$_2$, —$(CH_2)_n$CH=NR$^a$, —$(CH_2)_n$ CH=N—OR$^a$, —$(CH_2)_n$C(O)N(R$^c$)$_2$, —$(CH_2)_n$C(O)NR$^a$N(R$^c$)$_2$, —$(CH_2)_n$NR$^c$C(O)R$^c$, —$(CH_2)_n$COR$^c$, —$(CH_2)_n$CO$_2$R$^d$, —$(CH_2)_n$CO(O)R$^c$, —$(CH_2)_n$NR$^a$SO$_{0-2}$C$_{1-6}$alkyl, —$(CH_2)_n$SO$_{0-2}$C$_{1-8}$alkyl, —$(CH_2)_n$C$_{3-10}$cycloalkyl, —$(CH_2)_n$C$_{3-10}$-cycloalkenyl, —$(CH_2)_n$C$_{2-12}$heterocycloalkyl, —$(CH_2)_n$C$_{2-12}$heterocycloalkenyl, —$(CH_2)_n$aryl, —$(CH_2)_n$heteroaryl, —$(CH_2)_n$—O—$(CH_2)_n$ heteroaryl, —C(O)C$_{2-12}$heterocycloalkyl, —C(O)NR$^c$C$_{2-12}$heterocycloalkyl, and —C(O)NR$^c$heteroaryl, wherein alkyl, alkenyl, alkynyl, cycloalkyl, cycloalkenyl, heterocycloalkyl, heterocycloalkenyl, aryl, heteroaryl, —CH—, and $(CH_2)_n$ are unsubstituted or substituted with 1-5 substituents selected from R$^e$. In another embodiment of the present invention, each R$^5$ is independently selected from the group consisting of: hydrogen, F, Cl, Br, —$(CH_2)_{0-4}$CH$_3$, —C(OH)(CH$_3$)CH$_2$CH$_3$, —C(OH)(CH$_3$)CF$_3$, —CH(OH)CH(OH)CH$_3$, —CH$_2$CH(OH)C(OH)(CH$_3$)$_2$, —$(CH_2)_{0-1}$C(OH)(CH$_3$)$_2$, —CH(OH)CF$_3$, —CH(NH$_2$)CH$_3$, —CH=CH$_2$, —C(CH$_3$)=CH$_2$, —CH=CH(CH$_3$), —C≡CH, —$(CH_2)_{0-1}$C≡C(CH$_3$), —C≡CCH$_2$OH, —CH(OH)—C≡C(CH$_3$), —$(CH_2)_{0-1}$CN, —C(CH$_3$)$_2$CN, —$(CH_2)_{0-4}$OH, —$(CH_2)_{0-2}$OCH$_3$, —$(CH_2)_{0-2}$OCF$_3$, —CH(CH$_3$)OH, —C(CH$_3$)$_2$OH, —C(CF$_3$)$_2$OH, —C(CH$_3$)(CF$_3$)OH, —$(CH_2)_{0-1}$CH(OH)CH$_2$OH, —C(CH$_3$)$_2$CH(OH)CH$_2$OH, —C(CH$_3$)$_2$CH$_2$OH, —$(CH_2)_{0-1}$C(OH)(CF$_3$)CH$_2$OH, —$(CH_2)_{0-1}$C(OH)(CH$_3$)CH$_2$OH, —CF$_2$CH$_2$OH, —OCH$_2$CH=CH$_2$, —$(CH_2)_{0-1}$NH$_2$, —CH(CH$_3$)NH$_2$, —C(CH$_3$)$_2$CH$_2$NH$_2$, —NO$_2$, —C(NH$_2$)=NH, —C(CH$_3$)=N—OH, —C(CH$_3$)=N—OCH$_3$, —$(CH_2)_{0-1}$C(NH$_2$)=N—OH, —$(CH_2)_{0-1}$C(O)NH$_2$, —$(CH_2)_{0-1}$C(O)N(CH$_3$)$_2$, —C(CH$_3$)$_2$C(O)NH$_2$, —C(O)NHCH$_2$CO$_2$CH$_2$CH$_3$, —C(O)NHC(CH$_3$)$_2$OH, —C(O)NH(CH$_2$)$_2$OH, —C(O)NHNH$_2$, —C(O)NHN(CH$_3$)$_2$, —CH$_2$NHC(O)CH$_3$, —$(CH_2)_{0-1}$C(O)H, —$(CH_2)_{0-1}$C(O)CH$_3$, —C(O)CF$_3$, —C(O)CH$_2$CH$_3$, —$(CH_2)_{0-1}$CO$_2$H, —CO$_2$CH$_3$, —CH(CH$_3$)CO$_2$H, —C(CH$_3$)$_2$CO$_2$H, —C(CH$_3$)$_2$CO$_2$CH$_3$, —CH$_2$OC(O)CH$_3$, —CH$_2$NHSOC(CH$_3$)$_3$, —SO$_2$CH$_3$, —SO$_2$CF$_3$, cyclopropyl, cyclobutyl, cyclopentyl, cyclohexyl, cyclobutene, -piperidine, morpholine, —CH$_2$-morpholine, tetrahydropyran, —CH$_2$-aziridine, tetrahydropyran, tetrahydroisoxazole, dihydrooxadiazole, and dihydrotriazole, dihydropyran, tetrahydropyridine, dihydropyrazole, dihydroisoxazole, dihydrotriazole, phenyl, oxazole, -oxadiazole, triazole, thiadiazole, tetrazole, pyridine, —$(CH_2)_2$pyridine, pyrimidine, pyrazole, thiazole, isoxazole, imidazole, —CH$_2$CH(OH)CH$_2$OCH$_2$phenyl, —C(O)-aziridine, —C(O)-morpholine, —C(O)-piperazine, —C(O)-piperadine, —C(O)-pyrrolidine, —C(O)-azepane, —C(O)-isoxazolidine, —C(O)-thiamorpholine, —C(O)NH-piperazine, —C(O)NH-piperadine, —C(O)NH-morpholine, —C(O)NH-azepane, —C(O)NH-pyrrolidine, —C(O)NH-imidazolidine, —C(O)NH-thiazole, —C(O)NH-triazole, —C(O)NH-pyridine, —C(O)NH-pyrrole, —C(O)NH-tetrazole, and —C(O)-pyrazole, wherein each R$^5$ is independently unsubstituted or substituted with 1-5 substituents selected from R$^e$. In another embodiment of the present invention, R$^5$ is independently selected from the group consisting of: hydrogen, —$(CH_2)_n$halogen, —$(CH_2)_n$OR$^a$, —$(CH_2)_n$CN, —$(CH_2)_n$CF$_3$, —$(CH_2)_n$CHF$_2$, —$(CH_2)_n$CH$_2$F, —$(CH_2)_n$CCl$_3$, and —C$_{1-8}$alkyl. In another embodiment of the present invention, R$^5$ is independently selected from the group consisting of hydrogen, —$(CH_2)_n$halogen, and —C$_{1-8}$alkyl. In another embodiment of the present invention, R$^5$ is independently selected from the group consisting of: hydrogen, Cl, F, Br, and —CH$_3$. In another embodiment of the present invention, R$^5$ is hydrogen.

In another embodiment of the present invention, R$^6$ is independently selected from the group consisting of: C$_{1-8}$alkyl, —$(CH_2)_n$C$_{3-10}$cycloalkyl, —$(CH_2)_n$C$_{3-10}$cycloalkenyl, —$(CH_2)_n$C$_{2-12}$heterocycloalkyl, —$(CH_2)_n$C$_{2-12}$heterocycloalkenyl, —$(CH_2)_n$aryl, and —$(CH_2)_n$heteroaryl, wherein alkyl, cycloalkyl, cycloalkenyl, heterocycloalkyl, heterocycloalkenyl, aryl, heteroaryl, and $(CH_2)_n$ are unsubstituted or substituted with 1 to 5 substituents selected from R$^f$.

In another embodiment of the present invention, R$^6$ is independently selected from the group consisting of: —C$_{1-8}$alkyl, —$(CH_2)_n$aryl, and —$(CH_2)_n$heteroaryl, wherein alkyl, aryl, heteroaryl, and $(CH_2)_n$ are unsubstituted or substituted with 1 to 5 substituents selected from R$^f$.

In another embodiment of the present invention, R$^6$ is selected from the group consisting of: —C$_{1-8}$alkyl, —$(CH_2)_n$C$_{3-10}$cycloalkyl, —$(CH_2)_n$C$_{3-10}$cycloalkenyl, —$(CH_2)_n$C$_{2-12}$heterocycloalkyl, —$(CH_2)_n$C$_{2-12}$heterocycloalkenyl, —$(CH_2)_n$aryl, and —$(CH_2)_n$heteroaryl, wherein alkyl, cycloalkyl, cycloalkenyl, heterocycloalkyl, heterocycloalkenyl, aryl, heteroaryl, and $(CH_2)_n$ are unsubstituted or substituted with 1 to 5 substituents selected from R$^f$. In another embodiment of the present invention, R$^6$ is selected from the group consisting of: C$_{1-8}$alkyl, —$(CH_2)_n$aryl, and —$(CH_2)_n$heteroaryl, wherein alkyl, aryl, heteroaryl, and $(CH_2)_n$ are unsubstituted or substituted with 1 to 5 substituents selected from R$^f$. In another embodiment of the present invention, R$^6$ is selected from the group consisting of: —C(CH$_3$)$_3$, —$(CH_2)_3$ CH$_3$, phenyl, benxodioxole, 1,2,3,4-tetrahydronaphthalene, thiazole, thiophene, and pyridine, wherein R$^6$ is unsubstituted or substituted with 1 to 5 substituents selected from R$^f$. In another embodiment of the present invention, R$^6$ is phenyl, wherein phenyl is unsubstituted or substituted with 1 to 5 substituents selected from R$^f$.

In another embodiment of the present invention, each R$^a$ is independently selected from the group consisting of: hydrogen, and —C$_{1-6}$alkyl, wherein alkyl is unsubstituted or substituted with 1 to 3 substituents selected from —$(CH_2)_n$OH.

In another embodiment of the present invention, each R$^b$ is independently selected from the group consisting of: hydrogen, —C$_{1-6}$alkyl, —$(CH_2)_n$CF$_3$, —$(CH_2)_n$OC$_{1-6}$alkyl, —$(CH_2)_n$SO$_2$CF$_3$, —$(CH_2)_n$C$_{2-6}$alkenyl, —$(CH_2)_n$C$_{3-8}$cycloalkyl, —$(CH_2)_n$C$_{2-8}$heterocycloalkyl, —$(CH_2)_n$aryl, and —$(CH_2)_n$heteroaryl, wherein alkyl, alkenyl, cycloalkyl, heterocycloalkyl, aryl, heteroaryl, and —$(CH_2)_n$ are unsubstituted or substituted with 1-4 substituents selected from —OH, halogen, —CN, —CF$_3$, —C$_{1-6}$alkyl, and —CO$_2$H. In a class of this embodiment, R$^b$ is hydrogen.

In another embodiment of the present invention, each R$^c$ is independently selected from the group consisting of: hydrogen, —C$_{1-6}$alkyl, —$(CH_2)_n$CF$_3$, —$(CH_2)_n$CO$_2$R$^a$, —$(CH_2)_n$SO$_2$CF$_3$, —$(CH_2)_n$C$_{3-8}$cycloalkyl, —$(CH_2)_n$C$_{2-8}$heterocycloalkyl, —$(CH_2)_n$aryl, and —$(CH_2)_n$heteroaryl, wherein alkyl, cycloalkyl, heterocycloalkyl, aryl, heteroaryl, and —$(CH_2)_n$ are unsubstituted or substituted with 1-4 substituents selected from —OH, halogen, —CN, and C$_{1-6}$alkyl.

In another embodiment of the present invention, each R$^c$ is independently selected from the group consisting of: hydrogen, —C$_{1-6}$alkyl, —$(CH_2)_n$CF$_3$, —$(CH_2)_n$CO$_2$R$^a$, —$(CH_2)_n$C$_{3-8}$cycloalkyl, wherein alkyl, cycloalkyl, and —$(CH_2)_n$ are unsubstituted or substituted with 1-4 substituents selected from —OH, halogen, —CN, and C$_{1-6}$alkyl.

In another embodiment of the present invention, each R$^d$ is independently selected from the group consisting of: hydrogen, —C$_{1-6}$alkyl, and —C$_{3-8}$cycloalkyl, wherein alkyl and cycloalkyl are unsubstituted or substituted with 1-3 substituents selected from halogen, —CN, —OH, —N($R^a$)$_2$, and aryl. In a class of this embodiment, $R^d$ is independently selected from the group consisting of hydrogen and —C$_{1-6}$alkyl, wherein alkyl is unsubstituted or substituted with 1-3 substituents selected from halogen, —CN, —OH, —N($R^a$)$_2$, and aryl.

In another embodiment of the present invention, each $R^e$ is independently selected from the group consisting of: —(CH$_2$)$_n$halogen, —C$_{1-6}$alkyl, —(CH$_2$)$_n$CF$_3$, —(CH$_2$)$_n$CN, —(CH$_2$)$_n$C$_{2-8}$alkenyl, oxo, thio, —(CH$_2$)$_n$OR$^a$, —(CH$_2$)$_n$N(R$^a$)$_2$, —(CH$_2$)$_n$N(R$^a$)COR$^a$, —(CH$_2$)$_n$CON(R$^a$)$_2$, —(CH$_2$)$_n$COR$^a$, —(CH$_2$)$_n$N(R$^a$)CO$_2$R$^a$, —(CH$_2$)$_n$CO$_2$R$^a$, —(CH$_2$)$_n$OC(O)R$^a$, —(CH$_2$)$_n$C$_{3-8}$cycloalkyl, —(CH$_2$)$_n$C$_{2-8}$heterocycloalkyl, —(CH$_2$)$_n$aryl, —(CH$_2$)$_n$heteroaryl, —(CH$_2$)$_n$—O—(CH$_2$)$_n$aryl, —(CH$_2$)$_n$—O—(CH$_2$)$_n$heteroaryl, and —(CH$_2$)$_n$OP(O)(OH)$_2$, wherein alkyl, alkenyl, cycloalkyl, heterocycloalkyl, aryl, heteroaryl, and (CH$_2$)$_n$ are unsubstituted or substituted with 1 to 5 substituents selected from —(CH$_2$)$_{0-2}$OH, —F, —CF$_3$, —CO$_2$C$_{1-6}$alkyl, oxo, and —C$_{1-6}$ alkyl unsubstituted or substituted with —OH.

In another embodiment of the present invention, each $R^e$ is independently selected from the group consisting of: —(CH$_2$)$_n$halogen, —C$_{1-6}$alkyl, —(CH$_2$)$_n$CF$_3$, —(CH$_2$)$_n$CN, oxo, thio, —(CH$_2$)$_n$OR$^a$, —(CH$_2$)$_n$N(R$^a$)$_2$, —(CH$_2$)$_n$CON(R$^a$)$_2$, —(CH$_2$)$_n$COR$^a$, —(CH$_2$)$_n$CO$_2$R$^a$, —(CH$_2$)$_n$C$_{3-8}$cycloalkyl, —(CH$_2$)$_n$C$_{2-8}$heterocycloalkyl, —(CH$_2$)$_n$aryl, —(CH$_2$)$_n$heteroaryl, —(CH$_2$)$_n$—O—(CH$_2$)$_n$aryl, and —(CH$_2$)$_n$OP(O)(OH)$_2$, wherein alkyl, alkenyl, cycloalkyl, heterocycloalkyl, aryl, heteroaryl, and (CH$_2$)$_n$ are unsubstituted or substituted with 1 to 5 substituents selected from —(CH$_2$)$_{0-2}$OH, —F, —CF$_3$, —CO$_2$C$_{1-6}$alkyl, oxo, and —C$_{1-6}$ alkyl unsubstituted or substituted with —OH.

In another embodiment of the present invention, each $R^e$ is independently selected from the group consisting of —(CH$_2$)$_n$ halogen, —C$_{1-6}$alkyl, —(CH$_2$)$_n$CF$_3$, —(CH$_2$)$_n$CN, —(CH$_2$)$_n$C$_{2-8}$alkenyl, oxo, —(CH$_2$)$_n$OR$^a$, —(CH$_2$)$_n$N(R$^a$)$_2$, —(CH$_2$)CON(R$^a$)$_2$, —(CH$_2$)$_n$COR$^a$, —(CH$_2$)$_n$N(R$^a$)CO$_2$R$^a$, —(CH$_2$)$_n$CO$_2$R$^a$, —(CH$_2$)$_n$OC(O)R$^a$, —(CH$_2$)$_n$C$_{3-8}$cycloalkyl, —(CH$_2$)$_n$C$_{2-8}$heterocycloalkyl, —(CH$_2$)$_n$heteroaryl, —(CH$_2$)$_n$O—(CH$_2$)$_n$heteroaryl, and —(CH$_2$)$_n$OP(O)(OH)$_2$, wherein alkyl, alkenyl, cycloalkyl, heterocycloalkyl, heteroaryl, and (CH$_2$)$_n$ are unsubstituted or substituted with —(CH$_2$)$_{0-2}$OH, —F, —CF$_3$, —CO$_2$C$_{1-6}$alkyl, and —C$_{1-6}$alkyl unsubstituted or substituted with —OH. In another embodiment of the present invention, each $R^e$ is independently selected from the group consisting of: F, —(CH$_2$)$_{0-4}$CH$_3$, —CH(OH)CH(CH$_3$)$_2$, —C(OH)(CH$_2$CH$_3$)CH$_2$CH$_3$, —C(OH)(CH$_3$)CH$_2$CH$_3$, —C(CH$_3$)$_2$CH(OH)CH$_3$, CF$_3$, —CN, —C(CH$_3$)=CH$_2$, —CH=CHCH$_3$, oxo, —(CH$_2$)$_{0-4}$OCH$_3$, —(CH$_2$)$_{0-4}$OH, —CH(OH)$_2$, —CH(OH)CH$_2$OH, —C(OH)(CH$_3$)CH$_2$OH, —CH(CH$_3$)CH$_2$OH, —CH(CH$_3$)OH, —C(CH$_3$)$_2$OH, —(CH$_2$)$_{0-1}$NH$_2$, —(CH$_2$)$_{0-1}$N(CH$_3$)$_2$, —CH(CH$_3$)NH$_2$, —C(O)NH$_2$, —(CH$_2$)$_{0-1}$C(O)CH$_3$, —C(O)H, —C(O)CH$_2$OH, —C(OH)(CH$_3$)C(O)CH$_3$, —C(CH$_3$)$_2$C(O)CH$_3$, —CH(CH$_3$)NHCO$_2$C(CH$_3$)$_3$, —(CH$_2$)$_{0-1}$CO$_2$CH$_3$, —(CH$_2$)$_{0-1}$CO$_2$CH$_2$CH$_3$, —(CH$_2$)$_{0-1}$CO$_2$H, —(CH$_2$)$_{0-1}$CO$_2$C(CH$_3$)$_3$, —C(CH$_3$)$_2$CO$_2$H, —C(CH$_3$)$_2$CO$_2$CH$_2$CH$_3$, —OC(O)CH$_3$, cyclopropyl, cyclobutyl, dioxolane, aziridine, oxadiazole, —(CH$_2$)$_{0-3}$OCH$_2$phenyl, —CH(CH$_3$)OCH$_2$phenyl, and —CH$_2$OP(O)(OH)$_2$.

In another embodiment of the present invention, each $R^e$ is independently selected from the group consisting of: —C$_{1-6}$alkyl, —(CH$_2$)$_n$OR$^a$, and —(CH$_2$)$_n$CO$_2$R$^a$, wherein alkyl, and (CH$_2$)$_n$ are unsubstituted or substituted with —(CH$_2$)$_{0-2}$OH, —F, —CF$_3$, —CO$_2$C$_{1-6}$alkyl, —C$_{1-6}$alkyl unsubstituted or substituted with —OH. In a class of this embodiment, $R^e$ is selected from the group consisting of: —CH$_3$, —CH$_2$OH, —C(CH$_3$)$_2$OH, and —C(CH$_3$)$_2$CO$_2$H.

In another embodiment of the present invention, each $R^f$ is independently selected from the group consisting of: —(CH$_2$)$_n$halogen, —(CH$_2$)$_n$O$_m$C$_{1-8}$allyl, —(CH$_2$)$_n$O$_m$C$_{2-8}$alkenyl, —(CH$_2$)$_n$CN, —(CH$_2$)$_n$CCl$_3$, —(CH$_2$)$_n$OH, —(CH$_2$)$_n$C(O)H, —(CH$_2$)$_n$C(O)C$_{1-8}$alkyl, —(CH$_2$)$_n$CO$_2$H, —(CH$_2$)$_n$CO$_2$C$_{1-8}$alkyl, —(CH$_2$)$_n$O$_m$CF$_3$, —(CH$_2$)$_n$O$_m$CHF$_2$, —(CH$_2$)$_n$O$_m$CH$_2$F, —(CH$_2$)$_n$O$_m$C$_{3-10}$cycloalkyl, —(CH$_2$)$_n$O$_m$C$_{3-10}$cycloalkenyl, —(CH$_2$)$_n$O$_m$C$_{2-12}$heterocycloalkyl, —(CH$_2$)$_n$O$_m$C$_{2-12}$heterocycloalkenyl, —(CH$_2$)$_n$O$_m$aryl, —(CH$_2$)$_n$O$_m$heteroaryl, —SO$_{0-2}$C$_{1-8}$alkyl, —SO$_{0-2}$C$_{3-8}$cycloalkyl, —(CH$_2$)$_n$N(R$^c$)$_2$, —(CH$_2$)$_n$C(O)N(R$^c$)$_2$, and —(CH$_2$)$_n$NR$^c$C(O)R$^c$, wherein alkyl, alkenyl, cycloalkyl, cycloalkenyl, heterocycloalkyl, heterocycloalkenyl, aryl, heteroaryl, and —(CH$_2$)$_n$ are unsubstituted or substituted with 1 to 3 substituents selected from —OH, —CF$_3$, halogen, —C$_{1-6}$ alkyl and —CN.

In another embodiment of the present invention, each $R^f$ is independently selected from the group consisting of: —(CH$_2$)$_n$halogen, —(CH$_2$)$_n$O$_m$C$_{1-8}$alkyl, —(CH$_2$)$_n$O$_m$C$_{2-8}$alkenyl, —(CH$_2$)$_n$CN, —(CH$_2$)$_n$OH, —(CH$_2$)$_n$C(O)C$_{1-8}$alkyl, —(CH$_2$)$_n$O$_m$CF$_3$, —(CH$_2$)$_n$O$_m$CHF$_2$, —(CH$_2$)$_n$O$_m$CH$_2$F, —(CH$_2$)$_n$O$_m$C$_{3-10}$cycloalkyl, and —SO$_{0-2}$C$_{1-8}$alkyl, wherein alkyl, alkenyl, cycloalkyl, and —(CH$_2$)$_n$ are unsubstituted or substituted with 1 to 3 substituents selected from —OH, —CF$_3$, halogen, —C$_{1-6}$alkyl and —CN.

In another embodiment of the present invention, each $R^f$ is independently selected from the group consisting of: —(CH$_2$)$_n$halogen, —(CH$_2$)$_n$O$_m$C$_{1-8}$alkyl, —(CH$_2$)$_n$O$_m$C$_{2-8}$alkenyl, —(CH$_2$)$_n$CN, —(CH$_2$)$_n$CCl$_3$, —(CH$_2$)$_n$OH, —(CH$_2$)$_n$C(O)H, —(CH$_2$)$_n$C(O)C$_{1-8}$alkyl, —(CH$_2$)$_n$CO$_2$H, —(CH$_2$)$_n$CO$_2$C$_{1-8}$alkyl, —(CH$_2$)$_n$O$_m$CF$_3$, —(CH$_2$)$_n$O$_m$CHF$_2$, —(CH$_2$)$_n$O$_m$CH$_2$F, —(CH$_2$)$_n$O$_m$C$_{3-10}$cycloalkyl, —(CH$_2$)$_n$O$_m$C$_{3-10}$cycloalkenyl, —(CH$_2$)$_n$O$_m$C$_{2-12}$heterocycloalkyl, —(CH$_2$)$_n$O$_m$C$_{2-12}$heterocycloalkenyl, —(CH$_2$)$_n$O$_m$aryl, —(CH$_2$)$_n$O$_m$heteroaryl, —SO$_{0-2}$C$_{1-8}$alkyl, and —SO$_{0-2}$C$_{3-8}$cycloalkyl, wherein alkyl, alkenyl, cycloalkyl, cycloalkenyl, heterocycloalkyl, heterocycloalkenyl, aryl, heteroaryl, and —(CH$_2$)$_n$ are unsubstituted or substituted with 1 to 3 substituents selected from —OH, —CF$_3$, halogen, —C$_{1-6}$ alkyl and —CN. In another embodiment of the present invention, $R^f$ is selected from the group consisting of: —(CH$_2$)$_n$halogen, —(CH$_2$)$_n$O$_m$C$_{1-8}$alkyl, —(CH$_2$)$_n$O$_m$C$_{2-8}$alkenyl, —(CH$_2$)$_n$CN, —(CH$_2$)$_n$OH, —(CH$_2$)$_n$C(O)C$_{1-8}$alkyl, —(CH$_2$)$_n$O$_m$CF$_3$, —(CH$_2$)$_n$O$_m$CHF$_2$, —(CH$_2$)$_n$O$_m$C$_{3-10}$cycloalkyl, —(CH$_2$)$_n$O$_m$aryl, and —SO$_{0-2}$C$_{1-8}$alkyl, wherein alkyl, alkenyl, cycloalkyl, aryl, and —(CH$_2$), are unsubstituted or substituted with 1 to 3 substituents selected from —OH, —CF$_3$, halogen, —C$_{1-6}$alkyl and —CN. In another embodiment of the present invention, $R^f$ is selected from the group consisting of: Cl, Br, —C(CH$_3$)$_2$F, —CH$_3$, —CH$_2$CH$_3$, —C(CH$_3$)$_2$CH$_2$CH$_3$, —C(CH$_3$)$_3$, —CH(CH$_3$)$_2$, —OCH$_3$, —OCH(CH$_3$)$_2$, —C(CH$_3$)=CH$_2$, —C(CH$_3$)=CHCH$_3$, —CH(CH$_3$)$_2$CN, —C(CH$_3$)$_2$OH, —CH(CH$_3$)CH(CH$_3$)OH, —C(O)CH$_3$, —CF$_3$, —OCF$_3$, —OCHF$_2$, —C(CH$_3$)F$_2$, cyclopropyl, cyclobutyl, —O-phenyl, and —SO$_2$CH$_3$.

In another embodiment of the present invention, each $R^f$ is independently selected from the group consisting of: —(CH$_2$)$_n$O$_m$C$_{1-8}$alkyl, —(CH$_2$)$_n$O$_m$CF$_3$, and —(CH$_2$)$_n$O$_m$C$_{3-10}$cycloalkyl, wherein alkyl, cycloalkyl, and —(CH$_2$)$_n$ are unsubstituted or substituted with 1 to 3 substituents selected from —OH, —CF$_3$, halogen, —C$_{1-6}$alkyl and —CN. In a class of this embodiment, $R^f$ is —CF$_3$, —OCF$_3$, —C(CH$_3$)$_3$, and cyclopropyl substituted with CF$_3$.

In another embodiment of the present invention, each $R^f$ is independently selected from the group consisting of: —$C_{1-8}$alkyl, —$(CH_2)_nO_mCF_3$, and —$C_{3-10}$cycloalkyl, wherein alkyl, cycloalkyl, and —$(CH_2)_n$ are unsubstituted or substituted with 1 to 3 substituents selected from —OH, —$CF_3$, halogen, —$C_{1-6}$alkyl and —CN.

In another embodiment of the present invention, n is 0, 1, 2, 3, 4 or 5. In a class of this embodiment, n is 0, 1, 2, 3 or 4. In another class of this embodiment, n is 0. In another class of this embodiment, n is 1. In another class of this embodiment, n is 2. In another class of this embodiment, n is 3. In another embodiment of the present invention, m is independently 0 or 1. In a class of this embodiment, m is 0. In another class of this embodiment, n is 1. In another embodiment of the present invention, p is 0, 1, or 2. In a class of this embodiment, p is 1 or 2. In another class of this embodiment, p is 0. In another class of this embodiment, p is 1. In another class of this embodiment, p is 2. In another embodiment of the present invention, q is 0, 1, or 2. In a class of this embodiment, q is 1 or 2. In another class of this embodiment, q is 0. In another class of this embodiment, q is 1. In another subclass of this class, q is 2.

Illustrative but nonlimiting examples of compounds of the present invention that are useful as bombesin receptor subtype-3 agonists are the following:

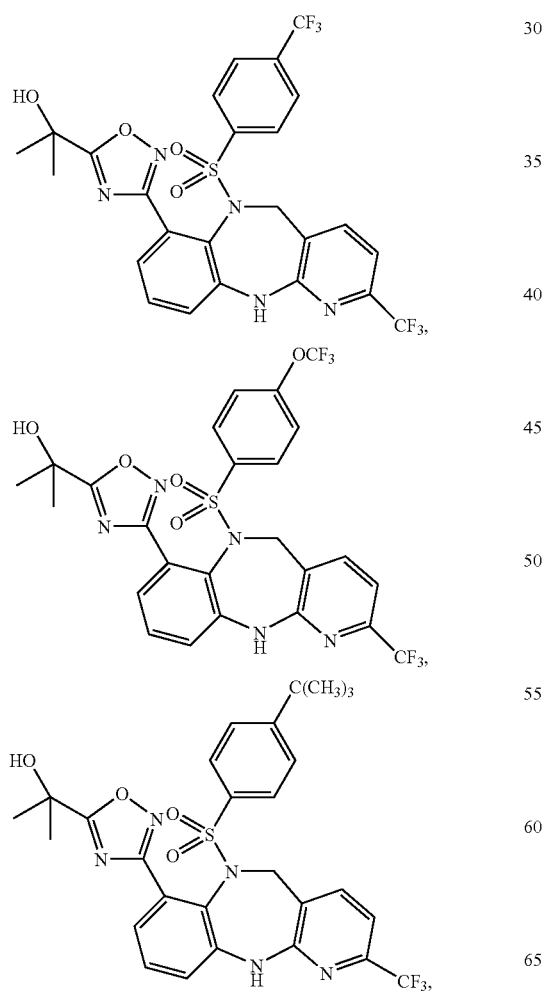

-continued

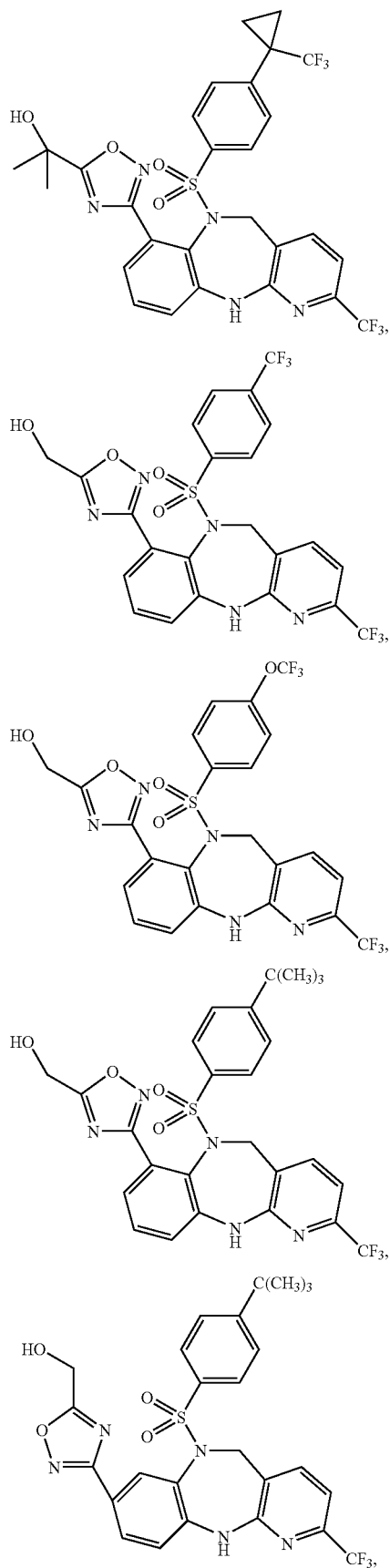

or a pharmaceutically acceptable salt thereof.

The compounds of formula I, II, III and IV are effective as bombesin receptor ligands and are particularly effective as selective ligands of the bombesin receptor subtype-3. They are therefore useful for the treatment and/or prevention of disorders responsive to the modulation of the bombesin receptor subtype-3, such as obesity, diabetes, and obesity-related disorders. More particularly, the compounds of formula I, II, III and IV are selective bombesin receptor subtype-3 (BRS-3) agonists useful for the treatment of disorders responsive to the activation of the bombesin receptor subtype-3, such as obesity, diabetes, as well as the treatment of gallstones.

One aspect of the present invention provides a method for the treatment or prevention of disorders, diseases or conditions responsive to the modulation of the bombesin receptor subtype-3 in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of obesity, diabetes, or an obesity related disorder in a subject in need thereof which comprises administering to said subject a therapeutically or prophylactically effective amount of a bombesin receptor subtype-3 agonist of the present invention. Another aspect of the present invention provides a method for the treatment or prevention of obesity in a subject in need thereof which comprises administering to the subject a therapeutically or prophylactically effective amount of a compound of formula I, II, III or IV, or a pharmaceutically acceptable salt thereof. Another aspect of the present invention provides a method for reducing food intake in a subject in need thereof which comprises administering to the subject a therapeutically or prophylactically effective amount of a compound of formula I, II, III or IV, or a pharmaceutically acceptable salt thereof. Another aspect of the present invention provides a method for increasing satiety in a subject in need thereof which comprises administering to the subject a therapeutically or prophylactically effective amount of a compound of formula I, II, III or IV, or a pharmaceutically acceptable salt thereof. Another aspect of the present invention provides a method for reducing appetite in a subject in need thereof which comprises administering to the subject a therapeutically or prophylactically effective amount of a compound of formula I, II, III or IV, or a pharmaceutically acceptable salt thereof. Another aspect of the present invention provides a method for reducing gastric emptying in a subject in need thereof which comprises administering to the subject a therapeutically or prophylactically effective amount of a compound of formula I, II, III or IV, or a pharmaceutically acceptable salt thereof. Another aspect of the present invention provides a method for the treatment or prevention of bulimia nervosa in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of diabetes mellitus in a subject in need thereof comprising administering to the subject a therapeutically or prophylactically effective amount of a compound of formula I, II, III or IV, or a pharmaceutically acceptable salt thereof. Another aspect of the present invention provides a method for the treatment or prevention of dyslipidemia in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of diabetes, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of an diabetes related disorder selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, II, III or IV, or a pharmaceutically acceptable salt thereof.

The present invention also relates to methods for treating or preventing obesity by administering a bombesin receptor subtype-3 agonist of the present invention in combination with a therapeutically or prophylactically effective amount of another agent known to be useful to treat or prevent the condition. The present invention also relates to methods for treating or preventing diabetes by administering the bombesin receptor subtype-3 agonist of the present invention in combination with a therapeutically or prophylactically effective amount of another agent known to be useful to treat or prevent the condition. The present invention also relates to methods for treating or preventing obesity related disorders by administering the bombesin receptor subtype-3 agonist of the present invention in combination with a therapeutically or prophylactically effective amount of another agent known to be useful to treat or prevent the condition.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, N-[3-(4-chlorophenyl)-2(S)-phenyl-1-(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl] oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl] azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1yl}methyl)-benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl] benzonitrile, and 5-((4-chlorophenyl){3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, II, III or IV and a pharmaceutically acceptable carrier.

Yet another aspect of the present invention relates to the use of a compound of formula I, II, III and IV for the manufacture of a medicament useful for the treatment or prevention, or suppression of a disease mediated by the bombesin receptor subtype-3 in a subject in need thereof.

Yet another aspect of the present invention relates to the use of a bombesin receptor subtype-3 agonist of the present invention for the manufacture of a medicament useful for the treatment or prevention, or suppression of a disease mediated by the bombesin receptor subtype-3, wherein the disease is selected from the group consisting of obesity, diabetes and an obesity-related disorder in a subject in need thereof.

Yet another aspect of the present invention relates to the use of a bombesin receptor subtype-3 agonist of the present invention for the manufacture of a medicament useful for the treatment or prevention of gallstones in a subject in need thereof. Yet another aspect of the present invention relates to the use of a bombesin receptor subtype-3 agonist of the present invention for the manufacture of a medicament useful for the treatment or prevention of dyslipidemia in a subject in need thereof. Yet another aspect of the present invention relates to the use of a bombesin receptor subtype-3 agonist of the present invention for the manufacture of a medicament useful for the treatment or prevention of bulimia nervosa in a subject in need thereof. Yet another aspect of the present invention relates to the use of a bombesin receptor subtype-3 agonist of the present invention for the manufacture of a medicament useful for the treatment or prevention of constipation in a subject in need thereof. Yet another aspect of the present invention relates to the use of a bombesin receptor subtype-3 agonist of the present invention for the manufacture of a medicament useful for the treatment or prevention of irritable bowel syndrome in a subject in need thereof.

Yet another aspect of the present invention relates to the use of a therapeutically effective amount of a bombesin receptor subtype-3 agonist of formula I, II, III or IV, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4)

inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a bombesin receptor subtype-3 agonist of formula I, II, III or IV, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes or an obesity-related disorder which comprises an effective amount of a bombesin receptor subtype-3 agonist of formula I, II, III or IV and an effective amount of the agent, together or separately. Yet another aspect of the present invention relates to a product containing a therapeutically effective amount of a bombesin receptor subtype-3 agonist of formula I, II, III or IV, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, or an obesity-related disorder.

The compounds of formula I, II, III or IV can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "alkoxy" means alkyl chains of the designated length which contain at least one ether linkage, in which any carbon of the alkyl chain may be substituted with an oxygen, and which may be linear or branched or combinations thereof. Examples of alkoxy include methoxy, ethoxy, 1-propoxy, 2-propoxy, 1-butoxy, 2-butoxy, methoxymethyl, methylethoxy, methyl-1-propoxy, methyl-2-propoxy, ethyl-2-methoxy, ethyl-1-methoxy and the like.

The term "halogen" includes fluorine, chlorine, bromine and iodine. The term "oxo" means=O. The term "thio" means=S.

The term "aryl" includes monocyclic aromatic rings containing only carbon atoms, and bicyclic aromatic ring systems, wherein at least one ring is an aromatic ring containing only carbon atoms. Examples of aryl include phenyl, naphthyl, benzodioxole and benzocyclobutene.

The term "heteroaryl" includes monocyclic aromatic rings that contain from 1 to 4 heteroatoms selected from nitrogen, oxygen and sulfur, and bicyclic heteroaromatic ring systems containing at least one aromatic ring that contains from 1 to 4 heteroatoms selected from nitrogen, oxygen and sulfur. Examples thereof include, but are not limited to, pyridinyl, furyl, thienyl, pyrrolyl, oxazolyl, thiophenyl, thiazolyl, isothiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, indazole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline, 1,2,3,4-tetrahydroquinoline; 1,2,3,4-tetrahydro-1,8-naphthyridine; 1-H-pyrrolo[2,3-b]pyridine; imidazo[1,2-a]pyrazine; benzopyrazole; benzodioxole; triazolopyridine; and benzopyrrole.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "cycloalkenyl" includes mono- or bicyclic non-aromatic rings containing only carbon atoms and containing at least one double bond. Examples of cycloalkenyl include, but are not limited to, cyclopropenyl, cyclobutenyl, cyclopentenyl, cyclohexenyl, and cycloheptenyl.

The term "heterocycloalkyl" includes non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane, azepane; thiazolidine; and hexahydropyridazine.

The term "heterocycloalkenyl" includes non-aromatic heterocycles containing one to four heteroatoms selected from nitrogen, oxygen and sulfur, and containing at least one double bond. Examples of heterocycloalkenyl include, but are not limited to, 3a,4,5,6,7,7a-hexahydro-1H-pyrazolo[3,4-b]pyridine; 1,2-dihydropyridine; and 1,2,3,4-tetrahydropyrazine.

The term "oxo" means a double bond to oxygen. The term "thio" means a double bond to sulfur.

Certain of the above defined terms may occur more than once in the above formula and upon such occurrence each term shall be defined independently of the other; thus for example, $NR^8R^8$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a bombesin receptor subtype 3 (BRS-3) "agonist" is meant an endogenous or drug substance or compound that can interact with a bombesin subtype 3 receptor and initiate a pharmacological or biochemical response characteristic of bombesin subtype 3 receptor activation. The "agonistic" properties of the compounds of the present invention were measured in the functional assay described below.

By "binding affinity" is meant the ability of a compound/drug to bind to its biological target, in the present instance, the ability of a compound of formula I, II, III and IV, to bind to the bombesin subtype 3 receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention were measured in the functional assay described below. Compounds of formula I, II, III or IV, may contain one chiral plane, one or more asymmetric or chiral centers and can exist in different stereoisomeric forms, such as racemates and racemic mixtures, single enantiomers, enantiomeric mixtures, individual diastereomers and diastereomeric mixtures. All stereoisomeric forms of the intermediates and compounds of the present invention as well as mixtures thereof, including racemic and diastereomeric mixtures, which possess properties useful in the treatment of the conditions discussed herein or are intermediates useful in the preparation of compounds having such properties, form a part of the present invention.

The compounds of formulas I, II, III and IV encompass any enantiomers and diastereomers. Compounds of structural formula I may be separated into their individual enantiomers and diastereoisomers by, for example, fractional crystallization from a suitable solvent, for example methanol or ethyl acetate or a mixture thereof, or via chiral chromatography using an optically active stationary phase. For example, racemic mixture XX can be separated into a faster eluting enantiomer and a slower eluting enantiomer by HPCL eluting on a chiral column. Enantiomers E1 and E2 have a chiral plane and are non-superimposable mirror images. Absolute stereochemistry may be determined by X-ray crystallography of crystalline products or crystalline intermediates which are derivatized, if necessary, with a reagent containing an asymmetric center of known absolute configuration.

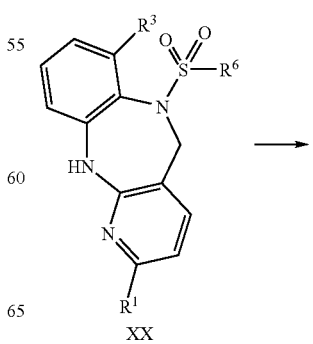

XX

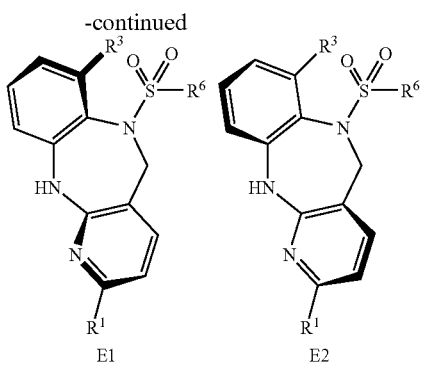

E1          E2

Alternatively, any stereoisomer of a compound of the general formula I, II, III and IV may be obtained by stereospecific synthesis using optically pure starting materials or reagents of known absolute configuration.

It will be understood that the compounds of the present invention include hydrates, solvates, polymorphs, crystalline, hydrated crystalline and amorphous forms of the compounds of the present invention, and pharmaceutically acceptable salts thereof.

Generally, one of the enantiomers will be more active biologically than the other enantiomer. Racemic mixtures can subsequently be separated into each enantiomer using standard conditions, such as resolution or chiral chromatography. Diastereomeric mixtures may be separated into their individual diastereoisomers on the basis of their physical chemical differences by methods well known to those skilled in the art, such as by chiral chromatography using an optically active stationary phase and/or fractional crystallization from a suitable solvent. Absolute stereochemistry may be determined by X-ray crystallography of crystalline products or crystalline intermediates which are derivatized, if necessary, with a reagent containing an asymmetric center of known absolute configuration. Enantiomers and diastereomers may be separated by use of a chiral HPLC column and by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Alternatively, any stereoisomer of a compound of the general formula I, II, III and IV may be obtained by stereospecific synthesis using optically pure starting materials or reagents of known absolute configuration.

The present invention is meant to comprehend all such isomeric forms of the compounds of formula I, II, III and IV, including the E and Z geometric isomers of double bonds and mixtures thereof. A number of the compounds of the present invention and intermediates therefor exhibit tautomerism and therefore may exist in different tautomeric forms under certain conditions. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is a diazepine moiety where the hydrogen may migrate between the ring nitrogens. Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also encompasses isotopically labeled compounds which are identical to the compounds of Formula (I) or intermediates thereof but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as 2H, 3H, 11C, 13C, 14C, 13N, 15N, 15O, 17O, 18O, 31P, 32P, 35S, 18F, 123I, 125I and 36Cl, respectively. Compounds of the present invention, prodrugs thereof and pharmaceutically acceptable salts, hydrates and solvates of said compounds and of said prodrugs which contain the aforementioned isotopes and/or other isotopes of other atoms are within the scope of the present invention. Certain isotopically labeled compounds of the present invention (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

The compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents. It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids. It will be understood that, as used herein, references to the compounds of formula I, II, III and IV are meant to also include the pharmaceutically acceptable salts, such as the hydrochloride salt.

Compounds of formula I, II, III and IV are bombesin receptor ligands and as such are useful in the treatment, control or prevention of diseases, disorders or conditions responsive to the modulation of one or more of the bombesin receptors. In particular, the compounds of formula I, II, III and IV act as bombesin receptor subtype-3 agonists useful in the treatment, control or prevention of diseases, disorders or conditions responsive to the activation of the bombesin receptor subtype-3. Such diseases, disorders or conditions include, but are not limited to, obesity (by reducing food intake, reducing appetite, increasing metabolic rate, increasing satiety, reducing carbohydrate craving, reducing gastric emptying), diabetes mellitus (by enhancing glucose tolerance, decreasing insulin resistance), bulimia nervosa and related eating disorders, dyslipidemia, hypertension, hyperlipidemia, osteoarthritis, cancer, gall stones, cholelithiasis, cholecystitis, gall bladder disease, sleep apnea, depression, anxiety, compulsion, neuroses, irritable bowel syndrome, inflammatory bowel syndrome, constipation, pain, neuroprotective and cognitive and memory enhancement including the treatment of Alzheimer's disease. Such diseases, conditions and disorders also include non-obese overweight conditions and normal weight conditions where weight control or management is desired in order to prevent an obese or overweight condition from developing, or to maintain a healthy weight.

The compounds and compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted bodyweight, and low self esteem), and other pathological conditions showing reduced metabolic activity or a decrease in resting energy expenditure as a percentage of total fat-free mass, e.g, children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by BRS-3 receptor agonists in an animal which comprises administering to the animal in need of such treatment a compound of formula I, II, III and IV, in particular a therapeutically or prophylactically effective amount thereof.

Some agonists encompassed by formula I, II, III and IV show highly selective affinity for the bombesin receptor subtype-3 (BRS-3) relative to the neuromedin 1 (BB1) receptor and the gastrin release peptide (BB2) receptor, which makes them especially useful in the prevention and treatment of obesity, diabetes, and obesity related disorders.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, BRS-3 agonists may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I, II, III and IV are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of formula I, II, III and N are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I, II, III and IV are useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating dyslipidemia, bulimia nervosa, and gallstones satisfactory results are obtained when the compounds of formula I, II, III and IV are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I, II, III and IV per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I, II, III and N in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I, II, III and N per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I, II, III and N in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Compounds of formula I, II, III and N may be used in combination with other drugs that are used in the treatment/prevention/suppression or amelioration of the diseases or conditions for which compounds of formula I, II, III and N are useful. Such other drugs may be administered, by a route and in an amount commonly used therefor, contemporaneously or sequentially with a compound of formula I, II, III and N. When a compound of formula I, II, III and N is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I, II, III or N.

Examples of other active ingredients that may be combined with a compound of formula I, II, III and N for the treatment or prevention of obesity and/or diabetes, either administered separately or in the same pharmaceutical compositions, include, but are not limited to:

(a) Anti-diabetic agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and A1-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR α/δ agonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTC0179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naflopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) (β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. Nos. 5,705,515, and 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294, 534; 6,350,760; 6,458,790; 6,472,398; 6,376,509; and 6,818, 658; US Patent Publication No. US2002/0137664; US2003/ 0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552, 524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11, Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4,179,337, 5,122,614, 5,349,052, 5,552,520, 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-G1u32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIRO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, (89) neuromedin U and analogs or derivatives thereof, (90) oxyntomodulin and analogs or derivatives thereof, (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; and (92) Qnexa; and (e) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro- 5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]

phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(R3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(R3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed with the BRS-3 receptor agonists of the present invention. NK-1 receptor antagonists of use in the present invention are fully described in the art. Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

Additionally, peptide analogs and mimetics of the incretin hormone glucagon-like peptide 1(GLP-1), such as oxyntomodulin and derivatives thereof, may also be of use in combination with a compound of the present invention.

Examples of other anti-obesity agents that can be employed in combination with a compound of formula I, II, III or IV are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity", *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The instant invention also includes administration of a single pharmaceutical dosage formulation which contains both the BRS-3 ligand or agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the BRS-3 ligand or agonist and the second active ingredient is realized by the patient at substantially the same time. Such beneficial effect is preferably achieved when the target blood level concentrations of each active ingredient are maintained at substantially the same time. It is preferred that the combination of the BRS-3 ligand or agonist and the second active ingredient be co-administered concurrently on a once-a-day dosing schedule; however, varying dosing schedules, such as the BRS-3 ligand or agonist once a day and the second active ingredient once, twice or more times per day or the BRS-3 ligand or agonist three times a day and the second active ingredient once, twice or more times per day, is also encompassed herein. A single oral dosage formulation comprised of both a BRS-3 ligand or agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the bombesin receptor subtype-3 agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of formula I, II, III or IV, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I, II, III and IV can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I, II, III or IV may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I, II, III and IV of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Reaction Scheme 1 illustrates the methods employed in the synthesis of the compounds of the present invention of formula I, II, III and IV. All substituents are as defined above unless indicated otherwise.

1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in CDCl$_3$ or CD$_3$OD as indicated and chemical shifts are reported as δ using the solvent peak as reference and coupling constants are reported in hertz (Hz).

Abbreviations used in the following Schemes, Intermediates, and Examples are: Ac is acetate; anhydr. or anhyd. is anhydrous; aq. is aqueous; API-ES is atmospheric pressure ionization-electrospray (mass spectrum term); BOC (Boc) is t-butyloxycarbonyl; BOP is (1H-1,2,3-benzotriazol-1-yloxy)[tris(dimethylamino)]phosphonium hexafluorophosphate; Bn is benzyl, Bu is butyl; tBu, t-Bu or $^t$Bu is tert-butyl; calc. or calc'd is Calculated; Celite is Celite™ diatomaceous earth, CBZ (Cbz) is benzyloxycarbonyl; cat. is catalytic; cone or conc is concentrated; DAST is diethyl amino sulfur trifluoride; DCC is dicyclohexylcarbodiimide, DCM is dichloromethane; DIC is diisopropylcarbodiimide; DIEA or

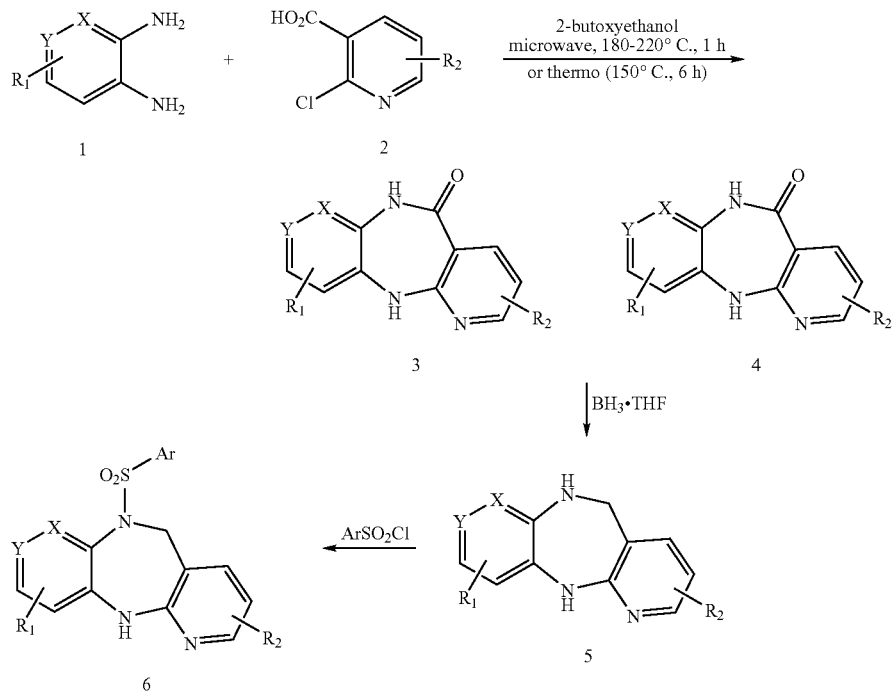

In Scheme 1, an appropriately substituted diamine 1 and acid 2 were heated with an oil bath or with microwave irradiation to give a mixture of 3 and 4. Reduction of the amide afforded the amine 5, which reacted to an sulfonyl chloride to give the product 6. Compounds of the present invention may be prepared by procedures illustrated in the accompanying scheme, intermediates and examples. In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

The LC/MS analyses were preformed using a MICROMASS ZMD mass spectrometer coupled to an AGILENT DIPEA is diisopropyl-ethylamine, DEAD is diethyl azodicarboxylate; DIBAL-His di-isobutyl aluminum hydride; DMAP is dimethylamino pyridine; DME is ethylene glycol dimethyl ether; DMF is dimethylformamide; DMSO is dimethylsulfoxide; dppf is 1,1'-bis(diphenylphosphino)ferrocene; EDC is 1-ethyl-3-(3-dimethylaminopropyl)-carbodiimide hydrochloride; ES-MS and ESI-MS are electron spray ion-mass spectroscopy, Et is ethyl, EPA is ethylene polyacrylamide (a plastic); eq is equivalent; Et$_2$O is diethyl ether; EA or EtOAc is ethyl acetate; g is gram(s); h or hr is hours; HATU is O-(7-Azabenzotriazol-1-yl)-N,N,N',N'-tetramethyluronium hexafluorophosphate; Hex is hexane; HOAT is 1-hydroxy-7-azabenzotriazole; HOBt is 1-hydroxybenzo-triazole; HPLC is high pressure liquid chromatography; HPLC/MS is high pressure liquid chromatography/mass spectrum; in vacuo is rotoevaporation; IPR or iPr is isopropyl; IPAC is isopropyl acetate; KHMDS is potassium hexamethyldisilazide; L is liter; LAH is lithium aluminum hydride; LC is Liquid chromatography; LCMS or LC-MASS is liquid chromatography mass spectrum; LDA is lithium diisopropylamide, M is molar; Me is methyl; MeCN is methyl cyanide; MeOH is methanol, MF is molecular formula, MW is molecular weight; min or min. is minutes; mg is milligram(s); mL is milliliter, MeOH is methanol; min is minute(s); mmol is millimole; MS or ms is mass spectrum; MTBE is tert-butyl methyl ether, NaHMDS is sodium hexamethyl disilazide, N is normal; NaHMDS is sodium hexamethyldisilazide; NBS is N-bromosuccinimide, NIS is N-iodosuccinimide, NMM is N-methylmorpholine, NMO is N-methylmorpholine-N-oxide; NMP is N-methylpyrrolidone; NaOtBu is sodium tert-butoxide, NMR is nuclear magnetic resonance; OTf is trifluoromethanesulfonyl, PCC is pyridinium chlorochromate; PE is petroleum ether; Pd(OAc)$_2$ is palladium acetate; Pd$_2$(dba)$_3$ is tris(dibenzylideneacetone) dipalladium (0); psi is pound per square inch; PyBOP is (benzotriazol-1-yloxy) tripyrrolidino-phosphonium hexafluorophosphate; rac or rac is racemate or racemic mixture; racemate or racemic mixture is a equal molar mixture of enantiomers; Rt or R$_t$ is retention time; rt, r.t. or RT is room temperature; sat, sat. or sat is saturated; SFC is Super Critical Fluid Chromatography; S-Phos is 2-dicyclohexylphosphino-2',6'-dimethoxybiphenyl; SEMCl is trimethylsilylethoxy methyl chloride; TBAF is tetrabutyl ammonium fluoride; TEA or Et$_3$N is triethylamine; TFA is trifluoroacetic acid; TEMPO is 2,2,6,6-tetramethyl-1-piperidinyloxy free radical; Tf$_2$O is triflic anhydride; THF is tetrahydrofuran; TLC is thin layer chromatography; TMC is 1-trifluoromethylcyclopropyl; TMS is trimethylsilyl; TosMIC or TOSMIC is tosylmethylisonitrile; v:v or v:v is volume to volume; v:v:v or v:v:v is volume to volume to volume; wt % is weight percent; and Xantphos is 9,9-Dimethyl-4,5-bis(diphenylphosphino)xanthene.

The following Intermediates and Examples are provided to illustrate the invention and are not to be construed as limiting the scope of the invention in any manner.

INTERMEDIATE 1

2-(Trifluoromethyl)-6,11-dihydro-5H-pyrido[2,3-b][1,5]benzodiazepin-7-ol

Step A: A mixture of 2,3-diaminophenol (79 g, 0.64 mol), 2-chloro-6-(trifluoromethyl)nicotinic acid (100 g, 0.44 mol) and sulfolane (1 L) was heated under nitrogen at 150° C. overnight. After cooling to rt, the reaction mixture was poured into water. The precipitate was collected by filtration, and was re-dissolved in EtOAc, washed with water and brine, dried over MgSO$_4$, filtered and concentrated to give 7-hydroxy-2-(trifluoromethyl)-6,11-dihydro-5H-pyrido[2,3-b][1,5]benzodiazepin-5-one.

Step B: To 7-hydroxy-2-(trifluoromethyl)-6,11-dihydro-5H-pyrido[2,3-b][1,5]benzodiazepin-5-one (113 g, 0.38 mol) in THF (1.7 L) at 0° C. was added BH$_3$ (1 M/THF, 1.5 L, 1.5 mol). After gas evolution subsided, the reaction was heated at 40° C. for 1 h. The reaction mixture was cooled to 0° C. and poured slowly into methanol. The resulting solution was partially concentrated, diluted with ethyl acetate, washed with 1 N HCl, saturated NaHCO$_3$ and brine, dried over MgSO$_4$, filtered and concentrated. The residue was slurried in heptane, and the solid was collected by filtration to give the title compound as a 1:1 mixture with 2-(trifluoromethyl)-6,11-dihydro-5H-pyrido[2,3-b][1,5]benzodiazepin-10-ol.

INTERMEDIATE 2

6-{[4-(Trifluoromethoxy)phenyl]sulfonyl}-2-(trifluoromethyl)-6,11-dihydro-5-pyrido[2,3-b][1,5]benzodiazepin-7-ol To a solution of intermediate 1 (25.0 g, 89.0 mmol) and 4-(trifluoromethoxy)benzenesulfonyl chloride (23.2 g, 89.0 mmol) in CH$_2$Cl$_2$ at 0° C. was added pyridine (22.0 mL, 270 mmol). After stirring at rt for 12 h, the reaction mixture was concentrated. The residue was diluted with EtOAc (3×400 mL), washed with saturated aqueous NaHCO$_3$ (300 mL) and brine, dried over MgSO$_4$, filtered and concentrated. The residue was triturated with CH$_2$Cl$_2$, and the solid was collected by filtration to afford the title compound. $^1$H NMR (500 MHz, (CD$_3$)$_2$CO): δ 8.53 (s, 1H), 7.82 (d, 1H), 7.55 (m, 3H), 7.26 (m, 3H), 7.19 (d, 1H), 7.12 (d, 1H), 5.33 (d, 1H), 5.11 (s, 1H), 4.80 (d, 1H). LCMS: m/z 506.0 (M+H)$^+$.

INTERMEDIATE 3

6-{[4-(Trifluoromethoxy)phenyl]sulfonyl}-2-(trifluoromethyl)-6,11-dihydro-5H-pyrido[2,3-b][1,5]benzodiazepin-7-yl trifluoromethanesulfonate To a suspension of intermediate 2 (23.6 g, 47 mmol), DMAP (8.60 g, 70 mmol) and TEA (9.75 mL, 70.0 mmol) in CH$_2$Cl$_2$ (1000 mL) at 0° C. was added Tf$_2$O (9.40 mL, 56.0 mmol). After stirring at 0° C. for 2 h, the reaction mixture was diluted with CH$_2$Cl$_2$ (400 mL), washed with H$_2$O (600 mL) and brine (600 mL), dried over MgSO$_4$, filtered and concentrated. The residue was triturated with CH$_2$Cl$_2$, and the solid was collected by filtration to afford the title compound. $^1$H NMR (500 MHz, (CD$_3$)$_2$CO): δ 8.80 (s, 1H), 7.86 (d, 1H), 7.55 (m, 2H), 7.32 (d, 2H), 7.23 (d, 1H), 7.15 (dd, 3H), 5.22 (d, 1H), 4.62 (d, 1H). LCMS: m/z 637.9 (M+H)$^+$.

INTERMEDIATE 4

2-(Trifluoromethyl)-6-{[4-(trifluoromethyl)phenyl]sulfonyl}-6,11-dihydro-5H-pyrido[2,3-b][1,5]benzodiazepin-7-yl trifluoromethanesulfonate The title compound was prepared following the procedures described for intermediates 2 and 3 replacing 4-(trifluoromethoxy)benzenesulfonyl chloride with 4-(trifluoromethyl)benzenesulfonyl chloride. LCMS: m/z 621.9 (M+H)$^+$.

INTERMEDIATE 5

6-[(4-tert-Butylphenyl)sulfonyl]-2-(trifluoromethyl)-6,11-dihydro-5H-pyrido[2,3-b][1,5]benzodiazepin-7-yl trifluoromethanesulfonate The title compound was prepared following the procedures described for intermediates 2 and 3 replacing 4-(trifluoromethoxy)benzenesulfonyl chloride with 4-(tert-butyl)-benzenesulfonyl chloride. LCMS: m/z 610.1 (M+H)+.

INTERMEDIATE 6

2-(Trifluoromethyl)-6-({4-[1-(trifluoromethyl)cyclopropyl]phenyl}sulfonyl)-6,11-dihydro-5H-pyrido[2,3-b][1,5]benzodiazepin-7-yl trifluoromethanesulfonate The title compound was prepared following the procedures described for intermediates 2 and 3 replacing 4-(trifluoromethoxy)benzenesulfonyl chloride with 4-(1-trifluoromethylcyclopropyl)benzenesulfonyl chloride. LCMS: m/z 661.9 (M+H)+.

INTERMEDIATE 7

7-Cyano-6-{[4-(trifluoromethoxy)phenyl]sulfonyl}-2-(trifluoromethyl)-6,11-dihydro-5H-pyrido[2,3-b][1,5]benzodiazepine A solution of intermediate 3 (13.2 g, 20.7 mmol), $Pd_2 dba_3$ (3.03 g, 3.30 mmol), S-Phos (3.40 g, 8.30 mmol), and $Zn(CN)_2$ (3.16 g, 27.0 mmol) in 99:1 DMF:$H_2O$ (60 mL) was stirred under $N_2$ for 15 min, and was then heated in a microwave reactor at 150° C. for 20 min. The reaction mixture was diluted with EtOAc (200 mL), washed with 1 N NaOH (200 mL) and saturated brine solution (200 mL), dried over $MgSO_4$, filtered and concentrated. The residue was recrystallized from MeOH and hexanes (200 mL) to yield the title nitrile. $^1H$ NMR (500 MHz, $(CD_3)_2CO$): δ 8.74 (s, 1H), 7.85 (d, 1H), 7.68 (d, 1H), 7.55 (t, 1H), 7.49 (dd, 1 H), 7.32 (d, 2 H), 7.22 (d, 1 H), 7.15 (d, 2 H), 5.3 (d, 1 H), 4.9 (d, 1 H), 2.8 (s, 6H). LCMS: m/z 515.1 (M+H)+.

INTERMEDIATE 8

N'-Hydroxy-6-{[4-(trifluoromethoxy)phenyl]sulfonyl}-2-(trifluoromethyl)-6,11-dihydro-5H-pyrido[2,3-b][1,5]benzodiazepine-7-carboximidamide A mixture of intermediate 7 (10.7 g, 20.7 mmol), hydroxylamine (50 wt % solution in water) (7 mL, 106 mmol), $K_2CO_3$ (0.20 mg, 0.14 mmol) and EtOH (40 mL) was heated in a microwave reactor at 120° C. for 20 min. The reaction mixture was concentrated to give the title compound. $^1H$ NMR (500 MHz, $(CD_3)_2CO$): δ 7.76 (d, 1H), 7.4 (m, 4H), 7.23 (dd, 1H), 7.16 (d, 3H), 5.30 (br s, 1H), 5.20 (d, 1H), 4.67 (d, 1H), 2.09 (s, 6H). LCMS: m/z 548.1 (M+H)+.

INTERMEDIATE 9

N'-Hydroxy-2-(trifluoromethyl)-6-{[4-(trifluoromethyl)phenyl]sulfonyl}-6,11-dihydro-5H-pyrido[2,3-b][1,5]benzodiazepine-7-carboximidamide The title compound was prepared from 2-(trifluoromethyl)-6-{[4-(trifluoromethyl)phenyl]sulfonyl}-6,11-dihydro-5H-pyrido[2,3-b][1,5]benzodiazepin-7-yl trifluoromethanesulfonate following the procedures as described for intermediates 7 and 8. LCMS: m/z 531.9 (M+H)+.

INTERMEDIATE 10

6-[(4-tert-Butylphenyl)sulfonyl]-N'-hydroxy-2-(trifluoromethyl)-6,11-dihydro-5H-pyrido[2,3-b][1,5]benzodiazepine-7-carboximidamide The title compound was prepared from 6-[(4-tert-butylphenyl)sulfonyl]-2-(trifluoromethyl)-6,11-dihydro-5H-pyrido[2,3-b][1,5]-benzodiazepin-7-yl trifluoromethanesulfonate following the procedures described for intermediates 7 and 8. LCMS: m/z 520.0 (M+H)+.

INTERMEDIATE 11

N'-Hydroxy-2-(trifluoromethyl)-6-({4-[1-(trifluoromethyl)cyclopropyl]phenyl}sulfonyl)-6,11-dihydro-5H-pyrido[2,3-b][1,5]benzodiazepine-7-carboximidamide The title compound was prepared from 2-(trifluoromethyl)-6-({4-[1-(trifluoromethyl)cyclopropyl]phenyl}sulfonyl)-6,11-dihydro-5H-pyrido[2,3-b][1,5]benzodiazepin-7-yl trifluoromethanesulfonate following the procedures described for intermediates 7 and 8. LCMS: m/z 572.0 (M+H)+.

INTERMEDIATE 12

Methyl-6-{[4-(trifluoromethoxy)phenyl]sulfonyl}-2-(trifluoromethyl)-6,11-dihydro-5H-pyrido[2,3-b][1,5]benzodiazepine-7-carboxylate A mixture of intermediate 3 (3.9 g, 6.2 mmol), 1:1 DMF/MeOH (60 mL), $Pd(OAc)_2$ (280 mg, 1.2 mmol), DPPF (1.3 g, 2.5 mmol) and TEA (2.6 mL, 18 mmol) was heated at 80° C. under a CO atmosphere (balloon) overnight. After cooling to rt, the reaction mixture was partitioned between brine (150 mL) and EtOAc (100 mL). The organic layer was separated, dried over $MgSO_4$, filtered and concentrated, and the residue was purified by flash column chromatography on silica gel eluting with 7-60% EtOAc to give the title compound. $^1H$ NMR (500 MHz, $(CD_3)_2CO$): δ 8.50 (s, 1H), 8.0 (s, 1H), 7.50 (m, 2H), 7.25 (m, 4H), 5.30 (d, 1 H), 4.71 (d, 1H), 3.9 (s, 3H). LCMS: m/z 548.1 (M+H)+.

INTERMEDIATE 13

Methyl 2-(trifluoromethyl)-6-{[4-(trifluoromethyl)phenyl]sulfonyl}-6,11-dihydro-5H-pyrido[2,3-b][1,5]benzodiazepine-7-carboxylate The title compound was prepared from intermediate 4 following the procedure described for intermediate 12. LCMS: m/z 532.0 (M+H)+.

INTERMEDIATE 14

Methyl 6-[(4-tert-butylphenyl)sulfonyl]-2-(trifluoromethyl)-6,11-dihydro-5H-pyrido[2,3-b][1,5]benzodiazepine-7-carboxylate The title compound was prepared from intermediate 5 following the procedure described for intermediate 12. LCMS: m/z 520.4 (M+H)+.

INTERMEDIATE 15

6-{[4-(Trifluoromethoxy)phenyl]sulfonyl}-2-(trifluoromethyl)-6,11-dihydro-5H-pyrido[2,3-b][1,5]benzodiazepine-7-carboxylic acid To a solution of intermediate 12 (1.0 g, 1.80 mmol) in 3:1 THF/H$_2$O (60 mL) was added LiOH (383 mg, 9.1 mmol), and the reaction was heated at 70° C. for 12 h. Additional LiOH (800 mg, 19.0 mmol) was added, and heating at 70° C. continued for 72 h. The reaction mixture was diluted with H$_2$O (200 mL), acidified to pH=1 with 6 N HCl, and the product was extracted with EtOAc (200 mL). The extracts were washed with H$_2$O and brine, dried over MgSO$_4$, filtered and concentrated to yield the title compound as a racemic mixture. $^1$H NMR (500 MHz, (CD$_3$)$_2$CO): δ 8.48 (s, 1H), 7.79 (d, 1H), 7.48 (m, 3H), 7.22 (m, 2H), 7.18 (d, 1H), 7.12 (d, 2H), 5.29 (d, 1H), 4.71 (d, 1H). LCMS: m/z 534.1 (M+H)$^+$.

INTERMEDIATE 16

6-{[4-(Trifluoromethyl)phenyl]sulfonyl}-2-(trifluoromethyl)-6,11-dihydro-5H-pyrido[2,3-b][1,5]benzodiazepine-7-carboxylic acid The title compound was prepared from intermediate 13 following the procedure described for intermediate 15. LCMS: m/z 517.9 (M+H)$^+$.

INTERMEDIATE 17

6-[4-(tert-Butylphenyl)sulfonyl]-2-(trifluoromethyl)-6,11-dihydro-5H-pyrido[2,3-b][1,5]benzodiazepine-7-carboxylic acid The title compound was prepared from intermediate 14 following the procedure described for intermediate 15. LCMS: m/z 506.0 (M+H)$^+$.

INTERMEDIATE 18

6-{[4-(Trifluoromethoxy)phenyl]sulfonyl}-2-(trifluoromethyl)-6,11-dihydro-5H-pyrido[2,3-b][1,5]benzodiazepine-7-carboxamide A solution of intermediate 15 (500 mg, 0.94 mmol), EDC (359 mg, 1.9 mmol) and DMAP (458 mg, 3.8 mmol) in CH$_2$Cl$_2$ was stirred at rt for 30 min, and was added NH$_3$/dioxane (0.5M, 15 mL, 7.5 mmol). The reaction was stirred at rt for 12 h, and was concentrated. The residue was diluted with H$_2$O, and the product was extracted with EtOAc. The extracts were washed with H$_2$O, brine, dried over MgSO$_4$, filtered and concentrated. The residue was purified by silica gel chromatography (40-80% EtOAc/hexanes) to give the title compound. $^1$H NMR (500 MHz, (CD$_3$)$_2$CO): δ 8.43 (s, 1H), 7.78 (d, 1H), 7.45 (dd, 1H), 7.39 (t, 1H), 7.30 (dd, 1H), 7.26 (m, 2H), 7.17 (d, 1H), 7.12 (d, 2H), 7.04 (br s, 1H), 6.68 (br s, 1H), 5.26 (d, 1H), 4.74 (d, 1H). LCMS: m/z 533.1 (M+H)$^+$.

INTERMEDIATE 19

7-(5-Isopropenyl-1,2,4-oxadiazol-3-yl)-2-(trifluoromethyl)-6-{[4-(trifluoromethyl)phenyl]sulfonyl}-6,11-dihydro-5H-pyrido[2,3-b][1,5]benzodiazepine A mixture of intermediate 9 (200 mg, 0.38 mmol) and methacryloyl chloride (100 μL, 0.38 mmol) in pyridine (8 ml) was heated at 80° C. overnight. The reaction mixture was concentrated and the residue was diluted with H$_2$O (50 mL), and EtOAc (50 mL). The organic layer was separated, washed with brine, dried over MgSO$_4$, filtered, and concentrated, and the residue was purified by silica gel chromatography (0-40% EtOAc/hexanes) to afford the title compound. $^1$H NMR (500 MHz, (CD$_3$)$_2$CO): δ 8.58 (s, 1H), 7.85 (d, 1H), 7.57 (m, 5H), 7.37 (d, 2H), 7.20 (d, 1H), 6.33 (s, 1H), 5.84 (s, 1H), 5.38 (d, 1H), 4.86 (d, 1H), 2.31 (d, 1H). LCMS: m/z 581.9 (M+H)$^+$.

INTERMEDIATE 20

7-(5-Isopropenyl-1,2,4-oxadiazol-3-yl)-6-{[4-(trifluoromethoxy)phenyl]sulfonyl}-2-(trifluoromethyl)-6,11-dihydro-5H-pyrido[2,3-b][1,5]benzodiazepine The title compound was prepared from intermediate 8 following the procedure described for intermediate 19. LCMS: m/z 598.0 (M+H)$^+$.

INTERMEDIATE 21

6-[(4-tert-Butylphenyl)sulfonyl]-2-(trifluoromethyl)-6,11-dihydro-5H-pyrido[2,3-b][1,5]benzodiazepine-7-carboximidamide To a suspension of NH$_4$Cl (180 mg, 3.4 mmol) in toluene (10 mL) at 80° C. was added Me$_3$Al (2.0 M/toluene, 1.7 mL, 3.4 mmol) resulting in a clear solution. The solution was cooled at 0° C. and intermediate 14 was added. The reaction was heated at 80° C. for 12 h, and was quenched with MeOH. The mixture was partitioned between brine (100 mL) and EtOAc (100 mL). The organic layer was separated, dried over MgSO$_4$, filtered, and concentrated. The residue was purified via reverse phase HPLC to give the title compound. $^1$H NMR (500 MHz, (CD$_3$)$_2$CO): δ 8.59 (s, 1H), 7.80 (d, 1H), 7.62 (dd, 1H), 7.54 (m, 1H), 7.38 (dd, 1H), 7.21 (d, 2H), 7.00 (d, 2H), 5.38 (d, 1H), 4.89 (d, 1H), 1.22 (s, 9H). LCMS: m/z 504.1 (M+H)$^+$.

INTERMEDIATE 22

6-{[4-(Trifluoromethoxy)phenyl]sulfonyl}-2-(trifluoromethyl)-6,11-dihydro-5H-pyrido[2,3-b][1,5]benzodiazepine-7-carboximidamide The title compound was prepared following the procedure described for intermediate 21 starting with intermediate 12. LCMS: m/z 532.0 (M+H)$^+$.

INTERMEDIATE 23

7-Ethynyl-6-{[4-(trifluoromethoxy)phenyl]sulfonyl}-2-(trifluoromethyl)-6,11-dihydro-5H-pyrido[2,3-b][1,5]benzodiazepine Step A: To a solution of intermediate 3 (750 mg, 1.20 mmol) in Et$_2$NH/DMF (15 mL/5 mL) was added trimethylsilylacetylene (231 mg, 2.40 mmol), Pd(Ph$_3$P)$_2$Cl$_2$ (83 mg, 0.20 mmol), Ph$_3$P (111 mg, 0.43 mmol) and CuI (22 mg, 0.20 mmol). The reaction was heated in a microwave reactor at 120° C. for 30 min. The reaction mixture was diluted with H$_2$O (100 mL) and the product was extracted with EtOAc (3×100 mL). The combined extracts were dried over MgSO$_4$, filtered and concentrated to give a residue, which was purified by silica gel chromatography (5-40% EtOAc/hexanes) to give 6-{[4-(trifluoromethoxy)phenyl]sulfonyl}-2-(trifluoromethyl)-7-[(trimethylsilyl)ethynyl]-6,11-dihydro-5H-pyrido[2,3-b][1,5]benzodiazepine. LCMS: m/z 586.1 (M+H)$^+$.

Step B: To a suspension of 6-{[4-(trifluoromethoxy)phenyl]sulfonyl}-2-(trifluoromethyl)-7-[(trimethylsilyl)ethynyl]-6,11-dihydro-5H-pyrido[2,3-b][1,5]benzodiazepine (414 mg, 0.75 mmol) in MeOH (40 mL) was added $K_2CO_3$ (306 mg, 3.00 mmol). The reaction was stirred at rt for 1.5 h, diluted with $H_2O$, and the product was extracted with EtOAc. The combined organic extracts were washed with $H_2O$, brine, dried over $MgSO_4$, filtered and concentrated. The resulting residue was purified by silica gel chromatography to give the title compound. $^1$H NMR (500 MHz, $(CD_3)_2CO$): δ 8.50 (s, 1H), 7.76 (d, 1H), 7.40 (m, 4H), 7.27 (m, 1H), 7.15 (d, 3H), 5.27 (d, 1H), 4.70 (d, 1H), 3.81 (s, 1H). LCMS: m/z 514.1 (m+H).

INTERMEDIATE 24

6-[(4-tert-Butylphenyl)sulfonyl]-7-ethynyl-2-(trifluoromethyl)-6,11-dihydro-5H-pyrido[2,3-b][1,5]benzodiazepine The title compound was prepared following the procedure described for intermediate 23 starting with intermediate 5. LCMS: m/z 486.1 (M+H)$^+$.

INTERMEDIATE 25

6-[(4-tert-Butylphenyl)sulfonyl]-7-chloro-2-(trifluoromethyl)-6,11-dihydro-5-pyrido[2,3-b][1,5]benzodiazepine To a solution of 7-chloro-2-(trifluoromethyl)-6,11-dihydro-5H-pyrido[2,3-b][1,5]benzodiazepine (intermediate 30, 2.60 g, 8.8 mmol) in $CH_2Cl_2$ (40 mL) at 0° C. was added 4-tert-butylbenzenesulfonyl chloride (6.2 g, 26.0 mmol), pyridine (3.7 mL) and DMAP (500 mg). After stirring at rt for 12 h, the reaction mixture was concentrated and the residue was purified by silica gel chromatography (40-80% $CH_2Cl_2$: hexanes) to give the title compound as a racemic mixture. $^1$H NMR (500 MHz, $(CD_3)_2CO$): δ 8.69 (s, 1H), 8.47 (s, 1H), 7.70 (d, 1H), 7.33 (m, 3H), 7.20 (dd, 1H), 7.15 (d, 2H), 5.19 (d, 1H), 4.59 (d, 1H), 1.22 (s, 9H). LCMS: m/z 496.0 (M+H)$^+$.

INTERMEDIATE 26

2-(Trifluoromethyl)-6,11-dihydro-5H-pyrido[2,3-b][1,5]benzodiazepine

Step A: A mixture of 1,2-diaminobenzene (5.4 g, 50 mmol), 2-chloro-6-(trifluoromethyl)nicotinic acid (11.25 g, 50 mmol) in 2-butoxyethanol (150 mL) was heated at 150° C. for 6 h. The reaction mixture was poured into water and made basic (pH=8) with 50% aqueous NaOH solution. The precipitate was collected by filtration, washed with water, and dried in a vacuum oven at 45° C. to give the diazepinone product, which was used without further purification. LCMS: m/e 280.1 (M+H)$^+$.

Step B: To the diazepinone of Step A in 100 mL of THF was added 1.0 M $BH_3$ in THF (150 mL, 150 mmol) at ° C. After stirring at it overnight, the reaction was carefully quenched with MeOH at 0° C. The resulting mixture was concentrated, and the residue was purified on silica gel eluting with 10-50% EtOAc in hexanes to give the title compound. LCMS: m/e 266.1 (M+H)$^+$.

INTERMEDIATE 27

7-Fluoro-2-(trifluoromethyl)-6,11-dihydro-5H-pyrido[2,3-b][1,5]benzodiazepine

Step A: A mixture of 3-Fluorobenzene-1,2-diamine (1.26 g, 10 mmol), 2-chloro-6-(trifluoromethyl)nicotinic acid (2.48 g, 11 mmol) in 2-butoxyethanol (14 mL) was heated in a microwave reactor at 150° C. for 30 min. The reaction mixture was concentrated to give the diazepinone, which was used without further purification. LCMS: m/e 298.1 (M+H)$^+$.

Step B: To the diazepinone of Step A in 10 mL of THF was added 1.0 M $BH_3$ in THF (30 mL, 30 mmol) at 0° C. After stirring at it overnight, the reaction was carefully quenched with MeOH at 0° C. The resulting mixture was concentrated, and the residue was purified on silica gel eluting with 10-50% EtOAc in hexanes to give the title compound. LCMS: m/e 284.1 (M+H)$^+$.

INTERMEDIATE 28

7-Methyl-2-(trifluoromethyl)-6,11-dihydro-5H-pyrido[2,3-b][1,5]benzodiazepine

The title compound was prepared from 3-methylbenzene-1,2-diamine following the procedure described for intermediate 26. LCMS: m/e 280.1 (M+H)$^+$.

INTERMEDIATE 29

7,8-Dimethyl-2-(trifluoromethyl)-6,11-dihydro-5H-pyrido[2,3-b][1,5]benzodiazepine Step A: A mixture of 3,4-dimethylbenzene-1,2-diamine (6.8 g, 50 mmol) and 2-chloro-6-(trifluoro-methyl)nicotinic acid (11 g, 50 mmol) in 2-butoxyethanol (150 mL) was heated at 150° C. for 6 h. The reaction mixture was poured into water and was made basic (pH=8) with 50% aqueous NaOH solution. The precipitate was collected by filtration, washed with water, and dried in a vacuum oven at 45° C. to give the diazepinone, which was used without further purification.

Step B: To the diazepinone of Step A in 100 mL of THF at ° C. was added 1.0 M $BH_3$ in THF (150 mL, 150 mmol). After stirring at it overnight, the reaction was carefully quenched with MeOH at 0° C. The resulting mixture was concentrated, and the residue was purified on silica gel eluting with 10-50% EtOAc in hexanes to give the title compound.

INTERMEDIATE 30

7-Chloro-2-(trifluoromethyl)-6,11-dihydro-5H-pyrido[2,3-b][1,5]benzodiazepine

Step A: A solution of 3-chloro-2-nitroanailine (8.6 g, 50 mmol) in 150 mL of EtOH was stirred with Pt(IV) oxide (0.9 g) under 1 atm hydrogen (balloon) for 4 h. The reaction mixture was filtered through Celite and the filtrate was concentrated to afford 3-chlorobenzene-1,2-diamine.

Step B: A mixture of 3-chlorobenzene-1,2-diamine and 2-chloro-6-(trifluoromethyl)nicotinic acid (11 g, 50 mmol) in 2-butoxyethanol (150 mL) was heated at 150° C. for 22 h. The reaction mixture was concentrated to give the diazepinone, which was used without further purification.

Step C: To the diazepinone of Step B in 100 mL of THF at 0° C. was added 1.0 M $BH_3$ in THF (150 mL, 150 mmol). After stirring at rt overnight, and reaction was carefully quenched with MeOH at 0° C. The resulting mixture was concentrated, and the residue was purified on silica gel eluting with 10-50% EtOAc in hexanes to give the title compound. LCMS: m/e 300.0 (M+H)+.

INTERMEDIATE 31

2-Chloro-6,11-dihydro-5H-pyrido[2,3-b][1,5]benzodiazepine

The title compound was prepared from 2,6-dichloronicotinic acid following the procedure described for intermediate 26. LCMS: m/e 232.1 (M+H)+.

INTERMEDIATE 32

7-Methyl-2-chloro-6,11-dihydro-5H-pyrido[2,3-b][1,5]benzodiazepine

The title compound was prepared from 2,6-dichloronicotinic acid following the procedure described for intermediate 28. LCMS: m/e 246.1 (M+H)+.

INTERMEDIATE 33

2-Chloro-7,8-dimethyl-6,11-dihydro-5H-pyrido[2,3-b][1,5]benzodiazepine

The title compound was prepared from 2,6-dichloronicotinic acid following the procedure described for intermediate 29. LCMS: m/e 260.1 (M+H)+.

INTERMEDIATE 34

2,7,8-Trimethyl-6,11-dihydro-5H-pyrido[2,3-b][1,5]benzodiazepine

The title compound was prepared from 2-chloro-6-methylnicotinic acid following the procedure described for intermediate 29. LCMS: m/e 240.1 (M+H)+.

INTERMEDIATE 35

1-[2-(Trifluoromethyl)-6,11-dihydro-5H-pyrido[2,3-b][1,5]benzodiazepin-8-yl]cyclopropanecarbonitrile Step A: To 1-phenylcyclopropanecarbonitrile (25 g, 0.17 mol) in concentrated sulfuric acid (100 ml) at 0-10° C. was added concentrated nitric acid (9.4 ml, 0.2 mol) dropwise. After stirring −5° C. for 15 min, the reaction mixture was poured onto ice, and the pH of the aqueous layer was adjusted to 7 with aqueous NaOH. The precipitate was collected by filtration to afford the desired product.

Step B: The product of Step A (50 g, 0.26 mol) in THF (2000 ml) was stirred at rt with Pd/C (5 g) under 45 psi of hydrogen for 48 h. The reaction mixture was filtered, and the filtrate was concentrated to afford the desired product.

Step C: To the solution of the product of Step B (45 g, 0.28 mol) in anhydrous THF (400 ml) at 0° C. was added acetic anhydride (32.3 ml, 0.34 mol) dropwise. After stirring at 15 t for 18 h, the solution was concentrated to afford the desired product.

Step D: To a solution of the product of Step C (20 g, 0.15 mol) in concentrated sulfuric acid (80 ml) at 0-10° C. was added concentrated nitric acid (5.4 ml, 0.12 mol). After stirring at −5° C. for 20 min, the reaction mixture was poured onto ice and the pH of the aqueous layer was adjusted to 7 with aqueous NaOH. The product was extracted with ethyl acetate, and the extracts were dried over sodium sulfate, and concentrated to afford the desired product.

Step E: A mixture of the product of Step D (24 g, 0.1 mol) and sodium hydroxide (24 g, 0.6 mol) in 1000 mL of methanol was stirred at rt overnight. The reaction mixture was concentrated and the residue was diluted with ethyl acetate, washed with water, dried over sodium sulfate, filtered and concentrated, and the residue was purified by on silica gel eluting with 1:1 DCM:PE to afford the desired product.

Step F: A mixture of the product of Step E (3 g, 14.76 mmol), 2-chloro-3-pyridinecarboxaldehyde (4.2 g, 29.53 mmol), potassium carbonate (2.45 g, 17.7 mmol), Pd$_2$(dba)$_3$ (0.2 g, 0.22 mmol), 2-dicyclohexylphosphino-2'-(N,N-dimethylamino) biphenyl (0.35 g, 0.89 mmol), and tert-butyl alcohol (90 ml) under nitrogen was heated at 95° C. for 20 h. The reaction mixture was diluted with ethyl acetate, washed with water, dried over sodium sulfate, filtered and concentrated, and the reside was purified on silica gel eluting with 2:1 DCM:PE to afford the desired product.

Step G: A solution of the product of Step F (6.2 g, 0.02 mol) in ethyl acetate (750 ml) and ethanol (750 ml) was stirred at 30° C. with Pd—C (1.4 g) under 15 psi of hydrogen for 20 h. The reaction mixture was filtered, the filtrate was concentrated, and the residue was purified by chromatography on silica gel eluting with 2:1 DCM:PE to afford the title compound. $^1$H-NMR: (DMSO-d$_6$ 300 MHz) δ 8.95 (s, 1 H, NH), 7.96 (dd, J=1.8 Hz, J=4.8 Hz, 1 H, Ar—H), 7.33 (dd, J=1.8 Hz, J=7.5 Hz, 1 H, Ar—H), 7.04 (d, J=8.4 Hz, 1 H, Ar—H), 6.79 (d, J=2.4 Hz, 1 H, Ar—H), 6.52~6.61 (m, 2 H, Ar—H), 5.92 (s, 1 H, NH), 3.98 (d, J=3.3 Hz, 2 H, CH$_2$), 1.58~1.62 (m, 2 H, CH$_2$), 1.28~1.33 (m, 2 H, CH$_2$).

INTERMEDIATE 36

8-Bromo-2-(trifluoromethyl)-6,11-dihydro-5H-pyrido[2,3-b][1,5]benzodiazepine Step A: To 2-(trifluoromethyl)-6,11-dihydro-5H-pyrido[2,3-b][1,5]benzodiazepine (intermediate 26, 3.43 g, 12.95 mmol) and 4-nitrobenzenesulfonyl chloride (5.7 g, 25.97 mmol) in CH$_2$Cl$_2$ (50 mL) was added pyridine (4.2 mL, 51.80 mmol). After stirring at rt overnight, the reaction mixture was concentrated and the residue was purified on silica gel eluting with 5-20% EtOAc in hexanes to afford the sulfonamide. LCMS: m/e 451.1 (M+H)+.

Step B: To the sulfonamide of step A (5.17 g, 11.5 mmol) in CH$_2$Cl$_2$ (50 mL) was added NBS (2.05 g, 11.5 mmol), and the reaction mixture was stirred at rt overnight. The reaction mixture was diluted with 200 mL of EtOAc, washed with water (100 mL×2) and brine (100 mL), dried over anhydrous MgSO$_4$, filtered and concentrated. The resulting residue was purified on silica gel eluting with 5-30% EtOAc in hexanes to give the bromo intermediate. LCMS: m/e 529.0 (M+H)+.

Step C: A mixture of the bromo intermediate of Step B (4.23 g, 8 mmol), K$_2$CO$_3$ (3.3 g, 24 mmol), thiophenol (0.98 mL, 9.6 mmol), and DMF (25 mL) was stirred at rt for 1 h. The reaction mixture was diluted with 100 mL of EtOAc, washed with water (2-100 mL) and brine (100 mL), dried over anhydrous MgSO$_4$, filtered and concentrated. The residue was purified on silica gel eluting with 10-35% EtOAc in hexanes to afford the title compound. LCMS: m/e 344.0 (M+H)+.

INTERMEDIATE 37

8-Iodo-2-(trifluoromethyl)-6,11-dihydro-5H-pyrido[2,3-b][1,5]benzodiazepine

The title compound was prepared according to the procedure described for intermediate 36 using NIS instead of NBS. LCMS: m/e 392.0 (M+H)$^+$.

INTERMEDIATE 38

2-Chloro-8-iodo-6,11-dihydro-5H-pyrido[2,3-b][1,5]benzodiazepine

The title compound was prepared according to the procedure described for intermediate 36 using NIS instead of NBS. LCMS: m/e 358.0 (M+H)$^+$.

INTERMEDIATE 39

(2E)-3-(dimethylamino)-1-[6-{[4-(trifluoromethoxy)phenyl]sulfonyl}-2-(trifluoromethyl)-6,11-dihydro-5H-pyrido[2,3-b][1,5]benzodiazepin-7-yl]prop-2-en-1-one Step A: A mixture of intermediate 3 (2.0 g, 3.14 mmol), tributyl(1-ethoxyvinyl)tin (2.27 g, 6.27 mmol), LiCl (0.4 g, 9.41 mmol), Pd(PPh$_3$)$_4$ (0.73 g, 0.63 mmol) and 10 mL of THF was heated under nitrogen at 70° C. overnight. The reaction mixture was diluted with water (50 mL) and the product was extracted with EtOAc (50 mL×2). The combined extracts were stirred with MgSO$_4$ and KF for 2 h, and were filtered through Celite. The filtrate was concentrated, and the residue was dissolved in 10 mL of EtOH. After the addition of 2N HCl (5 mL), the reaction was stirred for 2-3 h. The reaction mixture was diluted with EtOAc (100 mL), washed with water (50 mL×2) and brine (50 mL), dried over MgSO$_4$, filtered, and concentrated. The residue was purified on silica gel column eluting with 20-30% EtOAc in hexanes to afford the methyl ketone product. LCMS: m/e 532.1 (M+H)$^+$.

Step B: A mixture of the methyl ketone of Step A (2 g, 3.76 mmol), EtOH (14 mL), N,N-dimethylformamide dimethyl acetal (5 mL), and powdered 4A molecular sieves (500 mg) was heated in a microwave reactor for 2.5 h at 110° C. After cooling to rt, the reaction mixture was concentrated, and the residue was purified on silica gel column eluting with 5-30% EtOAc in hexanes to give the title compound. LCMS: m/e 587.1 (M+H)$^+$.

INTERMEDIATE 40

7,8-Dimethyl-6,11-dihydro-5H-pyrido[2,3-b][1,5]benzodiazepine

The title compound was prepared from 2-chloronicotinic acid following the procedure described for intermediate 29. LCMS: m/e 226.1 (M+H)$^+$.

INTERMEDIATE 41

2-Chloro-3-fluoro-7,8-dimethyl-6,11-dihydro-5H-pyrido[2,3-b][1,5]benzodiazepine The title compound was prepared from 2,6-dichloro-5-fluoronicotinic acid following the procedure described for intermediate 29. LCMS: m/e 278.1 (M+H)$^+$.

INTERMEDIATE 42

3-Methyl-2-trifluoromethyl-6,11-dihydro-5H-pyrido[2,3-b][1,5]benzodiazepine

Step A: To a solution of LDA (0.06 mol) in THF (60 ml) at −78° C. was added 2-chloro-6-trifluoromethylpyridine (9.1 g, 0.05 mol). After stirring at −78° C. 2h, I$_2$ (15.2 g, 0.06 mol) was added. The reaction was allowed to warm up to rt for 2 h and was quenched with water. The reaction mixture was partitioned between water and ether. The organic phase was separated, washed with water, diluted hydrochloric acid and brine, dried over Na$_2$SO$_4$, and concentrated to afford the desired product.

Step B: To a solution of LDA in THF at −78° C. was added a solution of the product of Step A in anhydrous THF, and the reaction was stirred −78° C. for 2 h and was added ethyl chloroformate in THF. The reaction was allowed to warm up to rt for 30 min, and was quenched with water. The reaction mixture was partitioned between water and ethyl acetate. The organic layer was separated, and the aqueous layer was extracted with EtOAc (3×30 ml). The combined extracts were washed with water and brine, dried with Na$_2$SO$_4$ and concentrated. The residue was purified on silica gel column eluting with PE to afford the desired product.

Step C: A mixture of the product of Step B (227 mg, 0.6 mmol), PPh$_3$ (10 mg) and Pd$_2$(dba)$_3$ (2 mg) and NMP was heated to 50° C. for 10 min. After the addition of CuI (11.4 mg, 0.06 mmol), the reaction was stirred at 50° C. for another 10 min. After cooling to rt, Me$_4$Sn (332 mg, 1.8 mmol) was added and the reaction was stirred at 65° C. overnight. The reaction was quenched with water, and the product was extracted with ethyl acetate (3×30 ml). The combined extracts were washed with water and brine, dried with Na$_2$SO$_4$ and concentrated. The residue was purified by silica gel column eluting with 10:1 PE:EA to afford the desired product.

Step D: A mixture of the product from Step C (1 g, 3.7 mmol), 1,2-diaminobenzene (2 g, 18.5 mmol), CuI (0.5 g, 2.7 mmol) and sulfolane was stirred at 140° C. overnight, and at 180° C. for 8 h. The reaction was quenched with water (20 ml), and the product was extracted with ethyl acetate (3×30 ml). The combined extracts were washed with water and brine, dried over Na$_2$SO$_4$ and concentrated to give the desired product, which was used without further purification. LCMS: m/294.1 (M+H)$^+$.

Step E: To a solution of the product of Step D (0.8 g, 2.7 mmol) in dry THF under N$_2$ was added dropwise BH$_3$—S(CH$_3$)$_2$ complex (10 M, 3 ml, 36 mmol), and the reaction was heated at reflux overnight. After cooling to rt, HCl (2 M, 50 ml) was added, and the resulting mixture was heated at reflux for 3 h. The pH of the aqueous layer was adjusted to 9 with aqueous ammonia, and the product was extracted with ethyl acetate (30 mL×3). The combined organic phases were washed with water and brine, dried over sodium sulfate and concentrated. The residue was purified by flash column chromatography on silica gel eluting with 20:1 PE:EA to afford the title compound. $^1$H-NMR: (CDCl$_3$, 400 MHz): δ 7.11 (br, 1 H, NH), 6.5-7.0 (m, 6 H, Ar), 4.27 (s, 2H, CH$_2$), 4.10 (br, 1 H, NH), 2.32 (s, 3H, CH$_3$). LCMS: m/e 280.1 (M+H)$^+$.

INTERMEDIATE 43

4-(1-Fluoro-1-methylethyl)benzenesulfonyl chloride

Step A: To 1-(4-bromophenyl)ethanone (8 g, 40.2 mmol) in 150 mL of THF was added MeMgCl (3.0 M in THF, 40 mL, 120 mmol) at −78° C. The reaction was stirred at rt overnight, and quenched with 150 mL of aqueous NH$_4$Cl. The product was extracted with 250 mL of EtOAc, and the extracts were dried over anhydrous MgSO$_4$, and concentrated to give 2-(4-bromophenyl)propan-2-ol, which was used without further purification.

Step B: To 2-(4-bromophenyl)propan-2-ol (8.3 g, 38.59 mmol) in 100 mL of CH$_2$Cl$_2$ was added DAST (6.1 mL, 46.31 mmol) at −78° C. The reaction was stirred to rt overnight, and quenched with 100 mL of water at 0° C. The product was extracted with EtOAc, and the extracts were washed with water (50 mL) and brine (50 mL), dried over anhydrous MgSO$_4$, and concentrated to give 1-bromo-4-(1-fluoro-1-methylethyl)benzene, which was used without further purification.

Step C: 1-Bromo-4-(1-fluoro-1-methylethyl)benzene was converted to the title compound according to the procedure described by T. Hamada et al (Synthesis, 1986, 852). $^1$H NMR (500 MHz, CD$_3$OD): δ 8.10 (2H, d), 7.79 (2H, d), 1.74 (3H, s), 1.70 (3H, s).

INTERMEDIATE 44

4-(1-Cyano-1-methylethyl)benzenesulfonyl chloride

The title compound was prepared as from 2-(4-bromophenyl)-2-methylpropanenitrile according to the procedure described for intermediate 43, step C.

INTERMEDIATE 45

4-(1-Cyanocyclopropyl)benzenesulfonyl chloride

To a solution of 1-phenylcyclopropanecarbonitrile (0.5 g, 3.5 mmol) in 5 mL of chloroform was added 0.5 mL of ClSO$_3$H at 0° C. After stirring at rt stirred overnight, the reaction mixture was poured into ice-water (50 mL) and the product was extracted with CHCl$_3$ (75 mL). The extracts were washed with water (50 mL) and brine (50 mL), dried over anhydrous MgSO$_4$, and concentrated to give the title compound. $^1$H NMR (500 MHz, CD$_3$OD): δ 8.08 (2H, d), 7.77 (2H, d), 1.60 (2H, t), 1.21 (2H, t).

INTERMEDIATE 46

4-(1-Cyanocyclobutyl)benzenesulfonyl chloride

The title compound was prepared from 1-phenylcyclobutanecarbonitrile according to the procedure described for intermediate 45. $^1$H NMR (500 MHz, CD$_3$OD): δ 8.07 (2H, d), 7.83 (2H, d), 2.86 (2H, m), 2.78 (2H, m), 2.44 (1H, m), 2.28 (1H, m).

INTERMEDIATE 47

4-(3,3-Difluorocyclobutyl)benzenesulfonyl chloride

Step A: 3-Phenylcyclobutanone was converted to (3,3-difluorocyclobutyl)benzene according to the procedure described for intermediate 43, Step B.

Step B: The product of Step A was converted to the title compound according to the procedure described for intermediate 45. $^1$H NMR (500 MHz, CD$_3$OD): δ 8.20 (2H, d), 7.82 (2H, d), 3.30 (2H, m), 2.78 (2H, m).

INTERMEDIATE 48

4-[1-(Trifluoromethyl)cyclopropyl]benzenesulfonyl chloride

The title compound was prepared from [1-(trifluoromethyl)cyclopropyl]benzene according to the procedure described for intermediate 45. $^1$H NMR (500 MHz, CD$_3$OD): δ 8.08 (2H, d), 7.83 (2H, d), 1.47 (2H, m), 1.21 (2H, m).

INTERMEDIATE 49

4-tert-Butyl-1,3-thiazole-2-sulfonyl chloride

To 50 mL of 33% AcOH/H$_2$O was bubbled Cl$_2$ gas at 0° C. until a precipitate formed, and a suspension of 4-tert-butylthiazole-2-thiol (5.0 g, 28.85 mmol) in 30 mL of 33% AcOH/H$_2$O was added over 0.5 h. Bubbling of Cl$_2$ continued for another 15 min. The reaction mixture was filtered, and the filtrate was extracted with CH$_2$Cl$_2$ (50 mL×2). The extracts were washed with water (50 mL), aqueous NaHCO$_3$ (50 mL), and brine (50 mL), dried over anhydrous MgSO$_4$, and concentrated to give the title compound. LCMS: m/e 240.0 (M+H)$^+$.

INTERMEDIATE 50

5-(Trifluoromethyl)thiophene-2-sulfonyl chloride

The title compound was prepared as the major regioisomer from 2-(trifluoromethyl)thiophene according to the procedure described for intermediate 45. $^1$H NMR (500 MHz, CD$_3$OD): δ 8.08 (1H, d), 7.79 (1H, d).

INTERMEDIATE 51

5-(Trifluoromethyl)thiophene-3-sulfonyl chloride

The title compound was prepared as the minor regioisomer from 2-(trifluoromethyl)thiophene according to the procedure described for intermediate 45. $^1$H NMR (500 MHz, CD$_3$OD): δ 8.88 (1H, s), 8.17 (1H, s).

INTERMEDIATE 52

6-[(4-tert-Butylphenyl)sulfonyl]-8-iodo-2-(trifluoromethyl)-6,11-dihydro-5H-pyrido[2,3-b][1,5]-benzodiazepine The title compound was prepared from intermediate 37 according to the procedure described for intermediate 53. LC/MS: m/e 588.0 (M+H)$^+$.

INTERMEDIATE 53

8-Bromo-6-[(4-tert-butylphenyl)sulfonyl]-2-(trifluoromethyl)-6,11-dihydro-5H-pyrido-[2,3-b][1,5]benzodiazepine A solution of 8-bromo-2-(trifluoromethyl)-6,11-dihydro-5H-pyrido[2,3-b][1,5]benzodiazepine (5.16 g, 15 mmol, intermediate 36), (4-tert-butylphenyl)sulfonyl chloride (10.5 g, 45 mmol), pyridine (7.11 g, 90 mmol), DMAP (0.366 g, 3 mmol in DCM (75 mL) was stirred at rt for 24 h. The reaction was quenched with water, and the product was extracted with EtOAc (3×). The combined extracts were washed with water and brine, dried (MgSO$_4$), filtered and concentrated. The residue was recrystallized from DCM and hexanes to afford the title compound. LC/MS: m/e 542.0 (M+H)$^+$. $^1$H NMR (500 MHz, CDCl$_3$): δ 7.76 (1H, d, J=2.3 Hz), 7.56 (1H, d, J=7.3 Hz), 7.36 (1H, dd, J=8.7, 2.3 Hz), 7.11 (2H, d, J=8.5 Hz), 7.09 (1H, d, J=7.5 Hz), 6.96 (2H, d, J=8.4 Hz), 6.72 (1H, s), 6.62 (1H, d, J=8.7 Hz), 4.70-4.90 (2H, br), 1.25 (9H, s).

INTERMEDIATE 54

6-[(4-tert-Butylphenyl)sulfonyl]-2-(trifluoromethyl)-6,11-dihydro-5H-pyrido-[2,3-b][1,5]benzodiazepine-8-carbonitrile A mixture of 8-bromo-6-[(4-tert-butylphenyl)sulfonyl]-2-(trifluoromethyl)-6,11-dihydro-5H-pyrido[2,3-b][1,5]benzodiazepine (0.860 g, 1.60 mmol, intermediate 53), zinc cyanide (0.112 g, 0.96 mmol), Pd$_2$(dba)$_3$ (0.293 g, 0.320 mmol), and dppf (0.443 g, 0.80 mmol) in NMP (6.5 mL) under nitrogen was stirred at rt for 0.5 h and at 100° C. overnight. After cooling to rt, the reaction mixture was diluted with EtOAc and filtered. The filtrate was washed with water (3×), brine, dried (MgSO$_4$), filtered and concentrated. The residue was purified by flash chromatography, eluting with mixtures of hexane and EtOAc, to provide the title compound. LC/MS: m/e 487.2 (M+H)$^+$. NMR (500 MHz, CDCl$_3$): δ 7.94 (1H, d, J=1.6 Hz), 7.66 (1H, d, J=7.5 Hz), 7.53 (1H, dd, J=8.4, 2.0 Hz), 7.19 (1H, d, J=7.3 Hz), 7.13 (2H, d, J=8.7 Hz), 7.04 (1H, s), 6.94 (2H, d, J=8.6 Hz), 6.83 (1H, d, J=8.5 Hz), 4.70-4.90 (2H, br), 1.26 (9H, s).

INTERMEDIATE 55

6-[(4-tert-Butylphenyl)sulfonyl]-N'-hydroxy-2-(trifluoromethyl)-6,11-dihydro-5H-pyrido[2,3-b][1,5]benzodiazepine-8-carboximidamide To a solution of 6-[(4-tert-butylphenyl)sulfonyl]-2-(trifluoromethyl)-6,11-dihydro-5H-pyrido[2,3-b][1,5]benzodiazepine-8-carbonitrile (0.60 g, 1.23 mmol, intermediate 54) in ethanol (6 mL) at rt was added hydroxylamine (0.24 mL of a 50% aqueous solution), and potassium carbonate (0.02 mL of a 0.8 M aqueous solution). After stirring at rt for 45 min, the reaction mixture was heated at 105° C. for 65 min in a microwave reactor. After cooling to rt, the precipitate was collected by filtration to provide the title compound. LC/MS: m/e 520.2 (M+H)$^+$.

INTERMEDIATE 56

Methyl 6-[(4-tert-butylphenyl)sulfonyl]-2-(trifluoromethyl)-6,11-dihydro-5H-pyrido[2,3-b][1,5]benzodiazepine-8-carboxylate To a solution of 8-bromo-6-[(4-tert-butylphenyl)sulfonyl]-2-(trifluoromethyl)-6,11-dihydro-5H-pyrido[2,3-b][1,5]benzodiazepine (0.168 g, 0.32 mmol, intermediate 53) in DMF (2.0 mL) under nitrogent (balloon) was added palladium acetate (0.072 g, 0.32 mmol), dppf (0.220 g, 0.40 mmol), triethylamine (0.080 g, 0.800 mmol), and methanol (2.0 mL). The nitrogen balloon was replaced with a carbon monoxide balloon and the reaction mixture was stirred at rt for 1 h, and at 80° C. for 15 h. After cooling to rt, the reaction mixture was diluted with EtOAc and filtered through a pad of silica gel. The filtrate was concentrated to dryness and the residue was purified by SiO$_2$ column chromatography eluting with EtOAc in hexanes to provide the title compound. LC/MS: m/e 520.1 (M+H)$^+$. $^1$H NMR (500 MHz, CDCl$_3$): δ 8.28 (1H, d, J=1.6 Hz), 7.94 (1H, dd, J=8.5, 1.8 Hz), 7.61 (1H, d, J=7.5 Hz), 7.13 (1H, d, J=7.6 Hz), 7.10 (2H, d, J=8.5 Hz), 6.99 (1H, s), 6.92 (2H, d, J=8.4 Hz), 6.80 (1H, m), 4.70-4.90 (2H, br), 3.95 (3H, s), 1.25 (9H, s).

INTERMEDIATE 57

6-[(4-tert-Butylphenyl)sulfonyl]-2-(trifluoromethyl)-6,11-dihydro-5H-pyrido-[2,3-b][1,5]benzodiazepine-8-carbohydrazide To a solution of methyl 6-[(4-tert-butylphenyl)sulfonyl]-2-(trifluoromethyl)-6,11-dihydro-5H-pyrido-[2,3-b][1,5]benzodiazepine-8-carboxylate (intermediate 56, 0.11 g, 0.21 mmol) in ethanol (1.0 mL) at rt was added hydrazine hydrate (0.460 mL). The mixture was heated at 80° C. for 18 h, cooled to rt, and the precipitate was collected by filtration to provide the title compound. LC/MS: m/e 520.1 (M+H)$^+$. $^1$H NMR (500 MHz, CD$_3$OD): δ 8.00 (1H, s), 7.78 (1H, d, J=8.3 Hz), 7.65 (1H, d, J=7.5 Hz), 7.10-7.16 (3H, m), 6.90-6.95 (3H, m), 4.45-4.70 (2H, br), 1.24 (9H, s).

INTERMEDIATE 58

6-[(4-tert-Butylphenyl)sulfonyl]-2-(trifluoromethyl)-6,11-dihydro-5H-pyrido[2,3-b][1,5]benzodiazepine-8-carboxylic acid A mixture of methyl 6-[(4-tert-butylphenyl)sulfonyl]-2-(trifluoromethyl)-6,11-dihydro-5H-pyrido-[2,3-b][1,5]benzodiazepine-8-carboxylate (90 mg, intermediate 56), water (0.63 mL), conc. HCl (1.25 mL), and glacial acetic acid (2.0 mL) was heated at 130° C. for 2 h. After cooling to rt, 4N aqueous NaOH was added until pH=6. The reaction mixture was extracted with DCM (3×), and the extracts were dried, filtered, and concentrated to provide the title compound. LC/MS: m/e 506.1 (M+H)$^+$. $^1$H NMR (500 MHz, CDCl$_3$): δ 8.12 (1H, s), 7.79 (1H, dd, J=8.5, 1.6 Hz), 7.49 (1H, d, J=7.5 Hz), 6.99 (3H, m), 6.79 (3H, m), 4.45-4.70 (2H, br), 1.11 (9H, s).

INTERMEDIATE 59

8-Iodo-2-(trifluoromethyl)-6-({4-[1-(trifluoromethyl)cyclopropyl]phenyl}sulfonyl)-6,11-dihydro-5H-pyrido[2,3-b][1,5]benzodiazepine The title compound was prepared following procedure described for intermediate 53 substituting 8-iodo-2-(trifluoromethyl)-6,11-dihydro-5H-pyrido[2,3-b][1,5]benzodiazepine (intermediate 37) and 4-[1-(trifluoromethyl)-cyclopropyl]benzenesulfonyl chloride (intermediate 48) for 8-bromo-2-(trifluoromethyl)-6,11-dihydro-5H-pyrido[2,3-b][1,5]benzodiazepine, and [(4-tert-butylphenyl)-sulfonyl chloride. LC/MS: m/e 639.8 (M+H)$^+$. $^1$H NMR (500 MHz, CDCl$_3$): δ 7.93 (1H, d, J=2.1 Hz), 7.58 (1H, d, J=7.8 Hz), 7.55 (1H, dd, J=8.5, 2.1 Hz), 7.22 (2H, d, J=8.2 Hz), 7.10 (1H, d, J=7.6 Hz), 7.03 (2H, d, J=8.5 Hz), 6.75 (1H, s), 6.52 (1H, d, J=8.5 Hz), 4.70-4.90 (2H, br), 1.37-1.40 (4H, m), 0.95-1.05 (4H, m).

INTERMEDIATE 60

8-Iodo-2-(trifluoromethyl)-6-{[4-(trifluoromethyl)phenyl]sulfonyl}-6,11-dihydro-5H-pyrido[2,3-b][1,5]benzodiazepine The title compound was prepared following procedure described for intermediate 53 substituting 8-iodo-2-(trifluoromethyl)-6,11-dihydro-5H-pyrido[2,3-b][1,5]benzodiazepine (intermediate 37) and 4-(trifluoromethyl)benzenesulfonyl chloride for 8-bromo-2-(trifluoromethyl)-6,11-dihydro-5H-pyrido[2,3-b][1,5]benzodiazepine and [(4-tert-butylphenyl)-sulfonyl chloride. LC/MS: m/e 599.8 (M+H)$^+$. $^1$H NMR (500 MHz, acetone-d$_6$): δ 8.56 (1H, s), 7.79-7.82 (2H, m), 7.66 (1H, dd, J=8.5, 2.1 Hz), 7.55 (2H, d, J=8.3 Hz), 7.29 (2H, d, J=8.3 Hz), 7.17 (1H, d, J=7.5 Hz), 7.15 (2H, d, J=8.7 Hz), 4.80-5.10 (2H, br).

INTERMEDIATE 61

8-Iodo-6-{[4-(trifluoromethoxy)phenyl]sulfonyl}-2-(trifluoromethyl)-6,11-dihydro-5H-pyrido[2,3-b][1,5]benzodiazepine The title compound was prepared following the procedure described for intermediate 53 substituting 8-iodo-2-(trifluoromethyl)-6,11-dihydro-5H-pyrido[2,3-b][1,5]benzodiazepine (intermediate 37) for 8-bromo-2-(trifluoromethyl)-6,11-dihydro-5H-pyrido[2,3-b][1,5]benzodiazepine, and 4-(trifluoromethoxy)benzenesulfonyl chloride substituted for [(4-tert-butylphenyl)-sulfonyl chloride. LC/MS: m/e 615.8 (M+H)$^+$. $^1$H NMR (500 MHz, acetone-d$_6$): δ 7.80 (1H, d, J=2.0 Hz), 7.79 (1H, d, J=7.8 Hz), 7.66 (1H, dd, J=8.5, 2.0 Hz), 7.55 (2H, d, J=8.4 Hz), 7.29 (2H, d, J=8.2 Hz), 7.17 (1H, d, J=7.6 Hz), 7.15 (2H, d, J=8.6 Hz), 4.70-4.90 (2H, br).

INTERMEDIATE 62

8-Amino-6-{[4-(trifluoromethoxy)phenyl]sulfonyl}-2-(trifluoromethyl)-6,11-dihydro-5H-pyrido[2,3-b][1,5]benzodiazepin-7-ol Step A: To a stirred suspension of Claycop (136 mg, prepared according to Synthesis, 1985, 909) in CCl$_4$ (0.85 mL) and acetic anhydride (0.43 mL) at −10° C. was added 6-{[4-(Trifluoromethoxy)phenyl]-sulfonyl}-2-(trifluoromethyl)-6,11-dihydro-5H-pyrido[2,3-b][1,5]benzodiazepin-7-ol (intermediate 2) in batches. After stirring at 5° C. for 5 h, the reaction mixture was diluted with EtOAc, filtered through Celite. The filtrate was washed with 5% aqueous NaHCO$_3$, brine, dried (MgSO$_4$), filtered and concentrated. The residue was triturated with DCM, and the solid was collected by filtration and dried to provide the nitro intermediate. LC/MS: m/e 551.0 (M+H)$^+$.

Step B: The nitro intermediate of Step A (30 mg, 0.055 mmol) was dissolved in 15 mL of MeOH and hydrogenated (10% Pd/C as catalyst, 10 atm of H$_2$, 50° C.), to provide the title compound. LC/MS: m/e 520.0 (M+H)$^+$. $^1$H NMR (500 MHz, CD$_3$OD): δ 7.57 (1H, d, J=7.5 Hz), 7.20 (2H, d, J=8.9 Hz), 7.03 (2H, d, J=8.7 Hz), 6.99 (1H, d, J=7.5 Hz), 6.73 (1H, d, J=8.7 Hz), 6.36 (1H, d, J=8.7 Hz), 5.17 (1H, d, J=16.4 Hz), 4.42 (1H, d, J=16.5 Hz).

INTERMEDIATE 63

8-Bromo-6-[(4-tert-butylphenyl)sulfonyl]-7-methyl-2-(trifluoromethyl)-6,11-dihydro-5H-pyrido[2,3-b][1,5]benzodiazepine The title compound was prepared following the procedure described for intermediates 36 and 53.

INTERMEDIATE 64

8-Bromo-6-[(4-tert-butylphenyl)sulfonyl]-7-chloro-2-(trifluoromethyl)-6,11-dihydro-5H-pyrido[2,3-b]-[1,5]benzodiazepine To a solution of 6-[(4-tert-butylphenyl)sulfonyl]-7-chloro-2-(trifluoromethyl)-6,11-dihydro-5H-pyrido[2,3-b][1,5]benzodiazepine (intermediate 25, 60 mg, 0.121 mmol) in DCM (1 mL) was added NBS (23.7 mg, 0.133 mmol) and a few drops of TFA. After stirring at rt for 3 h, the reaction mixture was concentrated to dryness, and the residue was dissolved in ether, washed with sodium thiosulfate, water and brine, dried over MgSO$_4$, filtered and concentrated. The residue was purified by reverse phase HPLC to provide the title compound. LC/MS: m/e 574 (M+H)$^+$.

INTERMEDIATE 65

8-Bromo-6-[(4-tert-butylphenyl)sulfonyl]-7-methyl-2-(trifluoromethyl)-6,11-dihydro-5H-pyrido[2,3-b][1,5]benzodiazepine Step A: A well-stirred mixture of 3-methyl-1,2-benzenediamine (4.0 g, 33 mmol) and 2-chloro-6-(trifluoromethyl)nicotinic acid (7.3 g, 33 mmol) in 2-butoxyethanol (60 ml) was heated at 140-150° C. for 6 h. The dark solution was then poured over crushed ice, and the resulting dark brown solid was collected, washed with water, and dried. Recrystallization from 50% dioxane/water afforded 7-methyl-2-(trifluoromethyl)-6,11-dihydro-5H-pyrido[2,3-b][1,5]benzodiazepin-5-one.

Step B: To a solution of the product of Step A (2.4 g, 9 mmol) was added BH$_3$•THF (20 ml, 20 mmol), and the resulting mixture was refluxed overnight. The reaction mixture was acidified with concentrated hydrochloric acid to pH=1. After refluxing for 3 h, the reaction mixture was neutralized to pH=8 with diluted aqueous NaOH, and the product was extracted with EtOAc (20 mL×3). The combined extracts were washed with water and brine, dried over sodium sulfate, and concentrated to give crude amine.

Step C: A solution of the amine of Step B (3.0 g, 12 mmol), 4-tert-butylphenylsulfonyl chloride (4.5 g, 19 mmol) and pyridine (5.0 ml, 66 mmol) in dichloromethane (100 ml) was stirred at rt overnight. The reaction mixture was diluted with dichloromethane (100 ml), separated, washed with dilute hydrochloric acid (1%), water and brine successively, dried over sodium sulfate, filtered and concentrated to give the crude product. Recrystallization from chloroform and methanol yielded 6-[(4-tert-butylphenyl)-sulfonyl]-7-methyl-2-(trifluoromethyl)-6,11-dihydro-5H-pyrido[2,3-b][1,5]benzodiazepine. $^1$H NMR (400 MHz, CDCl$_3$): δ 7.49 (d, J=8.0 Hz, 1H), 7.23 (d, J=8.4 Hz, 1H), 7.11 (d, J=8.4 Hz, 1H), 7.04 (m, 3H), 6.51~6.53 (m, 2H), 5.22 (d, J=16.8 Hz, 1H), 4.35 (d, J=16.8 Hz, 1H), 2.65 (s, 3H), 1.24 (s, 9H).

Step D: To a solution of the product of Step C (0.95 g, 2 mmol mol) in dichloromethane (5 ml) and acetonitrile (50 ml) was added NBS (0.35 g, 2 mmol mol) in portions at 0° C. After stirring at 5° C. for 12 h, the reaction mixture was concentrated, and the residue was partitioned between dichloromethane and water. The organic layer was separated, washed with water and brine, dried over anhydrous sodium sulfate, filtered and concentrated to afford the title compound. $^1$H NMR (400 MHz, CDCl$_3$) δ 7.50 (d, J=7.2 Hz, 1H), 7.40 (d, J=8.4 Hz, 1H), 7.13 (m, 5H), 6.52 (m, 2H), 5.20 (d, J=16.8 Hz, 1H), 4.34 (d, J=16.8 Hz, 1H), 2.65 (s, 3H), 1.24 (s, 9H).

EXAMPLE 1

2-{3-[6-{[4-(Trifluoromethoxy)phenyl]sulfonyl}-2-(trifluoromethyl)-6,11-dihydro-5H-pyrido[2,3-b][1,5]benzodiazepin-7-yl]-1,2,4-oxadiazol-5-yl}propan-2-ol

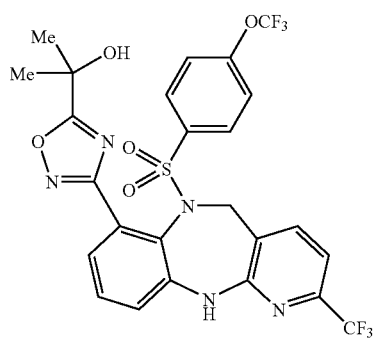

To a stirred solution of intermediate 8 (10.0 g, 18.3 mmol) in pyridine (200 mL) was added 2-acetoxyisobutyryl chloride (30.0 g, 182 mmol). The resulting solution was heated at 80° C. for 3 h and was then concentrated to give a residue, which was dissolved in MeOH (400 mL) and treated with $K_2CO_3$ (25.0 g, 181 mmol). The resulting slurry was heated at 50° C. for 2 hours, followed by the addition of another portion of $K_2CO_3$ (25.0 g, 181 mmol). The reaction was stirred for 2 hours, and the reaction mixture was concentrated, and diluted with EtOAc (400 mL) and $H_2O$ (400 mL). The organic layer was separated, dried over $MgSO_4$, filtered and concentrated to give an oil that was purified by silica gel chromatography (0-60% EtOAc in hexanes) to yield the title compound as a racemic mixture. The racemic mixture was separated by HPLC on a chiralcel OD column with 15% MeOH/liquid $CO_2$ as the mobile phase (SFC conditions). The faster eluting enantiomer (E1) has a retention time of 4.77 minutes, while the slower enantiomer (E2) has a retention time of 5.82 minutes. E1: $^1$H NMR (500 MHz, (CD$_3$)$_2$CO): δ 8.53 (s, 1H), 7.82 (d, 1H), 7.55 (m, 3H), 7.26 (m, 3H), 7.19 (d, 1H), 7.12 (d, 1H), 5.33 (d, 1H), 5.11 (s, 1H), 4.80 (d, 1H), 1.76 (d, 6H). LCMS: m/z 616.12 (M+H)$^+$.

EXAMPLE 2

2-[3-(2-(Trifluoromethyl)-6-{[4-(trifluoromethyl)phenyl]sulfonyl}-6,11-dihydro-5H-pyrido[2,3-b][1,5]benzodiazepin-7-yl)-1,2,4-oxadiazol-5-yl]propan-2-ol

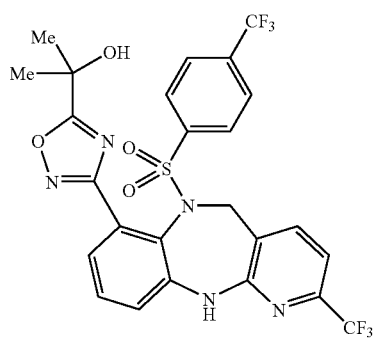

The title compound was prepared from intermediate 9 and acetoxyisobutyryl chloride following the procedure as described for Example 1. Racemic mixture: $^1$H NMR (500 MHz, (CD$_3$)$_2$CO): δ 8.53 (s, 1H), 7.84 (d, 1H), 7.56 (m, 5H), 7.35 (d, 2H), 7.19 (d, 1H), 5.37 (d, 1H), 5.10 (s, 1H), 4.84 (d, 1H), 1.77 (d, 6H). LCMS: m/z 600.0 (M+H)$^+$. The racemic mixture was separated by HPLC on a chiralcel OD column with 15% EtOH/hexanes as the mobile phase. The faster eluting enantiomer (E1) has a retention time of 15.0 min, while the slower eluting enantiomer (E2) has a retention time of 28.0 min.

EXAMPLE 3

2-{3-[6-[(4-tert-Butylphenyl)sulfonyl]-2-(trifluoromethyl)-6,11-dihydro-5H-pyrido[2,3-b][1,5]benzodiazepin-7-yl]-1,2,4-oxadiazol-5-yl}propan-2-ol

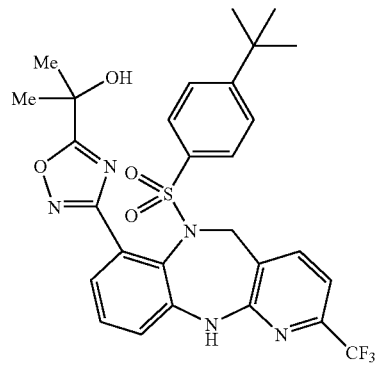

The title compound was prepared from intermediate 10 and acetoxyisobutyryl chloride following the procedure described for Example 1. Racemic mixture: $^1$H NMR (500 MHz, (CD$_3$)$_2$CO): δ 8.40 (s, 1H), 7.80 (d, 1H), 7.50 (m, 2H), 7.21 (d, 2H), 7.17 (d, 1H), 7.04 (d, 2H), 5.30 (d, 1H), 5.10 (s, 1H), 4.72 (d, 1H), 1.76 (d, 6H), 1.25 (s, 9H). LCMS: m/z 588.1 (M+H)$^+$. The racemic mixture was separated by HPLC on a chiralcel OD column with 15% EtOH/hexanes as the mobile phase. The faster eluting enantiomer (E1) has a retention time of 15.0 min, while the slower eluting enantiomer (E2) has a retention time of 28.0 min.

EXAMPLE 4

2-{3-[2-(Trifluoromethyl)-6-({4-[1-(trifluoromethyl)cyclopropyl]phenyl}sulfonyl)-6,11-dihydro-5H-pyrido[2,3-b][1,5]benzodiazepin-7-yl]-1,2,4-oxadiazol-5-yl}-2-propanol

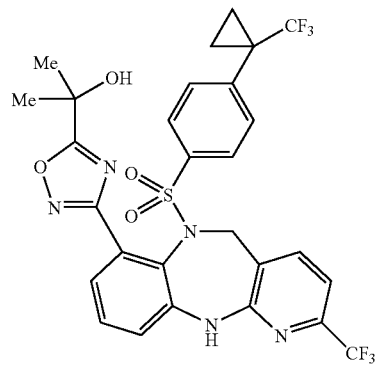

The title compound was prepared from intermediate 11 and acetoxyisobutyryl chloride following the procedure as described for Example 1. Racemic mixture: $^1$H NMR (500 MHz, (CD$_3$)$_2$CO): δ 8.44 (s, 1H), 7.82 (d, 1H), 7.51 (m, 3H), 7.19 (d, 1H), 7.12 (d, 2H), 5.34 (d, 1H), 5.10 (s, 1H), 4.76 (d, 1H), 1.76 (d, 6H), 1.10 (m, 4H). LCMS: m/z 640.1 (M+H)$^+$. The racemic mixture was separated by HPLC on a chiralcel OD column with 15% EtOH/hexanes as the mobile phase. The faster eluting enantiomer (E1) has a retention time of 12 min, while the slower eluting enantiomer (E2) has a retention time of 17 minutes.

EXAMPLE 5

{3-[6-[(4-tert-Butylphenyl)sulfonyl]-2-(trifluoromethyl)-6,11-dihydro-5H-pyrido[2,3-b]-[1,5]benzodiazepin-7-yl]-1,2,4-oxadiazol-5-yl}methanol

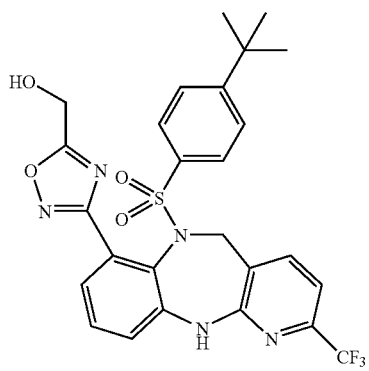

To a stirred solution of benzyloxyacetic acid (3.9 g, 24.0 mmol) in DMF (50 mL) was added Py-BOP (12.5 g, 24 mmol) and TEA (6.6 mL, 47 mmol). After 30 min, a solution of intermediate 10 (3.9 g, 7.5 mmol) was added in one portion. The resulting solution was heated to 70° C. and monitored by LC/MS. Once reaction is complete, the solution was diluted with brine (200 mL) and EtOAc (200 mL). The organic layer was separated, dried over MgSO$_4$, filtered and concentrated. The oily residue was dissolved in THF (50 mL) and treated with TBAF (25 mL, 25 mmol). After 1 h, the solution was concentrated and purified via flash chromatography (7-60% EtOAc:hexanes). The resulting benzyl protected intermediate was dissolved in CHCl$_3$ (40 mL) and treated with methanesulfonic acid (5 mL). After 15 min, the solution was quenched with sat NaHCO$_3$. The solution was then diluted with brine (100 mL) and EtOAc (100 mL). The organic layer was separated, dried over MgSO$_4$, filtered and concentrated to give an oil that was purified by silica gel chromatography (0-60% EtOAc in hexanes) to yield the title compound as a racemic mixture. $^1$H NMR (500 MHz, (CD$_3$)$_2$CO): δ 8.42 (s, 1H), 7.79 (d, 1H), 7.50 (m, 2H), 7.22 (d, 2H), 7.19 (d, 1H), 7.12 (d, 2H), 5.29 (d, 1H), 4.96 (s, 2H), 4.71 (d, 1H), 1.25 (s, 9H). LCMS: m/z 560.1 (M+H)$^+$. The racemic mixture was separated by HPLC on a chiralcel OD column to afford the respective enantiomers. The faster eluting enantiomer (E1) has a retention time of 8.7 min, while the slower eluting enantiomer (E2) has a retention time of 11.4 min.

EXAMPLE 6

[3-(2-(Trifluoromethyl)-6-{[4-(trifluoromethyl)phenyl]sulfonyl}-6,11-dihydro-5H-pyrido[2,3-b]-[1,5]benzodiazepin-7-yl)-1,2,4-oxadiazol-5-yl]methanol

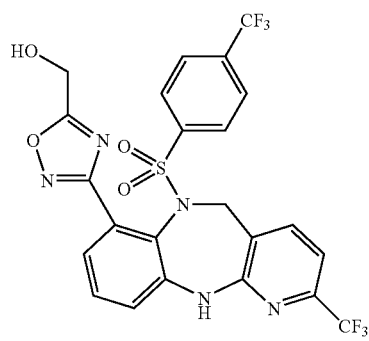

The title compound was prepared from intermediate 9 and benzyloxyacetic acid following the procedure as described for example 5 to give a racemic mixture. $^1$H NMR (500 MHz, (CD$_3$)$_2$CO): δ 8.54 (s, 1H), 7.83 (d, 1H), 7.55 (m, 3H), 7.23 (m, 3H), 7.13 (d, 2H), 5.33 (d, 1H), 5.17 (br s, 1H), 4.97 (s, 2H), 4.83 (d, 1H). LCMS: m/z 588.0 (M+H)$^+$. The racemic mixture was separated by HPLC using a chiralcel OD column and 20% EtOH/hexanes as mobile phase. The faster eluting enantiomer (E1) has a retention time of 20.0 min, while the slower eluting enantiomer (E2) has a retention time of 38.0 min.

EXAMPLE 7

{3-[6-{[4-(Trifluoromethoxy)phenyl]sulfonyl}-2-(trifluoromethyl)-6,11-dihydro-5H-pyrido[2,3-b]-[1,5]benzodiazepin-7-yl]-1,2,4-oxadiazol-5-yl}methanol

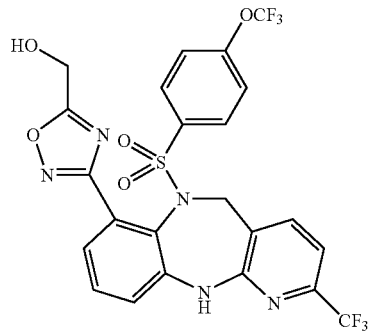

The title compound was prepared from intermediate 8 and benzyloxyacetic acid following the procedure described for example 5 to give a racemic mixture. $^1$H NMR (500 MHz, (CD$_3$)$_2$CO): δ 8.54 (s, 1H), 7.83 (d, 1H), 7.55 (m, 3H), 7.23 (m, 3H), 7.13 (d, 2H), 5.33 (d, 1H), 5.17 (br s, 1H), 4.97 (s, 2H), 4.83 (d, 1H). LCMS: m/z 588.0 (M+H)$^+$. The racemic mixture was separated by HPLC using a chiralcel OD-H column and 15% EtOH/hexanes as mobile phase. The faster eluting enantiomer (E1) has a retention time of 12.0 min, while the slower eluting enantiomer (E2) has a retention time of 17.0 min.

The compounds in Table 1 were prepared using the appropriate starting materials and reagents following procedures similar to that described for Example 5:

TABLE 1

| Example | Re | Rf | Enantiomer | LCMS: found m/e (M + H) |
|---|---|---|---|---|
| 8 | HO-CH(CH₃)- | CH₃ | E1 | 518.0 |
| 9 | HO-CH(CH₃)- | CH₃ | E2 | 518.0 |
| 10 | HO-CH(CH₃)- | (CH₃)₂CH | E1 | 531.1 |
| 11 | HO-CH(CH₃)- | (CH₃)₂CH | E2 | 531.1 |
| 12 | (CH₃)₂N-CH₂- | OCF₃ | E1 | 599.0 |
| 13 | (CH₃)₂N-CH₂- | OCF₃ | E2 | 599.0 |
| 14 | H | tBu | E1 | 530.0 |
| 15 | H | tBu | E2 | 530.0 |
| 16 | (R)-HO-CH(CH₃)- | tBu | E1 | 574.1 |
| 17 | (R)-HO-CH(CH₃)- | tBu | E2 | 574.1 |

TABLE 1-continued

| Example | Re | Rf | Enantiomer | LCMS: found m/e (M + H) |
|---|---|---|---|---|
| 18 | (R)-HO-CH(CH₃)- | CF₃ | E1 | 586.0 |
| 19 | (R)-HO-CH(CH₃)- | CF₃ | E2 | 586.0 |
| 20 | (R)-HO-CH(CH₃)- | OCF₃ | E1 | 602.0 |
| 21 | (R)-HO-CH(CH₃)- | OCF₃ | E2 | 602.0 |
| 22 | (R)-HO-CH(CH₃)- | TMC | E1 | 626.0 |
| 23 | (R)-HO-CH(CH₃)- | TMC | E2 | 626.0 |
| 24 | (S)-HO-CH(CH₃)- | tBu | E1 | 574.1 |
| 25 | (S)-HO-CH(CH₃)- | tBu | E2 | 574.1 |
| 26 | (S)-HO-CH(CH₃)- | CF₃ | E1 | 586.0 |

TABLE 1-continued

| Example | Re | Rf | Enantiomer | LCMS: found m/e (M + H) |
|---|---|---|---|---|
| 27 | HO—(R)— (dashed wedge) | CF$_3$ | E2 | 586.0 |
| 28 | HO—(R)— (dashed wedge) | OCF$_3$ | E1 | 602.0 |
| 29 | HO—(R)— (dashed wedge) | OCF$_3$ | E2 | 602.0 |
| 30 | HO—(R)— (dashed wedge) | TMC | E1 | 626.0 |
| 31 | HO—(R)— (dashed wedge) | TMC | E2 | 626.0 |
| 32 | HO-CH$_2$-CH(OH)- | tBu | E1 | 590.6 |
| 33 | HO-CH$_2$-CH(OH)- | tBu | E2 | 590.6 |
| 34 | HO-CH$_2$-CH(OH)- | CF$_3$ | E1 | 601.9 |
| 35 | HO-CH$_2$-CH(OH)- | CF$_3$ | E2 | 601.9 |

TABLE 1-continued

| Example | Re | Rf | Enantiomer | LCMS: found m/e (M + H) |
|---|---|---|---|---|
| 36 | HO-CH$_2$-CH(OH)- | OCF$_3$ | E1 | 617.9 |
| 37 | HO-CH$_2$-CH(OH)- | OCF$_3$ | E2 | 617.9 |
| 38 | HO-CH$_2$-CH(OH)- | TMC | E1 | 642.0 |
| 39 | HO-CH$_2$-CH(OH)- | TMC | E2 | 642.0 |
| 40 | HO-CH$_2$-CH(OH)- (dashed) | tBu | E1 | 590.6 |
| 41 | HO-CH$_2$-CH(OH)- (dashed) | tBu | E2 | 590.6 |
| 42 | HO-CH$_2$-CH(OH)- (dashed) | CF$_3$ | E1 | 601.9 |
| 43 | HO-CH$_2$-CH(OH)- (dashed) | CF$_3$ | E2 | 601.9 |
| 44 | HO-CH$_2$-CH(OH)- (dashed) | OCF$_3$ | E1 | 617.9 |

TABLE 1-continued

| Example | Re | Rf | Enantiomer | LCMS: found m/e (M + H) |
|---|---|---|---|---|
| 45 | HOCH2-CH(OH)- (stereo) | OCF3 | E2 | 617.9 |
| 46 | HOCH2-CH(OH)- (stereo) | TMC | E1 | 641.9 |
| 47 | HOCH2-CH(OH)- (stereo) | TMC | E2 | 641.9 |
| 48 | CH3-CH(OH)-CH(OH)- | OCF3 | E1 and E2 | 632.1 |
| 49 | 1-hydroxycyclopropyl | iPr | E1 | 572.5 |
| 50 | 1-hydroxycyclopropyl | iPr | E2 | 572.5 |
| 51 | H2N-C(CH3)2- | tBu | E1 | 587.2 |
| 52 | H2N-C(CH3)2- | tBu | E2 | 587.2 |
| 53 | H2N-CH(CH3)- (stereo) | iPr | E1 | 559.1 |
| 54 | H2N-CH(CH3)- (stereo) | iPr | E2 | 559.1 |
| 55 | H2N-CH(CH3)- (stereo) | iPr | E1 | 559.1 |
| 56 | H2N-CH(CH3)- (stereo) | iPr | E2 | 559.1 |
| 57 | MeO-CH2-CH2- | tBu | E1 | 419.2 |
| 58 | MeO-CH2-CH2- | tBu | E2 | 419.2 |
| 59 | HO-C(CH3)-C(=O)- | OCF3 | E1 and E2 | 644.5 |
| 60 | (CH3)2N-CH2- | OCF3 | E1 | 615.1 |
| 61 | (CH3)2N-CH2- | OCF3 | E2 | 615.1 |
| 62 | HOOC-C(CH3)2- | OCF3 | E1 and E2 | 644.1 |
| 63 | HO-CH2-CH2-CH2- | OCF3 | E1 | 600.1 |

TABLE 1-continued

[Structure with Re, Rf substituents on pyrido-benzodiazepine core with sulfonyl-phenyl group]

| Example | Re | Rf | Enantiomer | LCMS: found m/e (M + H) |
|---|---|---|---|---|
| 64 | HO~~~ (4-hydroxybutyl) | OCF₃ | E2 | 600.1 |
| 65 | HO-C(Et)(Me)- | CF₃ | E1 and E2 | 614.1 |
| 66 | CH₃CH(OH)CH₂- | OCF₃ | E1 | 616.1 |
| 67 | CH₃CH(OH)CH₂- | OCF₃ | E2 | 616.1 |
| 68 | CH₃CH(OH)CH₂- | OCF₃ | E1 | 616.1 |
| 69 | CH₃CH(OH)CH₂- | OCF₃ | E2 | 616.1 |
| 70 | azetidinyl-CH₂- | OCF₃ | E1 and E2 | 613.0 |

*E1 is the faster eluting enantiomer, and E2 is slower eluting enantiomer by HPLC on a chiralpak AD, OD, AD-H, or OD-H column eluting with ethanol/hexane, or by Super Critical Fluid Chromatography eluting with methanol/liquid CO₂ or isopropanol/liquid CO₂.

EXAMPLE 71

2-(2-(Trifluoromethyl)-6-{[4-(trifluoromethyl)phenyl]sulfonyl}-6,11-dihydro-5H-pyrido[2,3-b][1,5]benzodiazepin-7-yl)-2-propanol

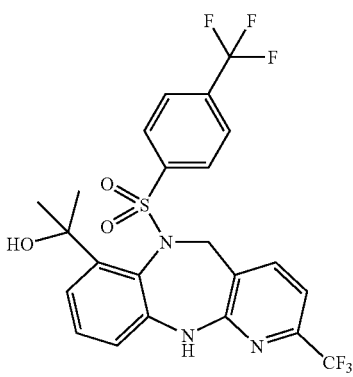

To a suspension of anhydrous CeCl₃ (2.3 g, 9.0 mmol) in THF (20 mL) at −78° C. was added MeLi (1.6M/Et₂O, 5.6 mL, 9.0 mmol) dropwise over 5 min. After 30 min, a solution of intermediate 13 (520 mg, 0.95 mmol) in THF (5 mL) was added in one portion. The solution was maintained at −78° C. for 1 h before warming to 0° C. After 1 h, the solution was quenched with 2N HCl (100 mL) and the product was extracted with EtOAc (3×50 mL). The combined extracts were dried over MgSO₄, filtered and concentrated to give an oil that was purified by silica gel chromatography (7-60% EtOAc in hexanes) to yield the title compound as a racemic mixture. The racemic mixture was separated by HPLC on a chiralcel OD-H column with 30% MeOH/liquid CO₂ as the mobile phase (SFC conditions). The faster eluting enantiomer (E1) has a retention time of 2.4 min, while the slower eluting enantiomer (E2) has a retention time of 3.6 min. E1: ¹H NMR (500 MHz, (CD₃)₂CO): δ 8.15 (s, 1H), 7.75 (d, 1H), 7.50 (m, 3H), 7.30 (m, 3H), 7.16 (d, 1H), 5.31 (d, 1H), 4.73 (d, 1H), 1.88 (s, 3H), 1.81 (s, 31-1). LCMS: m/z 531.9 (M+H)⁺.

The compounds in Table 2 were prepared using the appropriate starting materials and reagents following procedures similar to that described for Examples 71 and 241:

TABLE 2

| Example | R3 | Re | Enantiomer | LCMS: found m/e (M + H) |
|---|---|---|---|---|
| 72 | HO-C(CH3)2-CH2- (tert, HO) | OCF3 | E1 | 547.9 |
| 73 | HO-C(CH3)2-CH2- | OCF3 | E2 | 547.9 |
| 74 | HO-C(CH3)2-CH2- | tBu | E1 | 520.6 |
| 75 | HO-C(CH3)2-CH2- | tBu | E2 | 520.6 |
| 76 | HO-CH2-CH2- | tBu | E1 and E2 | 492.0 |
| 77 | HO-CH2-CH(OH)-CH2- | tBu | E1 | 522.0 |
| 78 | HO-CH2-CH(OH)-CH2- | tBu | E2 | 503.9 |
| 79 | HO-CH2-CH(OH)-CH2- | CF3 | E1 | 533.8 |
| 80 | HO-CH2-CH(OH)-CH2- | CF3 | E2 | 533.8 |

TABLE 2-continued

| Example | R3 | Re | Enantiomer | LCMS: found m/e (M + H) |
|---|---|---|---|---|
| 81 | NC-CH2- | CF3 | E1 and E2 | 512.9 |
| 82 | NC-CH2- | tBu | E1 and E2 | 501.1 |
| 83 | HO-CH(CH3)- | tBu | E1 | 506.0 |
| 84 | HO-CH(CH3)- | tBu | E2 | 506.0 |
| 85 | HO-CH(CH3)- | tBu | E1 | 506.0 |
| 86 | HO-CH(CH3)- | tBu | E2 | 506.0 |
| 87 | CF3-CH(OH)- | tBu | E1 | 559.9 |
| 88 | CF3-CH(OH)- | tBu | E2 | 559.9 |
| 89 | CF3-C(O)-CH2- | tBu | E1 and E2 | 557.9 |

TABLE 2-continued

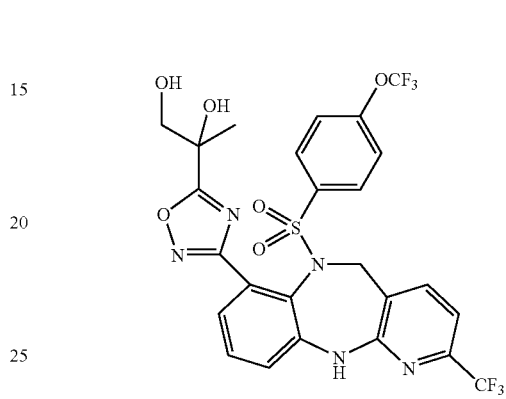

| Example | R3 | Re | Enantiomer | LCMS: found m/e (M + H) |
|---|---|---|---|---|
| 90 | HO─⟨⟩⧸ | OCF$_3$ | E1 | 547.9 |
| 91 | HO─⟨⟩⧸ | OCF$_3$ | E2 | 547.9 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid CO$_2$ or isopropanol/liquid CO$_2$; Racemic mixture refers to a mixture of enantiomers and/or diastereomers.

EXAMPLE 93

2-{3-[6-{[4-(Trifluoromethoxy)phenyl]sulfonyl}-2-(trifluoromethyl)-6,11-dihydro-5H-pyrido[2,3-b][1,5]benzodiazepin-7-yl]-1,2,4-oxadiazol-5-yl}-1,2-propanediol

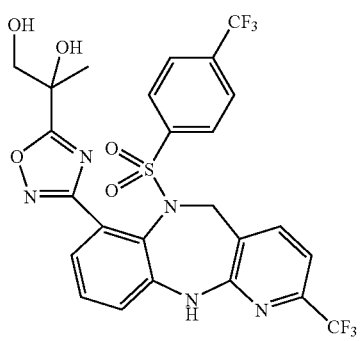

To a solution of intermediate 19 (186 mg, 0.30 mmol) in acetone/H$_2$O/tBuOH (5 mL/2.0 mL/0.8 mL) at rt was added NMO (75.0 mg, 0.60 mmol) followed by 1 crystal of OsO$_4$. After stirring at rt overnight, the solution was diluted with EtOAc (100 mL), washed with brine, dried over MgSO$_4$, filtered and concentrated. The resulting dark residue was purified by silica gel chromatography (50-100% EtOAC/hexanes) to afford the title compound as a racemic mixture. $^1$H NMR (500 MHz, (CD$_3$)$_2$CO): δ 8.54 (s, 1H), 7.84 (d, 1H), 7.57 (m, 5H), 7.18 (d, 1H), 5.36 (dd, 1H), 5.07 (s, 1H), 4.85 (d, 1H), 4.20 (m, 1H), 3.95 (m, 2H), 1.72 (d, 3H). LCMS: m/z 615.9 (M+H)$^+$. The racemic mixture was separated by HPLC using a chiralcel AD-H column and 20% iPrOH/CO$_2$ as the mobile phase (SFC conditions). The fastest eluting isomer (E1) has a retention time of 7.0 min, the second eluting isomer (E2) has a retention time of 8.7 min, the third eluting isomer (E4) has a retention time of 9.4 min and the last enantiomer (E4) has a retention time of 10.0 min.

EXAMPLE 94

2-{3-[6-{[4-(Trifluoromethoxy)phenyl]sulfonyl}-2-(trifluoromethyl)-6,11-dihydro-5H-pyrido[2,3-b][1,5]benzodiazepin-7-yl]-1,2,4-oxadiazol-5-yl}-1,2-propanediol

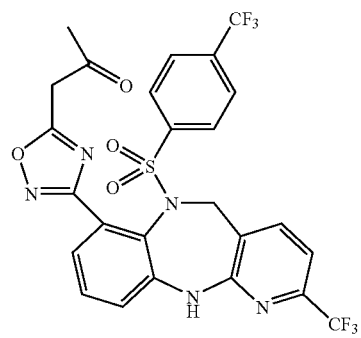

To a solution of intermediate 20 (186 mg, 0.30 mmol) in acetone/H$_2$O/tBuOH (5 mL/2.0 mL/0.8 mL) at rt was added NMO (75.0 mg, 0.60 mmol) followed by 1 crystal of OsO$_4$. After stirring at rt overnight, the solution was diluted with EtOAc (100 mL), washed with brine, dried over MgSO$_4$, filtered and concentrated. The residue was purified by silica gel chromatography (50-100% EtOAC/hexanes) to afford the title compound as a racemic mixture. $^1$H NMR (500 MHz, (CD$_3$)$_2$CO): δ 8.54 (s, 1H), 7.84 (d, 1H), 7.57 (m, 5H), 7.37 (d, 2H), 7.18 (d, 1H), 5.36 (dd, 1H), 5.07 (s, 1H), 4.85 (d, 1H), 4.20 (m, 1H), 3.95 (m, 2H), 1.72 (d, 3H). LCMS: m/z 615.9 (M+H)$^+$. The racemic mixture was separated by HPLC using a chiralcel AD-H column and 20% iPrOH/CO$_2$ as the mobile phase (SFC conditions). The fastest eluting isomer (E1) has a retention time of 7.0 min, the second eluting isomer (E2) has a retention time of 8.7 min, the third eluting isomer (E4) has a retention time of 9.4 min and the last enantiomer (E4) has a retention time of 10.0 min.

EXAMPLE 95

1-[3-(2-(Trifluoromethyl)-6-{[4-(trifluoromethyl)phenyl]sulfonyl}-6,11-dihydro-5H-pyrido[2,3-b][1,5]benzodiazepin-7-yl)-1,2,4-oxadiazol-5-yl]acetone A mixture of intermediate 9 (200 mg, 0.38 mmol) and tert-butylacetoacetate (2 mL) were heated at 120° C. for 4 h. After cooling to rt, the reaction mixture was loaded onto a silica gel column, eluting with 0-60% EtOAc/hexanes afforded the title compound as a racemic mixture. $^1$H NMR (500 MHz, (CD$_3$)$_2$CO): δ 8.54 (s, 1H), 7.84 (d, 1H), 7.56 (m, 5H), 7.33 (d, 2H), 7.19 (d, 1H), 5.34 (d, 1H), 4.83 (d, 1H), 4.37 (s, 2H), 2.40 (s, 3H). LCMS: m/z 598.0 (M+H)$^+$.

The compounds in Table 3 were prepared using the appropriate starting materials and reagents following procedures similar to that described above for Example 95:

TABLE 3

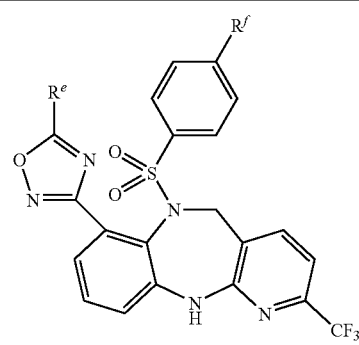

| Example | Re | Rf | Enantiomer | LCMS: found m/e (M + H) |
|---|---|---|---|---|
| 96 | methyl acetoacetate group | tBu | E1 | 602.1 |
| 97 | methyl acetoacetate group | tBu | E2 | 602.1 |
| 98 | 3-methyl-2-butanol group | CF$_3$ | E1 | 628.0 |
| 99 | 3-methyl-2-butanol group | CF$_3$ | E2 | 628.0 |
| 100 | 3-methyl-2-butanol group | CF$_3$ | E3 | 628.0 |
| 101 | 3-methyl-2-butanol group | CF$_3$ | E4 | 628.0 |
| 102 | 2-hydroxypropyl group | CF$_3$ | E1 | 600.0 |

TABLE 3-continued

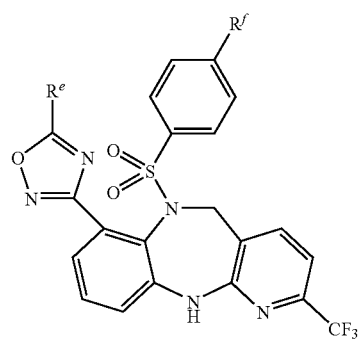

| Example | Re | Rf | Enantiomer | LCMS: found m/e (M + H) |
|---|---|---|---|---|
| 103 | 2-hydroxypropyl group | CF$_3$ | E2 | 600.0 |
| 104 | 2-hydroxypropyl group | CF$_3$ | E3 | 600.0 |
| 105 | 2-hydroxypropyl group | CF$_3$ | E4 | 600.0 |
| 106 | pivaloylmethyl group | CF$_3$ | E1 | 626.0 |
| 107 | pivaloylmethyl group | CF$_3$ | E2 | 626.0 |
| 108 | methyl ester group | CF$_3$ | E1 | 613.9 |
| 109 | methyl ester group | CF$_3$ | E2 | 613.9 |
| 110 | HOOC-CH$_2$- | CF$_3$ | E1 | — |
| 111 | HOOC-CH$_2$- | CF$_3$ | E2 | — |

*E1 is the faster eluting enantiomer, E2 is the slower eluting enantiomer. When more than one pair of enantiomers is present, E1 to E4 was used to denote the isomers that elute from the fastest to the slowest. on a chiralpak AD, OD, AD-H, or OD-H column eluting with ethanol/hexane, or by Super Critical Fluid Chromatography eluting with methanol/liquid CO$_2$ or isopropanol/liquid CO$_2$.

EXAMPLE 112

3-{3-[6-{[4-(Trifluoromethoxy)phenyl]sulfonyl}-2-(trifluoromethyl)-6,11-dihydro-5H-pyrido[2,3-b][1,5]benzodiazepin-7-yl]-1,2,4-oxadiazol-5-yl}cyclobutanol

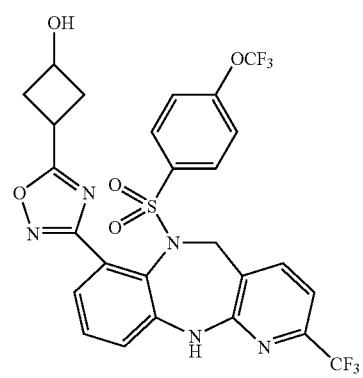

A mixture of intermediate 8 (1.0 g, 1.80 mmol), methyl 3-hydroxycyclobutanecarboxylate (713 mg, 5.50 mmol) and K$_2$CO$_3$ (303 mg, 2.20 mmol) in toluene (20 ml) was heated to reflux for 6 h. The reaction mixture was concentrated, diluted with H$_2$O (50 mL), and the product was extracted with EtOAc (3×100 mL). The combined extracts were washed with brine, dried over MgSO$_4$, filtered and concentrated. The residue was purified by silica gel chromatography (30-80% EtOAc/hexanes) to afford the title compound as a racemic mixture. $^1$H NMR (500 MHz, (CD$_3$)$_2$CO): δ 8.54 (s, 1H), 7.83 (d, 1H), 7.53 (m, 3H), 7.26 (d, 2H), 7.20 (d, 1H), 7.13 (d, 2H), 5.34 (d, 1H), 4.81 (d, 1H), 4.51 (br, 1H), 4.37 (m, 1H), 3.38 (m, 1H), 2.83 (m, 2H), 2.43 (m, 2H). LCMS: m/z 628.2 (M+H)$^+$. The racemic mixture was separated by chiral HPLC on a chiralcel OD-H column with 30% EtOH/heptane as the mobile phase. The faster eluting enantiomer (E1) has a retention time of 10.0 min, the slower eluting enantiomer (E2) has a retention time of 14 min.

The compounds in Table 4 were prepared using the appropriate starting materials and reagents following procedures similar to that described above for Example 112:

TABLE 4

| Example | Re | Rf | Enantiomer | LCMS: found m/e (M + H) |
|---|---|---|---|---|
| 113 | HO─⎍(S)─⁓ | CF$_3$ | E1 | 600.0 |
| 114 | HO─⎍(R)─⁓ | CF$_3$ | E2 | 600.0 |
| 115 | HO─⎍(S)─⁓ | OCF$_3$ | E1 | 616.1 |
| 116 | HO─⎍(R)─⁓ | OCF$_3$ | E2 | 616.1 |
| 117 | HO─⎍(S)─⁓ | CF$_3$ | E1 | 600.1 |
| 118 | HO─⎍(R)─⁓ | CF$_3$ | E2 | 600.1 |
| 119 | O=cyclobutyl─⁓ | OCF$_3$ | E1 | 626.1 |
| 120 | O=cyclobutyl─⁓ | OCF$_3$ | E2 | 626.1 |
| 121 | HO─(Me)cyclobutyl─⁓ | OCF$_3$ | E1 | 642.1 |
| 122 | HO─(Me)cyclobutyl─⁓ | OCF$_3$ | E2 | 642.1 |

TABLE 4-continued

| Example | Re | Rf | Enantiomer | LCMS: found m/e (M + H) |
|---|---|---|---|---|
| 123 | HO-methylcyclobutyl | OCF₃ | E3 | 642.1 |
| 124 | HO-methylcyclobutyl | OCF₃ | E4 | 642.1 |
| 125 | HO-cyclopropyl | OCF₃ | E1 | 614.1 |
| 126 | HO-cyclopropyl | OCF₃ | E2 | 614.1 |
| 127 | acetyl | CF₃ | E1 | 584.0 |
| 128 | acetyl | CF₃ | E2 | 584.0 |

*E1 is the faster eluting enantiomer, E2 is the slower eluting enantiomer. When more than one pair of enantiomers is present, E1 to E4 was used to denote the isomers that elute from the fastest to the slowest. on a chiralpak AD, OD, AD-H, or OD-H column eluting with ethanol/hexane, or by Super Critical Fluid Chromatography eluting with methanol/liquid $CO_2$ or isopropanol/ liquid $CO_2$.

EXAMPLES 129 AND 130

7-(4-Morpholinylcarbonyl)-6-{[4-(trifluoromethoxy)phenyl]sulfonyl}-2-(trifluoromethyl)-6,11-dihydro-5H-pyrido[2,3-b][1,5]benzodiazepine and N-(4-Morpholinyl)-6-{[4-(trifluoromethoxy)phenyl]sulfonyl}-2-(trifluoromethyl)-6,11-dihydro-5H-pyrido[2,3-b][1,5]benzodiazepine-7-carboxamide

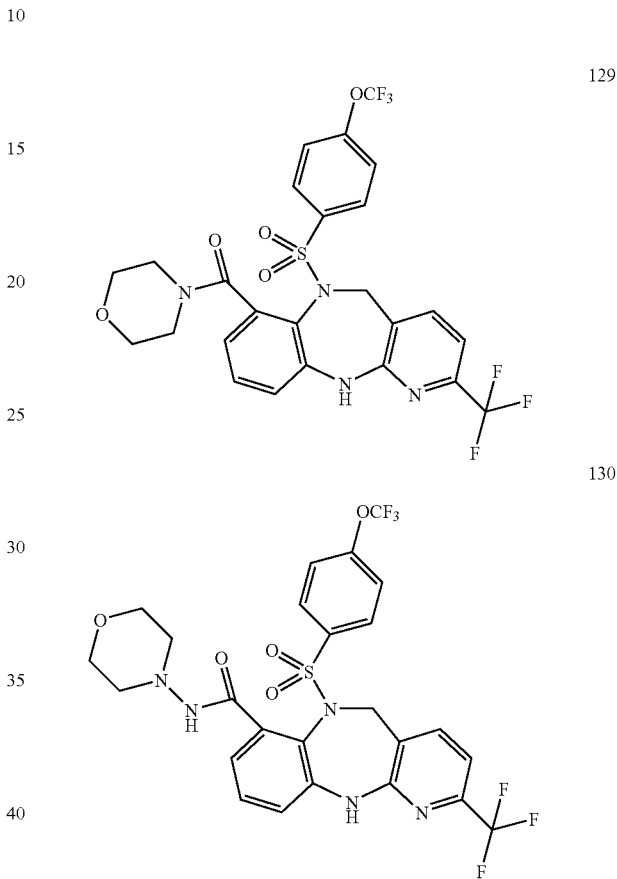

To intermediate 15 (40 mg, 0.08 mmol) in $CH_2Cl_2$ (3 mL) at rt was added oxalyl chloride (50 µL, 0.60 mmol) and two drops of DMF. The resulting solution was stirred at rt for 20 min, and was then concentrated. The resulting crude acid chloride was dissolved in $CH_2Cl_2$ (5 mL), and was treated with 1-aminomorpholine (43 µL, 0.50 mmol), and TEA (50 µL, 0.36 mmol). The solution was stirred at rt for 2 h, and was diluted with $CH_2Cl_2$ and water. The organic layer was separated, washed with brine, dried over $MgSO_4$, filtered and concentrated to give a residue which was purified by silica gel chromatography (0-100% EtOAc/hexanes) to afford the title amide 129 and the title hydrazide 130. Compound 129: $^1$H NMR (500 MHz, $(CD_3)_2CO$): δ 8.43 (s, 1H), 7.74 (d, 1H), 7.40 (m, 2H), 7.30 (d, 2H), 7.16 (d, 1H), 7.11 (d, 2H), 7.04 (d, 1H), 5.18 (d, 1H), 4.61 (d, 1H), 3.70 (m, 8H). LCMS: m/z 603.1 (M+H)⁺. Compound 130: $^1$H NMR (500 MHz, $(CD_3)_2CO$): δ 8.41 (s, 1H), 8.21 (s, 1H), 7.77 (d, 1H), 7.43 (d, 1H), 7.37 (t, 1H), 7.23 (d, 2H), 7.17 (t, 2H), 7.10 (d, 2H), 4.30 (d, 1H), 4.73 (d, 1H), 3.70 (m, 4H), 3.14 (m, 2H), 3.01 (m, 2H). LCMS: m/z 618.1 (M+H)⁺.

The compounds in Table 5 were prepared using the appropriate starting materials and reagents following procedures similar to that described above for Examples 129 and 130:

TABLE 5

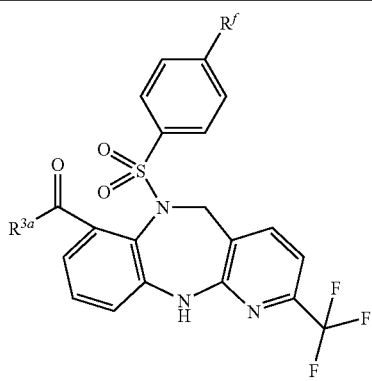

| Example | R3a | Rf | Enantiomer | LCMS: found m/e (M + H) |
|---|---|---|---|---|
| 131 | morpholine | $CF_3$ | E1 | 586.9 |
| 132 | morpholine | $CF_3$ | E2 | 586.9 |
| 133 | dimethylamino | $CF_3$ | E1 | 544.9 |
| 134 | dimethylamino | $CF_3$ | E2 | 544.9 |
| 135 | HOCH2CH2NH | $CF_3$ | E1 | 561.0 |
| 136 | HOCH2CH2NH | $CF_3$ | E2 | 561.0 |
| 137 | piperidine | $OCF_3$ | E1 | 601.2 |
| 138 | piperidine | $OCF_3$ | E2 | 601.2 |
| 139 | N-methylpiperazine | $OCF_3$ | E1 | 616.2 |
| 140 | N-methylpiperazine | $OCF_3$ | E2 | 616.2 |

TABLE 5-continued

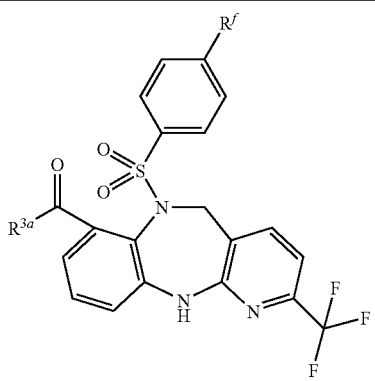

| Example | R3a | Rf | Enantiomer | LCMS: found m/e (M + H) |
|---|---|---|---|---|
| 141 | thiomorpholine | $OCF_3$ | E1 | 619.1 |
| 142 | thiomorpholine | $OCF_3$ | E2 | 619.1 |
| 143 | thiomorpholine-S,S-dioxide | $OCF_3$ | E1 | 651.1 |
| 144 | thiomorpholine-S,S-dioxide | $OCF_3$ | E2 | 651.1 |
| 145 | ethyl glycinate | $OCF_3$ | E1 | 619.2 |
| 146 | ethyl glycinate | $OCF_3$ | E2 | 619.2 |
| 147 | HOC(CH3)2CH2NH | $OCF_3$ | E1 | 605.1 |
| 148 | HOC(CH3)2CH2NH | $OCF_3$ | E2 | 605.1 |
| 149 | N-methylpiperazine | tBu | E1 | 588.0 |
| 150 | N-methylpiperazine | tBu | E2 | 588.0 |

TABLE 5-continued

| Example | R3a | Rf | Enantiomer | LCMS: found m/e (M + H) |
|---|---|---|---|---|
| 151 | morpholin-4-yl | tBu | E1 | 575.1 |
| 152 | morpholin-4-yl | tBu | E2 | 575.1 |
| 153 | pyrrolidin-1-yl | tBu | E1 | 558.9 |
| 154 | pyrrolidin-1-yl | tBu | E2 | 558.9 |
| 155 | piperidin-1-yl | tBu | E1 | 573.1 |
| 156 | piperidin-1-yl | tBu | E2 | 573.1 |
| 157 | azepan-1-yl | tBu | E1 | 587.1 |
| 158 | azepan-1-yl | tBu | E2 | 587.1 |
| 159 | N,N-dimethylamino | tBu | E1 | 533.1 |
| 160 | N,N-dimethylamino | tBu | E2 | 533.1 |
| 161 | thiomorpholin-4-yl | tBu | E1 | 591.1 |
| 162 | thiomorpholin-4-yl | tBu | E2 | 591.1 |
| 163 | 1,1-dioxo-thiomorpholin-4-yl | tBu | E1 | 623.0 |
| 164 | 1,1-dioxo-thiomorpholin-4-yl | tBu | E2 | 623.0 |
| 165 | HOCH(CH3)CH2- | tBu | E1 | 549.0 |
| 166 | HOCH(CH3)CH2- | tBu | E2 | 549.0 |
| 167 | EtO2CCH2- | tBu | E1 | 591.1 |
| 168 | EtO2CCH2- | tBu | E2 | 591.1 |
| 169 | HOC(CH3)2CH2- | tBu | E1 | 577.1 |

TABLE 5-continued

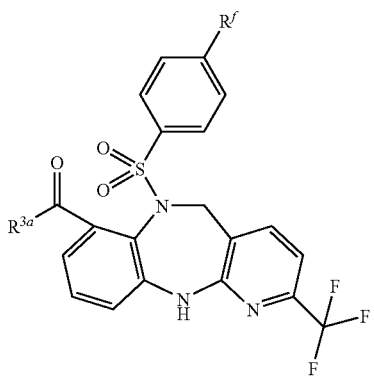

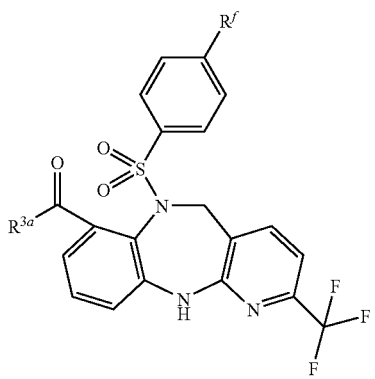

| Example | R3a | Rf | Enantiomer | LCMS: found m/e (M + H) | Example | R3a | Rf | Enantiomer | LCMS: found m/e (M + H) |
|---|---|---|---|---|---|---|---|---|---|
| 170 | HO-C(CH3)2-CH2- | tBu | E2 | 577.1 | 179 | morpholine-NH- | CF3 | E1 | 601.9 |
| 171 | 3-hydroxypyrrolidinyl | tBu | E1 | 575.1 | 180 | morpholine-NH- | CF3 | E2 | 601.9 |
| 172 | 3-hydroxypyrrolidinyl | tBu | E2 | 575.1 | 181 | (CH3)2N-NH- | CF3 | E1 | 559.9 |
| 173 | 3-hydroxypyrrolidinyl | tBu | E3 | 575.1 | 182 | (CH3)2N-NH- | CF3 | E2 | 559.9 |
| 174 | 3-hydroxypyrrolidinyl | tBu | E4 | 575.1 | 183 | piperidinyl-NH- | OCF3 | E1 | 616.2 |
| 175 | 3-methyl-5-hydroxypyrazolyl | tBu | E1 | 587.0 | 184 | piperidinyl-NH- | OCF3 | E2 | 616.2 |
| 176 | 3-methyl-5-hydroxypyrazolyl | tBu | E2 | 587.0 | 185 | 4-methylpiperazinyl-NH- | OCF3 | E1 | 631.2 |
| 177 | isoxazolidinyl | tBu | E1 | 561.0 | 186 | 4-methylpiperazinyl-NH- | OCF3 | E2 | 631.2 |
|  |  |  |  |  | 187 | pyrrolidinyl-NH- | OCF3 | E1 | 602.1 |
| 178 | isoxazolidinyl | tBu | E2 | 561.0 | 188 | pyrrolidinyl-NH- | OCF3 | E2 | 602.1 |

TABLE 5-continued

| Example | R3a | Rf | Enantiomer | LCMS: found m/e (M + H) |
|---|---|---|---|---|
| 189 | N,N-dimethylhydrazinyl | OCF₃ | E1 | 576.1 |
| 190 | N,N-dimethylhydrazinyl | OCF₃ | E2 | 576.1 |
| 191 | 4-methylpiperazin-1-ylamino | tBu | E1 | 603.1 |
| 192 | 4-methylpiperazin-1-ylamino | tBu | E2 | 603.1 |
| 193 | morpholin-4-ylamino | tBu | E1 | 590.1 |
| 194 | morpholin-4-ylamino | tBu | E2 | 590.1 |
| 195 | pyrrolidin-1-ylamino | tBu | E1 | 574.1 |
| 196 | pyrrolidin-1-ylamino | tBu | E2 | 574.1 |
| 197 | piperidin-1-ylamino | tBu | E1 | 588.1 |
| 198 | piperidin-1-ylamino | tBu | E2 | 588.1 |
| 199 | azepan-1-ylamino | tBu | E1 | 602.1 |
| 200 | azepan-1-ylamino | tBu | E2 | 602.1 |
| 201 | N,N-dimethylhydrazinyl | tBu | E1 | 548.1 |
| 202 | N,N-dimethylhydrazinyl | tBu | E2 | 548.1 |
| 203 | (2,4-dioxoimidazolidin-1-yl)amino | tBu | E1 | 602.1 |
| 204 | (2,4-dioxoimidazolidin-1-yl)amino | tBu | E2 | 602.1 |

*E1 is the faster eluting enantiomer, E2 is the slower eluting enantiomer. When more than one pair of enantiomers is present, E1 to E4 was used to denote the isomers that elute from the fastest to the slowest. on a chiralpak AD, OD, AD-H, or OD-H column eluting with ethanol/hexane, or by Super Critical Fluid Chromatography eluting with methanol/liquid CO₂ or isopropanol/liquid CO₂.

EXAMPLE 205

6-[(4-tert-Butylphenyl)sulfonyl]-7-(3-pyridinyl)-2-(trifluoromethyl)-6,11-dihydro-5H-pyrido[2,3-b]-[1,5]benzodiazepine

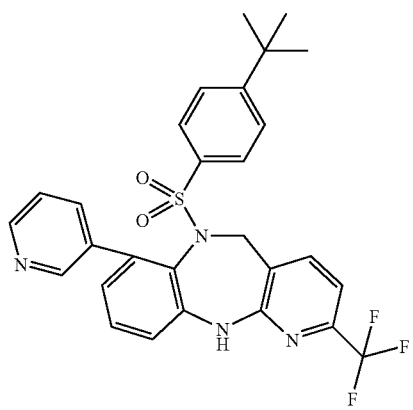

A mixture of intermediate 25 (30 mg, 0.06 mmol), 3-pyridine boronic acid (74 mg, 0.60 mmol), Pd(OAc)$_2$ (13 mg, 0.06 mmol), S-Phos (49 mg, 0.12 mmol) and K$_3$PO$_4$ (100 mg) in 4 mL 99:1 v:v toluene/H$_2$O was heated at 150° C. for 40 min in a microwave reactor. After cooling to rt, the reaction mixture was concentrated and the residue was purified by silica gel chromatography (10-100% EtOAC/hexanes) to afford the title compound as a racemic mixture. $^1$H NMR (500 MHz, (CD$_3$)$_2$CO): δ 8.62 (s, 1H), 8.58 (d, 1H), 8.42 (s, 1H), 7.82 (d, 1H), 7.75 (d, 1H), 7.40 (m, 2H), 7.20 (d, 2H), 7.16 (d, 1H), 7.14 (m, 1H), 7.02 (d, 2H), 5.20 (d, 1H), 4.85 (d, 1H), 1.23 (s, 9H). LC-MS: m/z 539.2 (M+H)$^+$. The racemic mixture was separated by HPLC using a chiralcel OD-H column and 20% EtOH/hexanes as the mobile phase. The fastest eluting isomer (E1) has a retention time of 12.0 min, the slower eluting isomer (E2) has a retention time of 20 min.

The compounds in Table 6 were prepared using the appropriate starting materials and reagents following procedures similar to that described above for Examples 1, 205, and 439:

TABLE 6

| Example | R3 | Rf | Enantiomer | LC-MS: found m/e (M + H) |
|---|---|---|---|---|
| 206 | 1-methyl-1H-pyrazol-4-yl | tBu | E1 | 542.3 |
| 207 | 1-methyl-1H-pyrazol-4-yl | tBu | E2 | 542.3 |
| 208 | 4-fluorophenyl | tBu | E1 | 556.1 |
| 209 | 4-fluorophenyl | tBu | E2 | 556.1 |
| 210 | cyclohexyl | tBu | E1 | 544.1 |
| 211 | cyclohexyl | tBu | E2 | 544.1 |
| 212 | pyrimidin-5-yl | tBu | E1 | 540.1 |

TABLE 6-continued

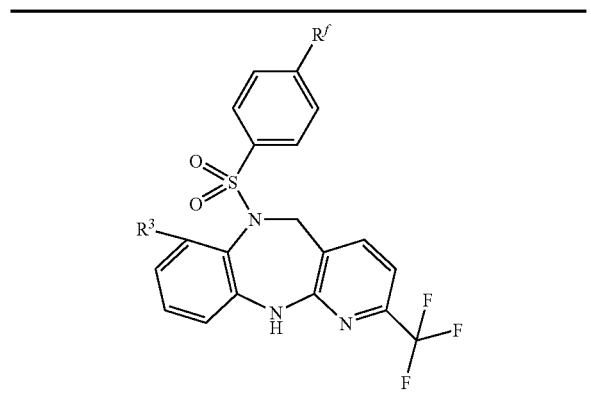

| Example | R3 | Rf | Enantiomer | LC-MS: found m/e (M + H) |
|---|---|---|---|---|
| 213 | pyrimidinyl | tBu | E2 | 540.1 |
| 214 | oxadiazolone | iPr | E1 | 532.1 |
| 215 | oxadiazolone | iPr | E2 | 532.1 |
| 216 | oxadiazolone | OCHF$_2$ | E1 | 556.1 |
| 217 | oxadiazolone | OCHF$_2$ | E2 | 556.1 |
| 218 | oxadiazolone | OCF$_3$ | E1 | 574.1 |
| 219 | oxadiazolone | OCF$_3$ | E2 | 574.1 |
| 220 | thienyl | OCF$_3$ | E1 | 572.1 |
| 221 | thienyl | OCF$_3$ | E2 | 572.1 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid CO$_2$ or isopropanol/liquid CO$_2$.

EXAMPLE 222

Methyl 2-[6-{[4-(Trifluoromethoxy)phenyl]sulfonyl}-2-(trifluoromethyl)-6,11-dihydro-5H-pyrido[2,3-b][1,5]benzodiazepin-7-yl]-5-pyrimidinecarboxylate

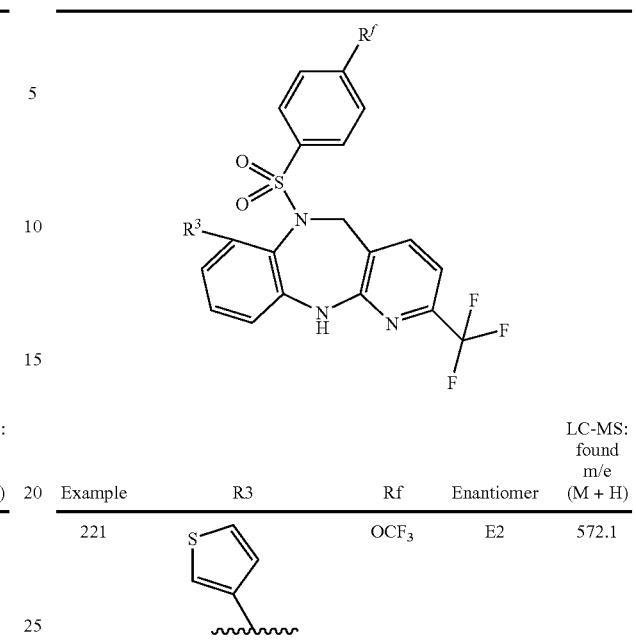

Step A: To a solution of 3,3-dimethoxy-2-methyl propionate (2.6 g, 17.6 mmol) in DME (12.5 mL) was added methyl formate (5 mL, 81 mmol), followed by NaH (880 mg, 0.02 mmol). The resulting yellow solution was heated to 50° C. for 3 h before cooling to rt and diluting with Et$_2$O.

A white solid precipitate was filtered and dried under vacuum to give sodium (1Z)-2-(dimethoxymethyl)-3-methoxy-3-oxo-1-propen-1-olate, which was used directly in the next step.

Step B: A solution of intermediate 22 (44 mg, 0.09 mmol) and sodium (1Z)-2-(dimethoxymethyl)-3-methoxy-3-oxo-1-propen-1-olate (26 mg, 0.13 mmol) in DMF (5 mL) were heated in a microwave reactor at 120° C. for 10 min. The reaction mixture was partitioned between water and EtOAc. The organic layer was separated, dried and concentrated, and the residue was purified by silica gel chromatography (7-60% EtOAc/hexanes) to give the title compound as a racemic mixture. $^1$H NMR (500 MHz, (CD$_3$)$_2$CO): δ 8.42 (s, 1H), 8.00 (s, 1H), 7.80 (d, 1H), 7.50 (m, 4H), 7.22 (m, 2H), 7.00 (d, 2H), 5.22 (d, 1H), 4.80 (d, 1H), 1.21 (s, 9H). LCMS: m/z 598.2 (M+H)$^+$.

The compounds in Table 7 were prepared using the appropriate starting materials and reagents following procedures similar to that described above for Examples 221 and 230:

TABLE 7

| Example | Re | Rf | Enantiomer | LCMS: found m/e (M + H) |
|---------|------|------|------------|----------------|
| 223 | MeO$_2$C– | OCF$_3$ | E1 | 626.1 |
| 224 | MeO$_2$C– | OCF$_3$ | E2 | 626.1 |
| 225 | HO-C(CH$_3$)$_2$– | tBu | E1 | 598.1 |
| 226 | HO-C(CH$_3$)$_2$– | tBu | E2 | 598.1 |
| 227 | HO-C(CH$_3$)$_2$– | OCF$_3$ | E1 | 626.1 |
| 228 | HO-C(CH$_3$)$_2$– | OCF$_3$ | E2 | 626.1 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid CO$_2$ or isopropanol/liquid CO$_2$.

EXAMPLE 229

Ethyl 2-[6-{[4-(Trifluoromethoxy)phenyl]sulfonyl}-2-(trifluoromethyl)-6,11-dihydro-5H-pyrido[2,3-b][1,5]benzodiazepin-7-yl]-1,3-oxazole-4-carboxylate

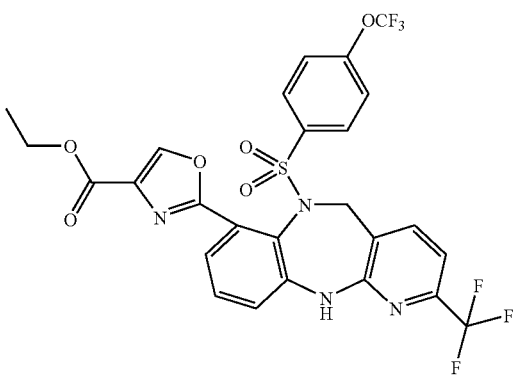

A mixture of intermediate 18 (100 mg, 0.19 mmol) and ethyl bromopyruvate (0.38 mL, 1.90 mmol) in EtOH was heated to 140° C. in a microwave reactor for 2 h. The reaction mixture was concentrated, and the residue was purified by silica gel chromatography (0-80% EtOAc/hexanes) to give the title compound. $^1$H NMR (500 MHz, (CD$_3$)$_2$CO): δ 8.69 (s, 1H), 8.57 (s, 1H), 7.85 (d, 1H), 7.66 (d, 1H), 7.54 (m, 2H), 7.22 (m, 3H), 7.13 (d, 2H), 5.38 (d, 1H), 4.88 (d, 1H), 4.39 (q, 2H), 1.39 (t, 3H). LC/MS: m/e 629.1 (M+H)$^+$.

EXAMPLE 230

2-{2-[6-{[4-(Trifluoromethoxy)phenyl]sulfonyl}-2-(trifluoromethyl)-6,11-dihydro-5H-pyrido[2,3-b][1,5]benzodiazepin-7-yl]-1,3-oxazol-4-yl}propan-2-ol

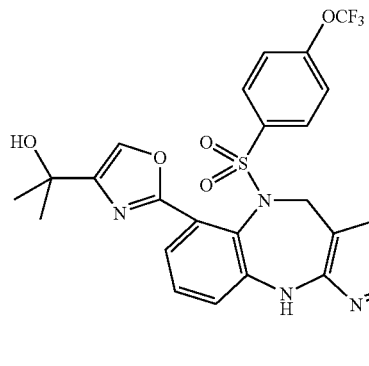

The title compound was prepared by methyl Grignard addition to ethyl 2-[6-{[4-(trifluoromethoxy)-phenyl]sulfonyl}-2-(trifluoromethyl)-6,11-dihydro-5H-pyrido[2,3-b][1,5]benzodiazepin-7-yl]-1,3-oxazole-4-carboxylate (Example 229). $^1$H NMR (500 MHz, (CD$_3$)$_2$CO): δ 8.50 (s, 1H), 7.83 (m, 2H), 7.64 (dd, 1H), 7.49 (m, 2H), 7.28 (m, 2H), 7.19 (d, 1H), 7.13 (d, 2H), 5.39 (d, 1H), 4.85 (d, 1H), 4.07 (m, 1H), 1.60 (d, 6H). LCMS: m/e 597.1 (M−18+H)$^+$.

EXAMPLE 231

Ethyl 5-[6-{[4-(trifluoromethoxy)phenyl]sulfonyl}-2-(trifluoromethyl)-6,11-dihydro-5H-Pyrido[2,3-b][1,5]benzodiazepin-7-yl]isoxazole-3-carboxylate

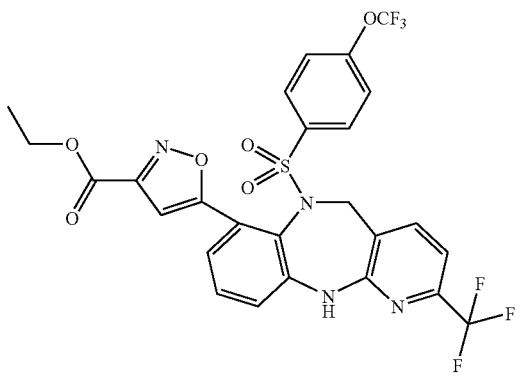

To intermediate 23 (301 mg, 0.59 mmol) in CHCl$_3$ at rt was added ethyl (2Z)-chloro(hydroxylimino)acetate (Skinner, G. S. *J. Am. Chem. Soc.* 1924, 46, 731) (444 mg, 2.9 mmol) and K$_2$CO$_3$ (405 mg, 2.90 mmol), and the reaction was stirred at rt overnight. The reaction was quenched with H$_2$O, and the product was extracted with EtOAc. The combined extracts were washed with H$_2$O, brine, dried over MgSO$_4$, filtered and concentrated. The residue was purified by silica gel chromatography (0-40% EtOAc/hexanes) to give the title compound. $^1$H NMR (500 MHz, (CD$_3$)$_2$CO): δ 8.59 (s, 1H), 7.88 (d, 1H), 7.58 (m, 3H), 7.30 (m, 2H), 7.24 (s, 1H), 7.22 (d, 1H), 7.14 (d, 2H), 5.44 (d, 1H), 4.96 (d, 1H), 4.49 (q, 2H), 1.44 (t, 3H). LC/MS: m/e 629.1 (M+H)$^+$.

EXAMPLE 232

2-{5-[6-{[4-(trifluoromethoxy)phenyl]sulfonyl}-2-(trifluoromethyl)-6,11-dihydro-5H-pyrido[2,3-b][1,5]benzodiazepin-7-yl]isoxazole-3-yl}propan-2-ol

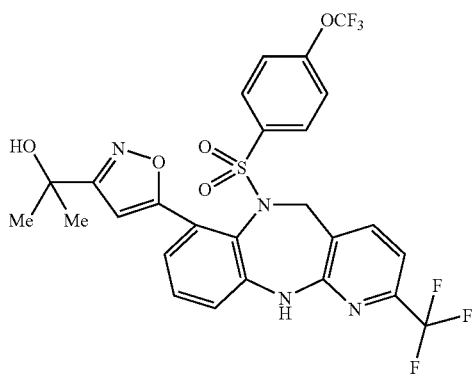

The title compound was prepared from ethyl 5-[6-{([4-(trifluoromethoxy)phenyl]sulfonyl}-2-(trifluoromethyl)-6,11-dihydro-5H-pyrido[2,3-b][1,5]benzodiazepin-7-yl]isoxazole-3-carboxylate (Example 238) following the procedure described for Example 233. LC/MS: m/e 615.1 (M+H)$^+$.

The compounds in Table 9 were prepared using the appropriate starting materials and reagents following procedures similar to that described above for Examples 231 and 232:

TABLE 9

| Example | R3 | Rf | Enantiomer | LCMS: found m/e (M + H) |
|---|---|---|---|---|
| 233 | ethyl isoxazole-3-carboxylate | tBu | E1 | 601.1 |
| 234 | ethyl isoxazole-3-carboxylate | tBu | E2 | 601.1 |
| 235 | HO-CH$_2$-isoxazole | tBu | E1 | 559.1 |
| 236 | HO-CH$_2$-isoxazole | tBu | E2 | 559.1 |
| 237 | HO-C(Me)$_2$-isoxazole | tBu | E1 | 587.1 |
| 238 | HO-C(Me)$_2$-isoxazole | tBu | E2 | 587.1 |
| 239 | acetyl-isoxazole | OCF$_3$ | E1 and E2 | 599.1 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid CO$_2$ or isopropanol/liquid CO$_2$.

EXAMPLE 240

6-[(4-tert-Butylphenyl)sulfonyl]-2-(trifluoromethyl)-7-vinyl-6,11-dihydro-5H-pyrido[2,3-b][1,5]benzodiazepine

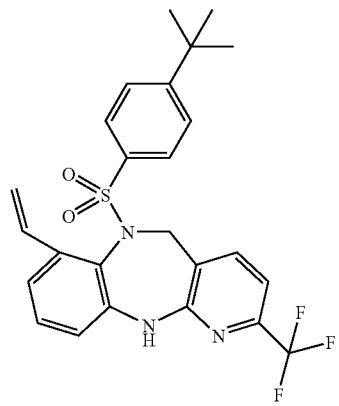

To a solution of vinyl magnesium bromide in THF (1.0 M, 3 mL, 3 mmol) at 0° C. was added ZnCl$_2$ (1.0 M in THF, 3 mL, 3 mmol) in a 5 mL, followed by the addition of intermediate 3 (321 mg, 0.50 mmol) and Pd(dppf)Cl$_2$ (15 mg). The mixture was heated in a microwave reactor at 120° C. for 1 h. After cooling to rt, the reaction was quenched with 1N HCl and was diluted with EtOAc. The organic layer was separated, dried over MgSO$_4$, filtered and concentrated. The oily residue was purified by silica gel chromatography to give the title compound. LCMS: m/e 488.1 (M+H)$^+$.

EXAMPLE 241

1-[6-[(4-tert-Butylphenyl)sulfonyl]-2-(trifluoromethyl)-6,11-dihydro-5H-pyrido[2,3-b][1,5]benzodiazepin-7-yl]-1,2-ethanediol

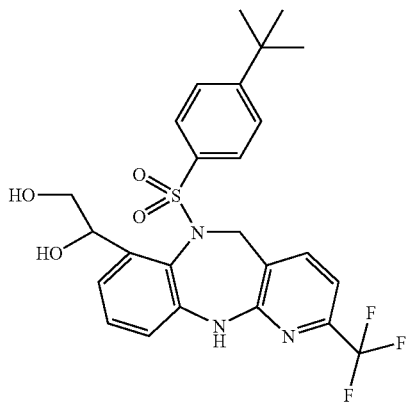

The title compound was prepared following the procedure outlined for Example 72. Racemic mixture: $^1$H NMR (500 MHz, (CD$_3$)$_2$CO): δ 8.14 (s, 1H), 7.71 (d, 1H), 7.30 (m, 5H), 7.10 (m, 2H), 5.45 (s, 2H), 5.22 (d, 1H), 4.54 (d, 1H), 4.10 (d, 1H), 3.84 (t, 1H), 2.83 (br s, 1H), 2.06 (m, 1H), 1.25 (s, 9H). LCMS: m/e 522.0 (M+H)$^+$.

EXAMPLE 242

1-[6-{[4-(Trifluoromethoxy)phenyl]sulfonyl}-2-(trifluoromethyl)-6,11-dihydro-5H-pyrido[2,3-b]-[1,5]benzodiazepin-7-yl]-1,2-ethanediol

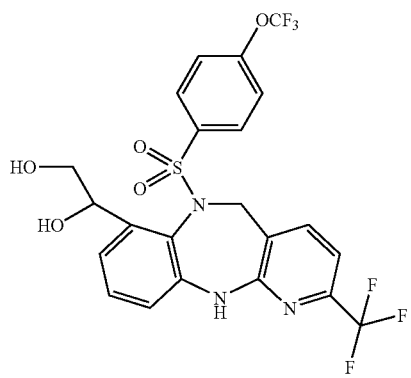

The title compound was prepared following the procedure outlined for Example 241. LCMS: m/e 533.8 (M+H)$^+$.

EXAMPLE 243

(1R)-1-[5-(2-(Trifluoromethyl)-6-{[4-(trifluoromethyl)phenyl]sulfonyl}-6,11-dihydro-5H-pyrido-[2,3-b][1,5]benzodiazepin-7-yl)-1,3,4-oxadiazol-2-yl]ethanol

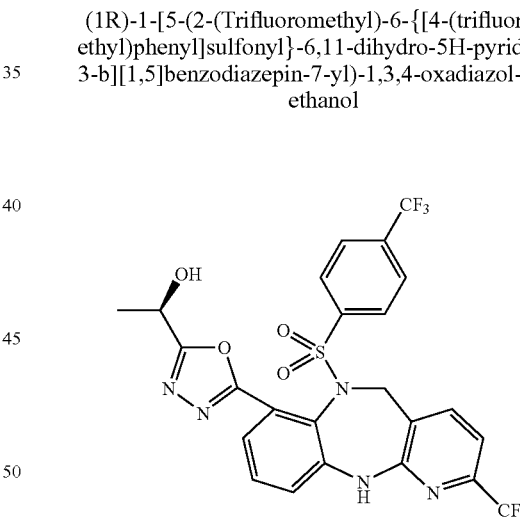

A solution of intermediate 13, hydrazine hydrate (2 mL) in EtOH (18 mL) was heated at 70° C. for 12 h. The reaction mixture was concentrated to afford the requisite hydrazide.

Step B: A mixture of the hydrazide from Step A (183 mg, 0.30 mmol), (R)-benzyloxypropionic acid (186 mg, 1 mmol), DMF (10 mL), Py-BOP (533 mg, 1 mmol) TEA (0.3 mL, 2 mmol) was heated at 70° C. overnight. The reaction mixture was partitioned between brine (200 mL) and EtOAc (200 mL). The organic layer was separated, dried over MgSO$_4$, filtered and concentrated. The oil residue was dissolved in CH$_3$CN (25 mL) and was added POCl$_3$ (15 mL). After stirring for 1 h, the reaction was quenched with saturated NaHCO$_3$. The product was extracted with EtOAc, and the extracts were concentrated. The residue was purified by flash chromatography on silica gel (7-60% EtOAc:hexanes) to give the desired product, which was dissolved in CHCl₃ (40 mL) and was treated with methanesulfonic acid (5 mL). After stirring at rt for 15 min, the reaction was quenched with saturated bicarbonate solution. The resulting solution was partitioned between brine (100 mL) and EtOAc (100 mL). The organic layer was separated, dried over MgSO₄, filtered and concentrated, and the residue was purified by silica gel chromatography (0-60% EtOAc in hexanes) to yield the title compound as a racemic mixture. $^1$H NMR (500 MHz, (CD₃)₂CO): δ 8.60 (s, 1H), 7.85 (t, 1H), 7.60 (m, 4H), 7.35 (d, 2H), 7.20 (d, 1H), 5.40 (m, 1H), 5.20 (m, 1H), 4.95 (m, 1H), 1.70 (m, 3H). LCMS: m/z 586.0 (M+H)⁺. The racemic mixture was separated by HPLC on a chiralcel OD column to afford the respective enantiomers. The faster eluting enantiomer (E1) has a retention time of 11.0 min, while the slower eluting enantiomer (E2) has a retention time of 17.0 min.

EXAMPLE 244

2-{2-Methyl-6-[6-{[4-(trifluoromethoxy)phenyl]sulfonyl}-2-(trifluoromethyl)-6,11-dihydro-5H-pyrido[2,3-b][1,5]benzodiazepin-7-yl]-3-pyridinyl}-2-propanol

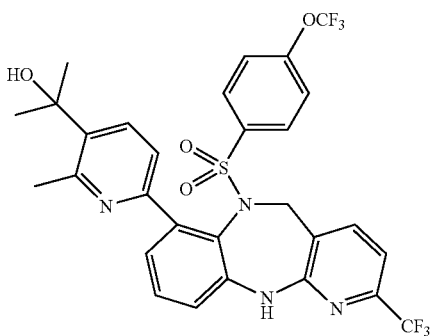

Step A: A solution of intermediate 39 (100 mg, 0.17 mmol), NH₄OAc (19 mg, 0.25 mmol), AcOH (2 mL) and ethyl acetoacetate (0.03 mL, 0.17 mmol) was heated at 110° C. for 13 h. The reaction mixture was partitioned between brine (50 mL) and EtOAc (50 mL). The organic layer was separated, dried over MgSO₄, filtered and concentrated to give the ester, which was used without further purification.

Step B: To a solution of the ester from Step A in THF (1.0 mL) was added MeMgBr (0.3 mL, 0.26 mmol) and the reaction was stirred at rt for 1 h. The reaction was quenched with saturated aqueous NH₄Cl and the product was extracted with EtOAc. The combined extracts were washed with water, brine, and dried over MgSO₄ and concentrated. The residue was purified by silica gel chromatography (0-60% EtOAc in hexanes) to provide the title compound as a racemic mixture. $^1$H NMR (500 MHz, CD₃OD): δ 8.60 (d, 1H), 7.80 (d, 1H), 7.70 (d, 1H), 7.50 (t, 1H), 7.35 (d, 1H), 7.25 (d, 1H), 7.15 (m, 3H), 7.0 (d, 2H), 5.20 (d, 1H), 4.90 (d, 1H), 3.1 (s, 3H), 1.80 (s, 3H), 1.79 (s, 3H). LCMS: m/z 639.2 (M+H)⁺. The racemic mixture was separated by HPLC on a chiralcel AD-H column to afford the respective enantiomers. The faster eluting enantiomer (E1) has a retention time of 4.8 min, while the slower eluting enantiomer (E2) has a retention time of 6.0 min.

EXAMPLE 245

4-[6-{[4-(Trifluoromethoxy)phenyl]sulfonyl}-2-(trifluoromethyl)-6,11-dihydro-5H-pyrido[2,3-b][1,5]benzodiazepin-7-yl]-2-pyrimidinamine

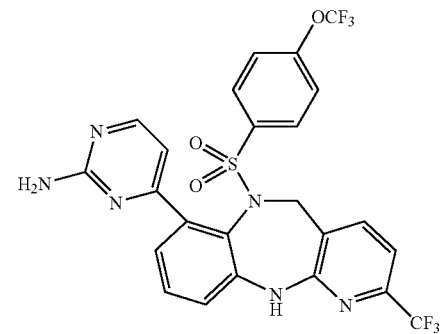

A solution of intermediate 39 (100 mg, 0.17 mmol) and guanidine hydrochloride (16 mg, 0.17 mmol), NaOMe (25 wt % in MeOH, 0.04 mL, 0.17 mmol) in EtOH (1 mL) was heated to 110° C. for 2.5 h. Once complete by LC/MS, the crude product was purified by reverse phase chromatography to provide the title compound as a racemic mixture. $^1$H NMR (500 MHz, CD₃OD): δ 8.30 (br s, 1H), 7.70 (d, 1H), 7.40 (t, 1H), 7.30 (d, 1H), 7.20 (m, 3H), 7.10 (d, 1H), 7.0 (d, 2H), 6.9 (d, 1H), 5.20 (d, 1H), 4.80 (d, 1H). LCMS: m/z 583.1 (M+H)⁺. The racemic mixture was separated by HPLC using a chiralcel AD-H column to afford the respective enantiomers. The faster eluting enantiomer (E1) has a retention time of 10.0 min, while the slower eluting enantiomer (E2) has a retention time of 14.8 min.

The compounds in Table 10 were prepared using the appropriate starting materials and reagents following procedures similar to that described for Examples 239 and 244:

TABLE 10

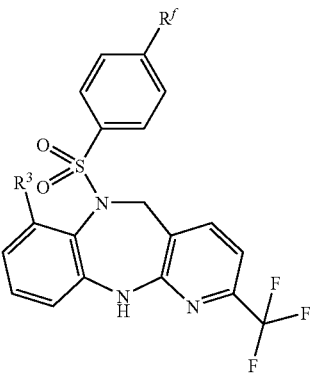

| Example | R3 | Rf | Enantiomer | LCMS: found m/e (M + H) |
|---------|----|----|-----------|------------------------|
| 246 |  | OCF₃ | E1 | 625.2 |
| 247 | 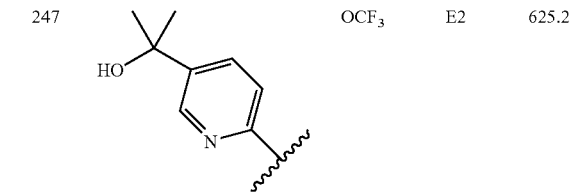 | OCF₃ | E2 | 625.2 |
| 248 | 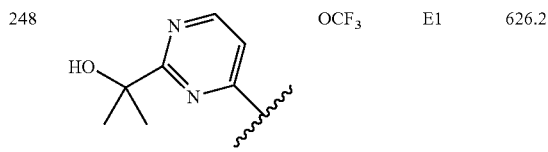 | OCF₃ | E1 | 626.2 |
| 249 | 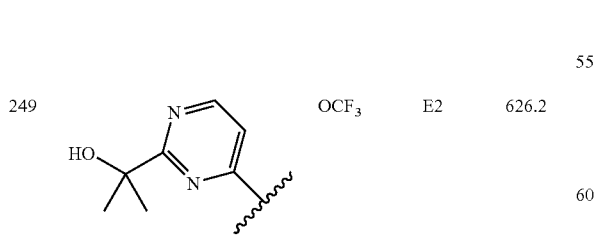 | OCF₃ | E2 | 626.2 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid CO₂ or isopropanol/liquid CO₂.

EXAMPLE 250

6-{[4-(Trifluoromethoxy)phenyl]sulfonyl}-2-(trifluoromethyl)-6,11-dihydro-5H-pyrido[2,3-b][1,5]benzodiazepine

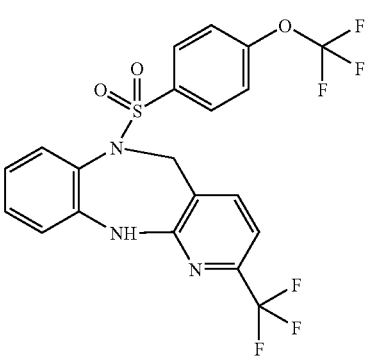

To a solution of intermediate 26 (3.98 g, 15 mmol) in DCM (75 mL) at rt was added sequentially (4-trifluoromethyl)sulfonyl chloride (9.75 g, 37.5 mmol), pyridine (7.11 g, 90 mmol), and DMAP (0.366 g, 3 mmol). The mixture was stirred at room temperature for 24 h and quenched with water. The product was extracted with EtOAc (3×), and the combined extracts were washed with water and brine, dried over MgSO₄ and concentrated. The solid residue was recrystallized from DCM and hexanes to afford the title compound. $^1$H NMR (500 MHz, CDCl₃): δ 8.03 (1H, d), 7.58 (1H, d), 7.43 (1H, d), 7.23 (1H, t), 7.10-6.96 (6H, m), 3.69 (2H, s). LC/MS: m/e 489.1 (M+H)⁺.

EXAMPLE 251

6-[(4-tert-Butylphenyl)sulfonyl]-7,8-dimethyl-2-(trifluoromethyl)-6,11-dihydro-5H-pyrido[2,3-b][1,5]benzodiazepine

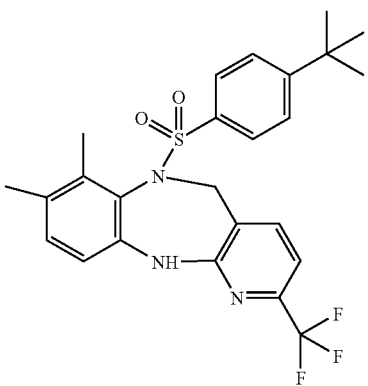

The title compound was prepared from intermediate 29 and [(4-tert-butylphenyl)sulfonyl] chloride following the same procedure as described for Example 250. Racemic mixture: $^1$H NMR (500 MHz, CD$_3$OD): δ 7.58 (1H, d), 7.19 (2H, d), 7.08 (2H, d), 7.07 (1H), 6.99 (1H, d), 6.79 (1H, d), 5.19 (1H, d), 4.42 (1H, d), 2.43 (3H, s), 2.28 (3H, s), 1.24 (9H, s); LCMS: m/e 490.2 (M+H)$^+$. The racemic mixture was separated by HPLC using a chiralcel OD column (10% IPA in heptane) to afford the respective enantiomers. The faster eluting enantiomer (E1) has a retention time of 10.6 min, while the slower eluting enantiomer (E2) has a retention time of 12.6 min.

EXAMPLE 252

6-[(4-tert-Butylphenyl)sulfonyl]-7-methyl-8-(1-methyl-1H-pyrazol-4-yl)-2-(trifluoromethyl)-6,11-dihydro-5H-pyrido[2,3-b][1,5]benzodiazepine

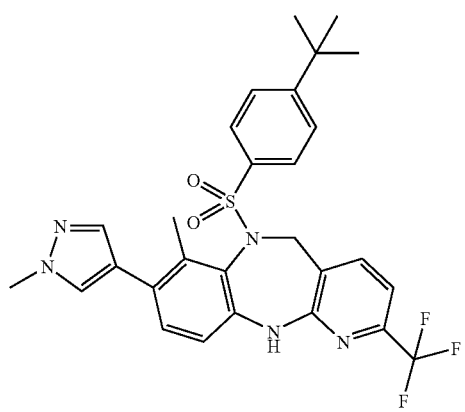

A mixture of intermediate 65 (140 mg, 0.25 mmol), 1-methyl-4-(4,4,5,5-tetramethyl-1,3,2-dioxaborolan-2-yl)-1H-pyrazole (105 mg, 0.50 mmol), K$_2$CO$_3$ (105 mg, 0.76 mmol), and Pd(dppf)Cl$_2$ (21 mg, 0.03 mmol) in DMSO (3 mL) was heated in a microwave reactor at 150° C. for 30 min. After cooling to rt, the reaction mixture was concentrated, and the residue was purified by silica gel chromatography (0-80% EtOAc/hexanes) to give the title compound as a racemic mixture. $^1$H NMR (500 MHz, (CD$_3$)$_2$CO): δ 8.12 (s, 1H), 7.70 (s, 1H), 7.69 (d, 1H), 7.61 (s, 1H), 7.32 (d, 2H), 7.22 (m, 1H), 7.14 (d, 2H), 7.07 (d, 1H), 5.22 (d, 1H), 4.55 (d, 1H), 3.97 (s, 3H), 2.57 (s, 3H), 1.26 (s, 9H). LC/MS: m/e 556.1 (M+H)$^+$. The racemic mixture was separated by HPLC on a chiralcel OD-H column to afford the respective enantiomers. The faster eluting enantiomer (E1) has a retention time of 14.5 min, while the slower eluting enantiomer (E2) has a retention time of 21.2 min.

The compounds in Table 11 were prepared using the appropriate starting materials and reagents following procedures similar to that described above for Examples 5 and 252:

TABLE 11

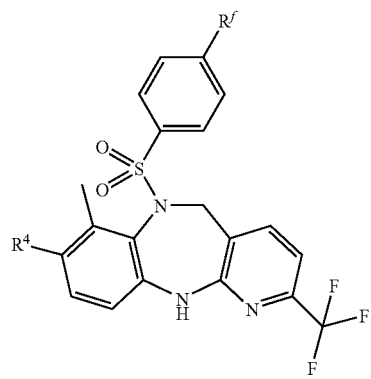

| Example | R4 | Rf | Enantiomer | LCMS: found m/e (M + H) |
|---|---|---|---|---|
| 253 | thiazol-2-yl | tBu | E1 | 558.9 |
| 254 | thiazol-2-yl | tBu | E2 | 558.9 |
| 255 | pyrimidin-5-yl | tBu | E1 | 554.0 |
| 256 | pyrimidin-5-yl | tBu | E2 | 554.0 |
| 257 | pyridin-3-yl | tBu | E1 | 553.6 |
| 258 | pyridin-3-yl | tBu | E2 | 553.6 |
| 259 | 2-chloropyridin-5-yl | tBu | E1 | 587.0 |

TABLE 11-continued

Common structure (Examples 260–272): diazepine core with Rf-phenylsulfonyl group, methyl, R4 substituent, and CF3-pyridine moiety.

| Example | R4 | Rf | Enantiomer | LCMS: found m/e (M + H) |
|---|---|---|---|---|
| 260 | 6-chloropyridin-3-yl | tBu | E2 | 587.0 |
| 260 | thiophen-3-yl | tBu | E1 | 558.0 |
| 262 | thiophen-3-yl | tBu | E2 | 558.0 |
| 263 | 3-phenylisoxazol-4-yl | tBu | E1 | 619.0 |
| 264 | 3-phenylisoxazol-4-yl | tBu | E2 | 619.0 |
| 265 | 3,5-dimethylisoxazol-4-yl | tBu | E1 | 570.9 |
| 266 | 3,5-dimethylisoxazol-4-yl | tBu | E2 | 570.9 |
| 267 | cyclopropylmethyl | tBu | E1 | 515.9 |
| 268 | cyclopropylmethyl | tBu | E2 | 515.9 |
| 269 | 3-(hydroxymethyl)-1,2,4-oxadiazol-5-yl | iPr | E1 | 560.1 |
| 270 | 3-(hydroxymethyl)-1,2,4-oxadiazol-5-yl | iPr | E2 | 560.1 |
| 271 | 3-(1-hydroxyethyl)-1,2,4-oxadiazol-5-yl | iPr | E1 | 574.1 |
| 272 | 3-(1-hydroxyethyl)-1,2,4-oxadiazol-5-yl | iPr | E2 | 574.1 |

TABLE 11-continued

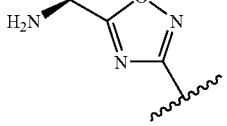

| Example | R4 | Rf | Enantiomer | LCMS: found m/e (M + H) |
|---|---|---|---|---|
| 273 | 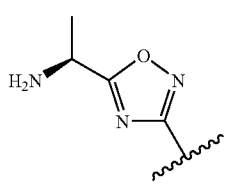 | | E1 | 573.1 |
| 274 | H2N (same oxadiazole group) | | E2 | 573.1 |

*E1 is the fastest eluting enantiomer, and E2 is the second fastest eluting enantiomer by HPLC on a chiralpak AD, OD, AD-H, or OD-H column eluting with ethanol/hexane, or by Super Critical Fluid Chromatography eluting with methanol/liquid $CO_2$ or isopropanol/liquid $CO_2$.

The compounds in Table 12 were prepared using the appropriate starting materials and reagents following procedures similar to that described above for Example 251.

TABLE 12

| Example | Structure | Starting materials | Enantiomer: E1 or E2 | LCMS: found m/e (M + H) |
|---|---|---|---|---|
| 275 | 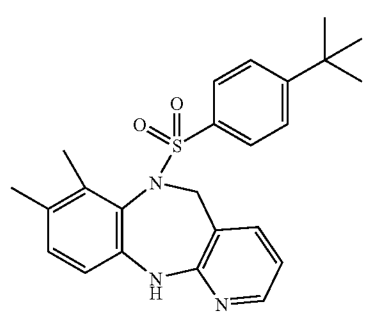 | Intermediate 40 and (4-tert-butylphenyl)-sulfonyl chloride | E1 | 422.2 |
| 276 | 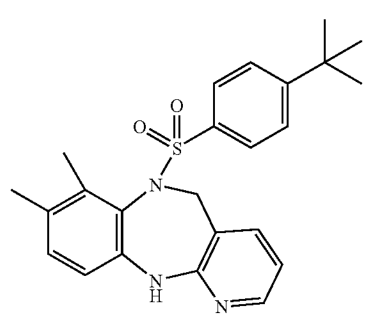 | Intermediate 40 and (4-tert-butylphenyl)-sulfonyl chloride | E2 | 422.2 |

TABLE 12-continued

| Example | Structure | Starting materials | Enantiomer: E1 or E2 | LCMS: found m/e (M + H) |
|---|---|---|---|---|
| 277 | 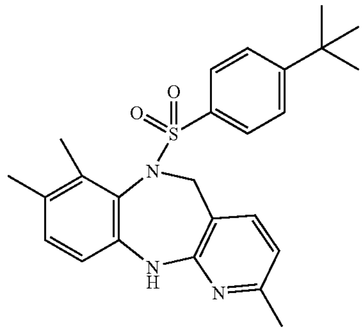 | Intermediate 34 and (4-tert-butylphenyl)-sulfonyl chloride | E1 | 436.2 |
| 278 | 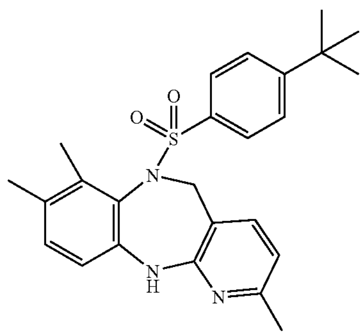 | Intermediate 34 and (4-tert-butylphenyl)-sulfonyl chloride | E2 | 436.2 |
| 279 | 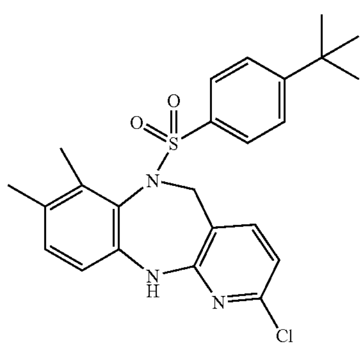 | Intermediate 33 and (4-tert-butylphenyl)-sulfonyl chloride | E1 | 456.1 |
| 280 | 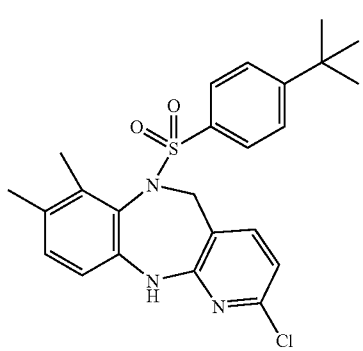 | Intermediate 33 and (4-tert-butylphenyl)-sulfonyl chloride | E2 | 456.1 |

TABLE 12-continued

| Example | Structure | Starting materials | Enantiomer: E1 or E2 | LCMS: found m/e (M + H) |
|---------|-----------|--------------------|-----------------------|--------------------------|
| 281 | 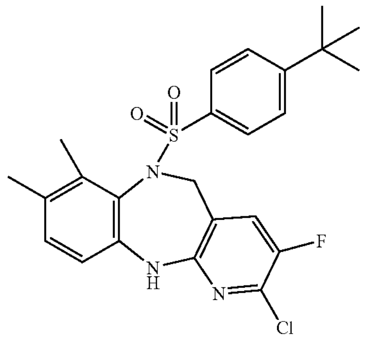 | Intermediate 41 and (4-tert-butylphenyl)-sulfonyl chloride | E1 | 474.1 |
| 282 | 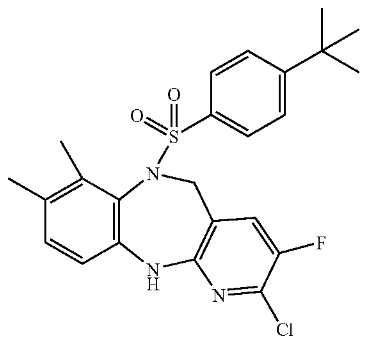 | Intermediate 41 and (4-tert-butylphenyl)-sulfonyl chloride | E2 | 474.1 |
| 283 | 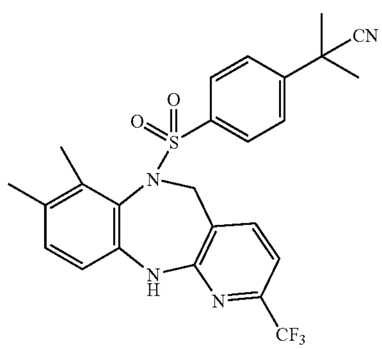 | Intermediates 29 and 44 | E1 | 501.2 |
| 284 | 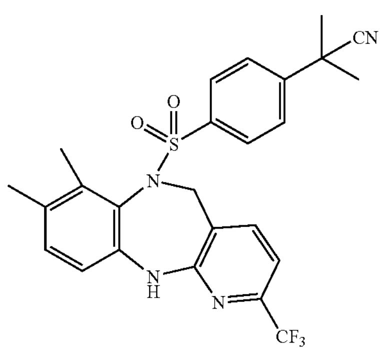 | Intermediates 29 and 44 | E2 | 501.2 |

TABLE 12-continued

| Example | Structure | Starting materials | Enantiomer: E1 or E2 | LCMS: found m/e (M + H) |
|---|---|---|---|---|
| 285 | 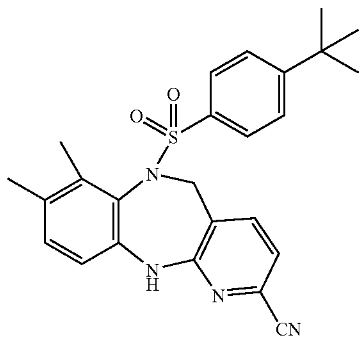 | Cyanation of Example 279 following the procedure described for intermediate 54 | E1 | 447.2 |
| 286 | 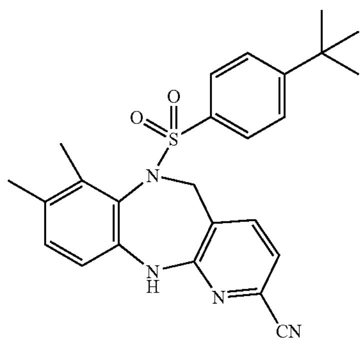 | Cyanation of Example 279 following the procedure described for intermediate 54 | E2 | 447.2 |
| 287 | 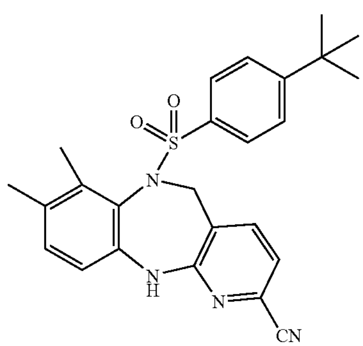 | Intermediate 28 and (4-trifluoromethyl-phenyl)sulfonyl chloride | E1 | 488.1 |
| 288 | 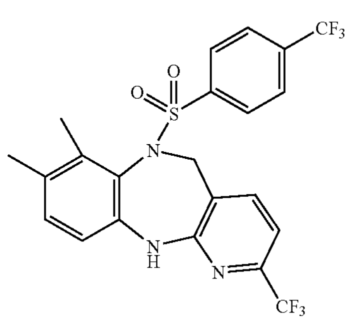 | Intermediate 28 and (4-trifluoromethyl-phenyl)sulfonyl chloride | E2 | 488.1 |

TABLE 12-continued

| Example | Structure | Starting materials | Enantiomer: E1 or E2 | LCMS: found m/e (M + H) |
|---|---|---|---|---|
| 289 | 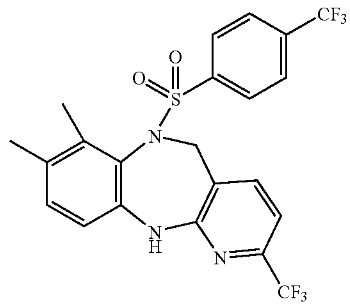 | Intermediate 29 and (4-trifluoromethyl-phenyl)sulfonyl chloride | E1 | 502.1 |
| 290 | 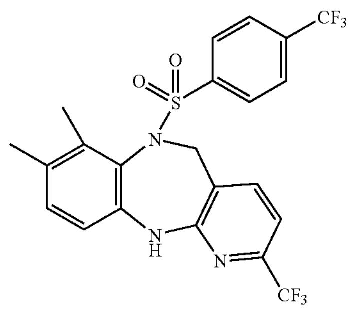 | Intermediate 29 and (4-trifluoromethyl-phenyl)sulfonyl chloride | E2 | 502.1 |
| 291 | 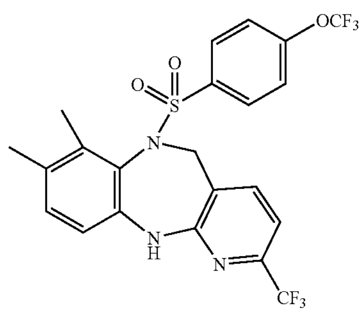 | Intermediate 29 and (4-trifluoromethoxy-phenyl)sulfonyl chloride | E1 | 518.1 |
| 292 | 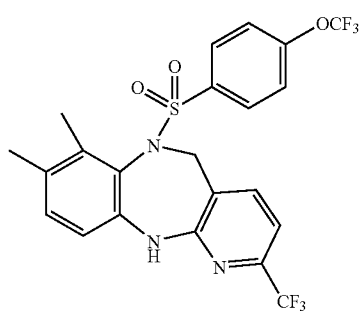 | Intermediate 29 and (4-trifluoromethoxy-phenyl)sulfonyl chloride | E2 | 518.1 |
| 293 | 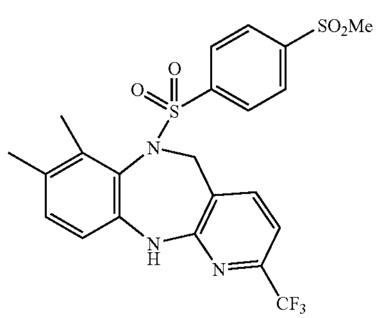 | Intermediate 29 and (4-methylsulfonyl-phenyl)sulfonyl chloride | E1 | 512.1 |

TABLE 12-continued

| Example | Structure | Starting materials | Enantiomer: E1 or E2 | LCMS: found m/e (M + H) |
|---|---|---|---|---|
| 294 | 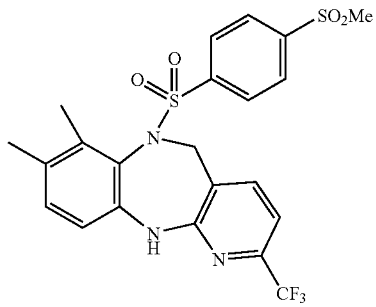 | Intermediate 29 and (4-methylsulfonyl-phenyl)sulfonyl chloride | E2 | 512.1 |
| 295 | 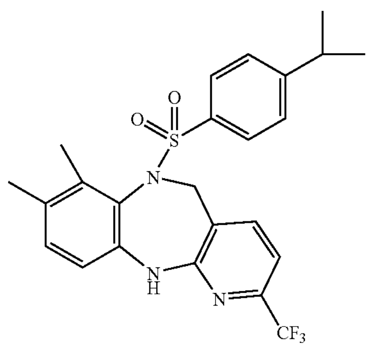 | Intermediate 29 and (4-isopropylphenyl)-sulfonyl chloride | E1 | 476.2 |
| 296 | 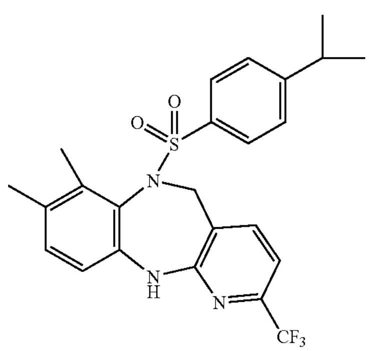 | Intermediate 29 and (4-isopropylphenyl)-sulfonyl chloride | E2 | 476.2 |
| 297 | 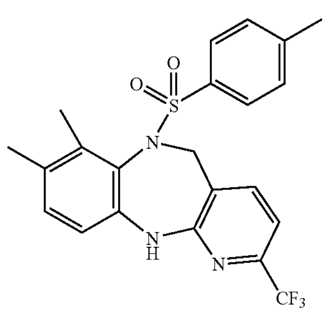 | Intermediate 29 and (4-methylphenyl)-sulfonyl chloride | E1 | 448.1 |

TABLE 12-continued

| Example | Structure | Starting materials | Enantiomer: E1 or E2 | LCMS: found m/e (M + H) |
|---|---|---|---|---|
| 298 | 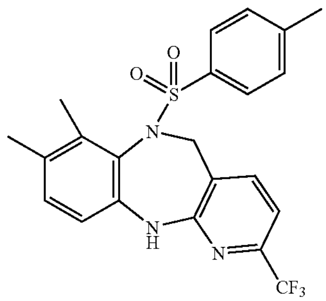 | Intermediate 29 and (4-methylphenyl)-sulfonyl chloride | E2 | 448.1 |
| 299 | 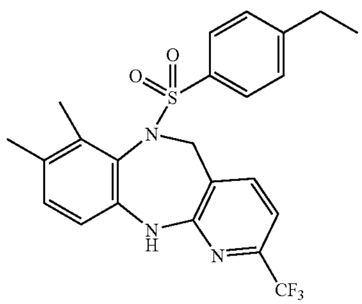 | Intermediate 29 and (4-ethylphenyl)-sulfonyl chloride | E1 | 462.1 |
| 300 | 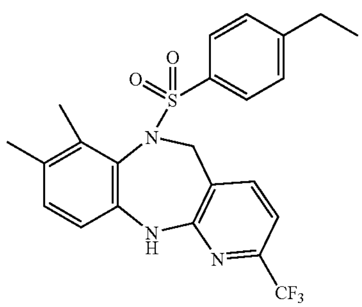 | Intermediate 29 and (4-ethylphenyl)-sulfonyl chloride | E2 | 462.1 |
| 301 | 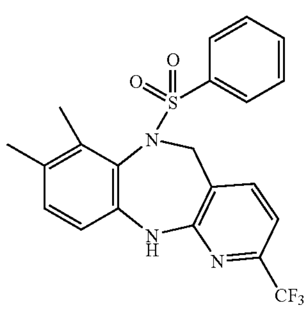 | Intermediate 29 and phenylsulfonyl chloride | E1 | 434.1 |
| 302 | 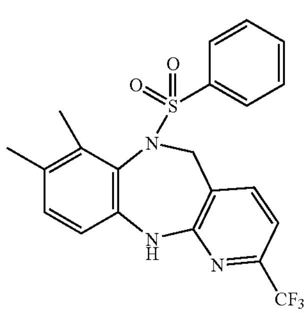 | Intermediate 29 and phenylsulfonyl chloride | E2 | 434.1 |

TABLE 12-continued

| Example | Structure | Starting materials | Enantiomer: E1 or E2 | LCMS: found m/e (M + H) |
|---|---|---|---|---|
| 303 | 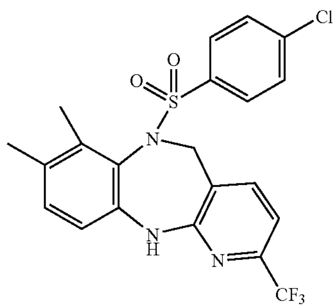 | Intermediate 29 and (4-chlorophenyl)-sulfonyl chloride | E1 | 468.1 |
| 304 | 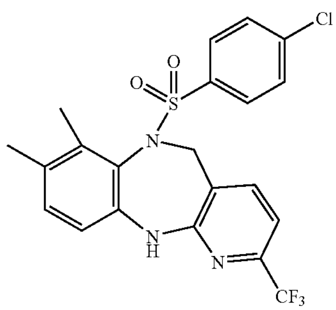 | Intermediate 29 and (4-chlorophenyl)-sulfonyl chloride | E2 | 468.1 |
| 305 | 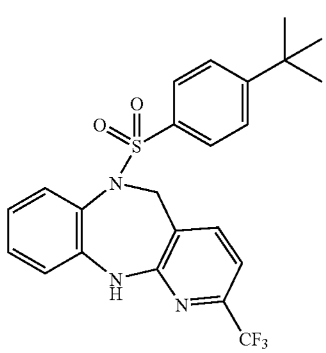 | Intermediate 42 and (4-tert-butylphenyl)-sulfonyl chloride | | 475.2 |
| 306 | 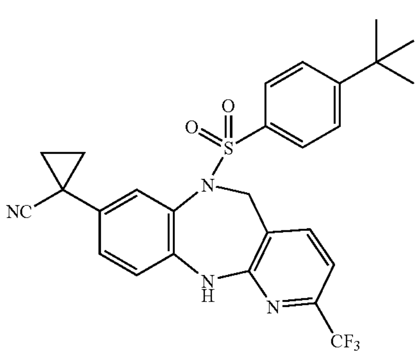 | Intermediate 35 and (4-tert-butylphenyl)-sulfonyl chloride | | 527.2 |

TABLE 12-continued

| Example | Structure | Starting materials | Enantiomer: E1 or E2 | LCMS: found m/e (M + H) |
| --- | --- | --- | --- | --- |
| 307 | 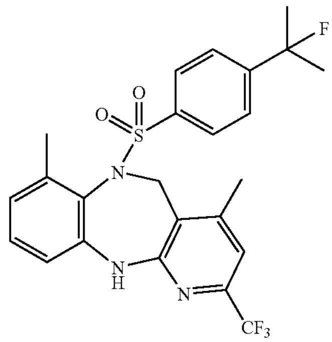 | Intermediates 28 and 43 | E1 | 494.1 |
| 308 | 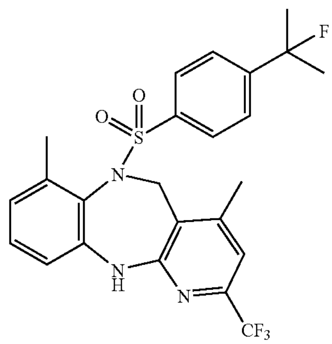 | Intermediates 28 and 43 | E2 | 494.1 |
| 309 | 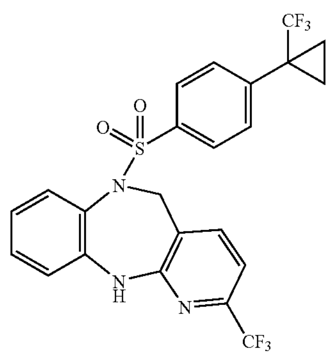 | Intermediates 26 and 48 | | 514.1 |
| 310 | 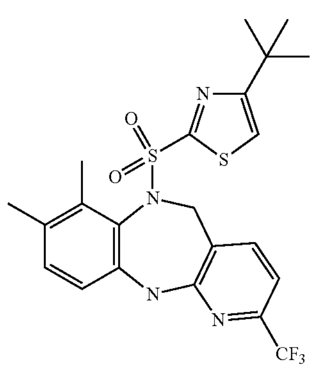 | Intermediates 29 and 49 | E1 | 497.1 |

TABLE 12-continued

| Example | Structure | Starting materials | Enantiomer: E1 or E2 | LCMS: found m/e (M + H) |
|---|---|---|---|---|
| 311 | 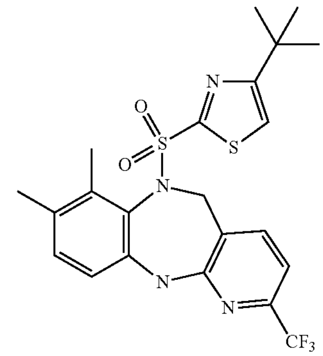 | Intermediates 29 and 49 | E2 | 497.1 |
| 312 | 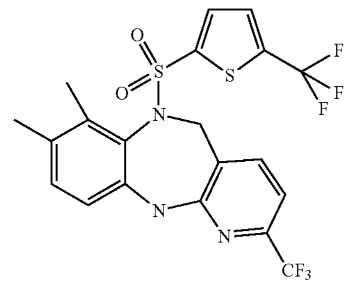 | Intermediates 29 and 50 | E1 | 508.1 |
| 313 | 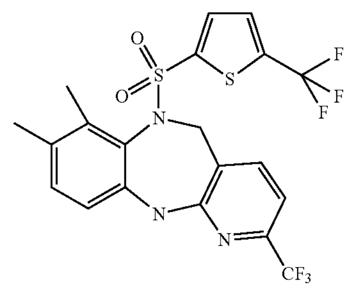 | Intermediates 29 and 50 | E2 | 508.1 |
| 314 | 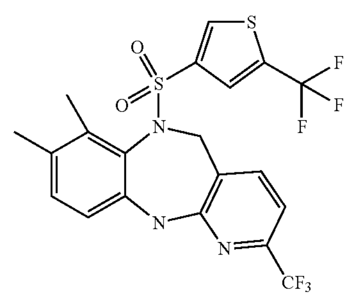 | Intermediates 29 and 51 | E1 | 508.1 |
| 315 | 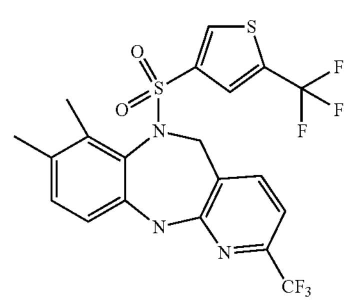 | Intermediates 29 and 51 | E2 | 508.1 |

*E1 is the faster eluting enantiomer by HPLC on a chiralpak OD or AD-H column eluting with isopropyl alcohol/heptane or ethanol/hexanes and E2 is the slower eluting enantiomer by HPLC on a chiralpak OD or AD-H column eluting with isopropyl alcohol/heptane or ethanol/hexanes.

EXAMPLE 316

13-[(4-tert-Butylphenyl)sulfonyl]-9-(trifluoromethyl)-12,13-dihydro-7H-pyrido[2',3':5,6][1,4]diazepino[2,3-f]quinoline

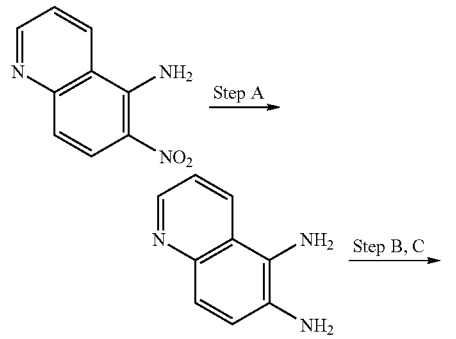

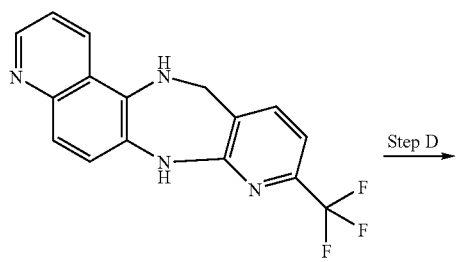

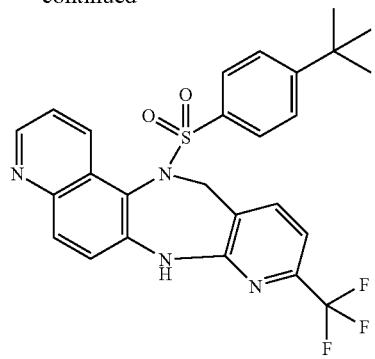

Step A: A mixture of 5-Amino-6-nitroquinoline (650 mg, 3.44 mmol), Pd/C (70 mg) and 15 mL of EtOH was stirred under $H_2$ (balloon) overnight. The reaction mixture was filtered through Celite and the filtrate was concentrated to give 5,6-diaminoquinoline.

Steps B: 5,6-Diaminoquinoline was converted to 9-(trifluoromethyl)-12,13-dihydro-7H-pyrido[2',3':5,6][1,4]diazepino[2,3-f]quinoline following the procedure described for intermediate 26.

Step C: 9-(Trifluoromethyl)-12,13-dihydro-7H-pyrido[2',3':5,6][1,4]diazepino[2,3-f]quinoline was converted to the title compound as a racemic mixture following the procedure as described for Example 250. $^1$H NMR (500 MHz, CD$_3$OD): δ 8.83 (1H, d), 8.75 (1H, d), 7.96 (1H, d), 7.72 (1H, d), 7.59 (1H, m), 7.53 (1H, d), 7.19 (2H, d), 7.17 (d, 1H), 6.97 (2H, d), 5.38 (1H, d), 4.53 (1H, d), 1.23 (9H, s). LCMS: m/e 513.2 (M+H)$^+$. The racemic mixture was separated by HPLC on a chiralcel OD column (30% EtOH in hexanes) to afford the two enantiomers with retention time of 7.6 min for E1 and 11.9 min for E2, respectively.

The compounds in Table 13 were prepared using the appropriate starting materials and reagents following procedures similar to that described above for Example 316.

TABLE 13

| Example | Structure | Enantiomer: E1 or E2 | LCMS: found m/e (M + H) |
|---|---|---|---|
| 317 | 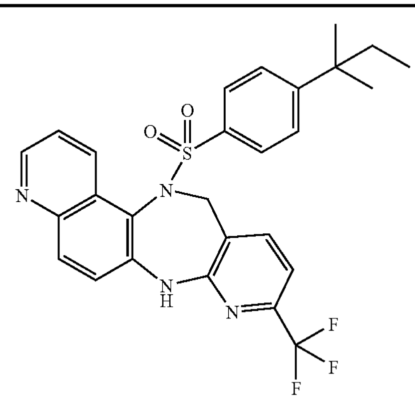 | E1 | 527.2 |

TABLE 13-continued

| Example | Structure | Enantiomer: E1 or E2 | LCMS: found m/e (M + H) |
|---------|-----------|----------------------|--------------------------|
| 318 | 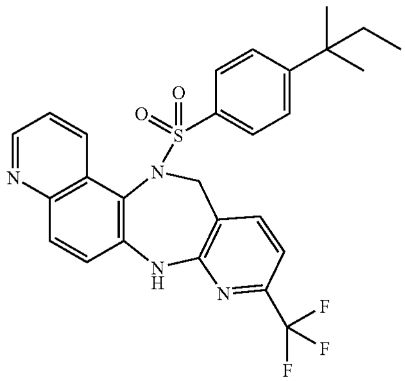 | E2 | 527.2 |
| 319 | 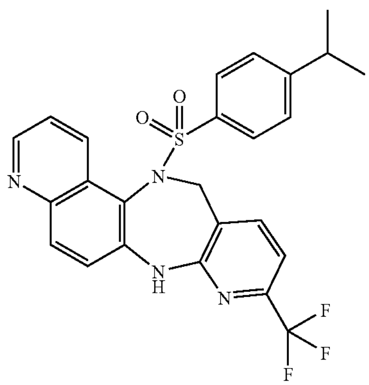 | E1 | 499.1 |
| 320 | 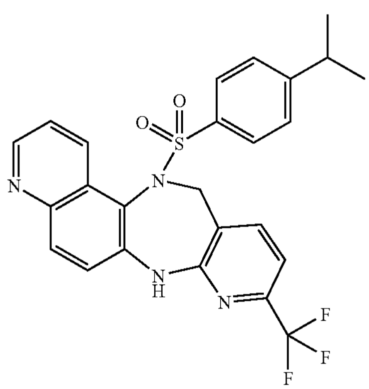 | E2 | 499.1 |
| 321 | 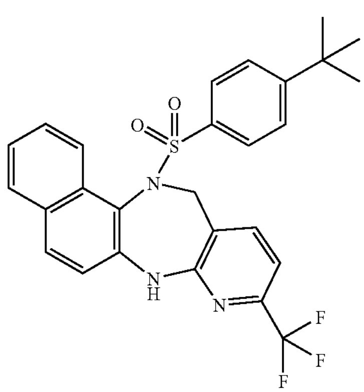 | E1 | 512.2 |

TABLE 13-continued

| Example | Structure | Enantiomer: E1 or E2 | LCMS: found m/e (M + H) |
|---|---|---|---|
| 322 | 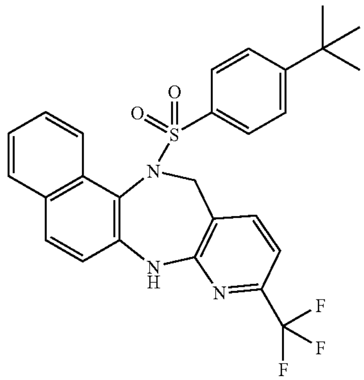 | E2 | 512.2 |

*E1 is the faster eluting enantiomer by HPLC on a chiralpak OD or AD-H column eluting with isopropyl alcohol/heptane or ethanol/hexanes and E2 is the slower eluting enantiomer by HPLC on a chiralpak OD or AD-H column eluting with isopropyl alcohol/heptane or ethanol/hexanes.

EXAMPLE 323

(1R)-1-(3-{1-[6-[(4-tert-Butylphenyl)sulfonyl]-2-(trifluoromethyl)-6,11-dihydro-5H-pyrido[2,3-b][1,5]benzodiazepin-8-yl]cyclopropyl}-1,2,4-oxadiazol-5-yl)ethanol

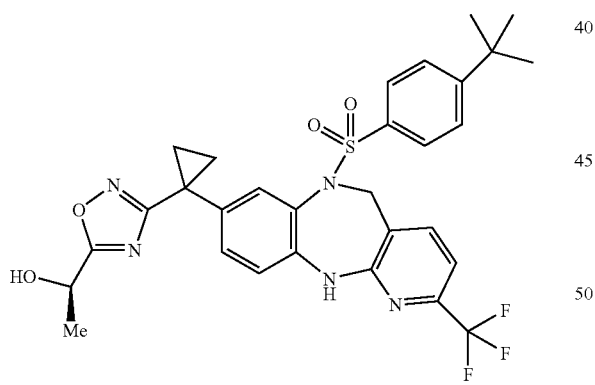

The title compound was prepared from the nitrile of Example 306 and (R)-2-benzyloxypropanoic acid following the procedure described for Example 437.

The compounds in Table 14 were prepared using the appropriate starting materials and reagents following procedures similar to that described for Example 471:

TABLE 14

[Structure: diazepine-pyridine core with R4 on benzene ring, sulfonyl-phenyl-Rf on N, and R1 on pyridine]

| Example | R4 | R1 | Rf | Enantiomer: E1 or E2 | LCMS: found m/e (M + H) |
|---|---|---|---|---|---|
| 324 | Me, Me, HO (C(Me)₂OH) | CF₃ | cyclopropyl-CF₃ | | 572.1 |
| 325 | Me, CF₃, HO | CF₃ | cyclopropyl-CF₃ | E1 | 626.1 |
| 326 | Me, CF₃, HO | CF₃ | cyclopropyl-CF₃ | E2 | 626.1 |
| 327 | 1-hydroxycyclobutyl | CF₃ | cyclopropyl-CF₃ | | 584.1 |
| 328 | HO, Me, HO-CH₂ | CF₃ | cyclopropyl-CF₃ | E1 | 588.1 |
| 329 | HO, Me, HO-CH₂ | CF₃ | cyclopropyl-CF₃ | E2 | 588.1 |
| 330 | HO, HO-CH₂ | CF₃ | cyclopropyl-CF₃ | E1 | 574.1 |
| 331 | HO, HO-CH₂ | CF₃ | cyclopropyl-CF₃ | E2 | 574.1 |
| 332 | 3-hydroxyazetidin-3-yl (HN, OH) | CF₃ | cyclopropyl-CF₃ | | 585.1 |
| 333 | 4-hydroxytetrahydropyran-4-yl (O, OH) | CF₃ | cyclopropyl-CF₃ | | 614.2 |

TABLE 14-continued

| Example | R4 | R1 | Rf | Enantiomer: E1 or E2 | LCMS: found m/e (M + H) |
|---|---|---|---|---|---|
| 334 | HO, CF₃, HO- (diol with CF₃) | CF₃ | cyclopropyl-CF₃ | E1 | 642.1 |
| 335 | HO, CF₃, HO- (diol with CF₃) | CF₃ | cyclopropyl-CF₃ | E2 | 642.1 |
| 336 | HO-CH₂-C(O)-N(azetidine)-OH | CF₃ | cyclopropyl-CF₃ |  | 643.1 |
| 337 | BnO-cyclobutyl-OH | CF₃ | cyclopropyl-CF₃ |  | 690.2 |
| 338 | HO-cyclobutyl-OH | CF₃ | cyclopropyl-CF₃ |  | 600.1 |
| 339 | HO-CH₂-C(O)-N(azetidine)-OH | CF₃ | ᵗBu |  | 591.2 |
| 340 | F-cyclobutyl-OH | CF₃ | ᵗBu |  | 550.2 |
| 341 | HO, HO- (diol) | CF₃ | ᵗBu | E1 | 522.2 |
| 342 | HO, HO- (diol) | CF₃ | ᵗBu | E2 | 522.2 |
| 343 | Me, CF₃, HO- | CF₃ | ᵗBu | E1 | 574.2 |

TABLE 14-continued

| Example | R4 | R1 | Rf | Enantiomer: E1 or E2 | LCMS: found m/e (M + H) |
|---|---|---|---|---|---|
| 344 | Me, CF₃, HO- | CF₃ | ᵗBu | E2 | 574.2 |
| 345 | cyclobutyl-OH | CF₃ | ᵗBu | | 532.2 |
| 346 | cyclohexyl-OH | CF₃ | ᵗBu | | 560.2 |
| 347 | tetrahydropyranyl-OH | CF₃ | ᵗBu | | 562.2 |
| 348 | N-methylpiperidinyl-OH | CF₃ | ᵗBu | | 575.2 |
| 349 | F₃C, CF₃, HO- | CF₃ | ᵗBu | | 628.1 |
| 350 | N-Boc-azetidinyl-OH | CF₃ | ᵗBu | | 633.2 |
| 351 | cyclopentyl-diol | CF₃ | ᵗBu | E1 | 562.2 |
| 352 | cyclopentyl-diol | CF₃ | ᵗBu | E2 | 562.2 |

TABLE 14-continued

| Example | R4 | R1 | Rf | Enantiomer: E1 or E2 | LCMS: found m/e (M + H) |
|---|---|---|---|---|---|
| 353 | 3-hydroxy-3-yl-azetidine (HN, OH) | CF₃ | ᵗBu | | 533.2 |
| 354 | C(Me)₂OH | Cl | ᵗBu | | 486.2 |
| 355 | 4-hydroxytetrahydropyran-4-yl | Cl | ᵗBu | | 528.2 |
| 356 | C(Me)₂OH | Cl | C(Me)(cyclopropyl)CF₃ | | 538.1 |
| 357 | 1-hydroxycyclobutyl | Cl | C(Me)(cyclopropyl)CF₃ | | 550.1 |
| 358 | HOCH₂-C(Me)(OH)- | Cl | C(Me)(cyclopropyl)CF₃ | E1 | 554.1 |

*E1 is the faster eluting enantiomer by HPLC on a chiralpak OD or AD-H column eluting with isopropyl alcohol/heptane or ethanol/hexanes and E2 is the slower eluting enantiomer by HPLC on a chiralpak OD or AD-H column eluting with isopropyl alcohol/heptane or ethanol/hexanes.

EXAMPLE 359

2-[6-[(4-tert-Butylphenyl)sulfonyl]-2-(trifluoromethyl)-6,11-dihydro-5H-pyrido[2,3-b][1,5]benzodiazepin-8-yl]propane-1,3-diol

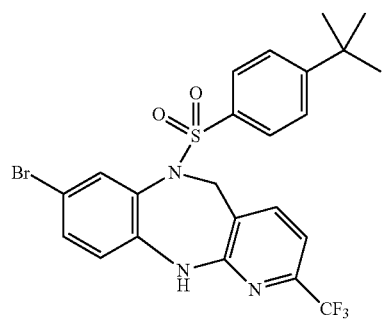

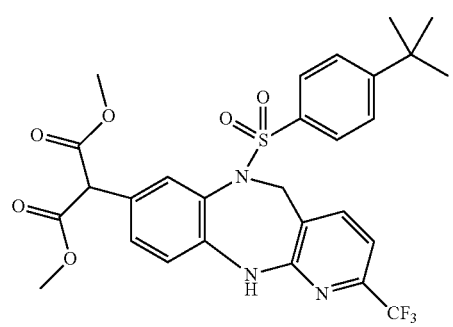

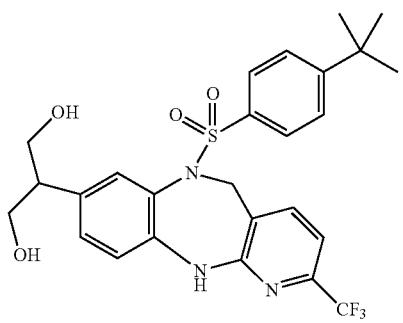

Step A: Intermediate 53 was reacted with dimethyl malonate following the procedure as described in Hartwig, John F. (*JOC* 2002, 67, 541-555) to afford the desired product.

Step B: To a solution of the product of Step A (80 mg, 0.135 mmol) in 1 mL THF was added lithium aluminum hydride (100 mg, 2.6 mmol). After stirring rt for 30 minutes, the reaction was quenched following the procedure described by Fieser, L. F. (Reagents for Organic Synthesis 1967, 581-595). The product was obtained after reverse phase HPLC purification. $^{1}$H NMR (CD$_3$OD): δ 1.2 (s, 9H-1), 3.8-3.9 (m, 2H-1), 4.0 (d, 1H), 4.2 (AB quartet, 2H), 6.9 (d, 1H), 7.0 (d, 1H), 7.9 (d, 1H), 7.2 (br, 2H), 7.38 (s, 1H), 7.4 (br, 2H), 7.6 (d, 1H). LCMS: m/e 536.1 (M+H)$^{+}$.

EXAMPLE 360

6-[(4-tert-Butylphenyl)sulfonyl]-8-(1-piperidin-4-yl)-2-(trifluoromethyl)-6,11-dihydro-5H-pyrido[2,3-b][1,5]benzodiazepine

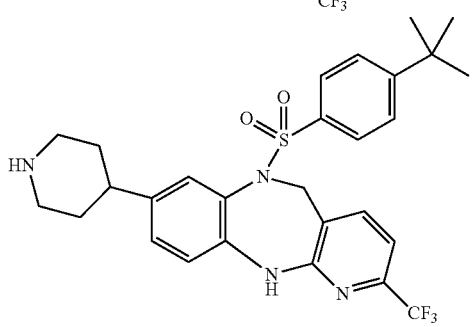

Step A: A mixture of intermediate 53 (200 mg, 0.37 mmol), potassium carbonate (153 mg, 1.11 mmol), tert-butyl 4-(4,4,5,5-tetramethyl-1,3,2-dioxaborolan-2-yl)-3,6-dihydropyridine-1(2H)-carboxylate (229 mg, 0.74 mmol), Pd(dppf)Cl2, (91 mg, 0.11 mmol), DMSO (2 mL) and water (3 drops) was heated in a microwave reactor at 120° C. for 30 minutes. After cooling to rt, the reaction mixture was diluted with ethyl acetate, washed with water and brine, dried over magnesium sulfate, filtered and concentrated. The residue was purified on silica gel column eluting 0-20% ethyl acetate/hexanes to afford the desired product.

Step B: A mixture of the product of Step A (100 mg, 0.156 mmol), palladium on activated carbon, in ethyl acetate (1 mL) and ethanol (1 mL) was stirred at rt under a hydrogen (balloon) overnight. The reaction mixture was diluted with ethyl acetate, filtered through a pad of Celite and silica, and the filtrate was concentrated to give the desired product.

Step C: To the product from Step B (100 mg, 0.155 mmol) in ethyl acetate (2 mL) was added 4N HCl in dioxane (0.5 mL). The reaction was stirred at rt for 2 hours, and was quenched with sodium bicarbonate. The product was extracted with ethyl acetate, and the combined extracts were concentrated. The residue was purified by reverse phase HPLC to afford the title compound. LCMS: m/e 545.1 (M+H)$^+$.

EXAMPLE 361

6-[(4-tert-butylphenyl)sulfonyl]-8-(1-methylpiperidin-4-yl)-2-(trifluoromethyl)-6,11-dihydro-5H-pyrido[2,3-b][1,5]benzodiazepine

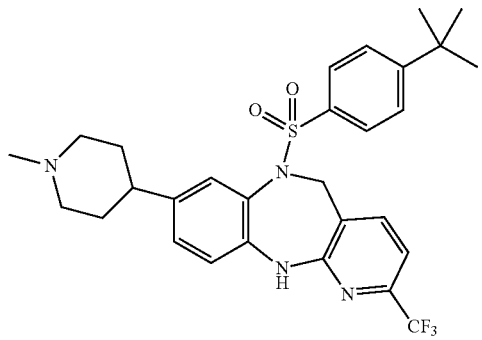

To 6-[(4-tert-butylphenyl)sulfonyl]-8-(1-piperidin-4-yl)-2-(trifluoromethyl)-6,11-dihydro-5H-pyrido[2,3-b][1,5] benzodiazepine (Example 360, 40 mg, 0.073 mmol) in acetonitrile (1 mL) was added sodium cyanoborohydride (4.6 mg, (0.073 mmol), diisopropyl ethyl amine (0.015 mL, 0.088 mmol), and aqueous formaldehyde (37%, 0.01 mL, 0.15 mmol). The reaction was stirred at room temperature for 2 hours, and the product was purified by reverse phase HPLC to afford the title compound. $^1$H NMR (CD$_3$OD): δ 1.2 (s, 9H), 2.0 (m, 2H), 2.2 (m, 2H), 2.95 (br, 4H), 3.2 (m, 2H), 3.65 (m, 2H), 6.9 (d, 2H), 7.0 (d, 1H), 7.05 (d, 1H), 7.2 (br, 3H), 7.4 (s, 1H), 7.6 (d, 1H). LCMS: m/e 559.2 (M+H)$^+$.

EXAMPLE 362

3-[6-[(4-tert-Butylphenyl)sulfonyl]-2-(trifluoromethyl)-6,11-dihydro-5H-pyrido[2,3-b][1,5]benzodiazepin-8-yl]propane-1,2-diol

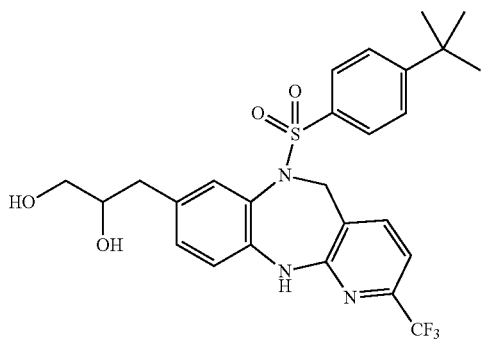

To intermediate 52 (100 mg, 0.17 mmol in 1 mL of THF at 0° C. was added $^i$PrMgCl (2.0 M in THF, 0.77 mL, 1.53 mmol), and CuCN (46 mg, 0.51 mmol). After stirring at 0° C. for 5 min, tert-butyl(dimethyl)(oxiran-2-ylmethoxy)silane (320 mg, 1.7 mmol) was added and the reaction was stirred for 30 min at rt, before quenching with aqueous NR$_4$Cl. The product was extracted with EtOAc, and the extracts were washed with water and brine, dried over MgSO$_4$, filtered, and concentrated. The residue was dissolved in 2 mL of THF and was added 1 mL of TBAF (1.0 M in THF). After stirring at rt for 2 h, the reaction mixture was quenched with aqueous NH$_4$Cl and the product was extracted with EtOAc. The combined extracts were washed with water and brine, dried over MgSO$_4$, filtered, and concentrated. The residue was purified on a silica gel column eluting with 50-90% EtOAc in hexanes to afford the title compound as a racemic mixture. $^1$H NMR (500 MHz, CD$_3$OD): δ 7.79 (1H, d), 7.38 (1H, s), 7.18 (2H, d), 7.16 (1H, d), 7.02 (1H, d), 6.93 (2H, d), 3.82 (m, 1H), 3.58-3.46 (2H, m), 2.82 (1H, dd), 2.67 (1H, dd), 1.22 (9H, s). LCMS: m/e 536.2 (M+H)$^+$. The racemic mixture was separated by HPLC using a chiralcel AD column (20% EtOH in hexanes) to afford the respective enantiomers with retention time of 18 min and 25 min, respectively.

The compounds in Table 15 were prepared using the appropriate starting materials and reagents following procedures similar to that described above for Example 362.

TABLE 15

| Example | R4 | Rf | Enantiomer: E1 or E2 | LCMS: found m/e (M + H) |
|---|---|---|---|---|
| 363 | HO-CH2-CH(OH)-C(CH3)- | cyclopropyl-CF3 | E1 | 588.1 |
| 364 | HO-CH2-CH(OH)-C(CH3)- | cyclopropyl-CF3 | E2 | 588.1 |
| 365 | HO-CH2-CH(OH)-C(CH3)- | OCF3 | E1 | 564.1 |
| 366 | HO-CH2-CH(OH)-C(CH3)- | OCF3 | E2 | 564.1 |
| 367 | HO-CH2-CH(OH)-C(CH3)- | CF3 | E1 | 548.1 |
| 368 | HO-CH2-CH(OH)-C(CH3)- | CF3 | E2 | 548.1 |
| 369 | HO-CH2-C(CH3)(OH)-C(CH3)- | cyclopropyl-CF3 | E1 | 602.2 |
| 370 | HO-CH2-C(CH3)(OH)-C(CH3)- | cyclopropyl-CF3 | E2 | 602.2 |
| 371 | HO-CH2-C(CH3)(OH)-C(CH3)- | CF3 | E1 | 562.1 |
| 372 | HO-CH2-C(CH3)(OH)-C(CH3)- | CF3 | E2 | 562.1 |

*E1 is the faster eluting enantiomer by HPLC on a chiralpak OD or AD-H column eluting with isopropyl alcohol/heptane or ethanol/hexanes and E2 is the slower eluting enantiomer by HPLC on a chiralpak OD or AD-H column eluting with isopropyl alcohol/heptane or ethanol/hexanes.

EXAMPLE 373

2-[6-[(4-tert-Butylphenyl)sulfonyl]-2-(trifluoromethyl)-6,11-dihydro-5H-pyrido[2,3-b][1,5]benzodiazepin-8-yl]-2-methylpropanoic acid methyl ester

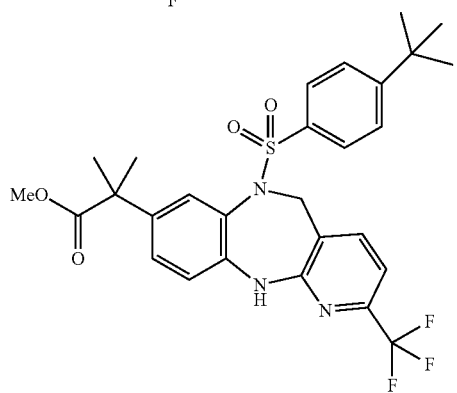

155

To methyl isobutyrate (128 mg, 1.25 mmol) in toluene (5 mL) was added 1.46 mL of LiHMDS (1.0 M in PhMe, 1.46 mmol) at 0° C. After stirring at rt for 10-15 min, the mixture was transferred via cannula to a mixture of intermediate 53 (225 mg, 0.416 mmol), Pd(dba)$_2$ (24 mg, 0.042 mmol), and tri-t-butylphosphonium tetrafluoroborate (12 mg, 0.042 mmol). After stirring at rt for 48 hrs, the reaction was quenched with aqueous NH$_4$Cl (20 mL) and the product was extracted with EtOAc (50 mL). The extracts were washed with water (30 mL) and brine (30 mL), dried over MgSO$_4$, filtered, and concentrated in vacuo. The residue was purified on silica gel column eluting with 5-30% EtOAc in hexanes to afford the title compound. LCMS: m/e 562.2 (M+H)$^+$.

EXAMPLE 374

2-[6-[(4-tert-Butylphenyl)sulfonyl]-2-(trifluoromethyl)-6,11-dihydro-5H-pyrido[2,3-b][1,5]benzodiazepin-8-yl]-2-methylpropanoic acid

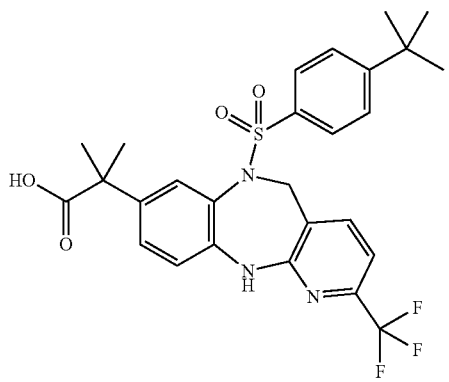

To the methyl ester (92 mg, 0.16 mmol) of Example 373 in 3 mL of H$_2$O/THF/acetonitrile (1:1:1) was added LiOH (16 mg, 0.65 mmol). After stirring at rt for 48 hrs, the reaction was quenched with aqueous NH$_4$Cl (25 mL) and the product was extracted with EtOAc (60 mL). The extracts were washed with water (30 mL) and brine (30 mL), dried over MgSO$_4$, filtered, and concentrated in vacuo. The residue was purified on silica gel column eluting with 20-50% EtOAc in hexanes to afford the title compound. $^1$H NMR (500 MHz, CD$_3$OD): δ 7.61 (1H, d), 7.46 (1H, s), 7.24 (1H, d), 7.17 (2H, d), 7.03 (1H, d), 6.93 (1H, d), 6.91 (2H, d), 1.58 (6H, s), 1.22 (9H, s). LCMS: m/e 548.2 (M+H)$^+$.

156

EXAMPLE 375

1-[6-[(4-Trifluoromethoxyphenyl)sulfonyl]-2-(trifluoromethyl)-6,11-dihydro-5H-pyrido[2,3-b][1,5]benzodiazepin-8-yl]cyclobutanecarboxamide and
1-[6-[(4-Trifluoromethoxyphenyl)sulfonyl]-2-(trifluoromethyl)-6,11-dihydro-5H-pyrido[2,3-b][1,5]benzodiazepin-8-yl]cyclobutanecarboxic acid

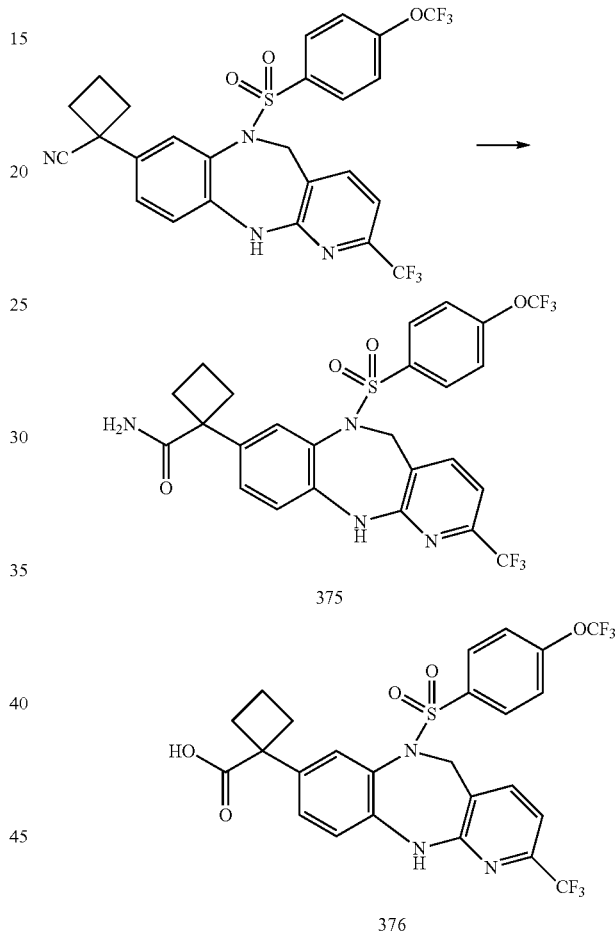

A solution of nitrile (prepared following the procedures described for Example 461, 100 mg) in ethanol (2 mL) and 5N NaOH (1 mL) was heated to 80° C. for 2.5 hours. The reaction was quenched with ammonium chloride, and the product was extracted with ethyl acetate. The combined extracts were washed with water and brine, dried over magnesium sulfate, filtered and concentrated. The residue was purified by reverse phase HPLC (eluting with 10 to 100% acetonitrile+0.05% TFA in water+0.05% TFA) to provide the title compounds. Example 375: $^1$H NMR (CD$_3$OD): δ 1.85-2.05 (br, 3H), 2.5 (m, 2H), 2.8 (m, 2H), 7.0 (br, 3H), 7.1 (d, 1H), 7.15 (d, 2H), 7.3 (d, 1H), 7.55 (s, 1H), 7.65 (d, 1H). LCMS: m/e 587.0 (M+H)$^+$. Example 376: $^1$H NMR (CD$_3$OD): δ 1.9-2.1 (br, 3H), 2.5 (m, 2H), 2.8 (m, 2H), 7.0 (d, 1H), 7.05 (d, 2H), 7.1 (d, 1H), 7.15 (d, 2H), 7.25 (d, 1H), 7.45 (s, 1H), 7.65 (d, 1H). LCMS: m/e 588.0 (M+H)$^+$.

The compounds in Table 16 were prepared using the appropriate starting materials and reagents following procedures similar to those described above for Examples 375 and 376.

TABLE 16

| Example | R4 | Rf | LCMS: found m/e (M + H) |
|---|---|---|---|
| 377 | 1-(HOOC)cyclobutyl | 1-(CF3)cyclopropyl | 611.1 |
| 378 | 1-(HOOC)cyclopropyl | OCF3 | 574.1 |
| 379 | C(CH3)2COOH | isopropyl | 534.2 |
| 380 | 1-(HOOC)cyclobutyl | OCF3 | 588.1 |
| 381 | C(CH3)2COOH | 1-(CF3)cyclopropyl | 600.1 |
| 382 | C(CH3)2COOH | OCF3 | 576.1 |
| 383 | C(CH3)2COOH | CF3 | 560.1 |
| 384 | 1-(H2NOC)cyclobutyl | OCF3 | 587.1 |

TABLE 16-continued

| Example | R4 | Rf | LCMS: found m/e (M + H) |
|---|---|---|---|
| 385 | C(CH3)2C(O)NH2 | t-Bu | 547.2 |
| 386 | C(CH3)2C(O)NH2 | OCF3 | 575.1 |
| 387 | C(CH3)2C(O)NH2 | CF3 | 559.1 |
| 388 | 1-(H2NOC)cyclobutyl | tBu | 559.2 |
| 389 | 1-(H2NOC)cyclopropyl | OCF3 | 573.1 |

The compounds in Table 17 were prepared using the appropriate starting materials and reagents following procedures similar to that described for Example 437.

TABLE 17

| Example | Re | Rf | LCMS: found m/e (M + H) |
|---|---|---|---|
| 390 | HO-C(CH3)2-CH2- | -O-iPr | 562.1 |
| 391 | HO-C(CH3)2-CH2- | -C(CH3)2-CH2CH3 | 574.1 |
| 392 | OMe | isopropyl | 534.0 |
| 393 | HO-C(CH3)2-CH2- | OCHF$_2$ | 570.0 |
| 394 | HO-C(CH3)2-CH2- | -C(=O)CH3 | 546.0 |
| 395 | HO-C(CH3)2-CH2- | -C(=CH2)CH3 | 544.1 |
| 396 | HO-C(CH3)2-CH2- | OH | 520.1 |
| 397 | HO-C(CH3)2-CH2- | 1-cyanocyclopropyl | 569.1 |
| 398 | HO-C(CH3)2-CH2- | 1-cyanocyclobutyl | 583.1 |
| 399 | HO-C(CH3)2-CH2- | 3,3-difluorocyclobutyl | 594.1 |

TABLE 17-continued

| Example | Re | Rf | LCMS: found m/e (M + H) |
|---|---|---|---|
| 400 | (R)-HO-CH(CH3)- | $^t$Bu | 574.1 |
| 401 | methyl propanoate (MeO-C(=O)-CH2CH2-) | $^t$Bu | 602.1 |
| 402 | (S)-HO-CH(CH3)- | $^t$Bu | 574.1 |
| 403 | (R)-H2N-CH(CH3)- | $^t$Bu | 573.1 |
| 404 | (S)-H2N-CH(CH3)- | $^t$Bu | 573.1 |
| 405 | HO-C(CH3)2- | $^t$Bu | 588.2 |
| 406 | H2N-C(CH3)2- | $^t$Bu | 587.2 |

The compounds in Table 18 were prepared using the appropriate starting materials and reagents following procedures similar to that described for Example 246:

TABLE 18

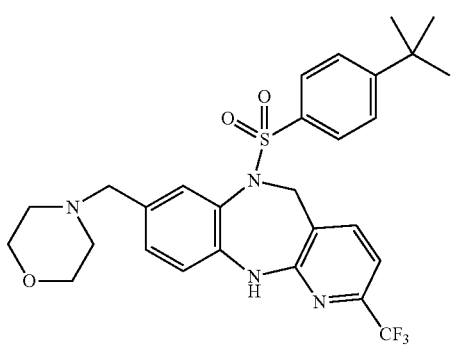

| Example | R4 | LCMS: m/e (M + H) |
|---|---|---|
| 407 | ethyl isoxazole-3-carboxylate-5-yl | 601.1 |
| 408 | 3-(hydroxymethyl)isoxazol-5-yl | 559.1 |
| 409 | 3-(2-hydroxypropan-2-yl)isoxazol-5-yl | 587.1 |
| 410 | ethyl 4,5-dihydroisoxazole-3-carboxylate-5-yl | 603.1 |
| 411 | 4,5-dihydroisoxazole-3-carboxylic acid-5-yl | 575.1 |
| 412 | 3-(hydroxymethyl)isoxazolidin-5-yl | 562.9 |

EXAMPLE 413

6-[(4-tert-Butylphenyl)sulfonyl]-8-(morpholin-4-ylmethyl)-2-(trifluoromethyl)-6,11-dihydro-5H-pyrido[2,3-b][1,5]benzodiazepine To a solution of 6-[(4-tert-butylphenyl)sulfonyl]-2-(trifluoromethyl)-6,11-dihydro-5H-pyrido[2,3-b][1,5]benzodiazepine-8-carbaldehyde (Step A, Example 453, 10 mg, 0.020 mmol) in EtOH (2 mL) at rt was added morpholine (10 uL, 0.12 mmol) and NaCNBH$_3$ (100 mg). After stirring at rt overnight, the reaction was diluted with sat. NaHCO$_3$, and product was extracted with EtOAc (3×). The combined extracts were washed with brine, dried with MgSO$_4$, filtered and concentrated. The residue was purified by silica gel chromatography (0-100% EtOAc/hexanes) to give the title compound. $^1$H NMR (500 MHz, (CD$_3$)$_2$CO): δ, 8.31 (s, 1H), 7.71 (d, 1H), 7.46 (s, 1H), 7.27 (s, 2H), 7.20 (d, 2H), 7.12 (d, 1H), 6.97 (d, 2H), 4.82 (br s, 2H), 3.66 (t, 4H), 3.51 (s, 2H), 2.46 (br, 4H), 1.24 (s, 9H). LCMS: m/e 561.1 (M+H)$^+$.

The compounds in Table 19 were prepared using the appropriate starting materials and reagents following procedures similar to that described above for Example 129.

TABLE 19

| Example | R4a | LCMS: found m/e (M + H) |
|---|---|---|
| 414 | piperazin-1-yl | 574.1 |
| 415 | morpholin-4-yl | 575.1 |

TABLE 19-continued

| Example | R4a | LCMS: found m/e (M + H) |
|---|---|---|
| 416 | piperidin-1-yl | 573.1 |
| 417 | thiomorpholin-4-yl | 591.0 |
| 418 | 1,1-dioxothiomorpholin-4-yl | 623.0 |
| 419 | HOCH2CH2NH- (on CMe) | 549.0 |
| 420 | EtO2CCH2NH- (on CMe) | 591.0 |
| 421 | HOC(Me)2CH2NH- (on CMe) | 577.1 |
| 422 | 3-hydroxypyrrolidin-1-yl | 575.0 |
| 423 | 1H-tetrazol-5-ylamino (on CMe) | 573.0 |
| 424 | thiazol-2-ylamino (on CMe) | 588.0 |
| 425 | pyridin-4-ylamino (on CMe) | 582.0 |

TABLE 20

| Example | R4b | LCMS: m/e (M + H) |
|---|---|---|
| 426 | 4-methylpiperazin-1-yl | 588.1 |
| 427 | morpholin-4-yl | 590.0 |
| 428 | pyrrolidin-1-yl | 574.1 |
| 429 | piperidin-1-yl | 588.1 |
| 430 | 1,2,4-triazol-4-yl | 572.0 |
| 431 | pyrrol-1-yl | 570.0 |

The compounds in Table 20 were prepared using the appropriate starting materials and reagents following procedures similar to that described above for Example 130.

EXAMPLE 432

{5-[6-[(4-tert-Butylphenyl)sulfonyl]-2-(trifluoromethyl)-6,11-dihydro-5H-pyrido[2,3-b][1,5]benzodiazepin-8-yl]-4H-1,2,4-triazol-3-yl}methanol

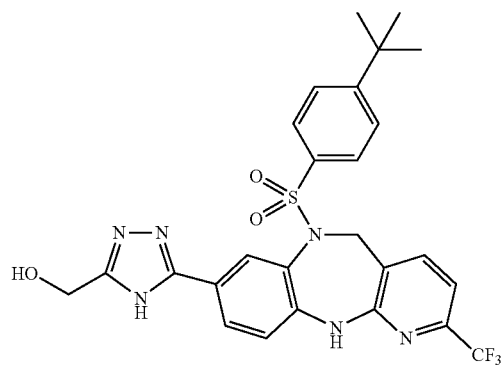

The title compound was prepared from intermediate 57 and methyl-2-(benzyloxy)ethanimidoate following the procedure described for Example 447. $^1$H NMR (500 MHz, (CD$_3$OD): δ 8.18 (s, 1H), 7.84 (d, 1H), 7.58 (d, 1H), 7.12 (d, 2H), 7.07 (d, 1H), 7.03 (d, 1H), 6.92 (d, 2H), 4.79 (s, 2H), 1.23 (s, 9H). LCMS: m/e 559.2 (M+H)$^+$.

EXAMPLE 433

Methyl {3-[6-[(4-tert-Butylphenyl)sulfonyl]-2-(trifluoromethyl)-6,11-dihydro-5H-pyrido[2,3-b][1,5]benzodiazepin-8-yl]-1H-pyrazol-1yl}acetate

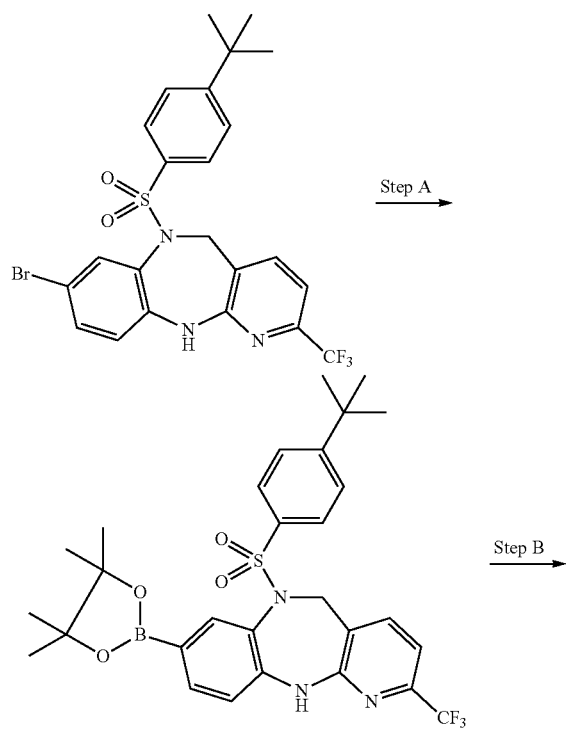

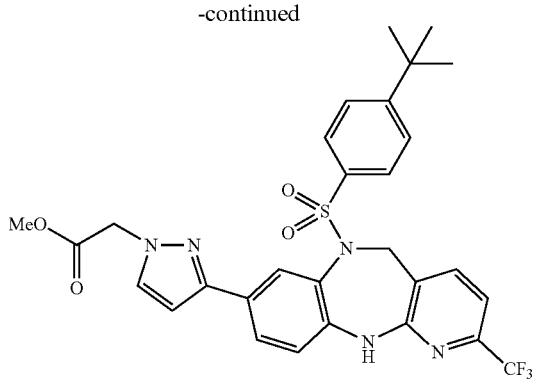

Step A: Intermediate 3 was converted to the boronic ester product following the procedure described by T. Ishiyama et al (*Tetrahedron*, 2001, 57, 9813). LCMS: m/e 590.2 (M+H)$^+$.

Step B: A mixture of the product of Step A (80 mg, 0.143 mmol), methyl (3-bromo-1H-pyrazol-1-yl)acetate (60 mg, 0.286 mmol), K$_2$CO$_3$ (57 mg, 0.411 mmol), and Pd(dppf)Cl$_2$ (34 mg, 0.04 mmol), DMSO (4 mL) and water (3 drops) was heated in a microwave reactor at 100° C. for 30 min. After cooling to rt, the reaction mixture was diluted with EtOAc (30 ml), washed with water and brine, dried over Na$_2$SO$_4$ and concentrated. The residue was purified by reverse phase HPLC to give the title compound. $^1$H NMR (500 MHz, (CD$_3$OD): δ 8.03 (s, 1H), 7.85 (s, 1H), 7.64 (s, 1H), 7.62 (d, 1H), 7.44 (d, 1H), 7.19 (d, 2H), 7.04 (d, 1H), 7.01 (d, 1H), 6.95 (d, 2H), 5.06 (s, 2H), 3.79 (s, 3H), 1.22 (s, 9H). LCMS: m/e 600.2 (M+H)$^+$.

EXAMPLE 434

{3-[6-[(4-tert-Butylphenyl)sulfonyl]-2-(trifluoromethyl)-6,11-dihydro-5H-pyrido[2,3-b]-[1,5]benzodiazepin-8-yl]-1H-pyrazol-1-yl}acetic acid

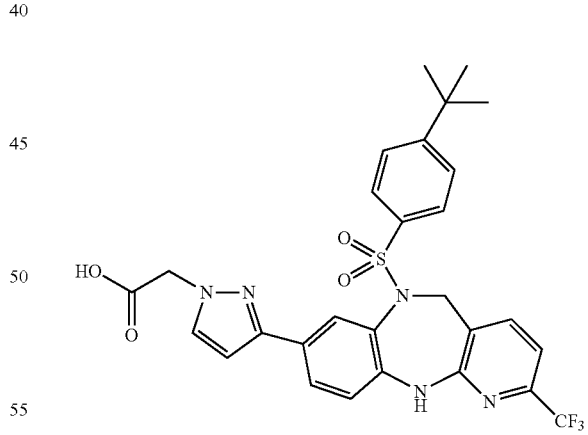

To methyl-{3-[6-[(4-tert-butylphenyl)sulfonyl]-2-(trifluoromethyl)-6,11-dihydro-5H-pyrido[2,3-b][1,5]benzodiazepin-8-yl]-1H-pyrazol-1-yl}acetate (Example 433, 3.5 mg, 0.006 mmol) in acetonitrile (0.5 mL) and water (0.5 mL) was added LiOH (2 mg, 0.005 mmol). After stirring overnight at rt, the reaction was diluted with 2 mL of brine, 0.5 mL of 2N HCl, and 20 mL of EtOAc. The organic layer was separated, washed with water and brine, dried with Na$_2$SO$_4$, and concentrated to give the title compound. $^1$H NMR (500 MHz, (CD$_3$OD): δ 8.05 (brd s, 1H), 7.91 (brd s, 1H), 7.63 (s, 1H), 7.61 (d, 1H), 7.44 (d, 1H), 7.18 (d, 2H), 7.06 (d, 1H), 7.02 (d, 1H), 6.96 (d, 2H), 5.02 (s, 2H), 1.23 (s, 9H). LCMS: m/e 586.2 (M+H)+.

EXAMPLE 435

2-Methyl-2-[6-{[4-(trifluoromethoxy)phenyl]sulfonyl}-2-(trifluoromethyl)-6,11-dihydro-5H-pyrido[2,3-b][1,5]benzodiazepin-7-yl]propanoic acid

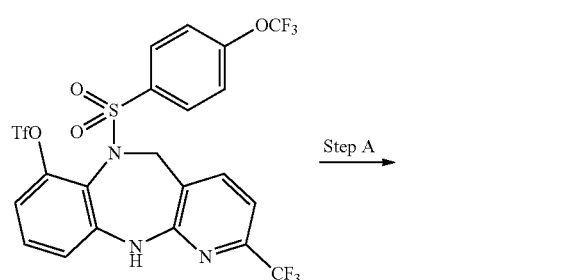

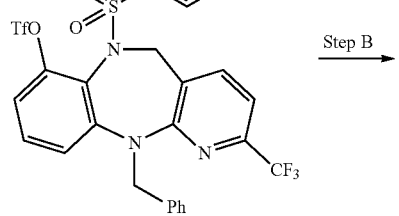

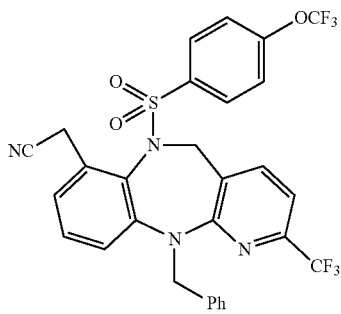

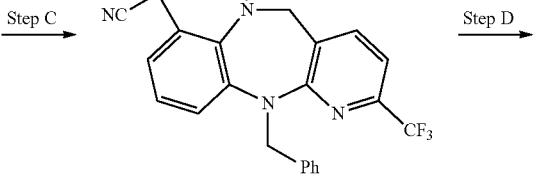

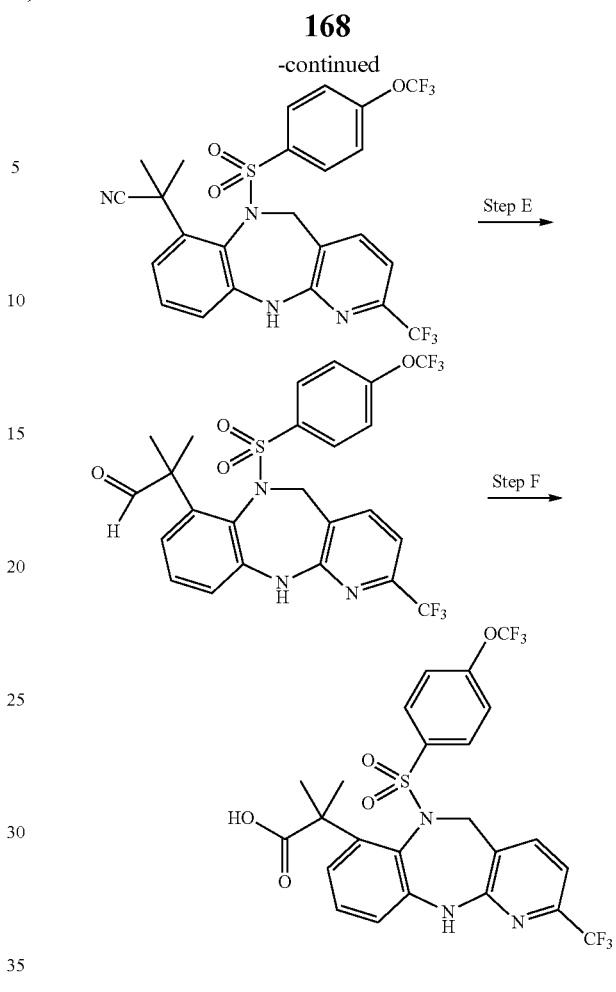

Step A: A mixture of intermediate 3 (1.0 g, 1.57 mmol), benzyl bromide (0.4 g, 2.4 mmol), and benzyltriethylamonium chloride (36 mg, 0.16 mmol), aqueous NaOH (5 mL, 50 weight %) and toluene (15 mL) was heated in a microwave reactor at 100° C. for 10 min. After cooling to rt, the reaction mixture was diluted with EtOAc (100 ml), washed with water and brine, dried over $Na_2SO_4$ and concentrated. The residue was purified on silica gel column eluting with 10-50% EtOAc in hexanes to give the desired product. LCMS: m/e 728.1 (M+H)+.

Step B: A mixture of the product of Step A (750 mg, 1.03 mmol), trimethylsilyl acetonitrile (350 mg, 3.1 mmol), S-phos (169 mg, 0.4 mmol), DMF (4 mL), $ZnF_2$ (160 mg, 1.55 mmol), and $Pd_2(dba)_3$ (189 mg, 0.21 mmol) was heated in a microwave reactor at 180° C. for 1 h. After cooling to rt, the reaction mixture was diluted with EtOAc (100 ml), washed with water and brine, dried with $Na_2SO_4$ and concentrated. The residue was purified on silica gel column eluting with 10-45% EtOAc in hexanes to give the desired product. LCMS: m/e 619.1 (M+H)+.

Step C: To a mixture of the product of Step B (375 mg, 0.61 mmol) in THF (4 mL) was added NaH (3 mmol), and MeI (4 mmol). The reaction was heated in a microwave reactor at 100° C. for 10 min. After cooling to rt, the reaction mixture was diluted with EtOAc (100 ml), washed with water and brine, dried with $Na_2SO_4$ and concentrated. The residue was purified on silica gel column eluting with 10-40% EtOAc in hexanes to give the desired product. LCMS: m/e 647.2 (M+H)+.

Step D: The benzyl protecting group was removed with TMSCl/NaI following the procedure described by O. Lohse et al (*Tetrahedron Lett.* 2001, 42, 385) to give the desired nitrile product.

Step E: To the product of Step D (22 mg, 0.04 mmol) in CH$_2$Cl$_2$ (1 mL) at −78° C. was added DIBAL-H (1M in PhMe, 0.24 mL, 0.24 mmol). After stirring for 30 min at −78° C., the reaction was quenched with aqueous sodium sulfate and the product was extracted with EtOAc (25 mL). The combined extracts were washed with water and brine, dried with Na$_2$SO$_4$ and concentrated to give the desired product, which was used without further purification.

Step F: The product from Step E was converted to the title compound acid following the procedure described by S. Akai et al (*J. Org. Chem.* 2002, 67, 411). $^1$H NMR (500 MHz, (CD$_3$OD): δ 7.58 (d, 1H), 7.24 (dd, 1H), 7.23 (d, 2H), 7.20 (d, 1H), 7.05 (d, 1H), 7.02 (d, 2H), 6.98 (d, 1H), 5.06 (d, 1H), 4.78 (d, 1H), 1.84 (s, 3H), 1.67 (s, 3H). LCMS: m/e 576.1 (M+H)$^+$.

EXAMPLE 436

{3-[6-[(4-tert-Butylphenyl)sulfonyl]-2-(trifluoromethyl)-6,11-dihydro-5H-pyrido[2,3-b][1,5]benzodiazepin-8-yl]-1,2,4-oxadiazole

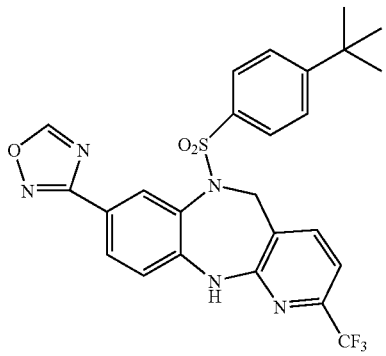

A mixture of 6-[(4-tert-butylphenyl)sulfonyl]-N'-hydroxy-2-(trifluoromethyl)-6,11-dihydro-5H-pyrido[2,3-b][1,5]benzodiazepine-8-carboximidamide (intermediate 55, 0.020 g, 0.0385 mmol) and triethylorthoformate (0.1 mL) was stirred at 130° C. overnight. The volatiles were removed under reduced pressure and the residue was purified via SiO$_2$ column chromatography to afford the title compound. LC/MS: m/e 530.1 (M+H)$^+$. $^1$H NMR (500 MHz, CDCl$_3$): δ 8.8 (1H, s), 8.39 (1H, d, J=2.1 Hz), 8.02 (1H, dd, J=8.5, 2.1 Hz), 7.63 (1H, d, J=7.6 Hz), 7.12-7.15 (3H, m), 6.97-6.99 (3H, m), 6.88 (1H, d, J=8.4 Hz), 4.60-4.90 (2H, br), 1.26 (9H, s).

EXAMPLE 437

{3-[6-[(4-tert-Butylphenyl)sulfonyl]-2-(trifluoromethyl)-6,11-dihydro-5H-pyrido[2,3-b][1,5]benzodiazepin-8-yl]-1,2,4-oxadiazol-5-yl}methanol

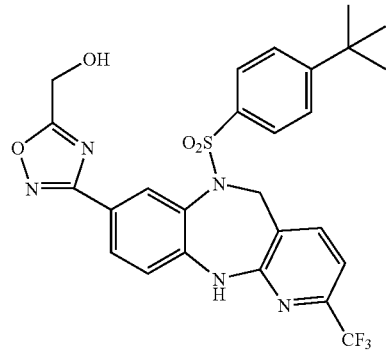

Step A: A mixture of 6-[(4-tert-butylphenyl)sulfonyl]-N'-hydroxy-2-(trifluoromethyl)-6,11-dihydro-5H-pyrido[2,3-b][1,5]benzodiazepine-8-carboximidamide (intermediate 55, 0.20 g, 0.38 mmol), 2-benzyloxyacetic acid (0.064 mg, 0.385 mmol), DIPEA (0.103 mg, 0.800 mmol), HOBt (0.108 g, 0.8 mmol), and DIC (0.073 g, 0.578 mmol) in DCM (3.85 mL) was stirred at rt for 4 h. The reaction mixture was diluted with EtOAc, washed with dilute NaOH, 5% citric acid, dried (MgSO$_4$) and concentrated to afford the desired product, which was used without further purification. LC/MS: m/e 667.5 (M+H)$^+$.

Step B: To a solution of the product from Step A in THF (2.0 mL) was added tetrabutylammonium fluoride (0.45 mL of a 1M solution in THF). After stirring at rt for 1 h, the reaction mixture was quenched with water and the product was extracted with EtOAc. The combined extracts were washed with water, brine, dried (MgSO$_4$) and concentrated. The residue was purified via SiO$_2$ column chromatography, eluting with hexane/EtOAc to afford the desired product. LC/MS: m/e 560.1 (M+H)$^+$.

Step C: To a solution of the product of Step B (0.48 g, 0.74 mmol) in chloroform (7 mL) at 0° was added methanesulfonic acid (1 mL). The ice bath was removed and the reaction mixture was stirred for 1 h. After cooling back to 0° C., EtOAc was added and the reaction was quenched with 4N aqueous NaOH until ~pH 7. The organic layer was separated, and the aqueous layer was extracted with EtOAc. The combined extracts were washed with water and brine, dried (MgSO$_4$) and concentrated. The residue was purified by SiO$_2$ chromatography, eluting with a mixture of hexane and EtOAc, to provide the title compound. LC/MS: m/e 560.1 (M+H)$^+$. $^1$H NMR (500 MHz, CDCl$_3$): δ 8.20 (1H, d, J=1.9 Hz), 7.86 (1H, dd, J=8.5, 2.1 Hz), 7.52 (1H, d, J=7.5 Hz), 7.03-7.05 (3H, m), 6.85-6.89 (3H, m), 4.58-5.10 (2H, br), 4.83 (2H, s), 1.15 (9H, s).

The compound in Table 21 was prepared from intermediate 55 and the appropriate acids following procedures described for Example 436.

TABLE 21

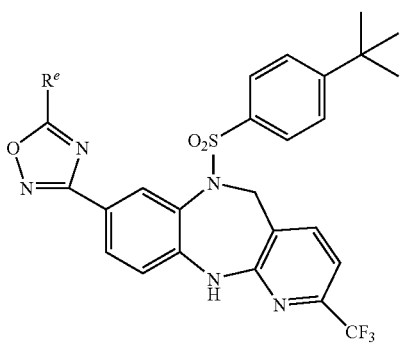

| Example | Re | LCMS: found m/e (M + H) |
|---|---|---|
| 438 | Me | 544.2 |

EXAMPLE 439

3-[6-[(4-tert-Butylphenyl)sulfonyl]-2-(trifluoromethyl)-6,11-dihydro-5H-pyrido-[2,3-b][1,5]benzodiazepin-8-yl]-1,2,4-oxadiazol-5(4H)-one

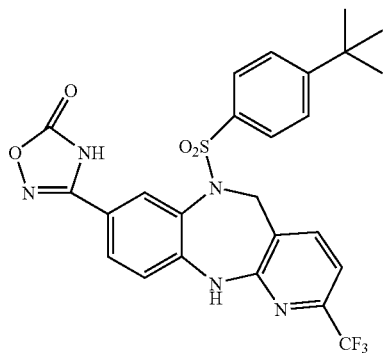

Step A: To 6-[(4-tert-butylphenyl)sulfonyl]-N'-hydroxy-2-(trifluoromethyl)-6,11-dihydro-5H-pyrido[2,3-b][1,5]benzodiazepine-8-carboximidamide (intermediate 55, 0.040 g, 0.0771 mmol) in DCM (0.7 mL) and DMF (1 mL) at 0° C. was added pyridine (7.9 mg, 0.100 mmol) and ethyl chloroformate (8.8 mg, 0.081 mmol), and the reaction was allowed to warm room temperature over 2 h. The volatiles were removed, and the residue was purified by $SiO_2$ column chromatography, eluting with 0-100% EtOAc in hexanes, to yield the desired product. LC/MS: m/e 592.2 $(M+H)^+$.

Step B: A solution of the product from Step A in p-xylene (0.5 mL) was heated at 130° C. for 3 h. The volatiles were removed and the residue was purified by $SiO_2$ column chromatography, eluting with mixtures of EtOAc in hexanes, to provide the title compound. LC/MS: m/e 546.1 $(M+H)^+$. $^1H$ NMR (500 MHz, $CDCl_3$): δ 7.75 (1H, d, J=2.1 Hz), 7.66 (1H, dd, J=8.7, 2.1 Hz), 7.53 (1H, d, J=7.6 Hz), 7.03-7.05 (3H, m), 6.90 (1H, d, J=8.7 Hz), 6.81-6.83 (2H, m), 4.5-5.0 (2H, br), 1.14 (9H, s).

EXAMPLE 440

{6-[(4-tert-Butylphenyl)sulfonyl]-8-(1,3,4-oxadiazol-2-yl)-2-(trifluoromethyl)-6,11-dihydro-5H-pyrido[2,3-b][1,5]benzodiazepine

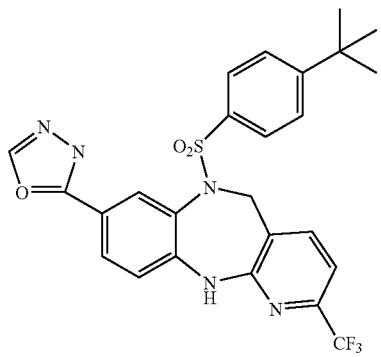

A mixture of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.023 g, 0.0443 mmol), triethylorthoformate (0.25 mL), and p-toluenesulfonic acid (5 mg) was stirred at rt for 2 h. Aqueous 1N HCl was added and stirring continued for 45 min. The reaction was quenched with saturated aqueous $NaHCO_3$, and the product was extracted with EtOAc. The combined extracts were washed with brine, dried ($MgSO_4$) and concentrated. The residue was purified by $SiO_2$ column chromatography to afford the title compound. LC/MS: m/e 530.1 $(M+H)^+$. $^1H$ NMR (500 MHz, $CDCl_3$): δ 8.5 (1H, s), 8.28 (1H, d, J=2.1 Hz), 8.06 (1H, dd, J=8.7, 2.0 Hz), 7.64 (1H, d, J=7.6 Hz), 7.16 (1H, d, J=7.5 Hz), 7.13 (2H, d, J=8.5 Hz), 7.04 (1H, s), 6.95 (2H, d, J=8.4 Hz), 6.91 (1H, d, J=8.5 Hz), 4.70-4.59 (2H, br), 1.26 (9H, s).

EXAMPLE 441

5-[6-[(4-tert-Butylphenyl)sulfonyl]-2-(trifluoromethyl)-6,11-dihydro-5H-pyrido-[2,3-b][1,5]benzodiazepin-8-yl]-1,3,4-oxadiazol-2(3H)-one

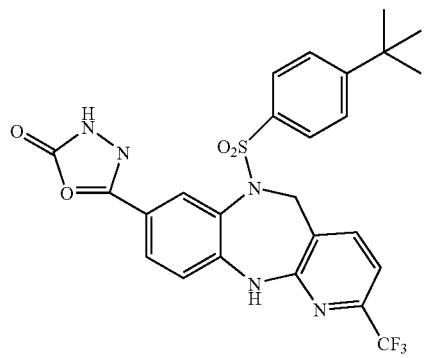

To a solution of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.040 g, 0.0771 mmol) in DCM (0.2 mL) at −78° C. was added phosgene (0.081 mL of a ~20% solution in toluene) dropwise. After stirring at −20° C. overnight, the reaction was quenched with saturated aqueous NaHCO$_3$, and the product was extracted with EtOAc and DCM. The combined extracts were washed with brine, dried (MgSO$_4$) and concentrated. The residue was purified via SiO$_2$ column chromatography, eluting with mixtures of EtOAc and hexane, to afford the title compound. LC/MS: m/e 546.1 (M+H)$^+$. $^1$H NMR (500 MHz, CDCl$_3$): δ 7.96 (1H, d, J=6.4 Hz), 7.62 (11-1, d, J=8.4 Hz), 7.54 (1H, d, J=7.8 Hz), 7.29 (1H, d, J=5.5 Hz), 7.03-7.04 (3H, m), 6.86-6.89 (3H, m), 4.50-4.90 (2H, br), 1.14 (9H, s).

EXAMPLE 442

5-[6-[(4-tert-Butylphenyl)sulfonyl]-2-(trifluoromethyl)-6,11-dihydro-5H-pyrido[2,3-b][1,5]benzodiazepin-8-yl]-3-methyl-1,3,4-oxadiazol-2(3H)-one

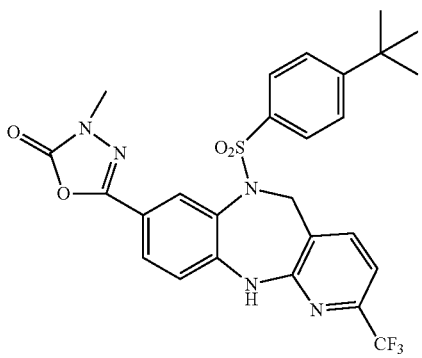

To a solution of 5-[6-[(4-tert-butylphenyl)sulfonyl]-2-(trifluoromethyl)-6,11-dihydro-5H-pyrido[2,3-b][1,5]benzodiazepin-8-yl]-1,3,4-oxadiazol-2(3H)-one (Example 441, 10 mg, 0.0183 mmol) in DMF (0.10 mL) was added cesium carbonate (6 mg, 0.0183 mmol) and iodomethane (0.0011 mL, 0.0183 mmol). After stirring at rt for 1.5 h, the reaction mixture was quenched with water, and the product was extracted with EtOAc (3×). The combined extracts were washed with water and brine, dried (MgSO$_4$) and concentrated. The residue was purified via SiO$_2$ chromatography, to provide the title compound. LC/MS: m/e 560.0 (M+H)$^+$. $^1$H NMR (500 MHz, CDCl$_3$): δ 8.09 (1H, d, J=2.0 Hz), 7,69 (1H, dd, J=8.5, 2.1 Hz), 7.61 (1H, d, J=7.5 Hz), 7.10-7.20 (3H, m), 6.94-6.98 (3H, m), 6.83 (1H, d, J=8.7 Hz), 4.65-4.95 (2H, br), 3.53 (3H, s), 1.25 (9H, s).

EXAMPLE 443

5-[6-[(4-tert-Butylphenyl)-sulfonyl]-2-(trifluoromethyl)-6,11-dihydro-5H-pyrido[2,3-b][1,5]benzodiazepin-8-yl]-3-ethyl-1,3,4-oxadiazol-2(3H)-one

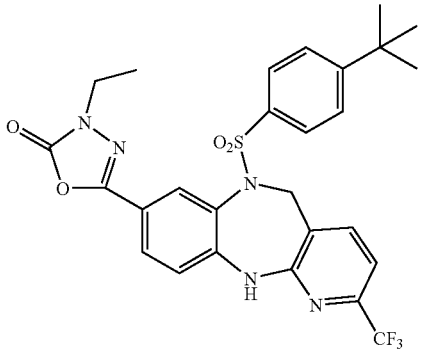

The title compound was prepared following the procedure described in Example 442 substituting iodoethane for iodomethane. LC/MS: m/e 574.1 (M+H)$^+$.

EXAMPLE 444

5-[6-[(4-tert-Butylphenyl)sulfonyl]-2-(trifluoromethyl)-6,11-dihydro-5H-pyrido[2,3-b]-[1,5]benzodiazepin-8-yl]-1,3,4-oxadiazole-2(3H)-thione

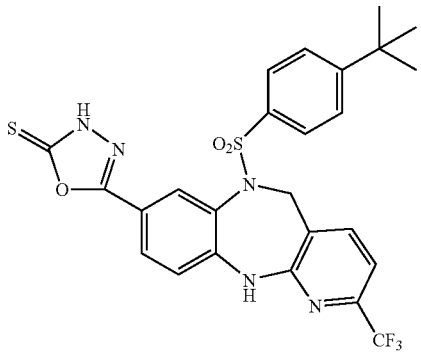

To a solution of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.040 g, 0.0771 mmol) in THF (0.6 mL) at −78° C was added thiophosgene (0.010 mL). After stirring for 1 h at −78° C, the reaction was quenched with saturated aqueous NaHCO$_3$ and the product was extracted with EtOAc. The combined extracts were washed with brine, dried (MgSO$_4$) and concentrated. The residue was purified by SiO$_2$ column chromatography, eluting with mixtures of EtOAc in hexanes, to provide the title compound. LC/MS: m/e 562.1 (M+H)$^+$. $^1$H NMR (500 MHz, CDCl$_3$): δ 8.22 (1H, d, J=1.8 Hz), 7.82 (1H, dd, J=8.4, 2.0 Hz), 7.65 (1H, d, J=7.4 Hz), 7.17 (1H, d, J=7.5 Hz), 7.13-7.16

(2H, m), 7.10 (1H, br s), 6.97-6.99 (2H, m), 6.88 (1H, d, J=8.5 Hz), 4.70-4.95 (2H, br), 1.25 (9H, s).

EXAMPLE 445

5-[6-[(4-tert-Butylphenyl)sulfonyl]-2-(trifluoromethyl)-6,11-dihydro-5H-pyrido[2,3-b][1,5]benzodiazepin-8-yl]-1,3,4-oxadiazol-2-amine

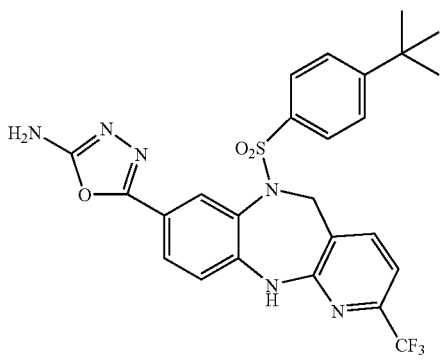

To a solution of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.040 g, 0.0771 mmol) and NaHCO$_3$ (7 mg in 0.187 mL of water) in dioxane (0.75 mL) was added cyanogen bromide (9 mg in 0.084 mL of dioxane) was in four equal portions over 5 min. After stirring at rt for 2 h, the reaction was quenched with saturated aqueous NaHCO$_3$ and the product was extracted with EtOAc and DCM. The combined extracts were washed with brine, dried (MgSO$_4$) and concentrated. The residue was purified by SiO$_2$ column chromatography to provide the title compound. LC/MS: m/e 545.1 (M+H)$^+$. $^1$H NMR (500 MHz, CD$_3$OD): δ 7.78 (1H, s), 7,76 (1H, d, J=8.5 Hz), 7.67 (1H, d, J=3.6 Hz), 7.63 (1H, d, J=7.3 Hz), 7.07-7.13 (3H, m), 6.91 (1H, d, J=8.5 Hz), 4.6-4.9 (2H, br), 3.53 (3H, s), 1.22 (9H, s).

EXAMPLE 446

5 6-[(4-tert-Butylphenyl)sulfonyl]-8-(5-methyl-1,3,4-oxadiazol-2-yl)-2-(trifluoromethyl)-6,11-dihydro-5H-pyrido[2,3-b][1,5]benzodiazepine

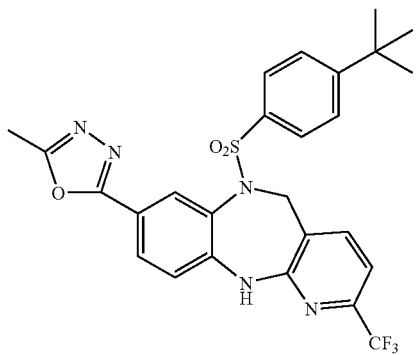

To a solution of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.040 g, 0.0771 mmol) and triethylamine (0.038 mL) in THF (0.65 mL) at rt was added acetyl chloride (8.5 mg, 0.108 mmol), and the reaction was stirred at rt overnight. The volatiles were removed and the residue was chromatographed on a SiO$_2$ column to provide acetyl product, which was mixed with POCl$_3$ (60 mg, 0.4 mmol) and acetonitrile (0.14 mL), and was stirred at 80° C. for 3 h. The volatiles were removed, and the residue was purified by SiO$_2$ column chromatography to provide the title compound. LC/MS: m/e 544.1 (M+H)$^+$. $^1$H NMR (500 MHz, CDCl$_3$): δ 8.21 (1H, d, J=1.9 Hz), 8.02 (1H, dd, J=8.5, 2.1 Hz), 7.63 (1H, d, J=7.5 Hz), 7.15 (1H, d, J=7.6 Hz), 7.13 (1H, d, J=8.7 Hz), 7.04 (1H, br s), 6.96 (2H, J=8.5 Hz), 6.90 (1H, d, J=8.6 Hz), 4.65-4.95 (2H, br), 2.67 (3H, s), 1.26 (9H, s).

EXAMPLE 447

6-[(4-tert-Butylphenyl)sulfonyl]-8-(5-methyl-4H-1,2,4-triazol-3-yl)-2-(trifluoromethyl)-6,11-dihydro-5H-pyrido[2,3-b][1,5]benzodiazepine

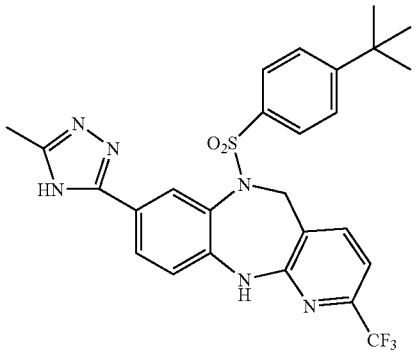

A mixture of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.025 g, 0.048 mmol), ethyl acetimidate hydrochloride (6.6 mg, 0.053 mmol), triethylamine (11 mg, 0.11 mmol), and MeCN (0.15 mL) was heated in a microwave reactor at 200° C. for 1 h. The reaction was partitioned between water and DCM, and the product was extracted with DCM. The combined extracts were washed with brine, dried (MgSO$_4$) and concentrated. The residue was purified by SiO$_2$ column chromatograph, elution with mixtures of EtOAc in hexanes to provide the title compound. LC/MS: m/e 543.1 (M+H)$^+$. $^1$H NMR (500 MHz, CDCl$_3$): δ 8.12 (1H, s), 7.92 (1H, s), 7.57 (1H, d, J=6.8 Hz), 7.20-7.60 (3H, m), 6.87-6.93 (3H, m), 4.40-5.20 (3H, br), 2.53 (3H, s), 1.22 (9H, s).

EXAMPLE 448

6-[(4-tert-Butylphenyl)sulfonyl]-8-(3-methyl-1,2,4-oxadiazol-5-yl)-2-(trifluoromethyl)-6,11-dihydro-5H-pyrido[2,3-b][1,5]benzodiazepine

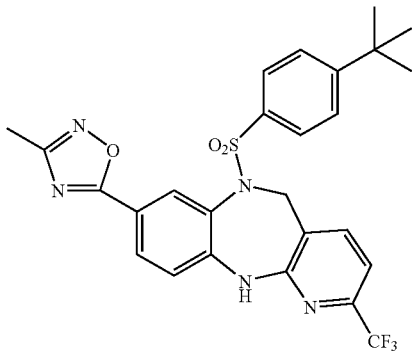

A mixture of 6-[(4-tert-butylphenyl)sulfonyl]-2-(trifluoromethyl)-6,11-dihydro-5H-pyrido[2,3-b][1,5]benzodiazepine-8-carboxylic acid (intermediate 58, 60 mg, 0.119 mmol), acetamide oxime (10 mg, 0.141 mmol), DIPEA (18 mg, 0.141 mmol), HOBt (19 mg, 0.14 mmol), DIC (23 mg, 0.18 mmol) in DCM (0.4 mL) and DMF (0.1 mL) was stirred at rt for 3 h. The reaction was quenched with water and the product was extracted with EtOAc. The combined extracts were washed with 5% NaHCO$_3$, brine, dried (MgSO$_4$) and concentrated. The residue was dissolved in NMP and was heated in a microwave reactor at 120° C. for 1 h. The reaction was quenched with water and the product was extracted with EtOAc. The extracts were washed with water and brine, dried (MgSO$_4$) and concentrated. Flash column purification of the residue on SiO$_2$ afforded the title compound. LC/MS: m/e 544.1 (M+H)$^+$. $^1$H NMR (500 MHz, CDCl$_3$): δ 8.38 (1H, d, J=1.6 Hz), 8.00 (1H, dd, J=8.4, 1.8 Hz), 7.63 (1H, d, J=7.4 Hz), 7.16 (1H, d, J=7.4 Hz), 7.13 (1H, d, J=8.4 Hz), 7.05 (1H, br s), 6.97 (2H, J=8.5 Hz), 6.90 (1H, d, J=8.4 Hz), 4.65-4.95 (2H, br), 2.51 (3H, s), 1.26 (9H, s).

EXAMPLE 449

{5-[6-[(4-tert-Butylphenyl)sulfonyl]-2-(trifluoromethyl)-6,11-dihydro-5H-pyrido[2,3-b][1,5]benzodiazepin-8-yl]-1,3,4-thiadiazol-2-yl}methanol

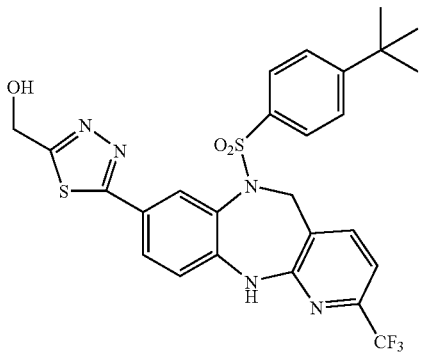

Step A: A solution of 6-[(4-tert-butylphenyl)sulfonyl]-2-(trifluoromethyl)-6,11-dihydro-5H-pyrido[2,3-b][1,5]benzodiazepine-8-carbohydrazide (intermediate 57, 0.170 g, 0.328 mmol), 2-benzyloxyacetic acid (60 mg, 0.360 mmol), DIPEA (106 mg, 0.82 mmol), PyBOP (187 mg, 0.360 mmol) in DCM (3 mL) and DMF (5 mL) was heated to 35° C. overnight. The volatiles were removed and the residue was dissolved in EtOAc and washed with aqueous 5% NaHCO$_3$, brine, dried (MgSO$_4$) and concentrated. The residue was purified by SiO$_2$ column chromatography, eluting with mixtures of EtOAc in hexanes, to provide the desired product. LC/MS: m/e 667.5 (M+H)$^+$.

Step B: To the product from Step A (18 mg) in toluene (0.15 mL) was added fresh Lawesson's reagent (15 mg). After refluxing for 2 h, the mixture was cooled to rt and the volatiles were removed under reduced pressure. The residue was purified via SiO$_2$ column chromatography, eluting with mixtures of EtOAc in hexanes, to provide the product.

Step C: The product of Step B was debenzylated according to the procedure in Example 437, Step C, to provide the title compound. LC/MS: m/e 576.0 (M+H)$^+$. $^1$H NMR (500 MHz, DMSO-d$_6$): δ 7.90 (1H, d, J=2.1 Hz), 7.81 (1H, dd, J=8.7, 2.1 Hz), 7.77 (1H, d, J=7.6 Hz), 7.42 (1H, d, J=8.6 Hz), 7.15-7.23 (3H, m), 7.09-7.15 (1H, m), 6.96 (2H, J=8.4 Hz), 4.65-5.15 (2H, br), 4.88 (2H, s), 1.17 (9H, s).

EXAMPLE 450

1-{[6[(4-tert-Butylphenyl)sulfonyl]-2-(trifluoromethyl)-6,11-dihydro-5H-pyrido[2,3-b][1,5]benzodiazepin-8-yl]carbonyl}azetidin-3-ol

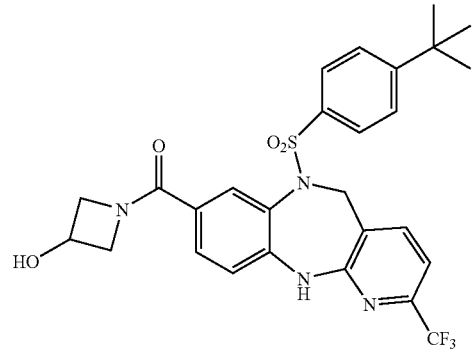

Step A: 6-[(4-tert-butylphenyl)sulfonyl]-2-(trifluoromethyl)-6,11-dihydro-5H-pyrido[2,3-b][1,5]benzodiazepine-8-carboxylic acid (intermediate 58, 14 mg, 0.0277 mmol) was treated with 3-benzyloxyazetidine hydrochloride (6 mg, 0.03 mmol) and PyBOP according to the procedure described in Example 13, Step A. The desired product was obtained by column chromatography on silica gel. LC/MS: m/e 651.1 (M+H)$^+$.

Step B: The product from Step A was treated according to the procedure described in Example 437, Step C, to provide the title compound. LC/MS: m/e 561.0 (M+H)$^+$. $^1$H NMR (500 MHz, CDCl$_3$): δ 7.80 (1H, s), 7.68 (1H, d, J=8.2 Hz), 7.58 (1H, d, J=7.6 Hz), 7.15-7.23 (3H, m), 7.08-7.11 (3H, m), 6.87 (2H, J=8.5 Hz), 6.82 (1H, J=8.3 Hz), 4.71 (2H, m), 4.69 (1H, m), 4.48 (1H, m), 4.35 (1H, m), 4.10 (1H, m), 2.90 (m, 1H), 1.22 (9H, s).

The compounds in Table 22 were prepared from intermediate 58 and azetidine following procedures described for Example 436.

TABLE 22

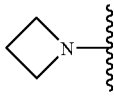

| Example | R4a | LCMS: found m/e (M + H) |
|---|---|---|
| 451 | azetidin-1-yl | 545.1 |

EXAMPLE 452

{3-[6-[(4-tert-Butylphenyl)sulfonyl]-10-iodo-2-(trifluoromethyl)-6,11-dihydro-5H-pyrido[2,3-b][1,5]benzodiazepin-8-yl]-1,2,4-oxadiazol-5-yl}methanol

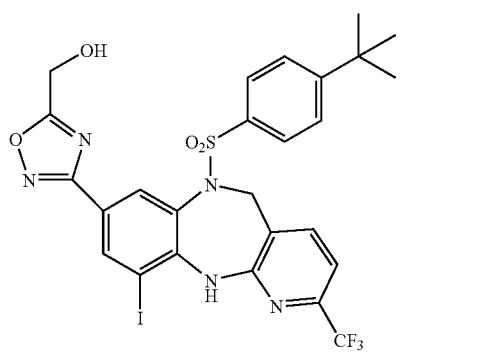

To a solution of {3-[6-[(4-tert-butylphenyl)sulfonyl]-2-(trifluoromethyl)-6,11-dihydro-5H-pyrido[2,3-b][1,5]benzodiazepin-8-yl]-1,2,4-oxadiazol-5-yl}methanol (Example 437, 49 mg, 0.0877 mmol) (1.5 mL) and N-iodosuccinimide (21 mg) in DCM at 0° C. was added trifluoroacetic acid (30 mg, 0.263 mmol). After stirring for 2 h, the reaction was quenched with 10% aqueous $Na_2S_2O_3$ and the product was extracted with EtOAc. The combined extracts were washed with water, brine, dried ($MgSO_4$) and concentrated. The residue was purified by $SiO_2$ column chromatography, eluting with 50% EtOAc in hexanes, to provide the title compound. LC/MS: m/e 586.0 (M+H)+. $^1$H NMR (500 MHz, CDCl$_3$): δ 8.55 (1H, d, J=1.8 Hz), 8.32 (1H, d, J=1.8 Hz), 7.64 (1H, d, J=7.6 Hz), 7.28 (1H, s), 7.20 (1H, J=7.5 Hz), 7.13 (2H, J=8.4 Hz), 6.86 (2H, J=8.5 Hz), 5.02 (2H, s), 4.30-5.0 (2H, br), 2.75 (1H, s br), 1.30 (9H, s).

EXAMPLE 453

8-(Azetidin-1-ylmethyl)-6-[(4-tert-butylphenyl)sulfonyl]-2-(trifluoromethyl)-6,11-dihydro-5H-pyrido[2,3-b][1,5]benzodiazepine

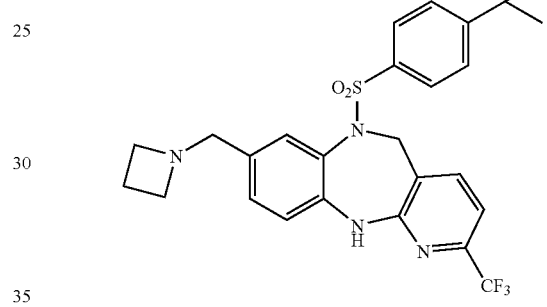

Step A: To 6-[(4-tert-Butylphenyl)sulfonyl]-2-(trifluoromethyl)-6,11-dihydro-5H-pyrido[2,3-b][1,5]benzodiazepine-8-carbonitrile (intermediate 54, 210 mg, 0.432 mmol) in DCM (4.0 mL) at −78° C., was added DIBAL-H (1.7 mL of a 1M solution in toluene). After 15 min, the reaction was quenched with saturated aqueous NH$_4$Cl, and the product was extracted with EtOAc. The combined extracts were washed with water, brine, dried (MgSO$_4$) and concentrated to provide the aldehyde product, which was used without further purification. LC/MS: m/e 490.0 (M+H)+.

Step B: A mixture of the aldehyde product from Step A (49 mg, 0.1 mmol), azetidine hydrochloride (9.4 mg, 0.1 mmol), dichloroethane (0.35 mL), sodium triacetoxyborohydride (30 mg, 0.14 mmol), and triethylamine (10 mg, 0.1 mmol) was stirred at rt overnight. The reaction was quenched with water and the product was extracted with ethyl acetate. The combined extracts were washed with water, brine, and dried (MgSO$_4$) and concentrated. The residue was purified by SiO$_2$ column chromatography (eluting with mixtures of MeOH in DCM) to afford the title compound. LC/MS: m/e 531.1 (M+H)+. $^1$H NMR (500 MHz, CDCl$_3$): δ 7.56 (1H, d, J=7.3 Hz), 7.52 (1H, s), 7.24 (1H, d, J=7.1 Hz), 7.10 (2H, d, J=8.5

Hz), 7.05 (1H, d, J=7.5 Hz), 6.92 (2H, J=8.4 Hz), 6.71 (2H, J=8.4 Hz), 4.65-4.9 (2H, br), 3.35 (4H, m), 2.17 (2H, m), 1.25 (9H, s).

EXAMPLE 454

1-[6-[(4-tert-Butylphenyl)sulfonyl]-2-(trifluoromethyl)-6,11-dihydro-5H-pyrido[2,3-b][1,5]benzodiazepin-8-yl]ethanone

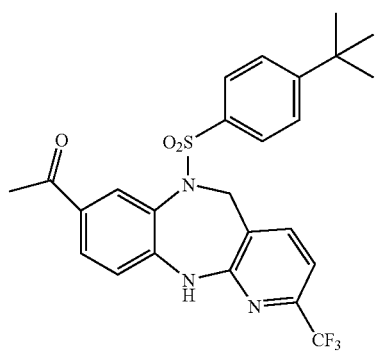

To a mixture of 8-bromo-6-[(4-tert-butylphenyl)sulfonyl]-2-(trifluoromethyl)-6,11-dihydro-5H-pyrido[2,3-b][1,5]benzodiazepine (270 mg, 0.5 mmol, from intermediate 53, Pd(dppf)Cl$_2$ (165 mg, 0.2 mmol), and LiCl (21 mg, 0.5 mmol) were dissolved in NMP (1.5 mL) under N$_2$ was added tri-n-butyl(1-ethoxyvinyl)tin (180 mg, 0.5 mmol), and the resulting mixture was stirred at 90° C. for 1 h. The cooled reaction mixture was poured into 1M HCl/Et$_2$O (5 mL) and stirred vigorously for 2 h. The product was extracted with EtOAc and the combined extracts were washed with water, brine, dried over MgSO$_4$, and concentrated. The residue was purified by SiO$_2$ column chromatography to provide the title compound. LC/MS: m/e 504.0 (M+H)$^+$. $^1$H NMR (500 MHz, CDCl$_3$): δ 8.19 (1H, s), 7.92 (1H, d, J=8.4 Hz), 7.64 (1H, d, J=7.6 Hz), 7.15 (1H, d, J=7.5 Hz), 7.12 (2H, d, J=8.4 Hz), 7.01 (1H, s), 6.94 (2H, d, J=8.2 Hz), 6.83 (1H, d, J=8.4 Hz), 4.65-4.9 (2H, br), 2.64 (3H, s), 1.25 (9H, s).

EXAMPLE 455

1-[6-[(4-tert-Butylphenyl)sulfonyl]-2-(trifluoromethyl)-6,11-dihydro-5H-pyrido[2,3-b][1,5]benzodiazepin-8-yl]ethanone oxime

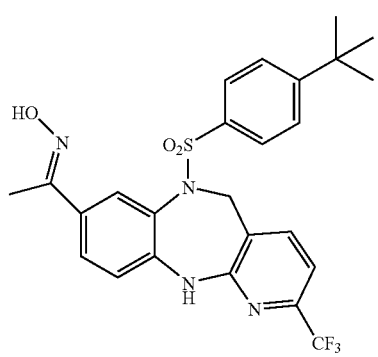

A mixture of 1-[6-[(4-tert-butylphenyl)sulfonyl]-2-(trifluoromethyl)-6,11-dihydro-5H-pyrido[2,3-b][1,5]benzodiazepin-8-yl]ethanone (Example 454, 19 mg, 0.0378 mmol), hydroxylamine hydrochloride (2.9 mg, 0.042 mmol), pyridine (0.15 mL), and ethanol (0.15 mL) was heated in a microwave reactor at 160° C. for 10 min. The volatiles were removed, and the residue was triturated with hexane/DCM. The solid was collected and dried to provide the title compound. LC/MS: m/e 504.0 (M+H)$^+$. $^1$H NMR (500 MHz, acetone-d6): δ 8.88 (1H, s), 8.45 (1H, s), 7.78 (1H, s), 7.73 (1H, d, J=7.5 Hz), 7.64 (1H, d, J=8.5 Hz), 7.27 (1H, d, J=8.4 Hz), 7.20 (2H, d, J=8.0 Hz), 7.14 (1H, d, J=7.3 Hz), 6.97 (2H, d, J=7.8 Hz), 4.70-4.95 (2H, br), 2.05 (3H, s), 1.23 (9H, s).

EXAMPLE 456

1-[6-[(4-tert-butylphenyl)sulfonyl]-2-(trifluoromethyl)-6,11-dihydro-5H-pyrido[2,3-b][1,5]benzodiazepin-8-yl]ethanone methoxime

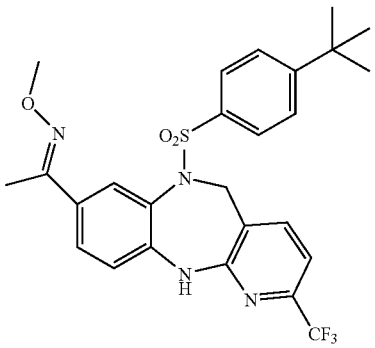

The title compound was obtained following the procedure of Example 455 substituting methoxylamine hydrochloride for hydroxylamine hydrochloride. LC/MS: m/e 533.0 (M+H)$^+$.

EXAMPLE 457

{3-[6-[(4-tert-Butylphenyl)sulfonyl]-2-(trifluoromethyl)-6,11-dihydro-5H-pyrido[2,3-b]-[1,5]benzodiazepin-8-yl]-1,2,4-oxadiazol-5-yl}methyl dihydrogen phosphate

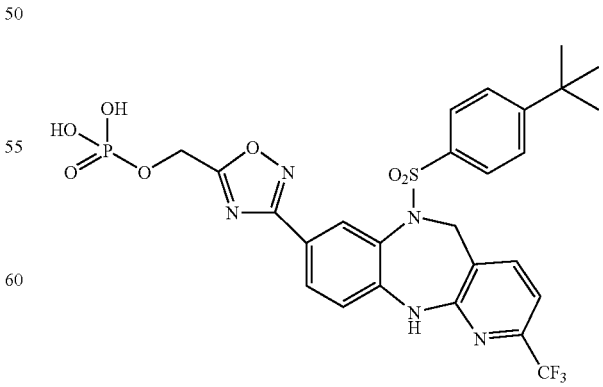

Step A: To a solution of {3-[6-[(4-tert-butylphenyl)sulfonyl]-2-(trifluoromethyl)-6,11-dihydro-5H-pyrido[2,3-b][1, 5]benzodiazepin-8-yl]-1,2,4-oxadiazol-5-yl}methanol (Example 437, 100 mg, 0.18 mmol) in chloroform (1.0 mL) was added 1H-tetrazole (28 mg, 0.39 mmol) and di-t-butyl diethylphosphoramidite (90 mg, 0.36 mmol). After stirring overnight at rt, the reaction mixture was cooled to −25° C. and was added peracetic acid (0.16 mL) dropwise. After stirring at rt for another 5 h, the reaction was quenched with aqueous 10% $NaHSO_3$ (4 mL). The organic layer was separated and the aqueous layer was extracted with EtOAc. The combined extracts were washed with 5% $NaHCO_3$, dried over $MgSO_4$ and concentrated. The residue was purified by $SiO_2$ column chromatography, eluting with mixtures of EtOAc in hexanes, to provide the desired protected phosphate ester.

Step B: To the phosphate ester product from Step A at 0° C. was added a 2M solution of HCl in EtOAc (1.0 mL), and the reaction was stirred at rt overnight. The volatiles were removed and the residue was triturated with a ether-hexane, and the product was obtained by filtration. LC/MS: m/e 640.0 $(M+H)^+$. $^1$H NMR (500 MHz, acetone-d6): δ 8.74 (1H, s), 8.21 (1H, s), 7.96 (1H, dd, J=8.7, 1.9 Hz), 7.79 (1H, d, J=7.3 Hz), 7.48 (1H, s), 7.43 (1H, d, J=8.7 Hz), 7.19-7.23 (3H, m), 6.98 (2H, d, J=8.4 Hz), 6.16 (1H, s), 5.33 (1H, br s), 4.90 (1H, br s), 1.24 (9H, s).

EXAMPLE 458

N-{(1R)-1-[6-[(4-tert-Butylphenyl)sulfonyl]-2-(trifluoromethyl)-6,11-dihydro-5H-pyrido[2,3-b][1,5]benzodiazepin-8-yl]ethyl}acetamide

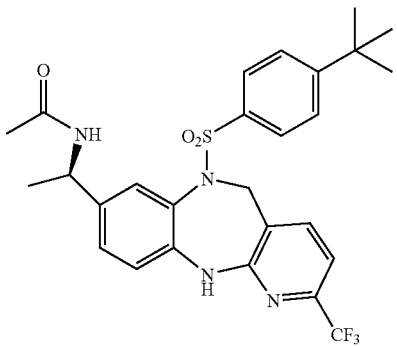

Step A: To a solution of (S)-(−)-2-methyl-2-propanesulfinamide (45 mg, 0.36 mmol) and titanium tetra(isopropoxide) (204 mg, 0.72 mmol) in THF (0.10 mL) was added 1-[6-[(4-tert-butylphenyl)sulfonyl]-2-(trifluoromethyl)-6,11-dihydro-5H-pyrido[2,3-b][1,5]benzodiazepin-8-yl]ethanone (Example 454, 30 mg, 0.060 mmol) in THF (0.24 mL), and the mixture was heated in a microwave reactor at 100° C. for 10 h. After cooling to rt, the mixture was added dropwise to a rapidly stirred mixture of sodium borohydride (36 mg) in THF (0.20 mL) at −78° C. The reaction was allowed to warm up to rt, and was quenched with MeOH. The resulting mixture was diluted with brine and EtOAc, filtered through Celite and the cake was washed with EtOAc. The filtrate was washed with brine, dried over $MgSO_4$ and concentrated. The residue was purified by $SiO_2$ column chromatography, eluting with mixtures of EtOAc in hexanes, to provide the sulfinamide. LC/MS: m/e 608.9 $(M+H)^+$.

Step B: To a solution of the sulfonamide product of Step A in MeOH (0.12 mL) was added a 2M solution of HCl(g) in EtOAc. After stirring for 2 h at rt, the volatiles were removed and the residue was triturated with ether. The desired amine product was collected by filtration. LC/MS: m/e 504.1 $(M+H)^+$.

Step C: To the amine of Step B in pyridine (0.075 mL) was added acetic anhydride (0.025 mL), and the reaction was stirred at rt for 5 h. The volatiles were removed under reduced pressure and azeotroped with heptane. The residue was purified on $SiO_2$, eluting with mixtures of EtOAc in hexane, to provide the title compound. LC/MS: m/e 547.1 $(M+H)^+$. $^1$H NMR (500 MHz, $CDCl_3$): δ 7.55 (1H, d, J=7.6 Hz), 7.54 (1H, d, J=1.9 Hz), 7.30 (1H, s), 7.25 (1H, dd, J=8.5, 2.1 Hz), 7.12 (2H, d, J=8.5 Hz), 7.06 (1H, s), 6.94 (2H, d, J=8.7 Hz), 6.89 (1H, s), 6.74 (1H, d, J=8.3 Hz), 5.85 (1H, br s), 5.12-5.17 (1H, m), 4.70-4.90 (2H, br), 2.07 (3H, s), 1.54 (3H, d, J=7.1 Hz) 1.25 (9H, s).

EXAMPLE 459

N-{(1S)-1-[6-[(4-tert-butylphenyl)sulfonyl]-2-(trifluoromethyl)-6,11-dihydro-5H-pyrido[2,3-b][1,5]benzodiazepin-8-yl]ethyl}acetamide

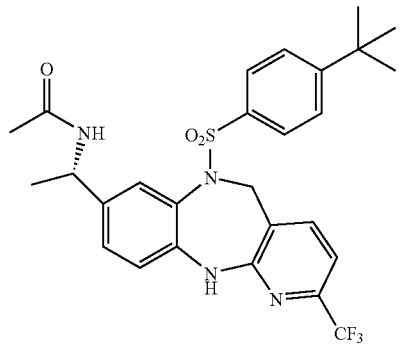

The title compound was prepared following the procedure described for Example 458 substituting (R)-(+)-2-methyl-2-propanesulfinamide for (S)-(−)-2-methyl-2-propanesulfinamide. LC/MS: m/e 547.1 $(M+H)^+$.

EXAMPLE 460

1-[6-[(4-tert-Butylphenyl)sulfonyl]-2-(trifluoromethyl)-6,11-dihydro-5H-pyrido[2,3-b][1,5]benzodiazepin-8-yl]ethanol

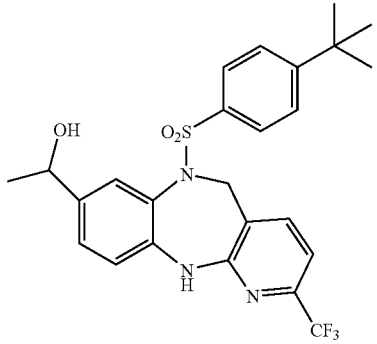

Step A: To a solution of 1-[6-[(4-tert-butylphenyl)sulfonyl]-2-(trifluoromethyl)-6,11-dihydro-5H-pyrido[2,3-b][1,5]benzodiazepin-8-yl]ethanone (Example 454, 100 mg, 0.200 mmol) in THF (0.50 mL) was added borane-THF complex (0.700 mL of 1M solution). After stirring at rt for 2 h, the reaction mixture was cooled to 0° C. and was quenched with 3N HCl, and the stirring continued at rt for 1 h. The product was extracted into EtOAc, and the combined extracts were washed with water, brine, dried over $MgSO_4$ and concentrated. The residue was purified by $SiO_2$ column chromatography, eluting with mixtures of EtOAc in hexane, to provide title compound as a racemic mixture. LC/MS: m/e 506.0 (M+H)+. $^1$H NMR (500 MHz, $CDCl_3$): δ 7.59 (1H, d, J=1.9 Hz), 7.56 (1H, d, J=7.3 Hz), 7.35 (1H, dd, J=8.4, 2.0 Hz), 7.12 (21-1, d, J=8.4 Hz), 7.05 (1H, d, J=7.5 Hz), 6.96 (2H, d, J=8.5 Hz), 6.85 (1H, s), 6.74 (1H, d, J=8.3 Hz), 4.95 (1H, q, J=6.4 Hz), 4.80 (1H, br s), 1.57 (3H, d, J=6.7 Hz), 1.26 (9H, s). The racemic mixture was separated into its enantiomers eluting on a Chiracel AD-H column (isocratic 15% EtOH in hexanes, 8 mL/min, 254 nM) with retention time of 22 min and 33 min, respectively. Faster enantiomer E1: LC/MS: m/e 506.0 (M+H)+. Slower enantiomer E2: LC/MS: m/e 506.0 (M+H).

EXAMPLE 461

2-[6-[(4-tert-Butylphenyl)sulfonyl]-2-(trifluoromethyl)-6,11-dihydro-5H-pyrido[2,3-b][1,5]benzodiazepin-8-yl]propanenitrile

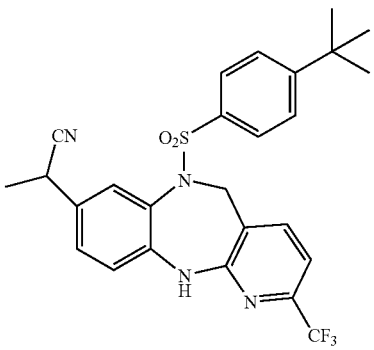

Step A: A mixture of 1-[6-[(4-tert-butylphenyl)sulfonyl]-2-(trifluoromethyl)-6,11-dihydro-5H-pyrido[2,3-b][1,5]benzodiazepin-8-yl]ethanol (Example 458, 105 mg) and acetic anhydride (0.15 mL) in pyridine (0.40 mL) was stirred at rt for 4 h. The volatiles were removed under reduced pressure and were azeotroped with heptane to afford the acetylated product. LC/MS: m/e 548.1 (M+H)+.

Step B: To a solution of the acetate product from Step A (54 mg, 0.100 mmol) in THF (1.5 mL) at 0° C. was added diethyl aluminum cyanide (1 mL of a 1M solution in toluene), and the reaction was heated at 40° C. for 4 h. After cooling to rt, the reaction was quenched with saturated aqueous ammonium chloride. The product was extracted with EtOAc, and the combined extracts were washed with water, brine, dried over $MgSO_4$ and concentrated. The residue was purified on $SiO_2$, eluting with EtOAc in hexanes, to provide the title compound as a racemic mixture. LC/MS: m/e 515.0 (M+H)+. $^1$H NMR (500 MHz, $CDCl_3$): δ 7.58 (1H, d, J=7.3 Hz), 7.55 (1H, d, J=2.2 Hz), 7.35 (1H, dd, J=8.2, 2.0 Hz), 7.13 (2H, d, J=8.5 Hz), 7.09 (1H, d, J=7.5 Hz), 6.5 (2H, d, J=8.4 Hz), 6.80 (3H, m), 4.70-4.95 (2H, br s), 1.72 (3H, d, J=7.3 Hz), 1.26 (9H, s).

The racemic mixture was separated into its individual enantiomers by eluting on a Chiracel AS column (isocratic 35% EtOH in hexanes, 8 mL/min, 254 nM). Faster enantiomer E1: LC/MS: m/e 515.0 (M+H)+. Slower enantiomer E2: LC/MS: m/e 515.0 (M+H).

EXAMPLE 462

2-[6-[(4-tert-Butylphenyl)sulfonyl]-2-(trifluoromethyl)-6,11-dihydro-5H-pyrido[2,3-b][1,5]benzodiazepin-8-yl]propanoic acid

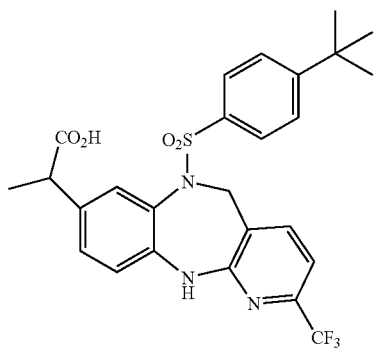

A solution of 2-[6-[(4-tert-butylphenyl)sulfonyl]-2-(trifluoromethyl)-6,11-dihydro-5H-pyrido[2,3-b][1,5]benzodiazepin-8-yl]propanenitrile (Example 461, 8 mg) and KOH (0.010 mL of a 10M aqueous solution) in EtOH (0.020 mL) was heated at 80° C. for 4 h. The mixture was acidified with 6N HCl until pH=1, and was extracted with EtOAc. The combined extracts were washed with brine, dried over $MgSO_4$ and concentrated. The residue was purified on $SiO_2$ to provide the title compound. LC/MS: m/e 534.0 (M+H)+. $^1$H NMR (500 MHz, $CDCl_3$): δ 7.74 (1H, m), 7.56 (1H, m), 7.26 (1H, dd, J=8.5, 2.1 Hz), 7.11 (2H, d, J=8.5 Hz), 7.05 (2H, m), 6.94 (2H, d, J=8.7 Hz), 6.77 (1H, d, J=8.2 Hz), 4.70-4.95 (2H, br s), 4.30 (1H, m), 1.60 (311, d, J=7.3 Hz), 1.26 (9H, s).

EXAMPLE 463

1-[6-[(4-tert-Butylphenyl)sulfonyl]-2-(trifluoromethyl)-6,11-dihydro-5H-pyrido[2,3-b][1,5]benzodiazepin-8-yl]-2,2,2-trifluoroethanone

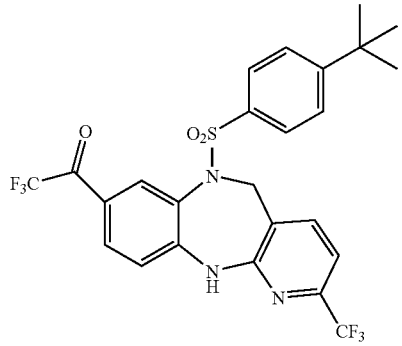

A solution of 8-bromo-6-[(4-tert-butylphenyl)sulfonyl]-2-(trifluoromethyl)-6,11-dihydro-5H-pyrido[2,3-b][1,5]benzodiazepine (intermediate 53, 540 mg, 1 mmol) in THF (1.0 mL) was added dropwise to an oil-free suspension of KH (48 mg, 1.2 mmol) in THF (2 mL) at 0° C. under nitrogen. After stirring at 0° C. for 15 minutes, the reaction mixture was cooled to −78° C. and was added t-BuLi in pentane (1.1 mL of a 1.7 M solution). After 15 min, trifluoroacetic anhydride (420 mg, 2 mmol) was added dropwise. After another 15 min, the reaction was quenched with aqueous saturated NH$_4$Cl, and the product was extracted with EtOAc. The combined extracts were washed with water, brine, dried over MgSO$_4$ and concentrated. The residue was purified by SiO$_2$ column chromatography, eluting with mixtures of EtOAc in hexane, to provide the title compound. LC/MS: m/e 557.9 (M+H)$^+$. $^1$H NMR (500 MHz, CDCl$_3$): δ 9.80 (1H, s), 8.77 (1H, d, J=8.5 Hz), 8.17 (1H, d, J=7.5 Hz), 8.09 (1H, d, J=8.3 Hz), 7.79 (2H, d, J=8.5 Hz), 7.60 (2H, m), 7.46 (2H, m), 5.70-6.30 (2H, br s), 1.35 (9H, s).

EXAMPLE 464

6-[(4-tert-Butylphenyl)sulfonyl]-2-(trifluoromethyl)-6,11-dihydro-5H-dipyrido[2,3-e:3',4'-b][1,4]diazepine

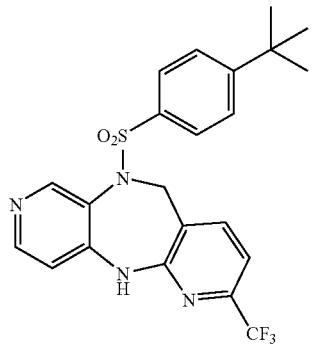

Step A: A mixture of 4-amino-3-nitropyridine (334 mg, 2.4 mmol), 2-chloro-6-(trifluoromethyl)-nicotinaldehyde (420 mg, 2.0 mmol), Xantphos (128 mg, 0.22 mmol), Pd$_2$(dba)$_3$ (92 mg, 0.10 mmol), and Na$_2$CO$_3$ (300 mg, 2.8 mmol) was flushed with nitrogen before addition of t-butanol (20 mL). The resulting mixture was heated at 100° C. for 15 h. After cooling to rt, the reaction mixture was diluted with EtOAc, filtered over a pad of silica gel, and the filter cake was washed with EtOAc. The filtrate was washed with water, brine, dried over MgSO$_4$ and concentrated. The residue was purified by SiO$_2$ column chromatography to provide the desired product. LC/MS: m/e 313.2 (M+H)$^+$.

Step B: A mixture of the product from Step A (117 mg) in EtOAc (5.5 mL), and 10% Pd/C (12 mg) was stirred for 2 days at 45° C. under a balloon of hydrogen. After cooling to rt, the reaction mixture was filtered through a pad of silica gel, and the cake was washed with EtOAc. The filtrate was concentrated, and the residue was purified via SiO$_2$ column chromatography to provide the desired product. LC/MS: m/e 267.1 (M+H)$^+$.

Step C: A mixture of the product of Step B (20 mg, 0.0752 mmol), 4-(t-butyl)phenylsulfonyl chloride (53 mg, 0.226 mmol), DMAP (9.2 mg, 0.0752 mmol) in DCM (0.030 mL) and t-amyl alcohol (0.300 mL) was heated in a microwave reactor at 120° C. for 1.5 h. After cooling to rt, the reaction was diluted with water and the product was extracted with EtOAc. The combined extracts were washed with water, brine, dried over MgSO$_4$ and concentrated. The residue was purified via SiO$_2$ column chromatography, eluting with mixtures of EtOAc in hexanes, to provide the title compound. LC/MS: m/e 463.0 (M+H)$^+$. $^1$H NMR (500 MHz, CDCl$_3$): δ 8.73 (1H, s), 8.37 (1H, d, J=5.4 Hz), 7.71 (1H, d, J=7.5 Hz), 7.40 (1H, s), 7.25 (1H, d, J=7.6 Hz), 7.14 (2H, d, J=8.7 Hz), 6.95 (2H, d, J=8.7 Hz), 6.83 (1H, d, J=5.7 Hz), 4.70-4.95 (2H, br s), 1.26 (9H, s).

EXAMPLE 465

7-(1H-Tetrazol-5-yl)-6-{[4-(trifluoromethoxy)phenyl]sulfonyl}-2-(trifluoromethyl)-6,11-dihydro-5H-pyrido[2,3-b][1,5]benzodiazepine

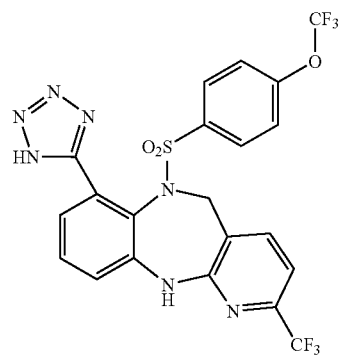

A mixture of 6-[(4-tert-butylphenyl)sulfonyl]-2-(trifluoromethyl)-6,11-dihydro-5H-pyrido[2,3-b][1,5]benzodiazepine-7-carbonitrile (400 mg, 0.778 mmol, from intermediate 7), trimethyltin azide (800 mg, 3.89 mmol), and p-xylene (2.0 mL) was stirred at 140° C. under argon for 2 h. After cooling to rt, the reaction mixture was treated with excess HCl in methanol. After stirring for 20 min, the volatiles were removed and the residue was purified by SiO$_2$ column chromatography, eluting with mixtures of MeOH in DCM, to provide the title compound. LC/MS: m/e 558.0 (M+H)$^+$. $^1$H NMR (500 MHz, acetone-d$_6$): δ 8.60 (1H, s), 7.81 (1H, d, J=7.5 Hz), 7.53-7.61 (3H, m), 7.20 (1H, d, J=7.6 Hz), 7.14-7.17 (2H, m), 7.09-7.11 (2H, m), 5.37 (1H, d, J=7.0 Hz), 4.91 (1H, d, J=6.7 Hz).

EXAMPLES 466A AND 466B 7-(1-Methyl-1H-tetrazol-5-yl)-6-{[4-(trifluoromethoxy)phenyl]sulfonyl}-2-(trifluoromethyl)-6,11-dihydro-5H-pyrido[2,3-b][1,5]benzodiazepine and 7-(2-Methyl-1H-tetrazol-5-yl)-6-{[4-(trifluoromethoxy)phenyl]sulfonyl}-2-(trifluoromethyl)-6,11-dihydro-5H-pyrido-[2,3-b][1,5]benzodiazepine

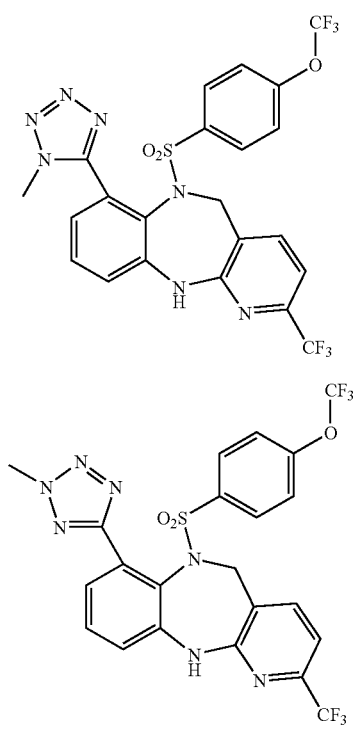

To a solution of 7-(1H-tetrazol-5-yl)-6-{[4-(trifluoromethoxy)phenyl]sulfonyl}-2-(trifluoromethyl)-6,11-dihydro-5H-pyrido[2,3-b][1,5]benzodiazepine (Example 462, 25 mg, 0.045 mmol) in DMF (0.30 mL) was added potassium carbonate (6.20 mg, 0.045 mmol). After stirring at room temperature for 1.5 h, the mixture was cooled to −25° C., and was added iodomethane (6.4 mg, 0.045 mmol). The reaction was allowed to warm up to 0° C. gradually. The reaction was quenched with water, and the product was extracted with EtOAc. The combined extracts were washed with water, brine, dried over MgSO$_4$, and concentrated. The residue was purified via SiO$_2$ column chromatography, eluting with mixtures of EtOAc in hexanes, to provide title compound 466A (TLC: Rf=0.10 in 33% EtOAc in hexanes) and title compound 466B (TLC: Rf=0.20 in 33% EtOAc in hexanes). Compound 466A: LC/MS: m/e 572.0 (M+H)$^+$. $^1$H NMR (500 MHz, acetone-d$_6$): δ 8.65 (1H, s), 7.79 (1H, d, J=7.6 Hz), 7.58-7.64 (2H, m), 7.35 (1H, dd, J=7.1, 1.6 Hz), 7.14-7.17 (2H, m), 7.20-7.24 (3H, m), 7.11 (2H, m), 5.21 (1H, d, J=6.7 Hz), 4.83 (1H, d, J=6.7 Hz), 4.20 (3H, s). Compound 466B: LC/MS: m/e 572.0 (M+H)$^+$. $^1$H NMR (500 MHz, acetone-d$_6$): δ 8.54 (1H, s), 7.82 (1H, d, J=7.5 Hz), 7.48-7.57 (3H, m), 7.23-7.25 (3H, m), 7.22-7.26 (2H, m), 7.19 (1H, d, J=7.5 Hz), 7.12 (1H, d, J=8.2 Hz), 5.35 (1H, d, J=7.2 Hz), 4.85 (1H, d, J=7.2 Hz), 4.48 (3H, s).

The compounds in Table 23 were prepared from Example 465 and the appropriate alkylating agents following procedures described for Examples 466A and 466B.

TABLE 23

| Example | Re | A: LC-MS: found m/e (M + H) | B: LC-MS: found m/e (M + H) |
|---------|-----|------------------------------|------------------------------|
| 467 | MeO—C(O)—CH$_2$— | 630.10 | 630.10 |
| 468 | CH$_3$CH(OH)CH$_2$— | 616.2 | 616.2 |

EXAMPLE 469A AND 469B

1-{5-[6-{[4-(Trifluoromethoxy)phenyl]sulfonyl}-2-(trifluoromethyl)-6,11-dihydro-5H-pyrido-[2,3-b][1,5]benzodiazepin-7-yl]-2H-tetrazol-2-yl}acetone and 2-Methyl-1-{5-[6-{[4-(trifluoromethoxy)-phenyl]sulfonyl}-2-(trifluoromethyl)-6,11-dihydro-5H-pyrido[2,3-b][1,5]benzodiazepin-7-yl]-2H-tetrazol-2-yl}propan-2-ol

469A

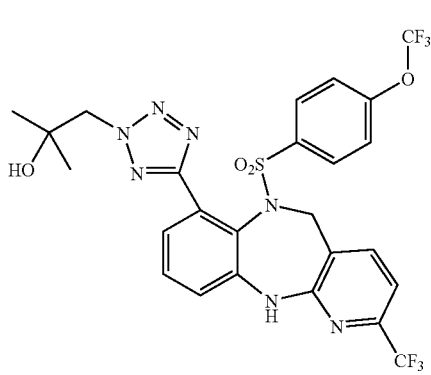

469B

To a solution of methyl {5-[6-{[4-(trifluoromethoxy)phenyl]sulfonyl}-2-(trifluoromethyl)-6,11-dihydro-5H-pyrido[2,3-b][1,5]benzodiazepin-7-yl]-2H-tetrazol-2-yl}acetate (Example 467B, 21 mg, 0.033 mmol) in THF (0.30 mL) was added methyl magnesium bromide (0.2 mmol) and the stirring continued at rt for 6 h. The reaction was quenched with water and the pH was adjusted to neutral with dilute citric acid. The mixture was extracted with EtOAc, and the combined organic layers were washed with water, brine, dried over MgSO$_4$, and concentrated. The residue was purified by SiO$_2$ column chromatography to provide compound 469A and compound 469B. Compound 469A: LC/MS: m/e 614.1 (M+H)$^+$. $^1$H NMR (500 MHz, CDCl$_3$): δ 7.68 (1H, d, J=7.5 Hz), 7.60 (1H, d, J=7.6 Hz), 7.45 (1H, m), 7.12-7.16 (2H, m), 6.92-7.00 (4H, m), 6.88 (1H, s), 5.51 (2H, m), 5.37 (1H, d, J=17 Hz), 4.75 (1H, d, J=17 Hz), 2.28 (3H, s). Compound 469B: LC/MS: m/e 630.1 (M+H)$^+$. $^1$H NMR (500 MHz, CDCl$_3$): δ 7.79 (1H, d, J=7.6 Hz), 7.54 (1H, d, J=7.3 Hz), 7.48 (1H, m), 7.06-7.24 (3H, m), 6.86-7.04 (4H, m), 5.35 (1H, d, J=14 Hz), 4.75 (1H, d, J=14 Hz), 1.44 (3H, s), 1.30 (3H, s).

EXAMPLE 470

2-[2-Trifluoromethyl)-6-({4-[1-(trifluoromethyl)cyclopropyl]phenyl}sulfonyl)-6,11-dihydro-5H-pyrido[2,3-b][1,5]benzodiazepin-8-yl]propanenitrile

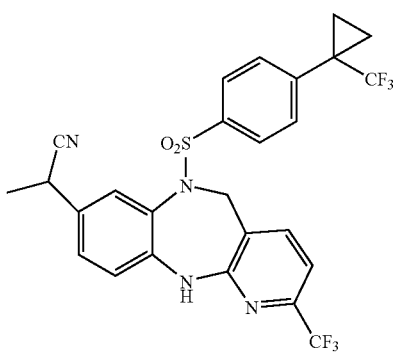

Step A: To a mixture of 8-bromo-2-(trifluoromethyl)-6,11-dihydro-5H-pyrido[2,3-b][1,5]benzodiazepine (intermediate 36, 1.00 g, 2.91 mmol), Pd(dppf)Cl$_2$ (990 mg, 1.2 mmol), LiCl (122 mg, 2.91 mmol) in NMP (6 mL) at rt was added tri-n-butyl(1-ethoxyvinyl)tin (1.08 g, 3.0 mmol) and the resulting mixture was stirred at 90° C. for 2.5 h. The reaction mixture was cooled and filtered over a pad of SiO$_2$ and the cake was washed with EtOAc. The filtrate was washed with water, brine, dried over MgSO$_4$ and concentrated. The residue was purified by SiO2 column chromatography to provide the desired product.

Step B: The product from Step A (25 mg) was treated with 4-[1-(trifluoromethyl)-cyclopropyl]-benzenesulfonyl chloride (intermediate 48) according to the procedure described for intermediate 53 to afford the sulfonylated ketone. LC/MS: m/e 555.9 (M+H)$^+$.

Step C: The sulfonylated ketone from Step B was treated with borane-THF complex according to the procedure of Example 460 to provide the alcohol product.

Step D: The alcohol from Step C was acetylated according to the procedure of Example 461, Step A to provide the acetate. LC/MS: m/e 599.9 (M+H)$^+$.

Step E: The acetate from Step D was converted to the title compound following the procedure described in Example 461, Step B. LC/MS: m/e 566.9 (M+H)$^+$. $^1$H NMR (500 MHz, CDCl$_3$): δ 7.59 (1H, d, J=7.3 Hz), 7.53 (1H, d, J=2.1 Hz), 7.34 (1H, dd, J=8.5, 2.3 Hz), 7.21 (2H, J=8.5 Hz), 7.09 (1H, d, J=7.6 Hz), 7.01 (2H, d, J=8.5 Hz), 6.80 (2H, m), 4.70-4.90 (2H, s, br), 3.95 (1H, d, J=7.3 Hz), 1.71 (3H, d, J=7.3 Hz).

EXAMPLE 471

2-[2-(Trifluoromethyl)-6-({4-[1-(trifluoromethyl) cyclopropyl]phenyl}sulfonyl)-6,11-dihydro-5H-pyrido[2,3-b][1,5]benzodiazepin-8-yl]propan-2-ol

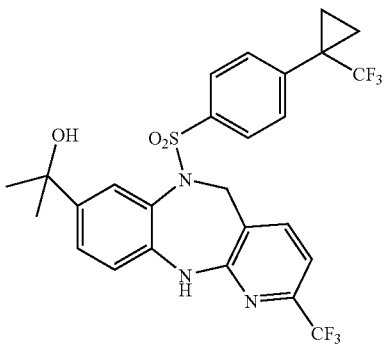

To a solution of 8-iodo-2-(trifluoromethyl)-6-({4-[1-(trifluoromethyl)-cyclopropyl]phenyl}sulfonyl)-6,11-dihydro-5H-pyrido[2,3-b][1,5]benzodiazepine (intermediate 59, 150 mg, 0.235 mmol) in THF (1.5 mL) at 0° C. was added isopropylmagnesium bromide (1.89 mmol of a 2M solution in ether). After stirred at 0° C. for 40 min, acetone (204 mg, 3.52 mmol) was added dropwise and the reaction mixture was gradually brought to rt. The reaction was quenched with saturated aqueous NH$_4$Cl and diluted with EtOAc. The organic layer was separated and the aqueous phase was extracted with EtOAc. The combined extracts were washed with water, brine, dried over MgSO$_4$ and concentrated. Purification of the residue via SiO$_2$ column chromatography provided the title compound. LC/MS: m/e 572.0 (M+H)$^+$. $^1$H NMR (500 MHz, CDCl$_3$): δ 7.65 (1H, d, J=2.1 Hz), 7.56 (1H, d, J=7.5 Hz), 7.44 (1H, dd, J=8.5, 1.6 Hz), 7.21 (2H, d, J=8.3 Hz), 7.05 (1H, d, J=7.3 Hz), 7.02 (2H, d, J=8.5 Hz), 6.77 (1H, s), 6.74 (1H, J=8.2 Hz), 4.70-4.90 (2H, s, br), 1.64 (6H, s), 1.35-1.42 (4H, m), 1.26-1.30 (4H, m).

EXAMPLE 472

2-Methyl-2-[2-(trifluoromethyl)-6-({4-[1-(trifluoromethyl)cyclopropyl]phenyl}sulfonyl)-6,11-dihydro-5H-pyrido[2,3-b][1,5]benzodiazepin-8-yl]propan-1-ol

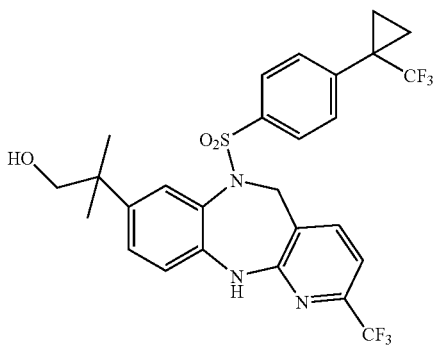

Step A: 2-[2-(Trifluoromethyl)-6-({4-[1-(trifluoromethyl)cyclopropyl]phenyl}sulfonyl)-6,11-dihydro-5H-pyrido[2,3-b][1,5]benzodiazepin-8-yl]propan-2-ol (Example 471) was acetylated according to the procedure of Example 461, Step A. LC/MS: m/e 614.0 (M+H)$^+$.

Step B: The acetylated material from Step A was converted to the cyanide according to the procedure of Example 461, Step B. LC/MS: m/e 581.0 (M+H)$^+$.

Step C: To a solution of cyanide from Step B (15 mg, 0.026 mmol) in DCM (0.26 mL) at −78° C. was added dropwise DIBAL-H (0.10 mmol, 1.0 M solution in DCM). After stirring for 20 min, the reaction mixture was quenched with saturated aqueous NH$_4$Cl and the product was extracted with EtOAc. The combined extracts were washed with water, brine, dried over MgSO$_4$, and concentrated to provide the aldehyde product. LC/MS: m/e 584.0 (M+H)$^+$.

Step D: The aldehyde obtained from Step C was reduced to the alcohol according to the procedure of Example 460, providing the title compound. LC/MS: m/e 586.0 (M+H)$^+$. $^1$H NMR (500 MHz, CDCl$_3$): δ 7.56 (2H, m), 7.31 (1H, dd, J=8.4, 2.0 Hz), 7.22 (2H, d, J=8.5 Hz), 7.05 (1H, d, J=7.5 Hz), 7.02 (2H, d, J=8.2 Hz), 6.83 (1H, s), 6.74 (1H, J=8.5 Hz), 4.70-4.90 (2H, s, br), 3.68 (2H, s), 1.38 (6H, s), 1.27-1.30 (4H, m), 0.94-1.03 (4H, m).

EXAMPLE 473

3-Hydroxy-2-methyl-2-[2-(trifluoromethyl)-6-({4-[1-(trifluoromethyl)cyclopropyl]phenyl}sulfonyl)-6,11-dihydro-5H-pyrido[2,3-b][1,5]benzodiazepin-8-yl]propanenitrile

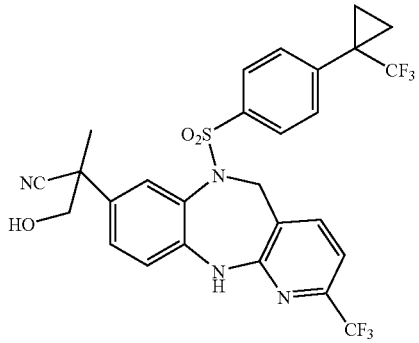

Step A: 8-Iodo-2-(trifluoromethyl)-6-({4-[1-(trifluoromethyl)-cyclopropyl]phenyl}sulfonyl)-6,11-dihydro-5H-pyrido[2,3-b][1,5]benzodiazepine (intermediate 59) reacted with t-butyldimethylsiloxypropanone according to the procedure of Example 471, providing the tertiary alcohol product. LC/MS: m/e 702.2 (M+H)$^+$.

Step B: The product obtained from Step A was acetylated according to the procedure of Example 461. Step C: The acetylated product from Step B was converted to the cyanide according to the procedure of Example 461, Step B. LC/MS: m/e 711.1 (M+H)$^+$.

Step D: The cyanide product from Step C (13 mg) was desilylated in acetonitrile and DCM at 0° C. by boron trifluoride etherate (0.020 mL, 0.15 mmol). The reaction mixture was partitioned between water and EtOAc. The organic layer was separated and the aqueous phase was extracted with EtOAc. Combined extracts were washed with water, brine, dried over MgSO$_4$, and concentrated. The residue was purified by a plug of SiO$_2$ providing the title compound. LC/MS: m/e 597.1 (M+H)$^+$. $^1$H NMR (500 MHz, CDCl$_3$): δ 7.58 (2H, m), 7.47 (1H, dd, J=8.5, 2.3 Hz), 7.23 (2H, d, J=8.2 Hz), 7.10 (1H, d, J=7.6 Hz), 7.02 (2H, d, J=8.2 Hz), 6.91 (1H, s), 6.83 (1H, d, J=8.5 Hz), 4.70-4.90 (2H, s, br), 3.91 (2H, m), 1.80 (6H, s), 1.35-1.40 (4H, m), 1.26-1.32 (4H, m).

EXAMPLE 474

2-(2-(Trifluoromethyl)-6-{[4-(trifluoromethyl)phenyl]sulfonyl}-6,11-dihydro-5H-pyrido[2,3-b][1,5]benzodiazepin-8-yl)propan-2-ol

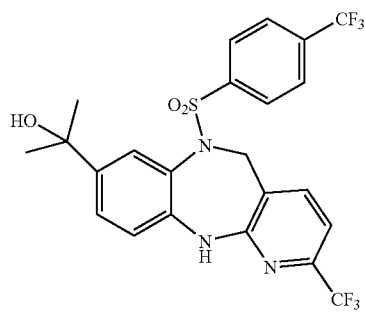

The title compound was prepared from 8-iodo-2-(trifluoromethyl)-6-{[4-(trifluoromethyl)phenyl]-sulfonyl}-6,11-dihydro-5H-pyrido[2,3-b][1,5]benzodiazepine (intermediate 60) according to the procedure of Example 471. MS: m/e 532.0 (M+H)$^+$.

EXAMPLE 475

3-Methyl-3-(2-(trifluoromethyl)-6-{[4-(trifluoromethyl)phenyl]sulfonyl}-6,11-dihydro-5H-pyrido[2,3-b][1,5]benzodiazepin-8-yl)butan-2-ol

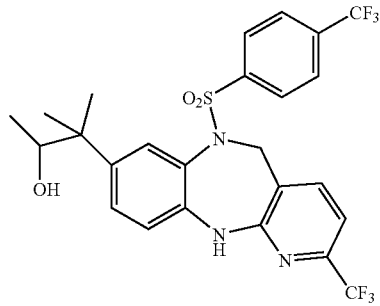

Step A: 2-(2-(Trifluoromethyl)-6-{[4-(trifluoromethyl)phenyl]sulfonyl}-6,11-dihydro-5H-pyrido[2,3-b][1,5]benzodiazepin-8-yl)propan-2-ol (from Example 474) was acetylated according to the procedure of Example 461, Step A. LC/MS: m/e 574.0 (M+H)$^+$.

Step B: The acetylated product from Step A was converted to the cyanide according to the procedure of Example 461, Step B. LC/MS: m/e 541.0 (M+H)$^+$.

Step C: The cyanide product from Step B was converted to the corresponding aldehyde according to the procedure from Example 472, Step C. LC/MS: m/e 544.0 (M+H)$^+$.

Step D: To the aldehyde from Step C (19 mg, 0.03 mmol) in THF (0.20 mL) at −78° C. was added dropwise methyl magnesium bromide (0.10 mmol, 0.075 mL of a 1.4 M solution in toluene/THF). After 20 min, the reaction was quenched by addition of saturated aqueous NH$_4$Cl. The product was extracted with EtOAc and combined extracts were washed with water, brine, and dried over MgSO$_4$, and concentrated. The residue was purified via SiO$_2$ column chromatography to provide the title compound as racemic mixture. LC/MS: m/e 560.0 (M+H)$^+$. $^1$H NMR (500 MHz, CDCl$_3$): δ 7.58-7.61 (2H, m), 7.40 (2H, d, J=8.5 Hz), 7.36 (1H, dd, J=8.5, 2.3 Hz), 7.32 (1H, s), 7.17 (2H, d, J=8.2 Hz), 7.08 (1H, d, J=7.6 Hz), 6.81 (1H, d, J=8.5 Hz), 4.70-4.90 (2H, s, br), 3.90 (1H, q, J=6.4 Hz), 1.39 (6H, s), 1.12 (3H, d, J=6.4 Hz). The racemic material was separated into its enantiomers via an AD-H column, using 10% isopropyl alcohol and hexanes as eluents, and a flow rate of 9 mL/min, with retention times of 26 min and 27.5 min, respectively.

EXAMPLE 476

2-Hydroxy-1-(2-(trifluoromethyl)-6-{[4-(trifluoromethyl)phenyl]sulfonyl}-6,11-dihydro-5H-pyrido[2,3-b][1,5]benzodiazepin-8-yl)propan-1-one

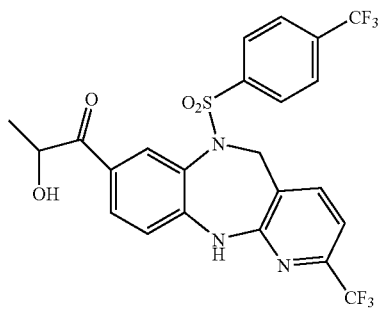

Step A: 8-Iodo-2-(trifluoromethyl)-6-{[4-(trifluoromethyl)phenyl]sulfonyl}-6,11-dihydro-5H-pyrido[2,3-b][1,5]benzodiazepine (intermediate 60) were coupled to (S)-2-(t-butyldimethylsiloxy)propionaldehyde according to the procedure of Example 471 to provide the corresponding mono-protected diol.

Step B: The diol product obtained from Step A (15 mg, 0.023 mmol) and DBU (6.90 mg, 0.045 mmol) were dissolved in DCM (0.110 mL) and cooled to −78° C. To this rapidly stirred solution was added dropwise 0.073 mL of a pre-made 10% solution of N-isopropylbenzenecarboximidoyl chloride (15 mg) in DCM (0.150 mL). The reaction was quenched by addition of 1% aqueous HCl, and the product was extracted with DCM. The combined organic extracts were washed with water, brine, dried over MgSO$_4$ and concentrated. The residue was purified via a plug of SiO$_2$ to provide the ketone intermediate. LC/MS: m/e 660.1 (M+H)$^+$.

Step C: The ketone intermediate obtained from Step B was deprotected according to the procedure of Example 473, Step D to provide the title compound. LC/MS: m/e 546.0 (M+H)$^+$. $^1$H NMR (500 MHz, CDCl$_3$): δ 8.16 (1H, d, J=2.1 Hz), 7.96 (1H, dd, J=8.5, 2.0 Hz), 7.66 (1H, d, J=7.5 Hz), 7.39 (2H, d, J=8.5 Hz), 7.19 (2H, d, J=8.5 Hz), 7.13-7.16 (3H, m), 6.90 (1H, d, J=8.5 Hz), 5.17 (1H, q, J=7.1 Hz), 4.70-5.10 (2H, s, br), 1.56 (3H, d, J=6.9 Hz).

EXAMPLE 477

2-[6-{[4-(Trifluoromethoxy)phenyl]sulfonyl}-2-(trifluoromethyl)-6,11-dihydro-5H-pyrido[2,3-b][1,5]benzodiazepin-8-yl]propan-2-ol

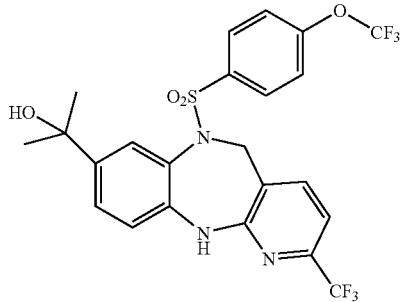

The title compound was prepared from 8-iodo-2-(trifluoromethyl)-6-{[4-(trifluoromethoxy)phenyl]-sulfonyl}-6,11-dihydro-5H-pyrido[2,3-b][1,5]benzodiazepine (intermediate 61) according to the procedure of Example 471. LC/MS: m/e 548.0 (M+H)+.

EXAMPLE 478

2-Methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanenitrile

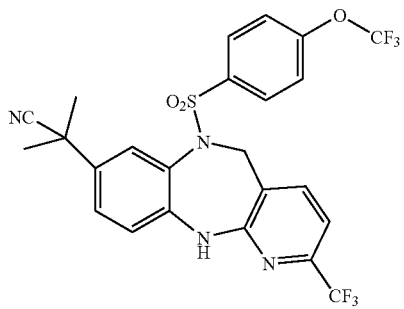

Step A: 2-[2-(Trifluoromethoxy)-6-({4-[1-(trifluoromethyl)cyclopropyl]phenyl}sulfonyl)-6,11-dihydro-5H-pyrido[2,3-b][1,5]benzodiazepin-8-yl]propan-2-ol (Example 477) was acetylated according to the procedure of Example 461, Step A. LC/MS: m/e 589.9 (M+H)+.

Step B: The acetylated product of Step A was converted to the title compound according to the procedure of Example 461, Step B. LC/MS: m/e 557.0 (M+H)+. 1H NMR (500 MHz, CDCl3): δ 7.62 (1H, d, J=2.3 Hz), 7.60 (1H, d, J=7.5 Hz), 7.47 (1H, dd, J=8.4, 2.3 Hz), 7.12 (1H, d, J=7.6 Hz), 7.07-7.09 (2H, m), 6.95 (2H, d, J=8.2 Hz), 6.84 (1H, m), 4.70-4.90 (2H, s, br), 1.80 (6H, s).

EXAMPLE 479

[12-{[4-(Trifluoromethoxy)phenyl]sulfonyl}-8-(trifluoromethyl)-11,12-dihydro-6H-[1,3]oxazolo[5,4-g]pyrido[2,3-b][1,5]benzodiazepin-2-yl]methanol

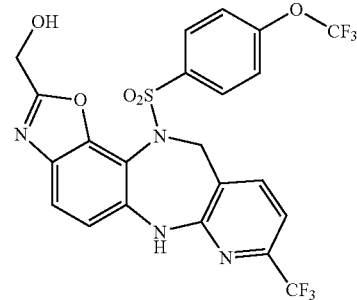

Step A: A mixture of 28-amino-6-{[4-(trifluoromethoxy)phenyl]sulfonyl}-2-(trifluoromethyl)-6,11-dihydro-5H-pyrido[2,3-b][1,5]benzodiazepin-7-ol (intermediate 62, 30 mg), benzyloxyacetyl chloride (11.7 mg, 0.063 mmol), pyridinium p-toluenesulfonate (4.35 mg, 0.017 mmol), triethyl amine (6.4 mg, 0.063 mmol) and p-xylene (0.20 mL) was heated at 170° C. for 8 h. Volatiles were removed and the residue was purified via SiO2 column chromatography, eluting with mixtures hexane and EtOAc, to provide the benzyl protected intermediate. LC/MS: m/e 651.2 (M+H)+.

Step B: The benzyl group was removed using the procedure described in Example 437, Step C to provide the title compound. LC/MS: m/e 561.0 (M+H)+. 1H NMR (500 MHz, DMSO-d6): δ 9.74 (1H, s), 7.75 (1H, d, J=7.3 Hz), 7.61 (1H, d, J=8.7 Hz), 7.34 (1H, d, J=8.7 Hz), 7.31 (2H, d, J=9.0 Hz), 7.18 (2H, J=8.7 Hz), 6.95 (2H, d, J=8.2 Hz), 7.09 (1H, d, J=7.5 Hz), 5.12 (1H, d, J=16.7 Hz), 4.76 (1H, d, J=16.5 Hz), 4.68 (2, t, J=5.8 Hz).

EXAMPLE 480

2-Methyl-12-{[4-trifluoromethoxy)phenyl]sulfonyl}-8-(trifluoromethyl)-11,12-dihydro-6H-[1,3]oxazolo[5,4-e]pyrido[2,3-b][1,5]benzodiazepine

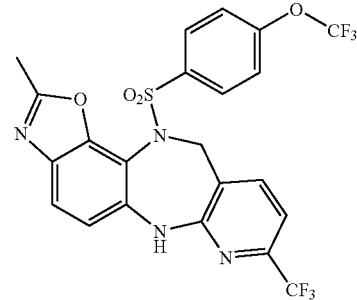

The title compound was prepared following the procedure described for Example 479 substituting acetyl chloride for 2-benzyloxyacetyl chloride. LC/MS: m/e 545.0 (M+H)+.

The compounds in Table 24 were prepared analogously to the compounds in Table 12, using the appropriate starting materials.

TABLE 24

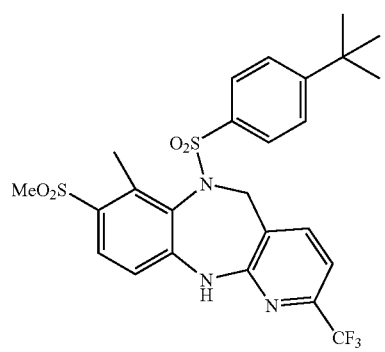

| Example | R₄ | R₅ₐ | LCMS: found m/e (M + H) |
|---|---|---|---|
| 481 | OCF₃ | H | 545.9 |
| 482 | H | OCF₃ | 545.9 |
| 483 | Cl | H | 495.9 |
| 484 | H | Cl | 495.9 |
| 485 | Br | H | 539.9 |
| 486 | H | Br | 539.9 |
| 487 | Cl | Cl | 529.8 |
| 488 | F | F | 497.9 |
| 489 | Cl | F | 514.3 |
| 490 | F | Cl | 514.3 |
| 491 | CH₃ | H | 476.0 |
| 492 | H | CH₃ | 476.0 |

EXAMPLE 493

6-[(4-tert-Butylphenyl)sulfonyl]-7-methyl-2-(trifluoromethyl)-6,11-dihydro-5H-pyrido[2,3-b][1,5]benzodiazepine-8-carbonitrile

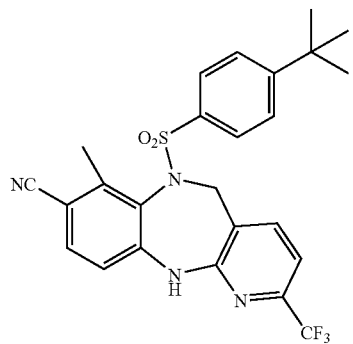

The title compound was prepared from 8-bromo-6-[(4-tert-butylphenyl)sulfonyl]-7-methyl-2-(trifluoromethyl)-6,11-dihydro-5H-pyrido[2,3-b][1,5]benzodiazepine (intermediate 63) according to the procedure described for intermediate 54. Racemic mixture: LC/MS: m/e 501.0 (M+H)⁺. ¹H NMR (500 MHz, CD₃OD): δ 7.63 (1H, d), 7.47 (1H, d), 7.19 (2H, d), 7.13 (1H, d), 7.00 (2H, d), 5.20 (1H, d), 4.45 (1H, d), 2.65 (3H, s), 1.25 (9H, s). The racemic mixture was separated into individual enantiomers via chromatography on a Chiracel OD column eluting with 15% EtOH in hexanes at 8.0 mL/min. The faster eluting enantiomer E1 has a retention time of 9.77 min. The slower eluting enantiomer E2 has a retention time of 12.04 min.

EXAMPLE 494

6-[(4-tert-Butylphenyl)sulfonyl]-7-methyl-8-(methylsulfonyl)-2-(trifluoromethyl)-6,11-dihydro-5H-pyrido[2,3-b][1,5]benzodiazepine

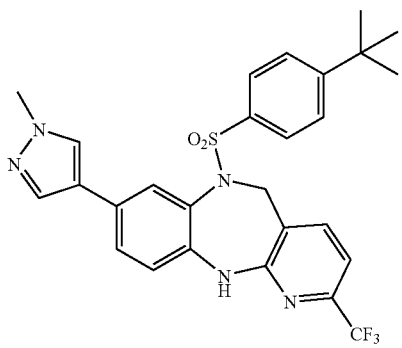

A mixture of 8-bromo-6-[(4-tert-butylphenyl)sulfonyl]-7-methyl-2-(trifluoromethyl)-6,11-dihydro-5H-pyrido[2,3-b][1,5]benzodiazepine (intermediate 63, 100 mg, 0.180 mmol) sodium methyl sulfinate (55.2 mg, 0.541 mmol) and copper (II) triflate benzene complex (27.2 mg, 0.054 mmol) was flushed with nitrogen and capped, and was added N,N'-dimethyl ethylenediamine (0.12 mL, 0.108 mmol), and DMSO (0.60 mL). The mixture was heated to 110° C. for 36 h. After cooling to rt, the reaction mixture was diluted with EtOAc, filtered through silica gel, the filtrated was washed with water and brine, and concentrated. The residue was purified by reverse phase HPLC to provide the title compound as a racemic mixture. LC/MS: m/e 553.9 (M+H)⁺; ¹H NMR (500 MHz, CD₃OD): δ 7.87 (1H, d), 7.63 (1H, d), 7.19 (2H, d), 7.13 (1H, d), 7.07 (1H, d), 7.02 (2H, d), 5.21 (1H, d), 4.45 (1H, d), 3.15 (3H, s), 2.87 (3H, s), 1.23 (9H, s). The racemic mixture was separated on a Chiracel OD-H column eluting with 20% EtOH in hexanes, at 8.0 mL/min. The faster eluting enantiomer E1 has a retention time of 15.7 min. The slower eluting enantiomer E2 has a retention time of 28.5 min.

EXAMPLE 495

6-[(4-tert-Butylphenyl)sulfonyl]-8-(1-methyl-1H-pyrazol-4-yl)-2-(trifluoromethyl)-6,11-dihydro-5H-pyrido[2,3-b][1,5]benzodiazepine A mixture of 8-bromo-6-[(4-tert-butylphenyl)sulfonyl]-2-(trifluoromethyl)-6,11-dihydro-5H-pyrido[2,3-b][1,5]benzodiazepine (intermediate 53, 50 mg, 0.0925 mmol), 1-methyl-4-(4,4,5,5-tetramethyl-1,3,2-dioxaborolan-2-yl)-1H-pyrazole (38.5 mg, 0.185 mmol), Pd(dppf)Cl$_2$ (22.7 mg, 0.0278 mmol), potassium carbonate (38.4 mg, 0.2775 mmol), DMSO (0.3 mL), and 3 drops of water was heated in a microwave reactor at 100° C. for 30 min. After cooling to room temperature, the reaction mixture was diluted with EtOAc, and the organic layer was separated, washed with water, brine, dried over MgSO$_4$ and concentrated. The residue was purified via reverse phase HPLC to provide the title compound. LC/MS: m/e 542.0 (M+H)$^+$. $^1$H NMR (500 MHz, CD$_3$OD): δ 7.93 (1H, s), 7.78 (1H, s), 7.60 (2H, m), 7.40 (1H, d), 7.16 (2H, d), 7.05 (1H, d), 6.95 (1H, d), 6.90 (2H, d), 4.60-5.00 (2H, br s), 3.90 (3H, s), 1.26 (9H, s).

EXAMPLE 496

7-Fluoro-8-(1-methyl-1H-pyrazol-4-yl)-6-[(4-iso-propylphenyl)sulfonyl]-2-(trifluoromethyl)-6,11-dihydro-5H-pyrido[2,3-b][1,5]benzodiazepine

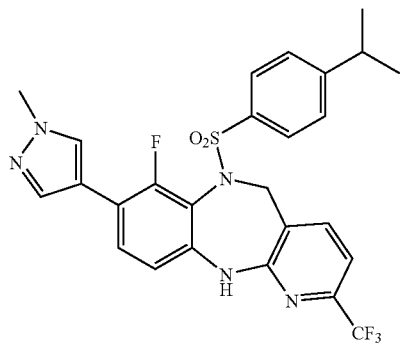

The title compound was prepared from 8-bromo-7-fluoro-6-[(4-iso-propylphenyl)sulfonyl]-2-(trifluoromethyl)-6,11-dihydro-5H-pyrido[2,3-b][1,5]benzodiazepine following the procedure described for Example 495. LC/MS: m/e 546.1 (M+H)$^+$.

EXAMPLE 497

6-[(4-tert-Butylphenyl)sulfonyl]-8-(2H-tetrazol-5-yl)-2-(trifluoromethyl)-6,11-dihydro-5H-pyrido[2,3-b][1,5]benzodiazepine

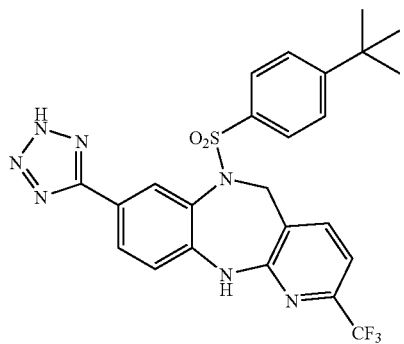

A mixture of 6-[(4-tert-butylphenyl)sulfonyl]-2-(trifluoromethyl)-6,11-dihydro-5H-pyrido[2,3-b][1,5]benzodiazepine-8-carbonitrile (intermediate 54, 26 mg, 0.0534 mmol), sodium azide (17.4 mg, 0.267 mmol), and ammonium chloride (14.3 mg, 0.267 mmol) in DMF (1 mL) was heated in a microwave reactor at 130° C. for 2 h. After cooling to room temperature, the reaction mixture was diluted with EtOAc, and organic layer was separated, washed with aqueous NaHCO$_3$, water, brine, dried over MgSO$_4$ and concentrated. The residue was purified via reverse phase HPLC to provide the title compound. LC/MS: m/e 530.0 (M+H)$^+$. $^1$H NMR (500 MHz, CD$_3$OD): δ 8.15 (1H, s), 7.88 (1H, d), 7.65 (1H, d), 7.10-7.20 (4H, m), 6.93 (2H, d), 4.60-5.00 (2H, br s), 1.25 (9H, s).

EXAMPLES 498A AND 498B

6-[(4-tert-Butylphenyl)sulfonyl]-8(1-methyl-2H-tetrazol-5-yl)-2-(trifluoromethyl)-6,11-dihydro-5H-pyrido[2,3-b][1,5]benzodiazepine and 6-[(4-tert-Butylphenyl)sulfonyl]-8-(2-methyl-2H-tetrazol-5-yl)-2-(trifluoromethyl)-6,11-dihydro-5H-pyrido[2,3-b][1,5]benzodiazepine

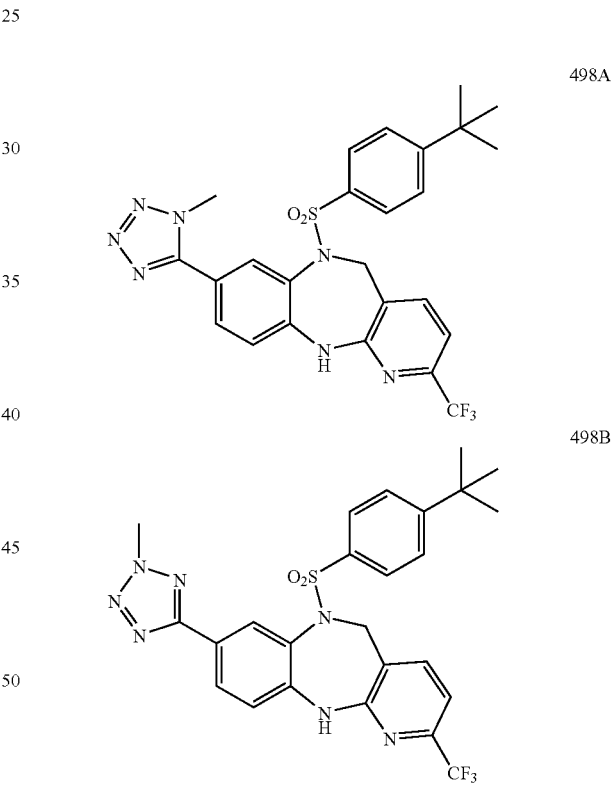

To a solution of 6-[(4-tert-butylphenyl)sulfonyl]-8-(2H-tetrazol-5-yl)-2-(trifluoromethyl)-6,11-dihydro-5H-pyrido[2,3-b][1,5]benzodiazepine (Example 497, 8 mg) in 1:1 MeOH/DCM (3 mL) was added dropwise trimethylsiyldiazomethane and the resulting mixture was stirred at room temperature for 2 h. The reaction was concentrated, and the residue was purified by reverse phase HPLC to give compound 498A (faster eluting) and compound 498B (slower eluting). 498A: LC/MS: m/e 544.1 (M+H)$^+$. $^1$H NMR (500 MHz, CD$_3$OD): δ 7.95 (1H, s), 7.73 (3H, m), 7.25 (1H, d), 7.13-7.20 (3H, m), 6.95 (2H, d), 4.60-5.00 (2H, br s), 3.25 (3H, s), 1.25 (9H, s). 498B: LC/MS: m/e 544.1 (M+H)$^+$. $^1$H NMR (500 MHz, CD$_3$OD): δ 8.20 (1H, s), 7.90 (1H, d), 7.65 (1H, d), 1.25 (2H, d), 7.08 (2H, m), 6.93 (2H, d), 4.60-5.00 (2H, br s), 4.40 (3H, s), 1.25 (9H, s).

EXAMPLE 499

6-[(4-tert-Butylphenyl)sulfonyl]-8-(1-methyl-1H-pyrazol-5-yl)-2-(trifluoromethyl)-6,11-dihydro-5H-pyrido[2,3-b][1,5]benzodiazepine

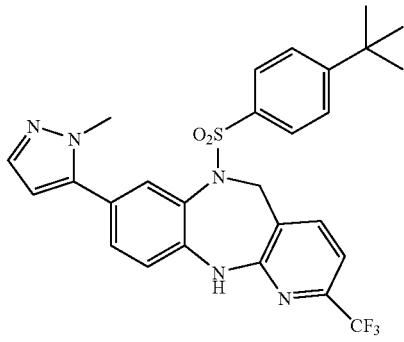

A mixture of 8-bromo-6-[(4-tert-butylphenyl)sulfonyl]-2-(trifluoromethyl)-6,11-dihydro-5H-pyrido[2,3-b][1,5]benzodiazepine (intermediate 53, 100 mg, 0.185 mmol), 1-methyl-3-(tributylstannyl)-1H-pyrazole (62.4 mg, 0.168 mmol, prepared according to Heterocycles, 1997, 45, 1463), and PdCl$_2$(PPh$_3$)$_2$ (11.8 mg, 0.0168 mmol) in THF (1.0 mL) was refluxed overnight. After cooling to room temperature, water was added, the reaction mixture was extracted with EtOAc, and the organic extracts were washed with water, brine, dried over MgSO$_4$ and concentrated. The residue was purified via reverse phase HPLC to provide the title compound. LC/MS: m/e 542.1 (M+H)$^+$. $^1$H NMR (500 MHz, CD$_3$OD): δ 7.66 (1H, d), 7.59 (1H, s), 7.50 (1H, s), 7.38 (1H, d), 7.18 (2H, d), 7.08-7.13 (2H, m), 6.97 (2H, d), 6.40 (1H, s), 4.60-5.00 (2H, br s), 3.97 (3H, s), 1.26 (9H, s).

EXAMPLE 500

6-[(4-tert-Butylphenyl)sulfonyl]-8-(1-methyl-1H-pyrazol-3-yl)-2-(trifluoromethyl)-6,11-dihydro-5H-pyrido[2,3-b][1,5]benzodiazepine

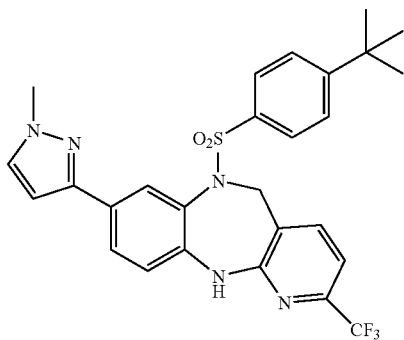

Step A: A mixture of 8-bromo-6-[(4-tert-butylphenyl)sulfonyl]-2-(trifluoromethyl)-6,11-dihydro-5H-pyrido[2,3-b][1,5]benzodiazepine (intermediate 53, 60 mg, 0.111 mmol) and (1H-pyrazol-3-yl)boronic acid (24.8 mg, 0.222 mmol), Pd(dppf)Cl$_2$ (27.2 mg, 0.0333 mmol), potassium carbonate (46 mg, 0.333 mmol), DMSO (0.3 mL), and 3 drops of water was heated in a microwave reactor at 100° C. for 30 min. After cooling to room temperature, the reaction mixture was diluted with EtOAc, the organic layer was separated, washed with water, brine, dried over MgSO$_4$ and concentrated. The residue was purified via reverse phase HPLC to provide the coupling product. LC/MS: m/e 528.0 (M+H)$^+$. $^1$H NMR (500 MHz, CD$_3$OD): δ 7.95 (1H, s), 7.56-7.65 (4H, m), 7.15 (2H, d), 7.00-7.10 (2H, m), 6.95 (2H, d), 6.60 (1H, s), 4.60-5.00 (2H, br s), 1.26 (9H, s).

Step B: The coupling product of Step A was methylated according to the procedure of Example 498. The major isomer isolated from reverse phase HPLC was identical to that obtained in Example 499. The title compound was isolated as the minor isomer. LC/MS: m/e 542.1 (M+H)$^+$. $^1$H NMR (500 MHz, CD$_3$OD): δ 7.85 (1H, s), 7.58-7.65 (4H, m), 7.08 (2H, d), 7.05 (1H, d), 7.00 (1H, d), 6.95 (2H, d), 6.57 (1H, s), 4.60-5.00 (2H, br s), 3.93 (3H, s), 1.26 (9H, s).

EXAMPLE 501

6-[(4-tert-Butylphenyl)sulfonyl]-7-chloro-8-(1-methyl-1H-pyrazol-4-yl)-2-(trifluoromethyl)-6,11-dihydro-5H-pyrido[2,3-b][1,5]benzodiazepine

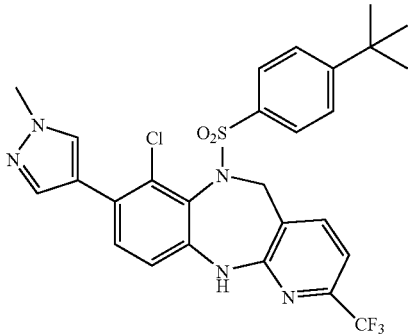

The title compound was prepared from 8-bromo-6-[(4-tert-butylphenyl)sulfonyl]-7-chloro-2-(trifluoromethyl)-6,11-dihydro-5H-pyrido[2,3-b][1,5]benzodiazepine (intermediate 64) and 1-methyl-4-(4,4,5,5-tetramethyl-1,3,2-dioxaborolan-2-yl)-1H-pyrazole according to the procedure of Example 495. Racemic mixture: LC/MS: m/e 576.1 (M+H)$^+$; $^1$H NMR (500 MHz, CD$_3$OD): δ 8.05 (1H, s), 7.80 (1H, s), 7.58 (1H, d), 7.41 (2H, d), 7.10 (3H, m), 7.05 (1H, d), 7.00-7.10 (2H, d), 5.19 (1H, d), 5.55 (1H, d), 3.96 (3H, s), 1.26 (9H, s). The racemic mixture was separated on a Chiracel OD-H column eluting with 20% EtOH in hexanes at 8.0 mL/min. The faster eluting enantiomer E1 had a retention time of 40 min. The slower eluting enantiomer E2 had a retention time of 50 min.

EXAMPLE 502

6-[(4-tert-Butylphenyl)sulfonyl]-7-methyl-2-(trifluoromethyl)-6,11-dihydro-5H-pyrido[2,3-b][1,5]benzodiazepine-8-carboxamide

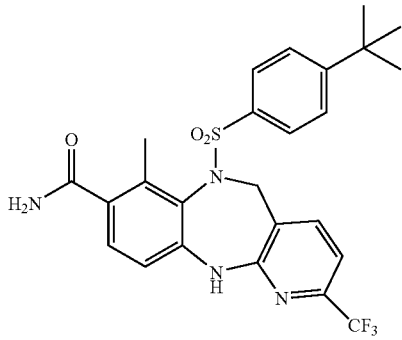

Step A: 8-Bromo-6-[(4-tert-butylphenyl)sulfonyl]-7-methyl-2-(trifluoromethyl)-6,11-dihydro-5H-pyrido[2,3-b][1,5]benzodiazepine (intermediate 63) was converted to 8-cyano-6-[(4-tert-butylphenyl)sulfonyl]-7-methyl-2-(trifluoromethyl)-6,11-dihydro-5H-pyrido[2,3-b][1,5]benzodiazepine according to the procedure described for intermediate 54. LC/MS: m/e 501.0 (M+H)$^+$.

Step B: A mixture of 8-cyano-6-[(4-tert-butylphenyl)sulfonyl]-7-methyl-2-(trifluoromethyl)-6,11-dihydro-5H-pyrido[2,3-b][1,5]benzodiazepine (199 mg, 0.398 mmol) and lithium hydroxide monohydrate (50.1 mg, 2.295 mmol) in 1:1 dioxane-water was heated in a microwave reactor for 15 min at 100° C., followed by 30 min at 120° C. The reaction mixture was cooled to room temperature, diluted with EtOAc, and the organic layer was separated, washed with water, brine, dried over MgSO$_4$ and concentrated. The residue was purified via reverse-phase HPLC to provide the title compound. LC/MS: m/e 519.1 (M+H)$^+$. $^1$H NMR (500 MHz, CD$_3$OD): δ 7.60 (1H, d), 7.35 (1H, d), 7.15 (2H, d), 7.03-7.10 (3H, m), 6.93 (1H, d), 5.19 (1H, d), 4.40 (1H, d), 2.60 (3H, s), 1.25 (9H, s).

EXAMPLE 503

6-[(4-tert-Butylphenyl)sulfonyl]-7-methyl-8-(1H-1,2,4-triazol-3-yl)-2-(trifluoromethyl)-6,11-dihydro-5H-pyrido[2,3-b][1,5]benzodiazepine

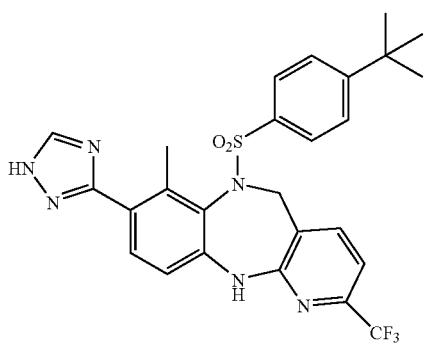

Step A: A mixture of 6-[(4-tert-butylphenyl)sulfonyl]-7-methyl-2-(trifluoromethyl)-6,11-dihydro-5H-pyrido[2,3-b][1,5]benzodiazepine-8-carboxamide (Example 502, 56 mg, 0.108 mmol) and dimethylformamide dimethylacetal (0.5 mL) was heated in a microwave reactor for 2 h at 120° C. The mixture was concentrated and the crude product was used without further purification.

Step B: To a solution of product of Step A (31 mg, 0.0544 mmol) in acetic acid (0.2 mL) was added hydrazine (0.005 mL, 0.163 mmol), and the mixture was heated to 90° C. for 1 h. The reaction mixture was cooled to room temperature and diluted with EtOAc, the organic layer was separated, washed with water, brine, dried over MgSO$_4$ and filtered. The residue was purified via silica gel chromatography, eluting with mixtures of EtOAc in hexanes to provide the title compound. LC/MS: m/e 543.1 (M+H)$^+$. $^1$H NMR (500 MHz, CD$_3$OD): δ 7.60 (1H, d), 7.15-7.20 (3H, m), 7.03-7.08 (4H, m), 6.98 (1H, m), 5.20 (1H, d), 4.42 (1H, d), 2.61 (3H, br s), 1.27 (9H, s).

EXAMPLE 504

6-[(4-tert-Butylphenyl)sulfonyl]-7-methyl-8-(1-methyl-1H-1,2,4-triazol-5-1-2-(trifluoromethyl)-6,11-dihydro-5H-pyrido[2,3-b][1,5]benzodiazepine

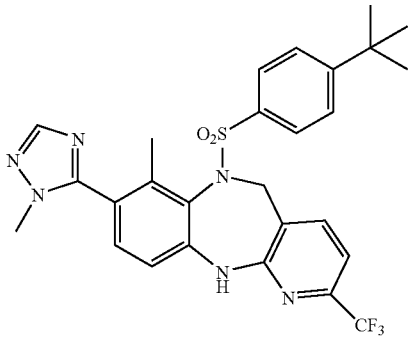

To a solution of the product of Example 503, Step A (31 mg, 0.0544 mmol) in acetic acid (0.2 mL) was added methyl hydrazine (0.0086 mL, 0.163 mmol), and the mixture was heated at 90° C. for 1 h. The reaction mixture was worked up as described for Example 503, Step B to provide the title compound. LC/MS: m/e 557.1 (M+H)$^+$. $^1$H NMR (500 MHz, CD$_3$OD): δ 8.0 (1H, s), 7.75 (1H, s), 7.59 (1H, d), 7.23 (1H, d), 7.18 (2H, d), 7.00-7.10 (3H, m), 5.40 (1H, s), 5.20 (1H, d), 4.42 (1H, d), 3.80 (3H, s), 2.38 (3H, s), 1.27 (9H, s).

EXAMPLE 505

6-[(4-tert-Butylphenyl)sulfonyl]-8-(1H-1,2,3-triazol-5-yl)-2-(trifluoromethyl)-6,11-dihydro-5H-pyrido[2,3-b][1,5]benzodiazepine

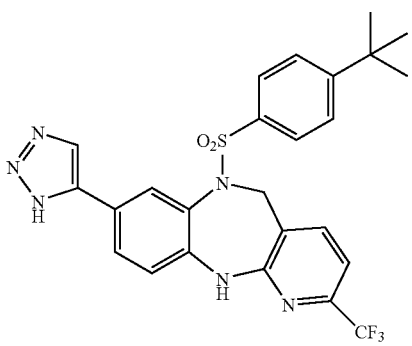

Step A: A mixture of 6-[(4-tert-butylphenyl)sulfonyl]-8-iodo-2-(trifluoromethyl)-6,11-dihydro-5H-pyrido[2,3-b][1,5]benzodiazepine (intermediate 52, 100 mg, 0.170 mmol), trimethylsilylacetylene (0.027 mL, 0.187 mmol), Pd(PPh$_3$)$_2$Cl$_2$ (23.9 mg, 0.034 mmol), copper (I) iodide (12.9 mg, 0.068 mmol), diethylamine (1.5 mL), and DMF (0.5 mL) was heated in a microwave reactor for 5 min at 120° C. After cooling to room temperature, the reaction mixture was diluted with EtOAc and poured into a mixture of 9:1 ammonium chloride in ammonium hydroxide. The reaction mixture was extracted with EtOAc, and the extracts were washed with water, brine, dried (anhydrous MgSO$_4$) and concentrated. The residue was dissolved in methanol (5 mL) and was treated with potassium carbonate at room temperature for 0.5 h. Volatiles were removed and the residue was partitioned between ether and water. The ether extracts were washed with brine, dried over MgSO$_4$ and concentrated, and the residue was purified by silica gel column chromatography to afford the acetylene intermediate. LC/MS: m/e 486.0 (M+H)$^+$.

Step B: A mixture of the product from Step A (30 mg, 0.062 mmol) and azidotrimethyltin (~1 mL) in DMF (1 mL) was heated in a microwave reactor at 120° C. for 1 h, followed by 150° C. for 2 h. The reaction mixture was cooled to room temperature, diluted with EtOAc, washed with water, brine, and dried over MgSO$_4$ and concentrated. The residue was purified via reverse-phase HPLC to provide the title compound. LC/MS: m/e 529.0 (M+H)$^+$. $^1$H NMR (500 MHz, CD$_3$OD): δ 8.20 (1H, br s), 7.70 (1H, d), 7.60 (1H, d), 7.18 (2H, d), 7.03-7.10 (2H, m), 6.95 (2H, d), 4.60-5.0 (2H, br), 1.25 (9H, s).

EXAMPLE 506

6-[(4-tert-Butylphenyl)sulfonyl]-8-(2H-1,2,3-triazol-2-yl)-2-(trifluoromethyl)-6,11-dihydro-5H-pyrido[2,3-b][1,5]benzodiazepine

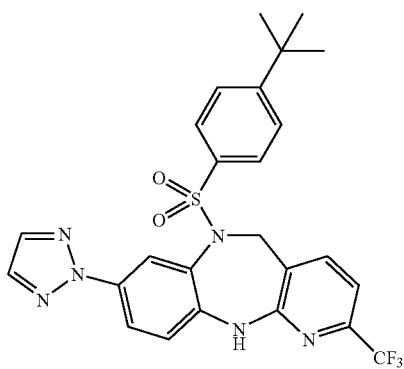

To a stirred solution of 6-[(4-tert-butylphenyl)sulfonyl]-8-iodo-2-(trifluoromethyl)-6,11-dihydro-5H-pyrido[2,3-b][1,5]benzodiazepine (intermediate 52, 109 mg, 0.19 mmol) in DMF (4 mL) was added 1,2,3-triazole (39 mg, 0.56 mmol), CuI (71 mg, 0.37 mmol), N,N'-dimethylethylenediamine (0.08 mL, 0.74 mmol), and KOtBu (1.0M/THF, 1.5 mL, 1.5 mmol). The resulting solution was heated to 180° C. in a microwave reactor for 1 h. The solution was diluted with EtOAc and washed with sat aqueous NaHCO$_3$. The organic layer was separated, washed with brine, dried over MgSO$_4$, filtered and concentrated, and the oily residue was purified by silica gel chromatography to give the title compound. $^1$H NMR (500 MHz, (CD$_3$)$_2$CO): δ 8.60 (s, 1H), 8.20 (s, 1H), 8.00 (m, 2H), 7.78 (d, 1H), 7.50 (d, 1H), 7.22 (d, 2H), 7.18 (d, 1H), 7.05 (d, 2H), 4.90 (br s, 2H), 1.20 (s, 9H). LCMS: m/e 529.0 (M+H)$^+$.

EXAMPLE 507

6-(Butylsulfonyl)-7,8-dimethyl-2-(trifluoromethyl)-6,11-dihydro-5H-pyrido[2,3-b][1,5]benzodiazepine

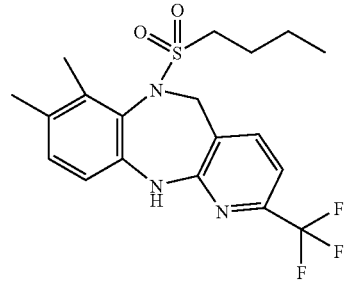

The title compound was prepared from intermediate 29 and butylsulfonyl chloride following the same procedure described for Example 250. $^1$H NMR (500 MHz, CD$_3$OD): δ 7.62 (1H, d), 7.13 (1H, d), 7.08 (1H, d), 6.93 (1H), 5.11 (1H, d), 4.42 (1H, d), 2.84 (1H, m), 2.46 (1H, m), 2.37 (3H, s), 2.37 (3H, s), 2.24 (3H, s), 1.62-1.46 (2H, m), 1.20 (2H, q), 0.77 (3H, t). LCMS: m/e 414.1 (M+H)$^+$.

EXAMPLE 508

6-[(4-tert-Butylphenyl)sulfonyl]-8-fluoro-7-methyl-2-(trifluoromethyl)-6,11-dihydro-5H-pyrido[2,3-b]-[1,5]benzodiazepine

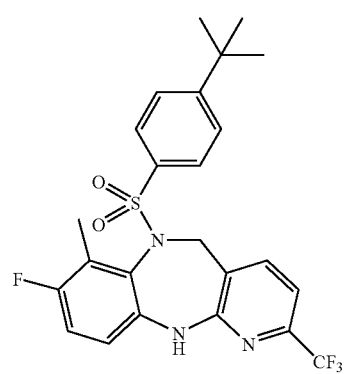

Step A: A solution of 4-fluoro-3-methyl-1,2-benzenediamine (1.66 g, 12.0 mmol) and 2-chloro-6-(trifluoromethyl)nicotinic acid (2.25 g, 10.0 mmol) in 25 mL of sec-butoxyethanol was heated to 150° C. for 4 h. Once complete, the solution was concentrated under reduced pressure to give the requisite amide, which was used without further purification. LCMS: m/z 312.1 (M+H)$^+$.

Step B: A solution of the amide from Step A in THF (40 mL) was treated with BH$_3$.THF (1.0 M/THF, 40 mL, 40.0 mmol) at 0° C. The dark solution was allowed to warm to rt. After 12 h, the solution was quenched carefully with MeOH. Once bubbling ceased, the solution was concentrated and purified by silica gel chromatography (0-60% EtOAc in hexanes) to provide the desired amine.

Step C: The amine from Step B was sulfonylated as previously described for intermediate 2 using 4-tert-butylbenzene sulfonyl chloride to give the title compound as a racemic mixture. $^1$H NMR (500 MHz, (CD$_3$OD): δ 7.55 (d, 1H), 7.19 (d, 2H), 7.09 (d, 2H), 6.99 (t, 2H), 6.89 (m, 1H), 5.15 (d, 1H), 4.43 (d, 1H), 2.42 (d, 3H), 1.26 (s, 9H). LCMS: m/z 493.9 (M+H)$^+$. The racemic mixture was separated by HPLC using a chiralcel OD-H column to afford the respective enantiomers. The faster eluting enantiomer (E1) has a retention time of 9.5 min; the slower eluting enantiomer (E2) has a retention time of 13.5 min.

EXAMPLES 509 AND 510

Ethyl 2-hydroxy-3-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]butanoate (509) and Ethyl oxo[6-{[4-(trifluoromethoxy)phenyl]sulfonyl}-2-(trifluoromethyl)-6,11-dihydro-5H-pyrido[2,3-b][1,5]benzodiazepin-8-yl]acetate (510)

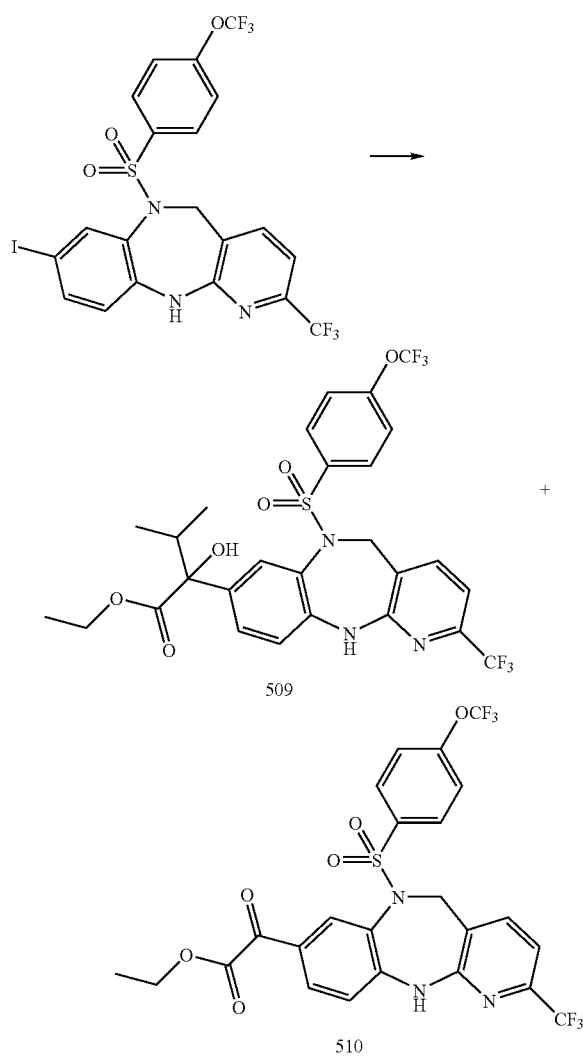

To a solution of 8-iodo-6-{[4-(trifluoromethoxy)phenyl]sulfonyl}-2-(trifluoromethyl)-6,11-dihydro-5H-pyrido[2,3-b][1,5]benzodiazepine (787 mg, 1.28 mmol, intermediate 61) in 2 ml of THF was added a solution of isopropyl magnesium chloride (5.12 ml, 10.24 mmol) in THF (2M) at 0° C. and stirred for 30 min. Then the reaction mixture was added to a solution of diethyl oxalate (4.34 ml, 32 mmol) in 8 mL of toluene and stirred for 30 min. at 0° C. Then the reaction mixture was poured into 3.5 mL of 2 N HCl and 5 mL of ice-water, and the pH was adjusted to pH=7-8 with aqueous NaHCO$_3$. The mixture was extracted with ethyl acetate (3×20 ml) and dried with Na$_2$SO$_4$. The combined organic layers were evaporated under reduced pressure. The resulting residue was purified by column chromatography on silica gel, eluting with hexane/ethyl acetate (4/1-3/1) to give title compound 509; Mass Spectrum: m/e=634 (M+1). Further elution of the column afforded the title compound 510; Mass Spectrum: m/e=590 (M+1).

EXAMPLE 511

2-hydroxy-3-methyl-2-[6-{[4-(trifluoromethoxy)phenyl]sulfonyl}-2-(trifluoromethyl)-6,11-dihydro-5H-pyrido[2,3-b][1.5]benzodiazepin-8-yl]butanoic acid

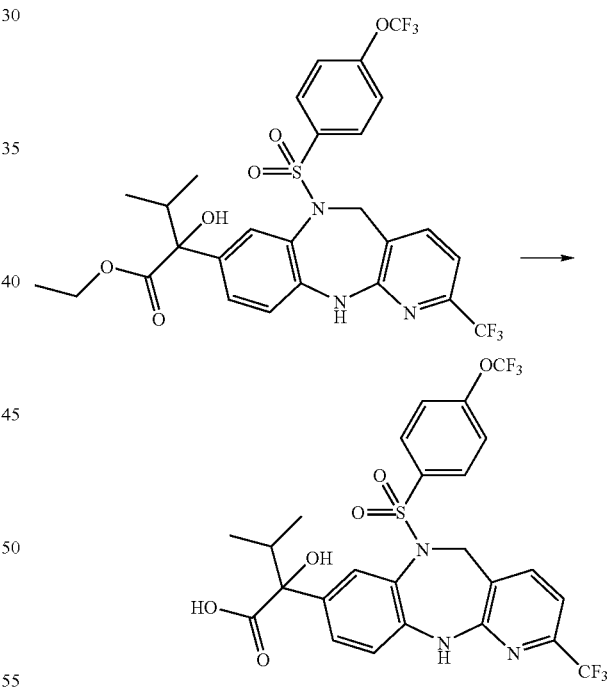

To a solution of ethyl 2-hydroxy-3-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]butanoate (153 mg, 0.242 mmol, Example 509) in 4 mL of EtOH was added a solution of 1N LiOH (2.5 ml) in water, and the solution was stirred for 48 h at rt. LC-MS showed the reaction complete. The reaction pH was adjusted to 6-7 with 1N HCl, and the mixture was concentrated. The resulting residue was dissolved in CH$_2$Cl$_2$ and filtered to remove the salt. The filtrate was concentrated and the residue was purified by chromatography to give the title compound as a white solid; Mass Spectrum: m/e=606 (M+1).

EXAMPLE 512

Oxo[6-{[4-(trifluoromethoxy)phenyl]sulfonyl}-2-trifluoromethyl)-6,11-dihydro-5H-pyrido[2,3-][1,5]benzodiazepin-8-yl]acetic acid

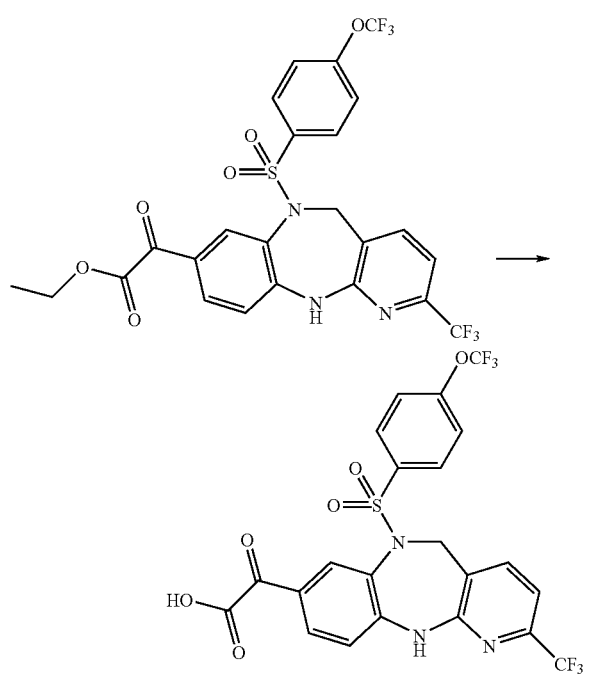

The title compound was prepared from ethyl oxo[6-{[4-(trifluoromethoxy)phenyl]sulfonyl}-2-(trifluoromethyl)-6,11-dihydro-5H-pyrido[2,3-b][1,5]benzodiazepin-8-yl]acetate (Example 510) using the procedure described in Example 511; Mass Spectrum: m/e=562 (M+1).

EXAMPLE 513

Hydroxy[6-{[4-(trifluoromethoxy)phenyl]sulfonyl}-2-(trifluoromethyl)-6,11-dihydro-5H-pyrido[2,3-b][1,5]benzodiazepin-8-yl]acetic acid

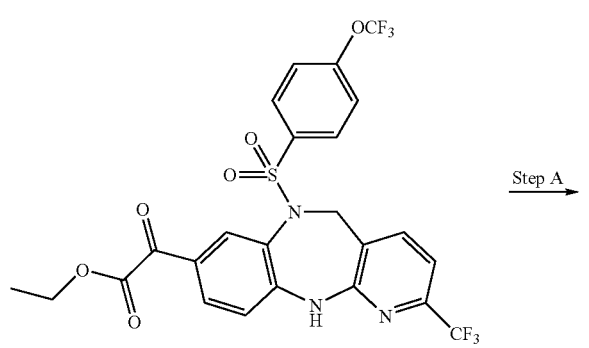

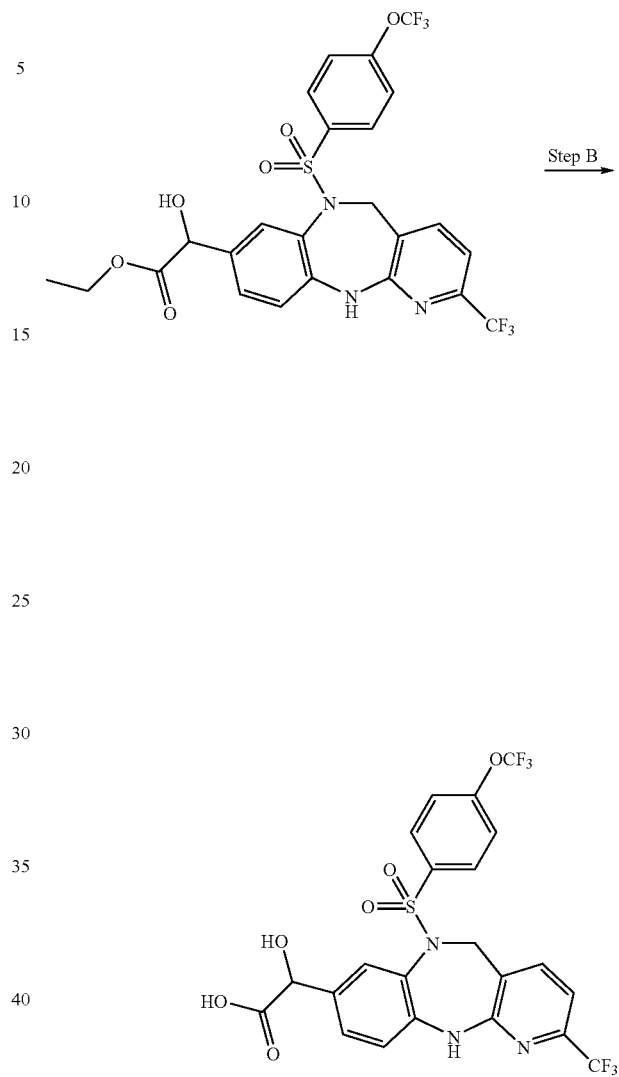

Step A: Ethyl hydroxy[6-{[4-(trifluoromethoxy)phenyl]sulfonyl}-2-(trifluoromethyl)-6,11-dihydro-5H-pyrido[2,3-b][1,5]benzodiazepin-8-yl]acetate To a solution of ethyl oxo[6-{[4-(trifluoromethoxy)-phenyl]-sulfonyl}-2-(trifluoromethyl)-6,11-dihydro-5H-pyrido[2,3-b][1,5]benzodiazepin-8-yl]acetate (61 mg, 0.103 mmol, Example 510) in 3 ml of THF/EtOH was added NaBH4 (2.74 mg, 0.072 mmol) at rt and the solution was stirred for 30 min. Then the reaction mixture was quenched with 0.3 mL of 1N HCl and 0.3 mL of water. The solution was concentrated and the crude residue was used directly in the next step; Mass Spectrum: m/e=592 (M+1).

Step B: Hydroxy[6-{[4-(trifluoromethoxy)phenyl]sulfonyl}-2-(trifluoromethyl)-6,11-dihydro-5H-pyrido[2,3-b][1,5]benzodiazepin-8-yl]acetic acid Prepared from ethyl hydroxy[6-{[4-(trifluoro-methoxy)phenyl]sulfonyl}-2-(trifluoromethyl)-6,11-dihydro-5H-pyrido[2,3-b][1,5]benzodiazepin-8-yl]acetate (the product of Step A) using the procedure described in Example 511: Mass Spectrum: m/e=564 (M+1).

EXAMPLE 514

Ethyl 6-{[4-(trifluoromethoxy)phenyl]sulfonyl}-2-(trifluoromethyl)-6,11-dihydro-5H-pyrido[2,3-b][1,5]benzodiazepine-8-carboxylate

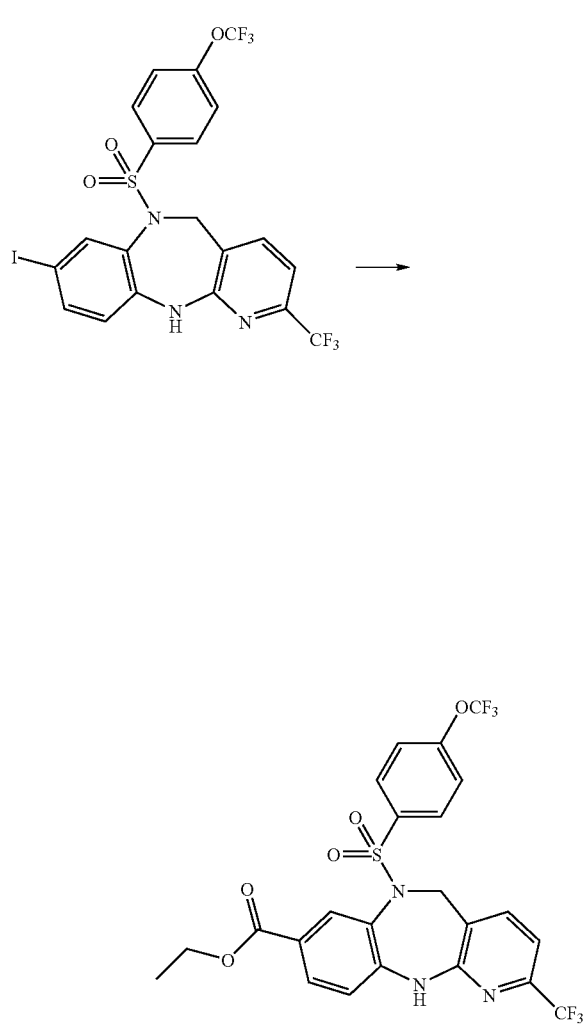

To a solution of 8-iodo-6-{[4-(trifluoromethoxy)phenyl]sulfonyl}-2-(trifluoromethyl)-6,11-dihydro-5H-pyrido[2,3-b][1,5]benzodiazepine (380 mg, 0.618 mmol, intermediate 61) in 2 ml of THF was added a solution of isopropyl magnesium chloride (1.54 ml, 3.08 mmol) in THF (2M) at 0° C. and the solution was stirred for 30 min at 0° C. Then the reaction mixture was added to a solution of ethyl cyanidocarbonate in 3 mL of THF and stirred for 30 min at 0° C. The reaction mixture was poured into 2 mL of 2N HCl and 5 mL of ice-water, and the pH was adjusted to 7-8 with aqueous NaHCO$_3$ at 0° C. The solution was extracted with ethyl acetate (3×20 ml), and the combined organic extracts were dried over Na$_2$SO$_4$. The solution was concentrated under reduced pressure and the residue was purified by silica gel chromatography using with hexane/ethyl acetate (6/1) to give the title compound as a white solid; Mass Spectrum: m/e=562 (M+1).

EXAMPLE 515

2-Hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid

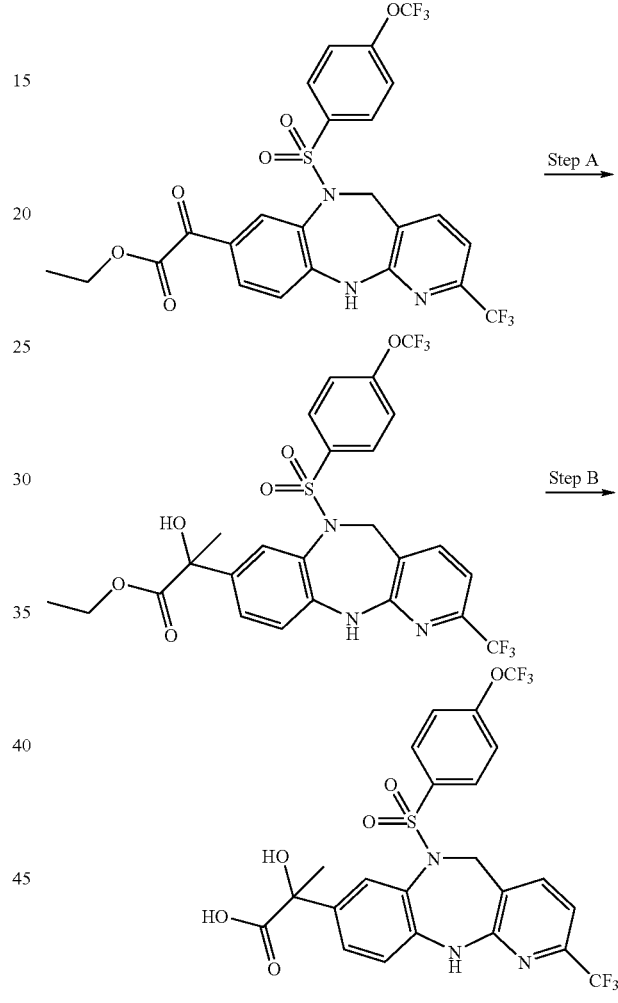

Step A: Ethyl 2-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoate To a solution of ethyl oxo[6-{[4-(trifluoro-methoxy)phenyl]sulfonyl}-2-(trifluoromethyl)-6,11-dihydro-5H-pyrido[2,3-b][1,5]benzodiazepin-8-yl]acetate (103 mg, 0.175 mmol, Example 510) in THF was added a solution of MeMgBr (0.25 ml, 0.35 mmol) in toluene (1.4 M) and the solution was stirred for 30 min. at 0° C. The LC-MS showed the reaction was almost complete. The solution was poured into aqueous NH$_4$Cl to quench the reaction, and the pH was adjusted to 7-8 with 1N aqueous NaHCO$_3$. The mixture was partitioned between 20 mL of CH$_2$Cl$_2$ and 5 mL of water, and the aqueous layer was extracted with CH$_2$Cl$_2$ (2×20 mL). The combined organic layers were dried over Na$_2$SO$_4$, and the solvent was evaporated under reduced pressure to give the title compound as white solid; Mass Spectrum: m/e=606 (M+1).

Step B: 2-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid Prepared from ethyl 2-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoate (the product of Step A) using the procedure described in Example 511; Mass Spectrum: m/e=578 (M+1).

EXAMPLE 516

2-Hydroxy-N-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]acetamide

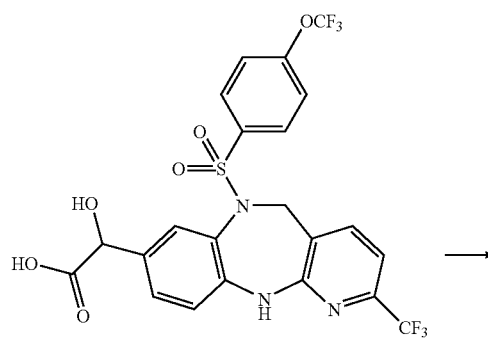

A mixture of hydroxy[6-{[4-(trifluoromethoxy)phenyl]sulfonyl}-2-(trifluoromethyl)-6,11-dihydro-5H-pyrido[2,3-b][1,5]benzodiazepin-8-yl]acetic acid (51 mg, 0.091 mmol, Example 513), BOP (60.1 mg, 0.136 mmol), MeNH₂—HCl (12.2 mg, 0.181 mmol), and diisopropylethylamine (0.08 ml, 0.453 mmol) in DMF was stirred for 2.5 h at rt. LC-MS showed the reaction complete. The solution was concentrated and the residue was purified by mass-directed HPLC eluting with H₂O/MeCN/TFA (90:10:0.1-10:90:0.1) to give the title compound; Mass Spectrum: m/e=576 (M+1).

EXAMPLES 517 AND 518

2-Hydroxy-N,3-dimethyl-2-[6-{[4-(trifluoromethoxy)phenyl]sulfonyl}-2-(trifluoromethyl)-6,11-dihydro-5H-pyrido[2,3-b][1,5]benzodiazepin-8-yl]butanamide (517) and N,3-dimethyl-2-[6-{[4-(trifluoromethoxy)phenyl]-sulfonyl}-2-(trifluoromethyl)-6,11-dihydro-5H-pyrido[2,3-b][1,5]benzodiazepin-8-yl]but-2-enamide (518)

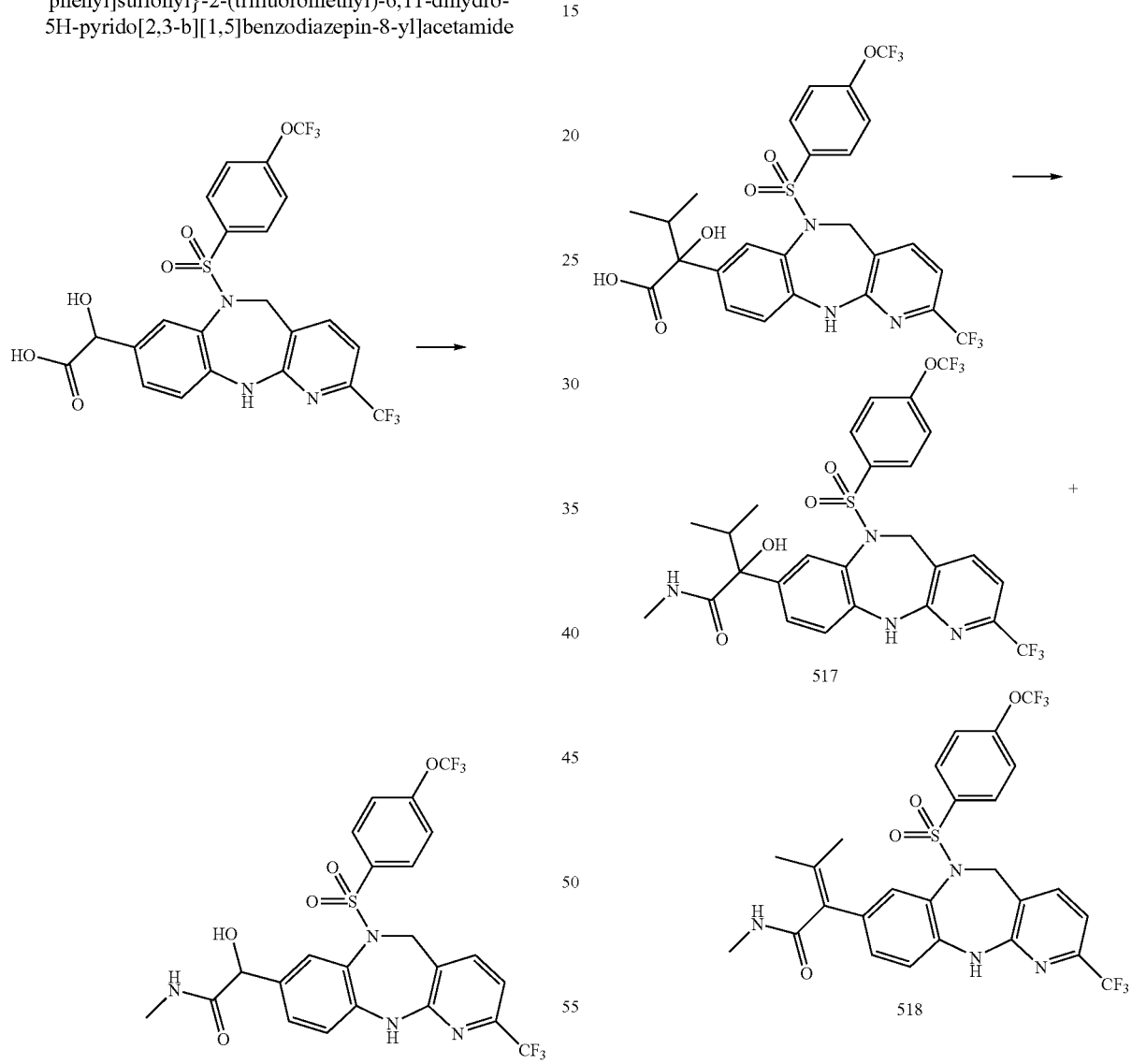

A mixture of 2-hydroxy-3-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]butanoic acid (71 mg, 0.117 mmol, Example 511), HATU (71.3 mg, 0.188 mmol), MeNH₂ (0.117 ml, 0.235 mmol, 2M in THF), and diisopropylethylamine (0.083 ml, 0.469 mmol) in DMF was stirred for 2.5 h at rt. LC-MS showed the reaction complete. The solution was concentrated and the residue was purified by mass-directed HPLC eluting with H₂O/MeCN/TFA (90/10/0.1-10/90/0.1) to give title compound 517; Mass Spectrum:

EXAMPLE 519

2-Hydroxy-N-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanamide

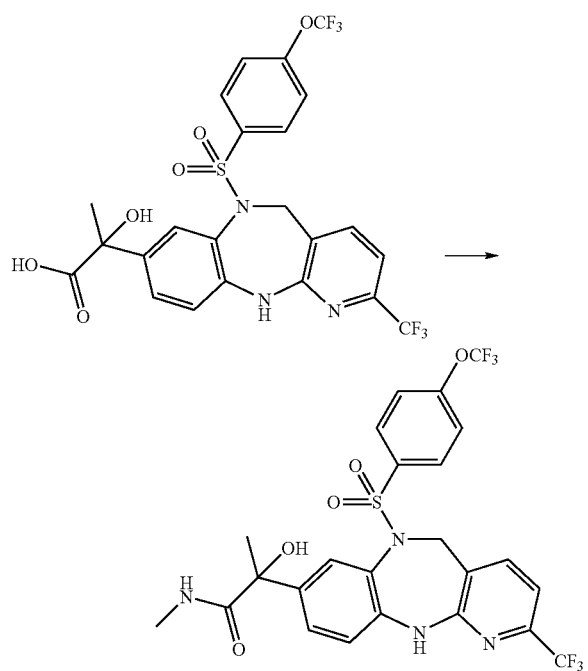

The title compound was prepared from 2-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid (Example 515) using the procedure described in Example 516 to afford the title compound; Mass Spectrum: m/e=591 (M+1).

EXAMPLE 520

1-[6-{[4-(Trifluoromethoxy)phenyl]sulfonyl}-2-(trifluoromethyl)-6,11-dihydro-5H-pyrido[2,3-b][1,5]benzodiazepin-8-yl]ethanone

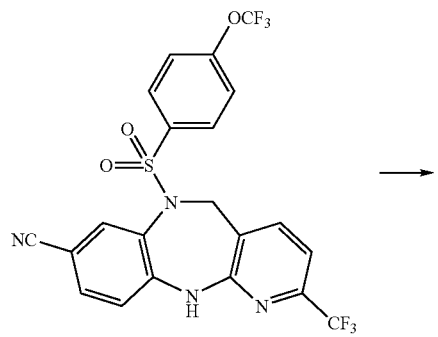

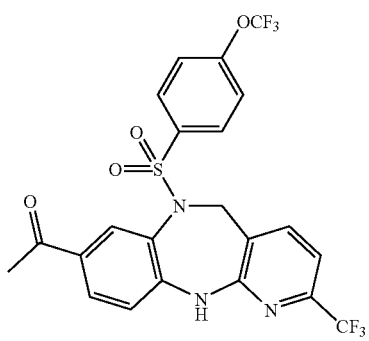

To a solution of 6-{[4-(trifluoromethoxy)phenyl]sulfonyl}-2-(trifluoromethyl)-6,11-dihydro-5H-pyrido[2,3-b][1,5]benzodiazepine-8-carbonitrile (702 mg, 1.365 mmol) in 5 ml of THF was added a solution of methyl magnesium bromide (4.87 ml, 6.82 mmol) in THF (1.4 M) at 0° C. The solution was heated to reflux for 8 h, then the solution was cooled to room temperature. Excess Grignard reagent was decomposed by the addition of 4 mL of 2N HCl and the solution was stirred for 1 hr at rt. The pH was adjusted to 7-8 with aqueous NaHCO$_3$. The resulting solution was filtered and the solids were washed with CH$_2$Cl$_2$. To the filtrate was added 30 mL of CH$_2$Cl$_2$, and the layers were separated. The aqueous layer was extracted with CH$_2$Cl$_2$ (3×20 ml), and the combined organic layers were dried with Na$_2$SO$_4$ and the solvent was evaporated under reduced pressure. The residue was purified by column chromatography on silica gel, eluting with hexane/ethyl acetate (6:1-4:1) to give the title compound as a white solid; Mass Spectrum: m/e=591 (M+1).

EXAMPLE 521

N,2-dimethyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanamide

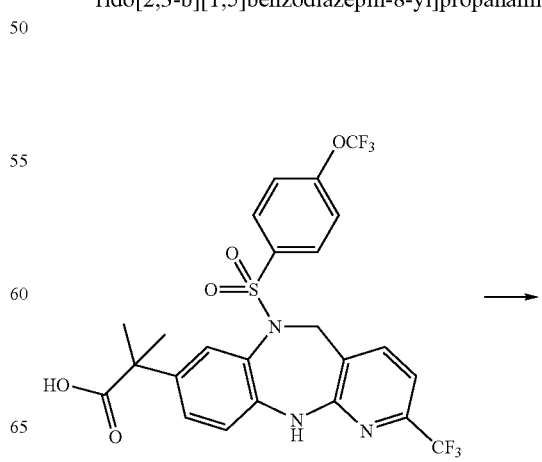

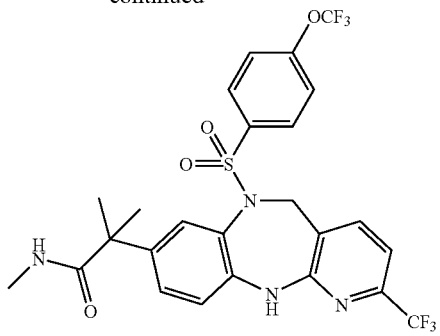

The title compound was prepared from 2-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid (Example 382) using the procedure described in Example 516 to afford the title compound; Mass Spectrum: m/e=589 (M+1).

EXAMPLE 522

N-Isopropyl-2-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanamide

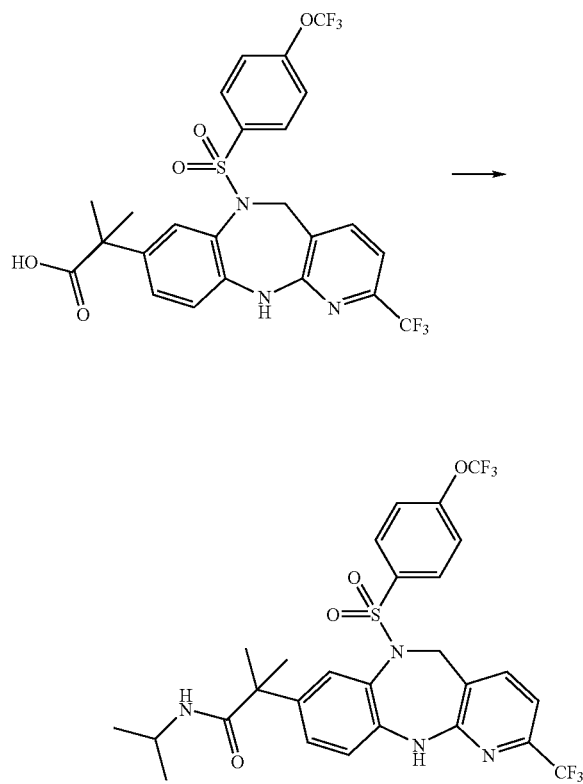

The title compound was prepared from 2-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid (Example 382) and isopropylamine using the procedure described in Example 516 to afford the title compound; Mass Spectrum: m/e=617 (M+1).

EXAMPLE 523

N,N,2-Trimethyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanamide

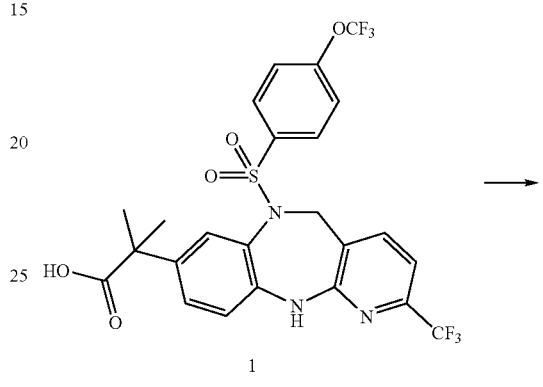

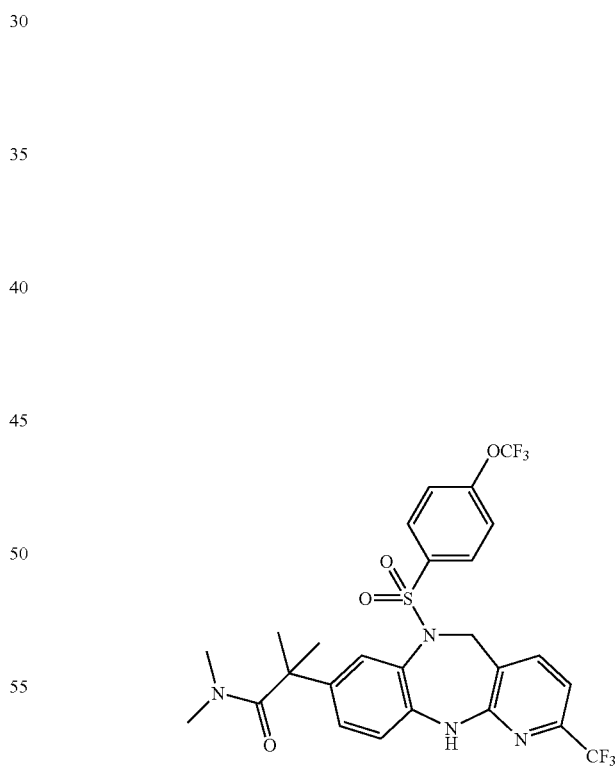

The title compound was prepared from 2-methyl-2-[6-{[4-(trifluoromethoxy)phenyl]sulfonyl}-2-(trifluoromethyl)-6,11-dihydro-5H-pyrido[2,3-b][1,5]benzodiazepin-8-yl]propanoic acid (Example 382) and dimethylamine using the procedure described in Example 516 to afford the title compound; Mass Spectrum: m/e=603 (M+1).

EXAMPLE 524

[6-{[4-(Trifluoromethoxy)phenyl]sulfonyl}-2-(trifluoromethyl)-6,11-dihydro-5H-pyrido[2,3-b][1,5]benzodiazepin-8-yl]acetonitrile

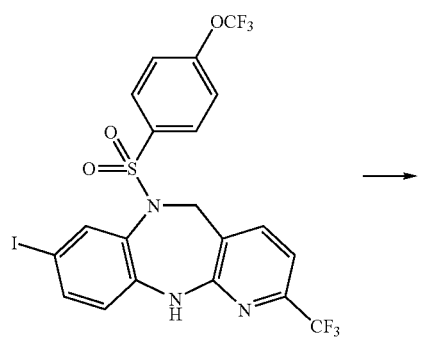

EXAMPLE 525

2-(3-{[6-{[4-(Trifluoromethoxy)phenyl]sulfonyl}-2-(trifluoromethyl)-6,11-dihydro-5H-pyrido[2,3-b][1,5]benzodiazepin-8-yl]methyl}-1,2,4-oxadiazol-5-yl)propan-2-ol

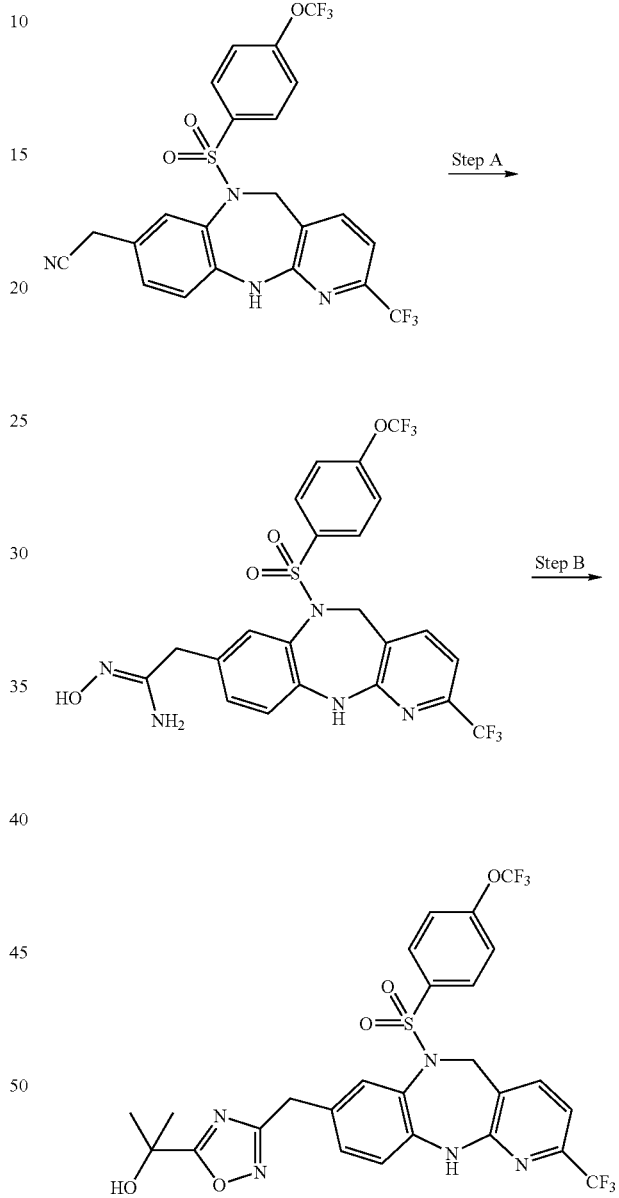

A sample of NaH (23.4 mg, 0.585 mmol) was put in a dried flask and 1.5 mL of DMSO (anhydrous) was added. Then ethyl cyanoacetate (0.062 ml, 0.585 mmol) was added slowly and stirred under $N_2$ for 20 minutes. Then a solution of 8-iodo-6-{[4-(trifluoromethoxy)phenyl]sulfonyl}-2-(trifluoromethyl)-6,11-dihydro-5H-pyrido[2,3-b][1,5]benzodiazepine (240 mg, 0.390 mmol, intermediate 61) in DMSO (2.0 ml) was added, followed by copper (I) iodide (111 mg, 0.585 mmol). The mixture was stirred for 2 hr at 90-95° C. Then 4 mL of water and 0.3 mL of 1N NaOH were added and the reaction mixture was stirred at 80-85° C. for 1 hr. The reaction mixture was poured into 50 mL of ethyl acetate and 10 mL of water, and the aqueous layer was extracted with ethyl acetate (20 mL×2). The combined organic layers were dried over $Na_2SO_4$ and concentrated. The resulting residue was purified by column chromatography on silica gel, eluting with hexane/acetone (6:1-4:1) to give the title compound.

Mass Spectrum: m/e=529 (M+1).

Step A: (1Z)-N'-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]ethanimidamide A mixture of [6-{[4-(trifluoromethoxy)-phenyl]sulfonyl}-2-(trifluoromethyl)-6,11-dihydro-5H-pyrido[2,3-b][1,5]benzodiazepin-8-yl]acetonitrile (86 mg, 0.163 mmol, Example 524), $NH_2OH$ (0.5 ml, 7.57 mmol; 50% in $H_2O$), and several crystals of $K_2CO_3$ in 4 mL of EtOH was heated at 120° C. in a microwave for 20 minutes. The resulting solution was concentrated to dryness to give a yellow solid, which was used in the next step without further purification; Mass Spectrum: m/e=562 (M+1).

Step B: 2-(3-{[6-{[4-(trifluoromethoxy)phenyl]sulfonyl}-2-(trifluoromethyl)-6,11-dihydro-5H-pyrido[2,3-b][1,5]benzodiazepin-8-yl]methyl}-1,2,4-oxadiazol-5-yl)propan-2-ol To a solution of (1Z)-N'-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]ethanimidamide (92 mg, 0.163 mmol, the product of Step A) in pyridine was added 2-acetoxyisobutyryl chloride (0.268 g, 1.63 mmol). The resulting mixture was heated at 80-84° C. for 1.5 hr, until LC-MS indicated the reaction was complete, and then the solution was concentrated to remove pyridine. The bright orange residue was dissolved in 5 mL of MeOH and K$_2$CO$_3$ was added. The mixture was stirred for 2 hr at 50° C., then another 0.5 g of K$_2$CO$_3$ was added and the solution was stirred for another 2 hr. The solution was filtered to remove solids and the filtrate was concentrated to remove MeOH. The residue was purified by column chromatography on silica gel, eluting with hexane/ethyl acetate (3:1-2:1) to give the title compound; Mass Spectrum: m/e=630 (M+1).

EXAMPLE 526

2-(3-{1Hydroxy-1-[6-{[4-(trifluoromethoxy)phenyl]sulfonyl}-2-(trifluoromethyl)-6,11-dihydro-5H-pyrido[2,3-b][1,5]benzodiazepin-8-yl]ethyl}-1,2,4-oxadiazol-5-yl)propan-2-ol

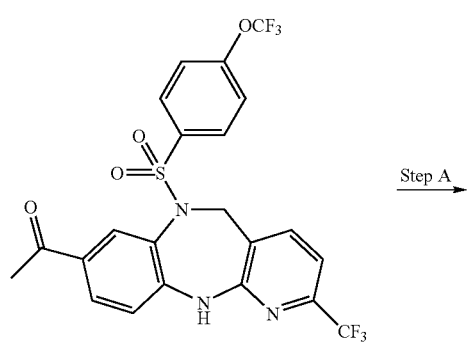

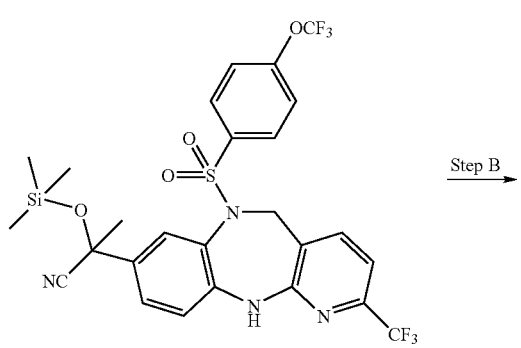

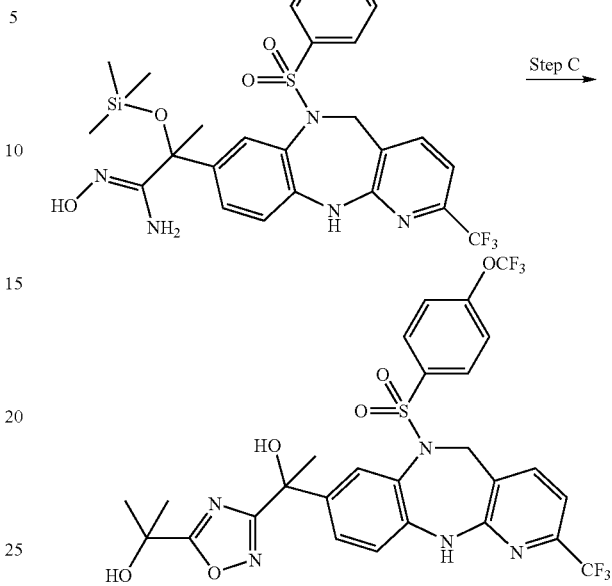

Step A: 2-[6-{[4-(trifluoromethoxy)phenyl]sulfonyl}-2-(trifluoromethyl)-6,11-dihydro-5H-pyrido[2,3-b][1,5]benzodiazepin-8-yl]-2-[(trimethylsilyl)oxy]propanenitrile A mixture of 1-[6-{[4-(trifluoro-methoxy)phenyl]sulfonyl}-2-(trifluoromethyl)-6,11-dihydro-5H-pyrido[2,3-b][1,5]benzodiazepin-8-yl]ethanone (62 mg, 0.117 mmol, Example 520), trimethylsilanecarbonitrile (23.15 mg, 0.233 mmol), and zinc diiodide (5.6 mg, 0.018 mmol) in benzene was stirred for 24 hr at rt. LC-MS showed the reaction was complete. The solution was concentrated to give the title compound, which was used directly in the next step.

Step B: (1Z)-N'-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]-2-[(trimethylsilyl)oxy]propanimidamide The mixture of crude 2-[6-{[4-(trifluoromethoxy)phenyl]sulfonyl}-2-(trifluoromethyl)-6,11-dihydro-5H-pyrido[2,3-b][1,5]-benzodiazepin-8-yl]-2-[(trimethylsilyl)oxy]propanenitrile (75 mg, 0.119 mmol, the product of Step A), NH$_2$OH (0.5 ml, 7.57 mmol, 50% in H$_2$O), and several crystals of K$_2$CO$_3$ in 4 mL of EtOH was heated at 120° C. in a microwave for 20 minutes. The solution was concentrated to dryness to give crude product as a yellow solid, which was used in the next step without further purification; Mass Spec: m/e=664 (M+1).

Step C: 2-(3-{1-hydroxy-1-[6-{[4-(trifluoromethoxy)phenyl]sulfonyl}-2-(trifluoromethyl)-6,11-dihydro-5H-pyrido[2,3-b][1,5]benzodiazepin-8-yl]ethyl}-1,2,4-oxadiazol-5-yl)propan-2-ol To a solution of dry (1Z)-N'-hydroxy-2-[6-{[4-(trifluoromethoxy)phenyl]sulfonyl}-2-(trifluoromethyl)-6,11-dihydro-5H-pyrido[2,3-b][1,5]benzodiazepin-8-yl]-2-[(trimethylsilyl)oxy]propanimidamide (108 mg, 0.163 mmol, the product of Step B) in pyridine was added 2-acetoxyisobutyrylchloride (0.268 g, 1.63 mmol) at rt. The resulting mixture was heated at 80-84° C. for 1.5 hr, until LC-MS indicated the reaction was complete. The bright orange residue was dissolved in 5 mL of MeOH and K$_2$CO$_3$ was added. The mixture was stirred for 2 hr at 50° C., then another 0.5 g of K$_2$CO$_3$ was added and the solution was stirred for another 2 hr. The solution was filtered to remove solids, and the filtrate was concentrated to remove MeOH. The residue was purified by column chromatography on silica gel, eluting with hexane/ethyl acetate (3:1-2:1) to give the title compound; Mass Spectrum: m/e=660 (M+1).

EXAMPLE 527

1-(5-Methyl-1H-pyrazol-3-yl)-1-[6-{[4-(trifluoromethoxy)phenyl]sulfonyl}-2-(trifluoromethyl)-6,11-dihydro-5H-pyrido[2,3-b][1,5]benzodiazepin-8-yl]ethanol

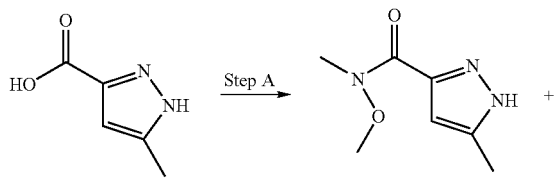

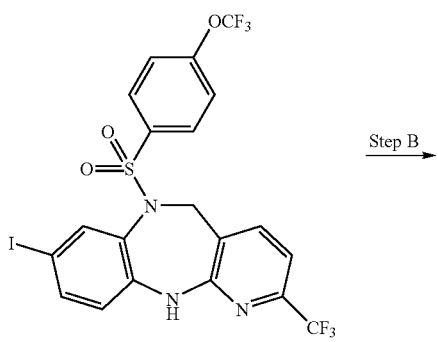

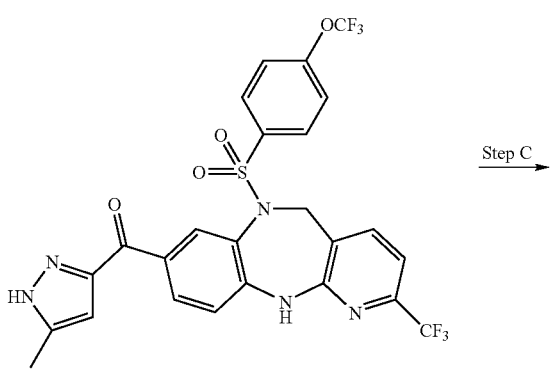

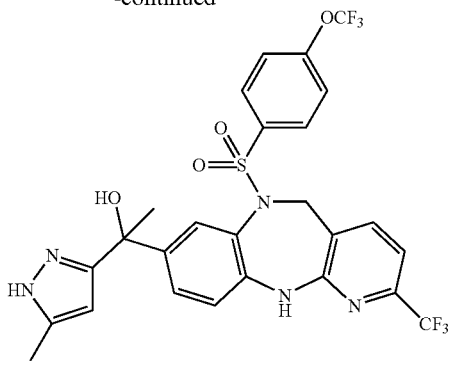

Step A: N-Methoxy-N,5-dimethyl-1H-pyrazole-3-carboxamide A mixture of 5-methyl-1H-pyrazole-3-carboxylic acid (995 mg, 7.89 mmol), N-methoxymethanamine hydrochloride (1539 mg, 15.78 mmol), DMAP (3856 mg, 31.6 mmol), and N-(3-dimethylaminopropyl)-N'-ethylcarbodiimide hydrochloride (3025 mg, 15.78 mmol) in $CH_2Cl_2$ was stirred for 12 h at rt. The mixture was poured into 30 mL of $CH_2Cl_2$ and 10 mL of water, and the pH was adjusted to 7.5 with aqueous $NaHCO_3$. The aqueous layer was extracted with $CH_2Cl_2$ (2×20 mL). The combined organic fractions were dried over $Na_2SO_4$, filtered and the solvent was evaporated under reduced pressure. The resulting residue was purified by column chromatography on silica gel eluting with $CH_2Cl_2$/acetone (5:1-3:1) to give the title compound as a white solid; Mass Spectrum: m/e=660 (M+1).

Step B: (5-Methyl-1H-pyrazol-3-yl)[6-{[4-(trifluoromethoxy)phenyl]sulfonyl}-2-(trifluoromethyl)-6,11-dihydro-5H-pyrido[2,3-b][1,5]benzodiazepin-8-yl]methanone
To a solution of 8-iodo-6-{[4-(trifluoromethoxy)phenyl]sulfonyl}-2-(trifluoromethyl)-6,11-dihydro-5H-pyrido[2,3-b][1,5]benzodiazepine (950 mg, 1.544 mmol, intermediate 61) in 5 ml of THF was added a solution of isopropyl magnesium chloride (3.47 ml, 6.95 mmol) in THF (2M) at 0° C. The solution was stirred at 0° C. for 30 min, then a mixture of N-methoxy-N,5-dimethyl-1H-pyrazole-3-carboxamide (261 mg, 1.544 mmol) in 3 mL of toluene was added. The reaction mixture was stirred for 2 hr at 0° C. and then allowed to warm to rt overnight. The reaction was quenched by the addition of 4 mL of 0.5 N HCl. The resulting viscous residue was washed with ethyl acetate (30 mL×2) and acetone (20 mL×2). The combined washes were evaporated under reduced pressure and the residue was crystallized from $CH_2Cl_2$ to give the title compound as a light yellow solid; Mass Spectrum: m/e=598 (M+1).

Step C: 1-(5-methyl-1H-pyrazol-3-yl)-1-[6-{[4-(trifluoromethoxy)phenyl]sulfonyl}-2-(trifluoromethyl)-6,11-dihydro-5H-pyrido[2,3-b][1,5]benzodiazepin-8-yl]ethanol To a solution of (5-methyl-1H-pyrazol-3-yl)[6-{[4-(trifluoromethoxy)phenyl]sulfonyl}-2-(trifluoromethyl)-6,11-dihydro-5H-pyrido[2,3-b][1,5]benzodiazepin-8-yl]methanone (105 mg, 0.177 mmol, the product of Step B) in THF was added a solution of methyl magnesium bromide (0.70 ml, 0.976 mmol) in toluene (1.4M). The solution was stirred for 1.5 min at 0° C. and then quenched by the addition of aqueous $NH_4Cl$ and the pH was adjusted to 7-8 with 1 N aqueous $NaHCO_3$. The mixture was poured in to 20 mL of $CH_2Cl_2$ and 5 mL of water and the aqueous layer was extracted with $CH_2Cl_2$ (2×20 mL). The combined organic fractions were dried over $Na_2SO_4$, filtered and the solvent was evaporated under reduced pressure. The residue was purified by mass-directed HPLC eluting with H₂O/MeCN/TFA (90:10:0.1-10:90:0.1) to give the title compound; Mass Spectrum: m/e=614 (M+1)

EXAMPLE 528

(5-methyl-1H-pyrazol-3-yl)[6-{[4-(trifluoromethoxy)phenyl]sulfonyl}-2-(trifluoromethyl)-6,11-dihydro-5H-pyrido[2,3-b][1,5]benzodiazepin-8-yl]methanol

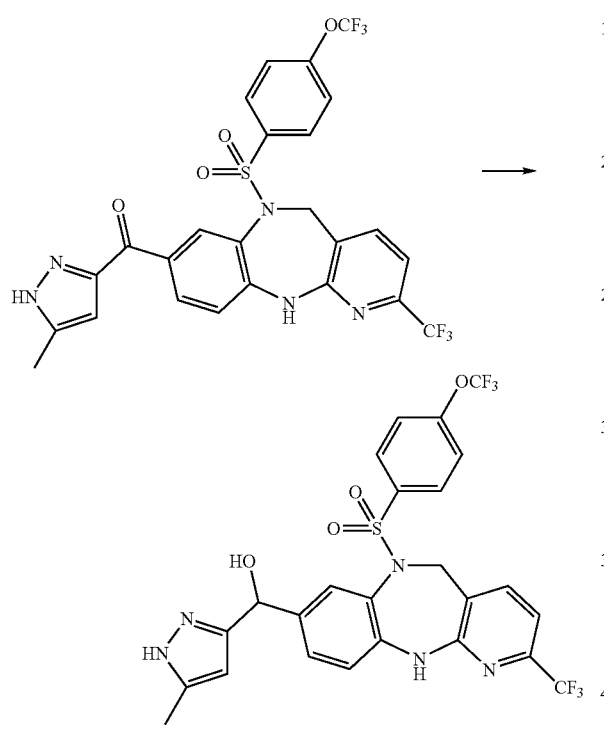

The title compound was prepared from (5-methyl-1H-pyrazol-3-yl)[6-{[4-(trifluoromethoxy)phenyl]sulfonyl}-2-(trifluoromethyl)-6,11-dihydro-5H-pyrido[2,3-b][1,5]benzodiazepin-8-yl]methanone (the product of Example 527, Step B) using the procedure described in Example 511; Mass Spectrum: m/e=600 (M+1).

EXAMPLE 529

1-(1,5-dimethyl-1H-pyrazol-3-yl)-1-[6-{[4-(trifluoromethoxy)phenyl]sulfonyl}-2-(trifluoromethyl)-6,11-dihydro-5H-pyrido[2,3-b][1,5]benzodiazepin-8-yl]ethanol

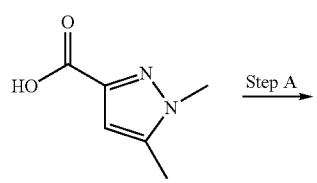

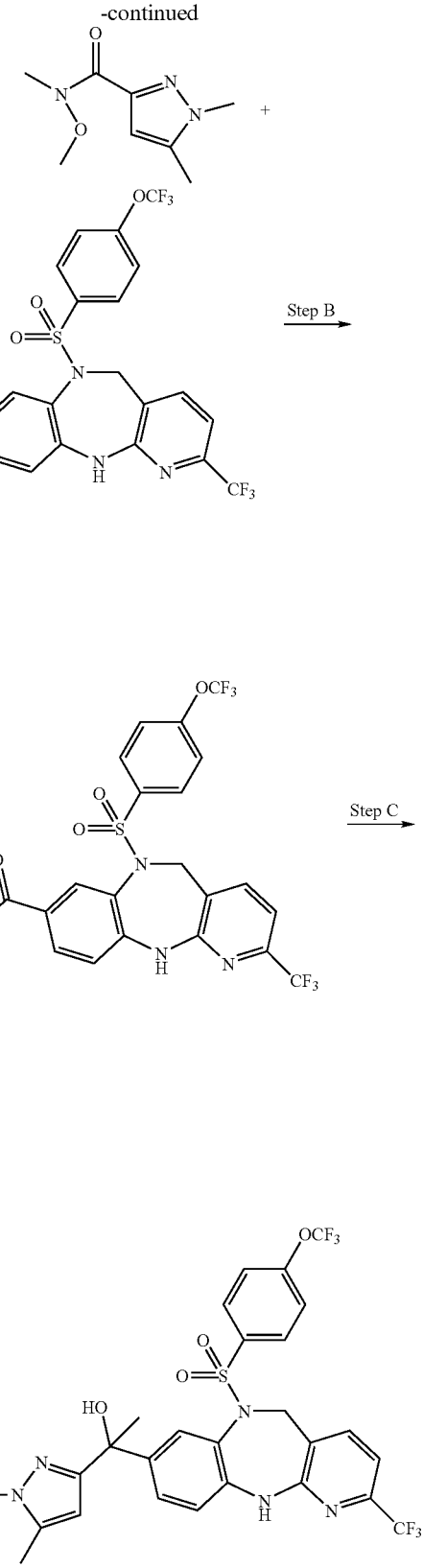

The title compound was prepared from 1,5-dimethyl-1H-pyrazole-3-carboxylic acid and 8-iodo-6-{[4-(trifluoromethoxy)phenyl]sulfonyl}-2-(trifluoromethyl)-6,11-dihydro-5H-pyrido[2,3-b][1,5]benzodiazepine (intermediate 61)

according to the procedures in Steps A-C of Example 527; Mass Spectrum: m/e=628 (M+1).

EXAMPLE 530

(1,5-dimethyl-1H-pyrazol-3-yl)[6-{[4-(trifluoromethoxy)phenyl]sulfonyl}-2-(trifluoromethyl)-6,11-dihydro-5H-pyrido[2,3-b][1,5]benzodiazepin-8-yl]methanol

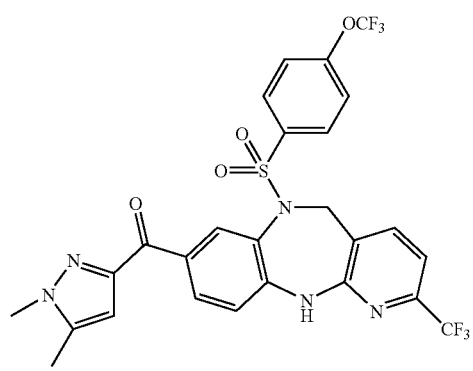

The title compound was prepared from (5-methyl-1H-pyrazol-3-yl)[6-{[4-(trifluoromethoxy)phenyl]sulfonyl}-2-(trifluoromethyl)-6,11-dihydro-5H-pyrido[2,3b][1,5]benzo- diazepin-8-yl]methanone (the product of Example 529, Step B) using the procedure described in Example 511; Mass Spectrum: m/e=614 (M+1).

EXAMPLE 531

2-(3-{1-[6-{[4-(Trifluoromethoxy)phenyl]sulfonyl}-2-(trifluoromethyl)-6,11-dihydro-5H-pyrido[2,3-b][1,5]benzodiazepin-7-yl]cyclobutyl}-1,2,4-oxadiazol-5-yl)propan-2-ol

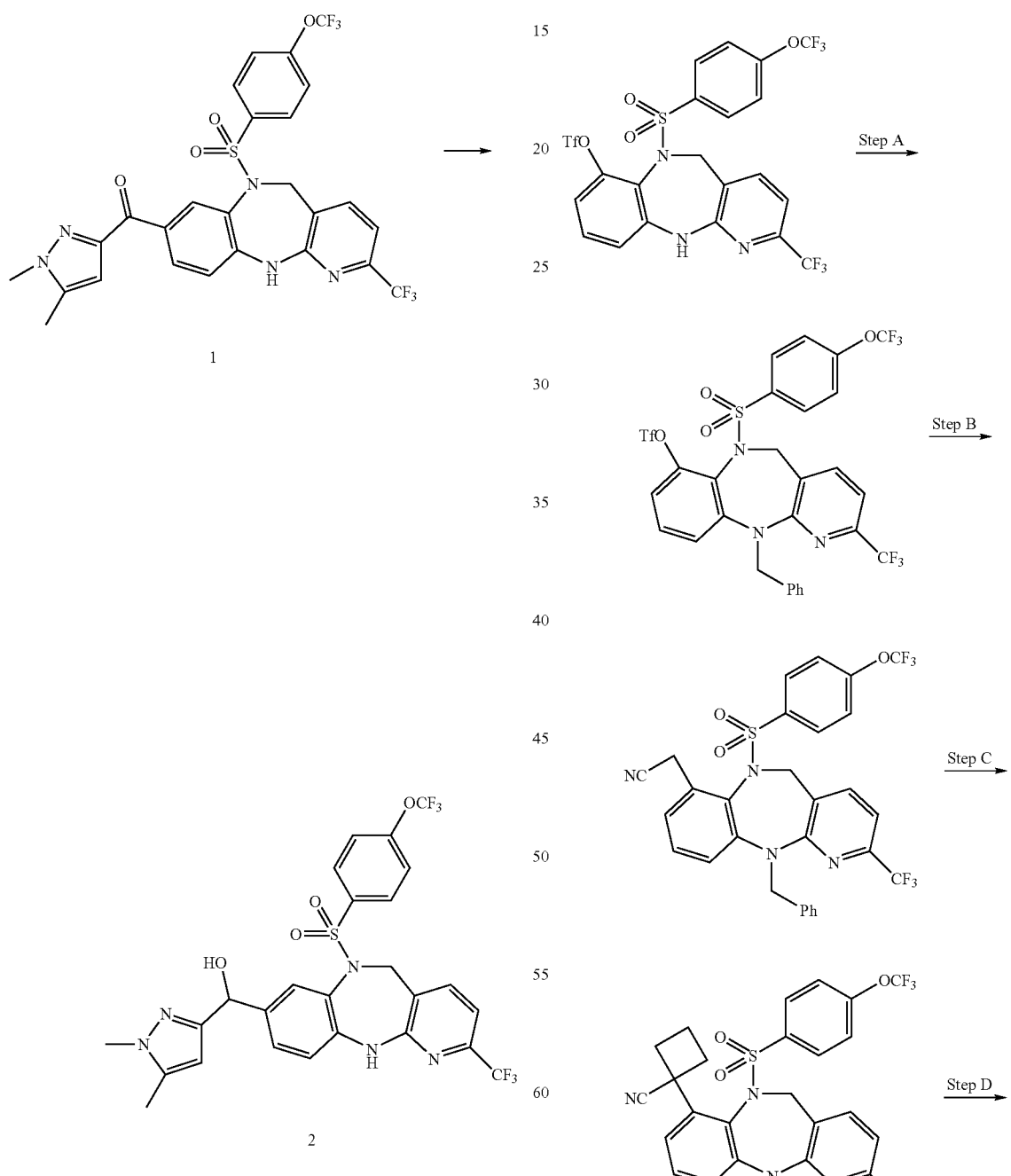

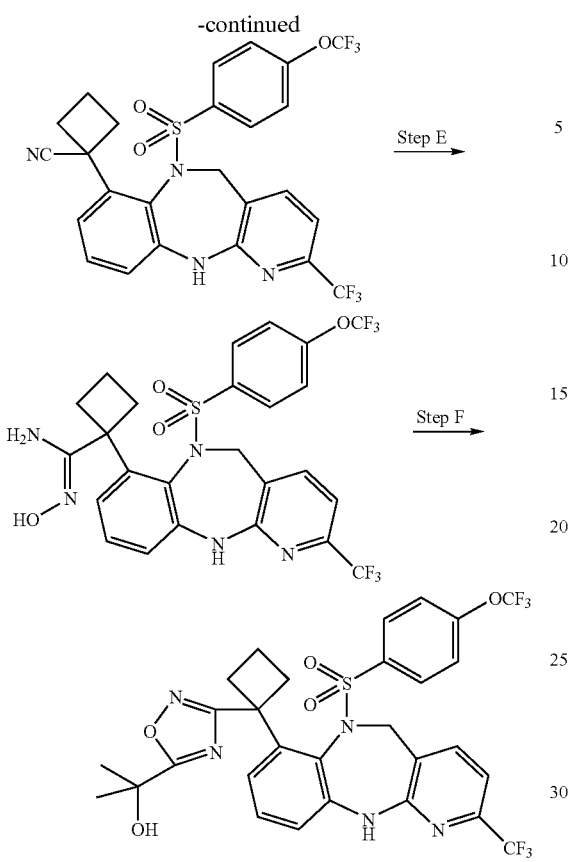

Step A: A mixture of intermediate 3 (1.0 g, 1.57 mmol), benzyl bromide (0.4 g, 2.4 mmol), benzyltriethylamonium chloride (36 mg, 0.16 mmol), aqueous NaOH (5 mL, 50 weight %) and toluene (15 mL) was heated in a microwave reactor at 100° C. for 10 minutes. After cooling to room temperature, the reaction mixture was diluted with EtOAc (100 ml), washed with water and brine, dried over $Na_2SO_4$ and concentrated. The residue was purified on silica gel column eluting with 10-50% EtOAc in hexanes to give the desired product. LCMS: m/e 728.1 $(M+H)^+$.

Step B: A mixture of the product from Step A (750 mg, 1.03 mmol), trimethylsilyl acetonitrile (350 mg, 3.1 mmol), S-phos (169 mg, 0.4 mmol), DMF (4 mL), $ZnF_2$ (160 mg, 1.55 mmol), and $Pd_2(dba)_3$ (189 mg, 0.21 mmol) was heated in a microwave reactor at 180° C. for 1 h. After cooling to room temperature, the reaction mixture was diluted with EtOAc (100 ml), washed with water and brine, dried with $Na_2SO_4$ and concentrated. The residue was purified on silica gel column eluting with 10-45% EtOAc in hexanes to give the desired product. LCMS: m/e 619.1 $(M+H)^+$.

Step C: To a mixture of the product from Step B (82 mg, 0.13 mmol) in THF (10 mL) was added NaH (0.6 mmol), and diodopropane (1.3 mmol). The reaction was heated in a microwave reactor at 120° C. for 15 min. After cooling to rt, the reaction mixture was diluted with EtOAc (50 ml), washed with water and brine, dried with $MgSO_4$ and concentrated. The residue was purified on silica gel column eluting with 7-60% EtOAc in hexanes to give the desired product. LCMS: m/e 659.1 $(M+H)^+$.

Step D: The benzyl protecting group was removed with TMSCl/NaI following the procedure described by O. Lohse et al (*Tetrahedron Lett.* 2001, 42, 385) to give the desired nitrile product.

Step E: The title compound was prepared from the product of Step D and hydroxylamine following the procedure as described for Intermediate 8.

Step F: The title compound was prepared from the product of Step E and 2-acetoxyisobutyryl chloride following the procedure as described for Example 1. The organic layer was separated, dried over $MgSO_4$, filtered and concentrated to give an oil that was purified by silica gel chromatography (0-60% EtOAc in hexanes) to yield the title compound as a racemic mixture. The racemic mixture was separated by HPLC on a chiralcel OD column with 15% EtOH/hexanes as the mobile phase. The faster eluting enantiomer (E1) has a retention time of 10.0 minutes, while the slower enantiomer (E2) has a retention time of 28.0 minutes. E1: $^1$H NMR (500 MHz, $(CD_3)_2CO$): δ 8.18 (s, 1H), 7.70 (d, 1H), 7.39 (m, 1H), 7.32 (m, 1H), 7.27 (d, 2H), 7.23 (m, 1H), 7.10 (d, 2H), 7.06 (d, 1H), 5.02 (d, 1H), 4.88 (s, 1H), 4.50 (d, 1H), 3.11 (m, 1H), 2.83 (m, 2H), 2.38 (s, 1H), 2.07 (s, 1H), 1.94 (m, 1H), 1.62 (d, 6H). LCMS: m/e 670.12 $(M+H)^+$.

EXAMPLE 532

2-(3-{1-Methyl-1-[6-{[4-(trifluoromethoxy)phenyl]sulfonyl}-2-(trifluoromethyl)-6,11-dihydro-5H-pyrido[2,3-b][1,5]benzodiazepin-7-yl]ethyl}-1,2,4-oxadiazol-5-yl)propan-2-ol

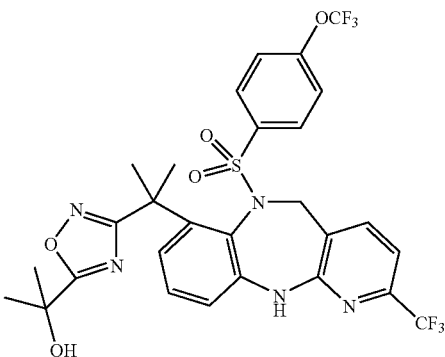

The title compound and the respective enantiomers were prepared from the intermediates of Example 435 following the general procedure described for Example 531. LCMS: m/e 658.0 $(M+H)^+$.

EXAMPLE 533

2-Methyl-2-[6-{[4-(trifluoromethoxy)phenyl]sulfonyl}-2-(trifluoromethyl)-6,11-dihydro-5H-pyrido[2,3-b][1,5]-benzodiazepin-7-yl]propanamide

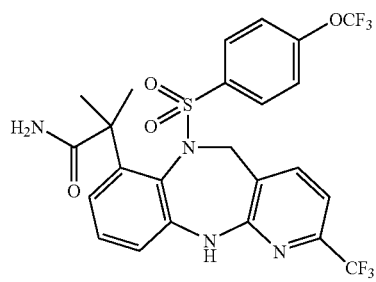

To a stirred solution of the product of Example 435 (217 mg, 0.4 mmol) in DMF (10 mL) was added HATU (169 mg, 0.4 mmol), Hunig's base (0.1 ml, 0.4 mmol) and $NH_3$ (0.5 M in dioxane) (2.2 mL, 0.7 mmol). The resulting solution was stirred at rt overnight, diluted with $H_2O$, and extracted with EtOAc(3×50 mL). The combined organic extracts were washed with brine, dried over $MgSO_4$, filtered and concentrated in vacuo to give an oil which was purified by flash chromatography (0-7% MeOH/$CH_2Cl_2$) to give the title compound as a racemic mixture. The racemic mixture was separated by HPLC on a chiralcel OD column with 20% MeOH/$CO_2$ as the mobile phase. The faster eluting enantiomer (E1) has a retention time of 4.0 minutes, while the slower enantiomer (E2) has a retention time of 4.6 minutes. E1: $^1$H NMR (500 MHz, $(CD_3)_2CO$): δ 8.11 (s, 1H), 7.73 (d, J=7.5 Hz, 1H), 7.31-7.35 (m, 3H), 7.28 (dd, J=1.5, 7.5 Hz, 1H), 7.18 (dd, J=1.5, 7.5 Hz, 1H), 7.13 (d, J=7.5 Hz, 1H), 7.09 (d, J=7.5 Hz, 2H), 6.55 (s, 1H), 6.31 (s, 1H), 5.11 (d, J=17.5 Hz, 1H), 4.81 (d, J=17.5 Hz, 1H), 1.85 (s, 3H), 1.74 (s, 3H). LCMS: m/e 587.08 (M+H)$^+$.

The following examples were prepared following the general procedure described for Example 533.

| | | | |
|---|---|---|---|
| 534 | 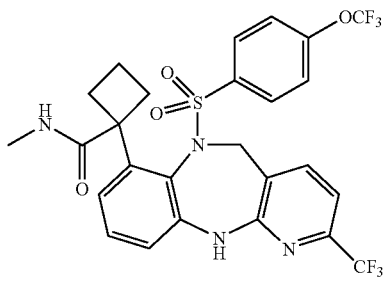 | E1 | 601.1 |
| 535 | 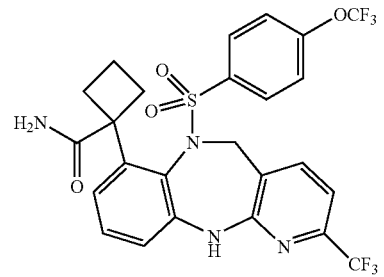 | E1 | 586.9 |

EXAMPLE 536

11-[4-tert-Butylphenyl)sulfonyl]-2-methyl-7-(trifluoromethyl)-10,11-dihydro-5H-dipyrido[2,3-b:2',3'-e][1,4]diazepine

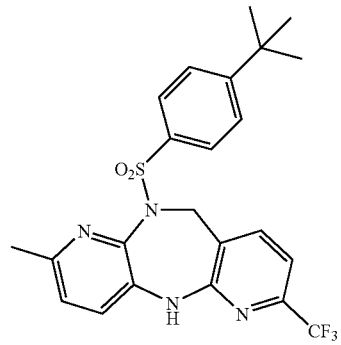

Step A: A mixture of 6-methyl-3-nitro-2-pyridinamine (3 g, 19.8 mmol) and Raney Ni (1 g) in MeOH (150 ml) was stirred in an autoclave filled with $H_2$ (50 psi) at 0° C. for 2 hours. When TLC showed the reaction was completed, the mixture was filtered, and the filtrate was concentrated to give 6-methyl-2,3-pyridinediamine.

Step B: A mixture of 6-methyl-2,3-pyridinediamine (2.1 g, 17 mmol), 2-chloro-6-(trifluoromethyl)nicotinic acid (3.8 g, 17 mmol) and Cu (1 g, 17 mmol) in $HOC_2H_5OBu$ was stirred at 160° C. overnight. When LCMS showed the reaction was complete, the mixture was filtered and concentrated to give a crude product, which was dissolved in THF (100 ml) in a flask equipped with a condenser and a nitrogen balloon. A solution of borane-$Me_2S$ (10 M, 10 ml, 0.1 mol) was added dropwise, and the resulting mixture was refluxed for 20 h before it was cooled, acidified to pH=1 with concentrated HCl, and refluxed for another 3 hours. The mixture was neutralized to pH=8 with saturated aqueous sodium bicarbonate, and the product was extracted with ethyl acetate (200 ml×3). The combined organic phases were washed with water and brine, dried over sodium sulfate and concentrated under reduced pressure. The residue was purified on silica gel eluting with pet ether:ethyl acetate (10:1) to afford the product 2-methyl-7-(trifluoromethyl)-10,11-dihydro-5H-dipyrido[2,3-b:2',3'-e][1,4]diazepine. $^1$H-NMR A27111 H02393-117-1 (400 MHz, DMSO) δ 10.83 (br, 1H, NH), 7.45 (d, J=7.6 Hz, 1H, Ar—H), 7.40 (d, J=8 Hz, 1H, Ar—H), 7.16 (d, J=7.6 Hz, 1H, Ar—H), 6.61 (t, J=7.6 Hz, 1H, Ar—H), 4.23 (s, 2H, $CH_2$), 2.51 (s, 3H, $CH_3$).

Step C: The title compound was prepared from 2-methyl-7-(trifluoromethyl)-10,11-dihydro-5H-dipyrido[[2,3-b:2',3'-e][1,4]diazepine and [(4-tert-butylphenyl)sulfonyl chloride following the same procedure as described for Example 250. $^1$H NMR (500 MHz, $CD_3OD$): δ 7.77 (1H, d), 7.68 (1H, d), 7.43 (1H, d), 7.26 (2H, d), 7.20 (2H, d), 7.17 (1H), 4.88 (2H, s), 2.59 (3H, s), 1.23 (9H, s); LCMS: m/e 477.0 (M+H)$^+$.

BIOLOGICAL ASSAYS

A. Bombesin Receptor Subtype 3 (BRS3) Binding Assays

Human embryonic kidney (HEK 293) cells expressing human BRS-3 were cultured to confluence and harvested by aspirating the culture medium and rinsing twice with 1×PBS without $Mg^{++}$ and $Ca^{++}$. Cellstriper Solution (Cellgrow #25-

056-Cl, 3 mL) was added to each T-175 flask until all cells dissociated and then an additional 15 mL 1×PBS without $Me^{++}$ and $Ca^{++}$ were added to each flask. Dissociated cells were collected by centrifuging at 1000 rpm for 10 minutes. Cell pellets were resuspended and homogenized at 4° C. using a Polytron homogenizer (setting 40, 20 stokes) in approximately 10 mL membrane preparation buffer (10 mM Tris pH 7.4, 0.01 mM Pefabloc, 10 µM phosphoramidon and 40 µg/mL Bacitracin) per T175 flask. After centrifugation at 2200 rpm (1000×g) for 10 minutes at 4° C., the supernatant was transferred to a clean centrifuge tube and spun at 18,000 rpm (38,742×g) for 15 minutes. at 4° C. Membranes were resuspended in the above membrane preparation buffer (1 mL/T-175 flask), homogenized, aliquoted, frozen in liquid nitrogen and stored at –80° C.

For the $[^{125}I]$-$[D$-$Tyr^6,\beta$-$Ala^{11},Phe^{13},Nle^{14}]$-Bombesin(6-14), "$[^{125}I]$-dY-peptide", radioligand assay the specific binding of $[^{125}I]$-dY-peptide to human BRS3 was measured by filtration assay in 96-well plate format. The receptor membrane (2 µg/well) in binding buffer (50 mM Tris pH 7.4, 5 mM $MgCl_2$, 0.1% BSA and protease inhibitor cocktail) was mixed with compound in DMSO (1% final concentration) and 30 pM $[^{125}I]$-dY-peptide. After incubation for 1-2 hours at room temperature, membrane-bound $[^{125}I]$-dY-peptide was separated from free $[^{125}I]$-dY-peptide by filtering through GF/C filters presoaked in 1% PEI solution. The filters were washed five times with ice-cold washing buffer (1×PBS without $Mg^{++}$ and $Ca^{++}$). The radioactivity was determined by adding 30 µl of microscintillant/well after each plate was dried at room temperature overnight or placed at 50° C. for 1 hr.

The radioligand, $[^3H]$-1-{4-[(4,5-difluoro-2-hydroxycarbonylphenyl)phenyl]}-2-(4-cyclohexylmethyl-1H-imidazol-2-yl)ethane, was used for binding to receptor membranes generated with BRS3 from other species and was also utilized for the human receptor. Cell membranes (5 to 20 µg/well) were added to binding buffer (25 mM Tris pH 7.4, 10 mM $MgCl_2$, 2 mM EDTA and protease I cocktail) containing compound in DMSO (1% final concentration) and 660 pM $[^3H]$-biphenyl. After incubation for 1-2 hours at room temperature, membrane bound $[^3H]$-biphenyl was separated from free radiologand by filtering through GF/C filters presoaked in 1% PEI solution. The filters were washed five times with ice-cold washing buffer (50 mM Tris pH 7.4, 10 mM $MgCl_2$, 2.5 mM EDTA and 0.02% Triton X-100). The radioactivity was determined by adding 30 µl of microscintillant/well after each plate was dried at room temperature overnight or placed at 50° C. for 1 hr.

A Packard Top Count was used to read the filter plates. The data in % inhibition of binding was plotted vs. the log molar concentration of receptor ligand (compound). The $IC_{50}$ was reported as the inflection point of the resulting sigmoidal curve. The maximum inhibition observed at the highest compound concentration tested was reported for compounds which did not generate a curve. The binding assays for the rat and mouse Bombesin Receptor Subtype 3 (BRS3) were performed in a similar fashion.

The racemates and chiral HPLC separated enantiomers of the present invention, including the racemates and chiral HPLC separated enantiomers in Examples 1-508, were tested and found to bind to the bombesin subtype 3 receptor with $IC_{50}$ values less than 10 µM. Preferred racemates and chiral HPLC separated enantiomers of the present invention, including the racemates and chiral HPLC separated enantiomers in Examples 1-508, were tested and found to bind to the bombesin subtype 3 receptor with $IC_{50}$ values less than 1 µM.

B. Cell Culture of Human, Rat and Mouse BRS3 Expressing Cell Lines

An NFATCHO cell line stably expressing human BRS3 cDNA was generated using standard cell biology techniques and used to prepare receptor membranes for the human "$[^{125}I]$-dY-peptide binding assay. The cell line was cultured in T175 flasks in Iscove's Modified Dulbecco's Medium with L-glutamine and 25 mM HEPES buffer (Gibco #12440-046) supplemented with 10% FBS (cat#SH30070.03, Hyclone, Logan, Utah), 1×HT Supplement (0.1 mM Sodium Hypoxanthine and 16 µM Thymidine Gibco #11067-030), 2 mM L-glutamine (Gibco #25030-081), 100 units/mL Pennicillin-G and 100 µg/mL Streptomycin (Gibco #15140-122) and 1 mg/mL Geneticin (Gibco #10131-027).

HEK293/AEQ cell lines stably expressing either human, rat or mouse BRS3 cDNA were generated using standard cell biology techniques and were used for all functional assays and to prepare membranes for the rat BRS3 binding assay. The cell lines were routinely cultured in T75 or T175 flasks in Dulbecco's Modified Eagle Medium (Gibco #11965-084) supplemented with 10% FBS, 25 mM HEPES buffer solution (Gibco #15630-080), 0.5 mg/mL Geneticin and 50 µg/mL Hygromycin B (Boehringer Mannheim #14937400). Transient transfection of mouse BRS3 cDNA, as well as BRS3 cDNA from other species, in the HEK293AEQ cell line was achieved using the Lipofectamine transfection method following the recommended protocol (Invitrogen Lipofectamine 2000 #11668-027). The transfected cells were used to prepare membranes for the $[^3H]$-biphenyl binding assay and for the functional assays. The cells were maintained in culture under the same conditions used for the human and rat stable BRS3 HEK293AEQ cell lines. All cells were grown as attached monolayers to approximately 90% confluency in tissue culture flasks under the appropriate media in an incubator at 37° C. with 5% $CO_2$. Cells were passed 1:3 to 1:5 twice a week depending on the rate of growth.

C. BRS3 Functional Assays

1) Aequorin Bioluminescent Assay to Measure Intracellular $Ca^{++}$

The apoaequorin containing HEK293AEQ cell lines expressing BRS3 were first charged with coelenterazine (Molecular Probes #C-14260) by rinsing confluent T75 flasks with 12 mL Hams F-12 media (Gibco #11765-054) containing 300 mM glutathione and 0.1% FBS. The same media (8 mL) containing 20 µM coelenterzine was added to the cells and incubated at 37° C. for 1 hr. The media was aspirated and the flasks rinsed with 6 mL ECB buffer (140 mM NaCl, 20 mM KCl, 20 mM HEPES, 5 mM glucose, 1 mM MgCl, 1 mM CaCl, 0.1 mg/mL BSA, pH 7.4). The cells were dissociated with a rubber-tipped scraper in 6 mL of fresh ECB buffer and collected by centrifugation at 2500 rpm for 5 minutes. The cell pellets were resuspended in ECB buffer to a concentration of 200,000 cells/mL and were either used right away or quickly frozen in liquid nitrogen for storage at –80° C. for up to six weeks.

The Aequorin assay itself was performed in 96-well format using a Wallac Microbeta luminometer equipped with microinjector module. Compounds in DMSO (0.5% final concentration) were titrated in the plates at 2× concentration in a volume of 0.1 mL ECB buffer. The cells (20,000 per well) were then injected in 0.1 mL ECB buffer and the bioluminescence monitored for 30 seconds. Alternatively, total bioluminescence was determined over 10 minutes. The bioluminescent readings were plotted vs. the log molar concentration of receptor ligand (compound). The $EC_{50}$ for activation was reported as the inflection point of the resulting sigmoidal curve.

2) Inositol Phosphate SPA Assay (IP) to Measure 1P3 Accumulation

The IP functional assay was performed in 96-well format. The BRS3 expressing HEK293AEQ cells were plated on poly-D-lysine plates (25,000 cells/0.15 mL) and kept in culture for 24 hours. The media from each well was aspirated and the cells were washed with PBS without $Mg^{++}$ and $Ca^{++}$. Inositol labeling media consisting of Inositol-free DMEM media (ICN #1642954) supplemented with 10% FBS, 1×HT Supplement, 2 mM glutamine, 70 mM HEPES buffer solution and 0.02% BSA to which $^3$H-myo-inositol (NEN #NET114A 1mCi/mL, 25 Ci/mmol) was added so that there was 1 µCi $^3$H-myo-inositol in 150 µL media per well. After 18 hours of labeling, 5 µl 300 mM LiCl was added to each well, mixed, and incubated for 20 minutes at 37° C. Compound (1.5 µl of 100× compound in DMSO) was added and incubated for an additional 60 minutes at 37° C. The labeled media was aspirated, and the reaction terminated by lysing the cells with the addition of 60 µl 10 mM formic acid for 60 minutes at room temperature. A 20 µl aliquot of the lysate was transferred from each well to a clear-bottom Opti-plate which contained 70 µL RNA binding YSi SPA-beads (Amersham RPNQ0013) that had been suspended in 10% glycerol at 1 mg beads/70 µl of solution. After mixing, the plates were left at room temperature for 2 hours and were then counted using a Wallac Microbeta luminometer. The data in cpm (counts per minute) as plotted vs. the log molar concentration of receptor ligand (compound). The $EC_{50}$ for activation was reported as the inflection point of the resulting sigmoidal curve.

The racemates and chiral HPLC separated enantiomers of the present invention, including the racemates and chiral HPLC separated enantiomers in Examples 1-508, were tested and found to agonize the bombesin subtype 3 receptor with $EC_{50}$ values less than 10 µM. Preferred racemates and chiral HPLC separated enantiomers of the present invention, including the racemates and chiral HPLC separated enantiomers in Examples 1-508, were tested and found to agonize the bombesin subtype 3 receptor with $EC_{50}$ values less than 1 µM.

D. In-Vivo Overnight Food Intake and Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. On the day of study, mice were orally dosed (n=6-8/group) with either vehicle only (10% Tween-water) or BRS-3 agonists (various doses). A known CB1R inverse agonist, AM251 (3 mg/kg), was used as the positive control for inter- and intra-experimental control. BRS-3 agonists were dosed approximately 60 minutes prior to the onset of the dark cycle. Overnight food intake and body weight were measured and analyzed. All data are presented as mean±SEM. Statistical significance was calculated using Student's t-test with differences considered significant when 2-tailed p<0.05.

Compounds useful in the present invention decrease overnight food intake by at least 10% and/or decrease body weight overnight by at least 1% relative to placebo.

E. In-Vivo Chronic Administration on Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. During the study, mice were orally dosed (n=7-9/group) with either vehicle only (10% Tween-water) or BRS-3 agonists (various doses). A known anorectic agent, dexfenfluramine (10-15 mg/kg) was used as the positive control for inter- and intra-experimental control. Two doses (PO) of BRS-3 agonist were administered each day for 14 days. The first dose was given approximately 60 minutes prior to the onset of the dark cycle and the second, 5 hours after the first dose. A single dose of dexfenfluramine was given approximately 60 minutes prior to the onset of the dark cycle and vehicle was dosed for the second dose, 5 hours after the first dose. Daily food intake and body weight were measured and analyzed. All data are presented as mean±SEM. Statistical significance was calculated using Student's t-test with differences considered significant when 2-tailed p<0.05.

Compounds useful in the present invention, by day 14, decrease cumulative food intake by at least 10% and/or decrease body weight by at least 2% relative to placebo.

The compounds of the invention were tested according to method A and method C and the compounds tested were found to bind to and to agonize the bombesin subtype-3 receptor. The results of the racemic mixture or the more potent enantiomer after HPLC separation are shown in the following Table.

TABLE

Bombesin Subtype-3 Receptor Binding ($IC_{50}$) and agonism ($EC_{50}$)

| Compound | human BRS-3 $IC_{50}$ | human BRS-3 $EC_{50}$ |
|---|---|---|
| Example 2 | 8.3 nM | 158 nM |
| Example 1 | 3.6 nM | 73 nM |
| Example 3 | 1.9 nM | 63 nM |
| Example 4 | 3.3 nM | 139 nM |
| Example 6 | 6.4 nM | 52 nM |
| Example 7 | 2.9 nM | 33 nM |
| Example 5 | 0.75 nM | 34 nM |
| Example 437 | 4.1 nM | 121 nM |
| Example 251 | 1.0 nM | 100 nM |
| Example 464 | 38 nM | 196 nM |
| Example 374 | 4.9 nM | 130 nM |
| Example 316 | 0.64 nM | 48 nM |
| Example 533 | 2.2 nM | 16 nM |
| Example 531 | 0.65 nM | 94 nM |
| Example 536 | 5.3 nM | 66 nM |

EXAMPLES OF PHARMACEUTICAL COMPOSITIONS

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:
1. A compound of formula I:

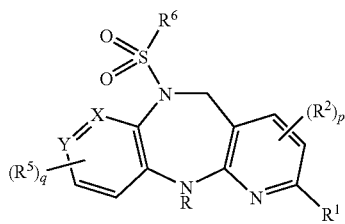

or a pharmaceutically acceptable salt thereof; wherein
X is selected from the group consisting of:
  (1) $CR^3$, and
  (2) N;
Y is selected from the group consisting of:
  (1) $CR^4$, and
  (2) N;
R is selected from the group consisting of:
  (1) hydrogen,
  (2) $-(CH_2)_nC_{2-6}$alkenyl, and
  (3) $-COC_{1-6}$alkyl;
$R^1$, $R^2$, $R^3$, $R^4$ and $R^5$ are each independently selected from the group consisting of:
  (1) hydrogen,
  (2) $-(CH_2)_n$halogen,
  (3) $-C_{1-8}$alkyl,
  (4) $-(CH_2)_nC_{2-8}$alkenyl,
  (5) $-(CH_2)_nC_{2-8}$alkynyl,
  (6) $-(CH_2)_nCN$,
  (7) $-(CH_2)_nCF_3$,
  (8) $-(CH_2)_nCHF_2$,
  (9) $-(CH_2)_nCH_2F$,
  (10) $-(CH_2)_nOCF_3$,
  (11) $-(CH_2)_nOR^b$,
  (12) $-(CH_2)_nCOR^c$,
  (13) $-(CH_2)_nCO_2R^d$,
  (14) $-(CH_2)_nOC(O)R^c$,
  (15) $-(CH_2)_nN(R^c)_2$,
  (16) $-(CH_2)_nNO_2$,
  (17) $-(CH_2)_nCH=NR^a$,
  (18) $-(CH_2)_nCH=N-OR^a$,
  (19) $-(CH_2)_nC(O)N(R^c)_2$,
  (20) $-(CH_2)_nC(O)NR^aN(R^c)_2$,
  (21) $-(CH_2)_nC(O)_{1-2}(CH_2)_nCO_2R^a$,
  (22) $-(CH_2)_nC(O)NR^a(CH_2)_nCO_2R^a$,
  (23) $-(CH_2)_nNR^cC(O)R^c$,
  (24) $-(CH_2)_nNR^aSO_{0-2}C_{1-6}$alkyl,
  (25) $-(CH_2)_nSO_{0-2}N(R^c)_2$,
  (26) $-(CH_2)_nSO_{0-2}C_{1-8}$alkyl,
  (27) $-(CH_2)_nSO_{0-2}C_{3-8}$cycloalkyl,
  (28) $-(CH_2)_nSO_{0-2}$aryl,
  (29) $-(CH_2)_nSO_{0-2}$heteroaryl,
  (30) $-(CH_2)_nC_{3-10}$cycloalkyl,
  (31) $-(CH_2)_nC_{3-10}$cycloalkenyl,
  (32) $-(CH_2)_nC_{2-12}$heterocycloalkyl,
  (33) $-(CH_2)_nC_{2-12}$heterocycloalkenyl,
  (34) $-(CH_2)_n$aryl,
  (35) $-(CH_2)_n$heteroaryl,
  (36) $-(CH_2)_nO(CH_2)_n$heteroaryl,
  (37) $-C(O)C_{3-10}$cycloalkyl,
  (38) $-C(O)C_{3-10}$cycloalkenyl,
  (39) $-C(O)C_{2-12}$heterocycloalkyl,
  (40) $-C(O)C_{2-12}$heterocycloalkenyl,
  (41) $-C(O)$aryl,
  (42) $-C(O)$heteroaryl,
  (43) $-C(O)NR^cC_{3-10}$cycloalkyl,
  (44) $-C(O)NR^cC_{3-10}$cycloalkenyl,
  (45) $-C(O)NR^cC_{2-12}$heterocycloalkyl,
  (46) $-C(O)NR^c$aryl, and
  (47) $-C(O)NR^c$heteroaryl,
wherein alkyl, alkenyl, alkynyl, cycloalkyl, cycloalkenyl, heterocycloalkyl, heterocycloalkenyl, aryl, heteroaryl, $-CH$, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and $NR^a$, wherein the 3-6 membered aromatic or non-aromatic ring is unsubstituted or substituted with 1 to 5 substituents selected from $R^e$;
$R^6$ is independently selected from the group consisting of:
  (1) $C_{1-8}$alkyl,
  (2) $-(CH_2)_nC_{3-10}$cycloalkyl,
  (3) $-(CH2)_nC3-10$cycloalkenyl,
  (4) $-(CH2)_nC_{2-12}$heterocycloalkyl,
  (5) $-(CH2)_nC_{2-12}$heterocycloalkenyl,
  (6) $-(CH_2)_n$aryl, and
  (7) $-(CH2)_n$heteroaryl,
wherein alkyl, cycloalkyl, cycloalkenyl, heterocycloalkyl, heterocycloalkenyl, aryl, heteroaryl, and $(CH_2)_n$ are unsubstituted or substituted with 1 to 5 substituents selected from $R^f$;
each $R^a$ is independently selected from the group consisting of:
  (1) hydrogen, and
  (2) $-C_{1-6}$alkyl,
wherein alkyl is unsubstituted or substituted with 1 to 3 substituents selected from $-(CH_2)_nOH$;
each $R^b$ is independently selected from the group consisting of:
  (1) hydrogen,
  (2) $-C_{1-6}$alkyl,
  (3) $-(CH_2)_nCF_3$,
  (4) $-(CH_2)_nOC_{1-6}$alkyl,
  (5) $-(CH2)_nSO_2CF_3$,
  (6) $-(CH_2)_nC_{2-6}$alkenyl,
  (7) $-(CH2)_nC_{3-8}$cycloalkyl,
  (8) $-(CH_2)_nC_{2-8}$heterocycloalkyl,
  (9) $-(CH2)_n$aryl, and
  (10) $-(CH_2)_n$heteroaryl,
wherein alkyl, alkenyl, cycloalkyl, heterocycloalkyl, aryl, heteroaryl, and $-(CH_2)_n$ are unsubstituted or substituted with 1-4 substituents selected from $-OH$, halogen, $-CN$, $-CF_3$, $-C_{1-6}$alkyl, and $-CO_2H$;
each $R^c$ is independently selected from the group consisting of:

(1) hydrogen,
(2) —$C_{1-6}$alkyl,
(3) —$(CH_2)_nCF_3$,
(4) —$(CH_2)_nCO_2R^a$,
(5) —$(CH_2)_nSO_2CF_3$,
(6) —$(CH_2)_nC_{3-8}$cycloalkyl,
(7) —$(CH_2)_nC_{2-8}$heterocycloalkyl,
(8) —$(CH_2)_n$aryl, and
(9) —$(CH_2)_n$heteroaryl,
wherein alkyl, cycloalkyl, heterocycloalkyl, aryl, heteroaryl, and —$(CH_2)_n$ are unsubstituted or substituted with 1-4 substituents selected from —OH, halogen, —CN, and $C_{1-6}$alkyl;
each $R^d$ is independently selected from the group consisting of:
(1) hydrogen,
(2) —$C_{1-6}$alkyl, and
(3) —$C_{3-8}$cycloalkyl,
wherein alkyl and cycloalkyl are unsubstituted or substituted with 1-3 substituents selected from halogen, —CN, —OH, —$N(R^a)_2$, and aryl;
each $R^e$ is independently selected from the group consisting of:
(1) —$(CH_2)_n$halogen,
(2) —$C_{1-6}$alkyl,
(3) —$(CH_2)_nCF_3$,
(4) —$(CH_2)_nCN$,
(5) —$(CH_2)_nC_{2-8}$alkenyl,
(6) oxo,
(7) thio,
(8) —$(CH_2)_nOR^a$,
(9) —$(CH_2)_nN(R^a)_2$,
(10) —$(CH_2)_nN(R^a)COR^a$,
(11) —$(CH_2)_nCON(R^a)_2$,
(12) —$(CH_2)_nCOR^a$,
(13) —$(CH_2)_nN(R^a)CO_2R^a$,
(14) —$(CH_2)_nCO_2R^a$,
(15) —$(CH_2)_nOC(O)R^a$,
(16) —$(CH_2)_nC_{3-8}$cycloalkyl,
(17) —$(CH_2)_nC_{2-8}$heterocycloalkyl,
(18) —$(CH_2)_n$aryl,
(19) —$(CH_2)_n$heteroaryl,
(20) —$(CH_2)_nO(CH_2)_n$aryl,
(21) —$(CH_2)_nO(CH_2)_n$heteroaryl, and
(22) —$(CH_2)_nOP(O)(OH)_2$,
wherein alkyl, alkenyl, cycloalkyl, heterocycloalkyl, aryl, heteroaryl, and $(CH_2)_n$ are unsubstituted or substituted with 1 to 5 substituents selected from —$(CH_2)_{0-2}$OH, —F, —$CF_3$, —$CO_2C_{1-6}$alkyl, oxo, and —$C_{1-6}$alkyl unsubstituted or substituted with —OH;
each $R^f$ is independently selected from the group consisting of:
(1) —$(CH_2)_n$halogen,
(2) —$(CH_2)_nO_mC_{1-8}$alkyl,
(3) —$(CH_2)_nO_mC_{2-8}$alkenyl,
(4) —$(CH_2)_nCN$,
(5) —$(CH_2)_nCCl_3$,
(6) —$(CH_2)_nOH$,
(7) —$(CH_2)_nC(O)H$,
(8) —$(CH_2)_nC(O)C_{1-8}$alkyl,
(9) —$(CH_2)_nCO_2H$,
(10) —$(CH_2)_nCO_2C_{1-8}$alkyl,
(11) —$(CH_2)_nO_mCF_3$,
(12) —$(CH_2)_nO_mCHF_2$,
(13) —$(CH_2)_nO_mCH_2F$,
(14) —$(CH_2)_nO_mC_{3-10}$cycloalkyl,
(15) —$(CH_2)_nO_mC_{3-10}$cycloalkenyl,
(16) —$(CH_2)_nO_mC_{2-12}$heterocycloalkyl,
(17) —$(CH_2)_nO_mC_{2-12}$heterocycloalkenyl,
(18) —$(CH_2)_nO_m$aryl,
(19) —$(CH_2)_nO_m$heteroaryl,
(20) —$SO_{0-2}C_{1-8}$alkyl,
(21) —$SO_{0-2}C_{3-8}$cycloalkyl,
(22) —$(CH_2)_nN(R^c)_2$,
(23) —$(CH_2)_nC(O)N(R^c)_2$, and
(24) —$(CH_2)_nNR^cC(O)R^c$,
wherein alkyl, alkenyl, cycloalkyl, cycloalkenyl, heterocycloalkyl, heterocycloalkenyl, aryl, heteroaryl, and —$(CH_2)_n$ are unsubstituted or substituted with 1 to 3 substituents selected from —OH, —$CF_3$, halogen, —$C_{1-6}$alkyl and —CN;
each n is independently 0, 1, 2, 3, 4, or 5;
each m is independently 0 or 1;
each p is independently 0, 1 or 2; and
each q is independently 0, 1 or 2.

2. The compound of claim 1 wherein R is hydrogen or —$CH_2CH=CH_2$; or a pharmaceutically acceptable salt thereof.

3. The compound of claim 1 wherein R is hydrogen; or a pharmaceutically acceptable salt thereof.

4. The compound of claim 1 wherein $R^5$ is independently selected from the group consisting of: hydrogen, —$(CH_2)_n$halogen, —$(CH_2)_nOR^b$, —$(CH_2)_nCN$, —$(CH_2)_nCF_3$, —$(CH_2)_nCHF_2$, —$(CH_2)_nCH_2F$, —$(CH_2)CCl_3$, and —$C_{1-8}$alkyl; or a pharmaceutically acceptable salt thereof.

5. The compound of claim 1 wherein $R^1$ and $R^2$ are each independently selected from the group consisting of: hydrogen, —$(CH_2)_n$halogen, —$(CH_2)_nOR^b$, —$(CH_2)_nCN$, —$(CH_2)_nCF_3$, —$(CH_2)_nCHF_2$, —$(CH_2)_nCH_2F$, —$C_{1-8}$alkyl, —$SC_{1-8}$alkyl, —$SC_{3-8}$cycloalkyl, wherein alkyl, cycloalkyl, and $(CH^2)_n$ are unsubstituted or substituted with 1 to 5 substituents selected from —$C_{1-6}$alkyl, halogen, and —OH; or a pharmaceutically acceptable salt thereof.

6. The compound of claim 5 wherein $R^2$ is hydrogen or —$(CH_2)_n$halogen, wherein $(CH^2)_n$ is unsubstituted or substituted with 1 to 5 substituents selected from —$C_{1-6}$alkyl, halogen, and —OH; or a pharmaceutically acceptable salt thereof.

7. The compound of claim 1 wherein $R^6$ is selected from the group consisting of:
$C_{1-8}$alkyl, —$(CH_2)_n$aryl, and —$(CH_2)_n$heteroaryl, wherein alkyl, aryl, heteroaryl, and $(CH_2)_n$ are unsubstituted or substituted with 1 to 5 substituents selected from $R^f$; or a pharmaceutically acceptable salt thereof.

8. The compound of claim 1 wherein $R^3$ and $R^4$ are each independently selected from the group consisting of: hydrogen, —$(CH_2)_n$halogen, —$C_{1-8}$alkyl, —$(CH_2)_nC_{2-8}$alkenyl, —$(CH_2)_nCN$, —$(CH_2)_nCF_3$, —$(CH_2)_nCHF_2$, —$(CH_2)_nCH_2F$, —$(CH_2)_nOCF_3$, —$(CH_2)_nOR^b$, —$(CH_2)_nCOR^c$, —$(CH_2)_nCO_2R^d$, —$(CH_2)_nN(R^c)_2$, —$(CH_2)_nCH=NR^a$, —$(CH_2)_nCH=N—OR^a$, —$(CH_2)_nC(O)N(R^c)_2$, —$(CH_2)_nC(O)NR^aN(R^c)_2$, —$(CH_2)_nC(O)_{1-2}(CH_2)_nCO_2R^a$, —$(CH_2)_nC(O)NR^a(CH_2)_nCO_2R^a$, —$(CH_2)_nNR^cC(O)R^c$, —$(CH_2)_nSO_{0-2}C_{1-8}$alkyl, —$(CH_2)_nC_{3-10}$cycloalkyl, —$(CH_2)_nC_{2-12}$heterocycloalkyl, —$(CH_2)_nC_{2-12}$heterocycloalkenyl, —$(CH_2)_n$aryl, —$(CH_2)_n$heteroaryl, —$C(O)C_{2-12}$heterocycloalkyl, —$C(O)$heteroaryl, —$C(O)NR^cC_{2-12}$heterocycloalkyl, and —$C(O)NR^c$heteroaryl, wherein alkyl, alkenyl, cycloalkyl, heterocycloalkyl, heterocycloalkenyl, aryl, heteroaryl, —CH, and $(CH_2)_n$ are unsubstituted or substituted with 1-5 substituents selected from $R^e$, and wherein $R^3$ and $R^4$ or $R^4$ and $R^5$ together with the atoms to which they are attached may form a 3-6 membered aromatic or non-aromatic ring containing 0 to 3 heteroatoms independently selected from oxygen, sulfur, nitrogen, and NRa, wherein the 3-6 membered aromatic or non-aromatic ring is unsubstituted or substituted with 1 to 5 substituents selected from R$^e$; or a pharmaceutically acceptable salt thereof 9. The compound of claim 1 of formula I:

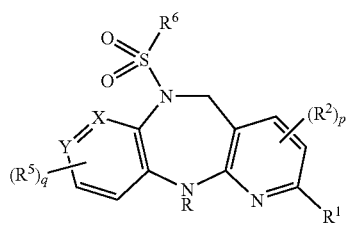

or a pharmaceutically acceptable salt thereof; wherein
X is selected from the group consisting of:
  (1) CR$^3$, and
  (2) N;
Y is CR$^4$;
R, R$^2$ and R$^5$ are hydrogen;
R$^1$ is CF$_3$;
R$^3$ and R$^4$ are each independently selected from the group consisting of:
  (1) hydrogen,
  (2) —C$_{1-8}$alkyl, and
  (3) —(CH$_2$)$_n$heteroaryl,
wherein alkyl, heteroaryl, and (CH$_2$)$_n$ are unsubstituted or substituted with 1-5 substituents selected from R$^e$, and wherein R$^3$ and R$^4$ together with the atoms to which they are attached may form a 3-6 membered aromatic or non-aromatic ring containing 0 to 3 heteroatoms independently selected from oxygen, sulfur, nitrogen, and NR$^a$, wherein the 3-6 membered aromatic or non-aromatic ring is unsubstituted or substituted with 1 to 5 substituents selected from R$^e$;
R$^6$ is phenyl, wherein phenyl is unsubstituted or substituted with 1 to 5 substituents selected from R$^f$;
each R$^a$ is independently selected from the group consisting of:
  (1) hydrogen, and
  (2) —C$_{1-6}$alkyl,
wherein alkyl is unsubstituted or substituted with 1 to 3 substituents selected from —(CH$_2$)$_n$OH;
each R$^e$ is independently selected from the group consisting of:
  (1) —C$_{1-6}$alkyl,
  (2) —(CH$_2$)$_n$OR$^a$, and
  (3) —(CH$_2$)$_n$CO$_2$R$^a$,
wherein alkyl and (CH$_2$)$_n$ are unsubstituted or substituted with —(CH$_2$)$_{0-2}$OH, —F, —CF$_3$, —CO$_2$C$_{1-6}$alkyl, —C$_{1-6}$alkyl unsubstituted or substituted with —OH;
each R$^f$ is independently selected from the group consisting of:
  (1) —C$_{1-8}$alkyl,
  (2) —(CH$_2$)$_n$O$_m$CF$_3$, and
  (3) —C$_{3-10}$cycloalkyl,
wherein alkyl, cycloalkyl, and —(CH$_2$)$_n$are unsubstituted or substituted with 1 to 3 substituents selected from —OH, —CF$_3$, halogen, —C$_{1-6}$alkyl and —CN;
each n is independently 0, 1, 2, 3, 4, or 5;
each m is independently 0 or 1;
each p is 0 or 1; and
each q is 0 or 1.

10. The compound of claim 1 selected from the group consisting of:

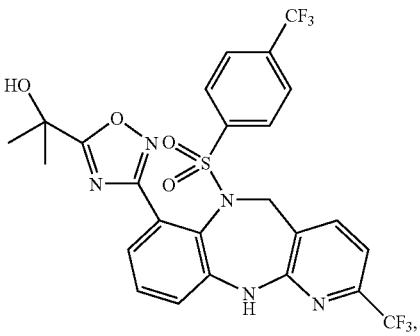

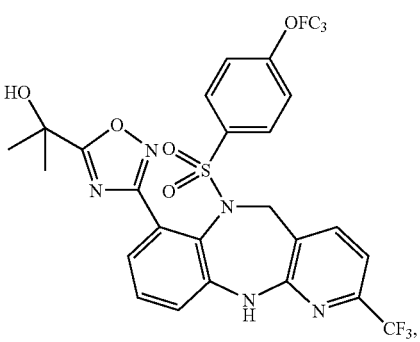

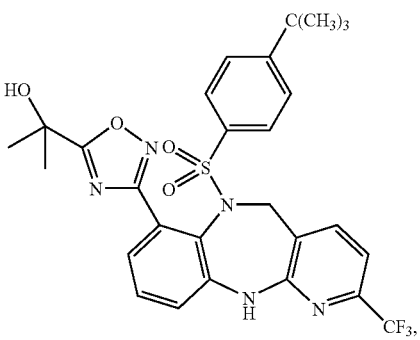

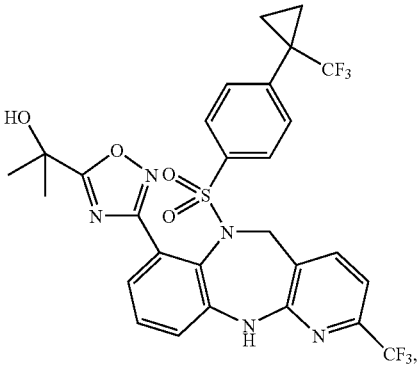

245
-continued
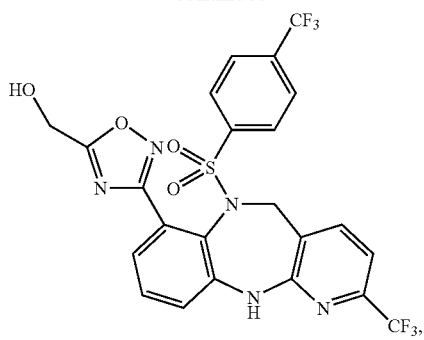
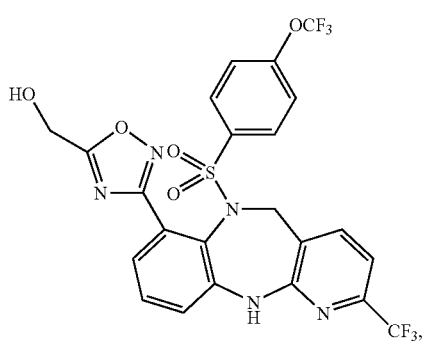
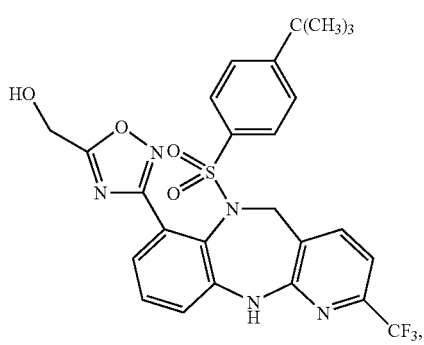
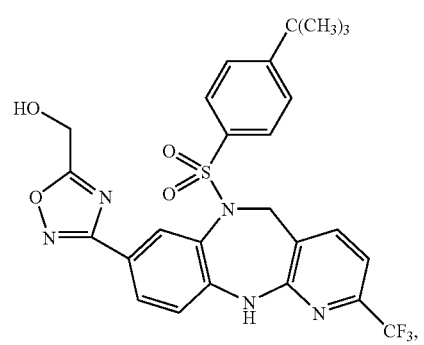
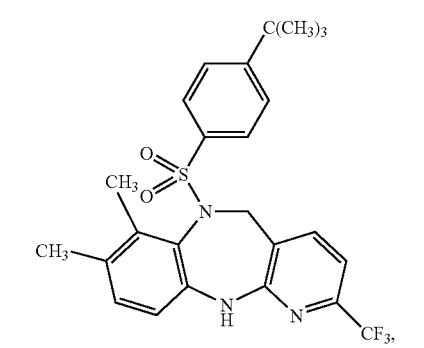
246
-continued
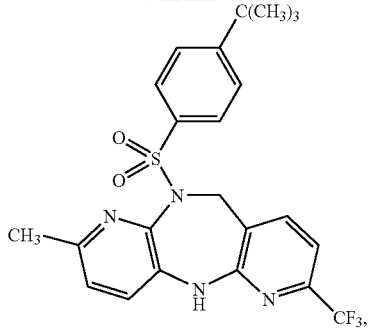
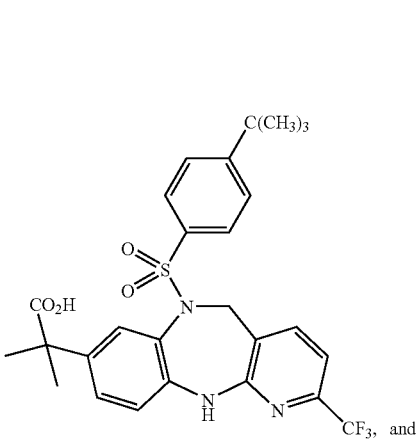
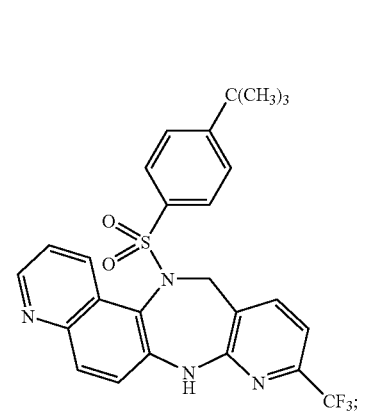
or a pharmaceutically acceptable salt thereof
11. The compound of claim 10 which is:
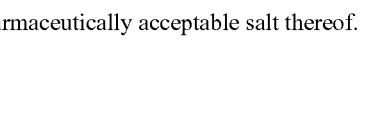
or a pharmaceutically acceptable salt thereof.

12. The compound of claim 10 which is:

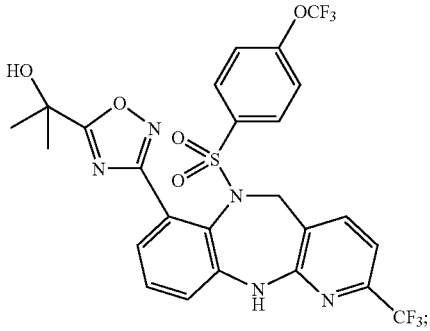

or a pharmaceutically acceptable salt thereof.

13. The compound of claim 10 which is:

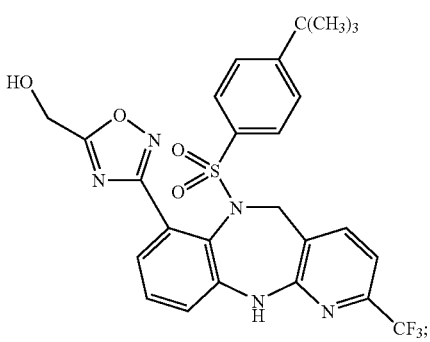

or a pharmaceutically acceptable salt thereof.

14. The compound of claim 10 which is:

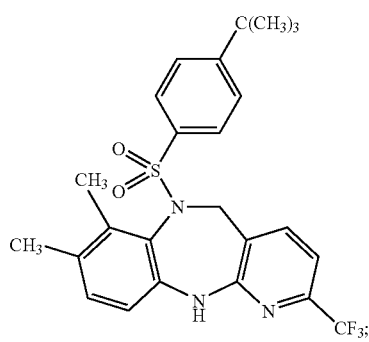

or a pharmaceutically acceptable salt thereof.

15. The compound of claim 10 which is:

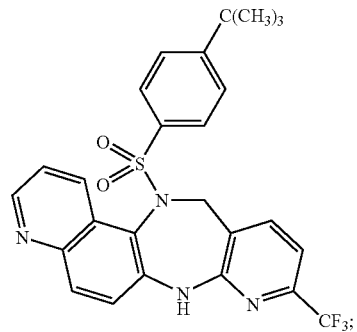

or a pharmaceutically acceptable salt thereof.

16. The compound of claim 1 selected from the group consisting of:

or a pharmaceutically acceptable salt thereof.

17. The compound of claim 10 wherein the pharmaceutically acceptable salt is a hydrochloride salt.

18. A composition which comprises a compound of claim 1, or a pharmaceutically acceptable salt thereof, and a pharmaceutically acceptable carrier.

19. A compound according to claim 1, or a pharmaceutically acceptable salt thereof, for use in medicine.

20. A method of treating obesity comprising administering a compound according to claim 1, or a pharmaceutically acceptable salt thereof, to a subject in need thereof.

* * * * *